(12) United States Patent
Dodge et al.

(10) Patent No.: US 6,828,331 B1
(45) Date of Patent: Dec. 7, 2004

(54) GROWTH HORMONE SECRETAGOGUES

(75) Inventors: Jeffrey Alan Dodge, Indianapolis, IN (US); Charles Willis Lugar, III, McCordsville, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/890,163
(22) PCT Filed: Feb. 18, 2000
(86) PCT No.: PCT/US00/04274
§ 371 (c)(1),
(2), (4) Date: Jul. 25, 2001
(87) PCT Pub. No.: WO00/49037
PCT Pub. Date: Aug. 24, 2000

Related U.S. Application Data
(60) Provisional application No. 60/120,813, filed on Feb. 19, 1999.

(51) Int. Cl.$^7$ .................. A61K 41/445; C07D 401/06
(52) U.S. Cl. ............. 514/326; 514/323; 514/397; 514/398; 546/201; 546/210; 548/312.1; 548/314.7; 548/326.5
(58) Field of Search ............... 514/323, 326, 514/397, 398; 546/201, 210; 548/312.1, 314.7, 326.5

(56) References Cited

U.S. PATENT DOCUMENTS

| | | | |
|---|---|---|---|
| 3,711,495 A | 1/1973 | Kulsa et al. | 548/241 |
| 3,984,426 A | 10/1976 | Winkelmann et al. | 548/136 |
| 5,206,235 A | 4/1993 | Fisher et al. | 514/213 |
| 5,242,903 A | 9/1993 | Bender et al. | 514/18 |
| 5,380,866 A | 1/1995 | Barnett et al. | 548/330.1 |
| 5,401,851 A | 3/1995 | Boyd et al. | 548/112 |
| 5,459,156 A | 10/1995 | Muller-Gliemann et al. | 514/397 |

(List continued on next page.)

FOREIGN PATENT DOCUMENTS

| | | |
|---|---|---|
| EP | 0 662 481 B1 | 8/1993 |
| EP | 0 615977 A1 | 9/1994 |
| EP | 0 761219 A1 | 8/1996 |
| EP | 0 761 219 A | 3/1997 |
| EP | 0 761 220 A | 3/1997 |
| WO | WO 94/13696 A | 6/1994 |
| WO | WO 95/11029 A | 4/1995 |
| WO | WO 96/15148 A | 5/1996 |
| WO | WO 96/35713 A1 | 11/1996 |
| WO | WO 96/38471 A1 | 12/1996 |
| WO | WO 97/15573 A | 5/1997 |
| WO | WO 97/24369 A1 | 7/1997 |
| WO | WO 97/34604 A1 | 9/1997 |
| WO | WO 97/41878 A1 | 11/1997 |
| WO | WO 98/16527 A1 | 4/1998 |
| WO | WO 99 08697 A1 | 2/1999 |
| WO | WO 99/08699 A1 | 2/1999 |
| WO | WO 99/08699 | 2/1999 |
| WO | WO 00/10565 | 3/2000 |
| WO | WO 00/12047 A2 | 3/2000 |
| WO | WO 00/49037 | 8/2000 |

OTHER PUBLICATIONS

*Synthesis of 4–Nitroimidazoles with 1–Substituents Containing Acid, Ester or Phenol Functions, and Radiosensitizing Efficiency of Some of These Compounds,* Suwinski, et al., Arch. Pharm., vol. 325, pp. 317–324 (1992).

*Synthetic Approaches to the 'Azole' Peptide Mimetics,* Gordon, et al., Tetrahedron Letters, vol. 34, NO. 12, pp. 1901–1904 (1993).

Chem. Abst. No. 130:209977, Kaufffman, et al. *Treatment of Congestive Heart Failure with Growth Hormone Secretagogues,* Kauffman et al., application of WO 99/08697, Aug. 19, 1998.

Chem. Abst. No. 130:182769, Dodge, et al., *Preparation of Heterocyclic Peptide Derivatives as Growth Hormone Secretagogues,* application of WO 9908699, Aug. 19, 1998.

Chem. Abst. No. CA 119:261758, Uzundo, et al., *Some Aspects of the Enantiorecognition of Derivatized Primary Amines on a Pirkle–type Chiral Stationary Phase Utilizing Tocainide and Mexiletine as Model Compounds,* J. Chromatogr. (1993).

*Primary Examiner*—Celia Chang
(74) *Attorney, Agent, or Firm*—William R. Boudreaux; Scott A. McNeil

(57) ABSTRACT

What is disclosed are growth hormone secretagogues, and their uses, of the formula

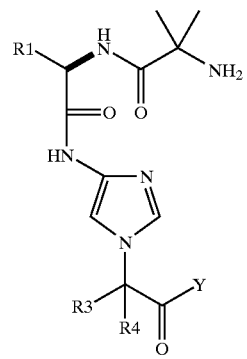

wherein R1 is $C_6H_5CH_2OCH_2—$, $C_6H_5$ $(CH_2)3—$ or indol-3-ylmethyl; Y is pyrrolidin-1-yl, 4-$C_1$–$C_6$ alkylpiperidin-1-yl or NR2R2; R2 are each independently a $C_1$ to $C_6$ alkyl; R3 is 2-napthyl or phenyl para-substituted by W; W is H, F, $CF_3$, $C_1$–$C_6$ alkoxy or phenyl; and R4 is H or $CH_3$, or a pharmaceutically acceptable salt or solvate thereof.

8 Claims, No Drawings

U.S. PATENT DOCUMENTS

| | | | |
|---|---|---|---|
| 5,492,916 A | 2/1996 | Marriello et al. | 514/318 |
| 5,492,920 A | 2/1996 | Chen et al. | 514/323 |
| 5,494,919 A | 2/1996 | Marriello et al. | 514/323 |
| 5,559,128 A | 9/1996 | Chakravarty et al. | 514/323 |
| 5,574,167 A | 11/1996 | Jaber | 548/327.1 |
| 5,578,593 A | 11/1996 | Chen et al. | 514/212 |
| 5,583,130 A | 12/1996 | Bochis et al. | 514/183 |
| 5,652,235 A | 7/1997 | Chen et al. | 514/215 |
| 5,661,161 A | 8/1997 | Anthony et al. | 514/326 |
| 5,663,146 A | 9/1997 | Bowers et al. | 514/16 |
| 5,663,171 A | 9/1997 | Chen et al. | 514/19 |
| 5,700,827 A | 12/1997 | Schnorrenberg et al. | 514/414 |
| 5,721,250 A | 2/1998 | Morriello et al. | 514/318 |
| 5,756,528 A | 5/1998 | Anthony et al. | 514/399 |
| 5,773,441 A | 6/1998 | Hipskind et al. | 514/253 |
| 5,798,337 A | 8/1998 | Somers et al. | 514/19 |
| 5,830,855 A | 11/1998 | Takemoto | 514/11 |
| 6,046,333 A | 4/2000 | Dorziotis et al. | 546/18 |
| 6,329,342 B1 * | 12/2001 | Kauffman et al. | 514/16 |
| 6,639,076 B1 | 10/2003 | Heiman et al. | 546/210 |

* cited by examiner

GROWTH HORMONE SECRETAGOGUES

This application claims benefit of Provisional 60/120,813 filed Feb. 19, 1999.

BACKGROUND OF THE INVENTION

Growth hormone is a secretory protein of the pituitary gland of animals having wide ranging developmental effects on the organism. Artificial manipulation of growth hormone levels has been demonstrated to have significant therapeutic utility. Human growth hormone supplementation has been shown to be an effective treatment for growth hormone deficiencies and their related disease states in humans. Apart from this application, studies have uncovered new and significant properties of growth hormone which lend further importance to the ability to control growth hormone levels. For example, recent clinical studies indicate that growth hormone supplementation may be useful in combating the maladies of aging in humans. Elevated growth hormone levels in animals have been shown to result in increased lean muscle mass. One application of this latter observation could result in higher production of leaner meat products or in the production of larger and/or stronger animals.

While growth hormone is naturally produced by the pituitary gland, the secretion of growth hormone into the bloodstream is controlled by a second protein, Growth Hormone Releasing Factor (GRF). This hormone is also commonly known in the art as somatocrinin, Growth Hormone Releasing Hormone (GHRH), and Growth Releasing Hormone (GRH).

There are two ways to approach the problem of increasing circulating levels of growth hormone: (1) increase the level of human growth hormone in the organism directly or (2) increase the organism's natural tendency to produce growth hormone. The latter strategy may be achieved via supplementation with GRF. GRF has been demonstrated to increase the circulatory levels of growth hormone in vivo. (Rivier, et al., *Nature* (London). 300:276 (1982). The effect of GRF, including structural analogs thereof, on growth hormone production has been widely studied. A primary obstacle to the use of GRF as a direct supplement is its short lifespan in vivo. L. A. Frohman, et al., *Journal of Clinical Investigation*, 78:906 (1986). More potent and/or longer lasting GRF molecules are therefore desirable for the development of effective human therapeutic or animal husbandry agents.

The structure of GRF has been modified in numerous ways resulting in longer lasting and/or more potent GRF analogs. It has been demonstrated that the first 29 amino acids from the N-terminus are sufficient to retain full GRF activity. Speiss, et al., *Biochemistry*, 21:6037 (1982). One strategy has been the incorporation of novel D-amino acid residues in various regions of the GRF molecule. V. A. Lance, et al., *Biochemical and Biophysical Research Communications*, 119:265 (1984); D. H. Coy, et al., *Peptides*, 8(suppl. 1):49 (1986). Another strategy has modified the peptide backbone of GRF by the incorporation of peptide bond isosteres in the N-terminal region. D. Tourwe, *Janssen. Chim. Acta*, 3:3 (1985); S. J. Hocart, et al., *Journal of Medicinal Chemistry*, 33:1954–58 (1990). A series of very active analogs of GHRH is described in European Patent Publication 511,003, published Oct. 28, 1992.

In addition to the actions of GHRH there are various ways known to release growth hormone. For example, chemicals such as arginine, L-3,4-dihydroxyphenylalanine (L-DOPA), glucagon; vasopressin, and insulin-induced hypoglycemia, as well as activities such as sleep and exercise, indirectly cause growth hormone to be released from the pituitary by acting in some fashion on the hypothalamus, perhaps either to decrease somatostatin secretion or to increase the secretion of GHRH.

In cases where increased levels of growth hormone are desired, the problem has generally been solved by providing exogenous growth hormone or by administering GHRH, or a related peptidyl compounds which stimulates growth hormone production or release. In either instance the peptidyl nature of the compound has necessitated that it be administered by injection.

Other compounds have been developed which stimulate the release of endogenous growth hormone, such as analogous peptidyl compounds related to GHRH. These peptides, while considerably smaller than growth hormones are still susceptible to metabolic instability.

Administration of the hexapeptide growth hormone releasing peptide-6 (GHRP-6) results in the secretion of growth hormone in many species, including humans. This peptide is one of a series of synthetic peptides, the structures of which were based on the pentapeptide Met-enkephalin. It has been shown that GHRP binds specifically to the pituitary, although the binding does not involve the opioid, GHRH, or the somatostatin receptors.

In recent years significant efforts have been taken to develop nonpeptidyl analogs of this series of compounds. Such compounds, termed growth hormone secretagogues, should be orally bioavailable, induce the production or release of growth hormone, and act in concert, or synergistically with GHRH.

Representative growth hormone secretagogues are disclosed in U.S. Pat. No. 3,239,345; U.S. Pat. No. 4,036,979; U.S. Pat. No. 4,411,890; U. S. Pat. No. 5,206,235; U.S. Pat. No. 5,248,841; U.S. Pat. No. 5,310,737; U.S. Pat. No. 5,310,017; European Patent Publication 144,230; European Patent Publication 513,974; Patent Cooperation Treaty Patent Publication WO 94/07486; Patent Cooperation Treaty Patent Publication WO 94/08583; Patent Cooperation Treaty Patent Publication WO 94/13696; U.S. Ser. No. 08/704,494, filed Aug. 20, 1996, U.S. Ser. No. 08/700,206, filed Aug. 20, 1996, and *Science*, 260:1640–1643 (1993).

U.S. Pat. No. 5,206,235, issued Apr. 27, 1993, describes a series of benzolactam compounds typified by the following structure.

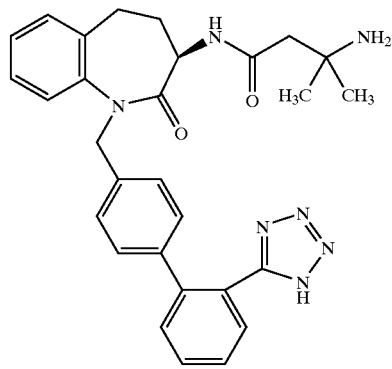

These compounds have demonstrated clinical activity in humans in raising the growth hormone secretory levels. B. J. Gertz, *Journal of Clinical Endocrinology and Metabolism*, 77:1393–1397 (1993).

Another group of growth hormone secretagogues is described in Patent Cooperation Treaty Patent Publication WO 94/13696, published Jun. 23, 1994. These compounds are typified by the following two structures.

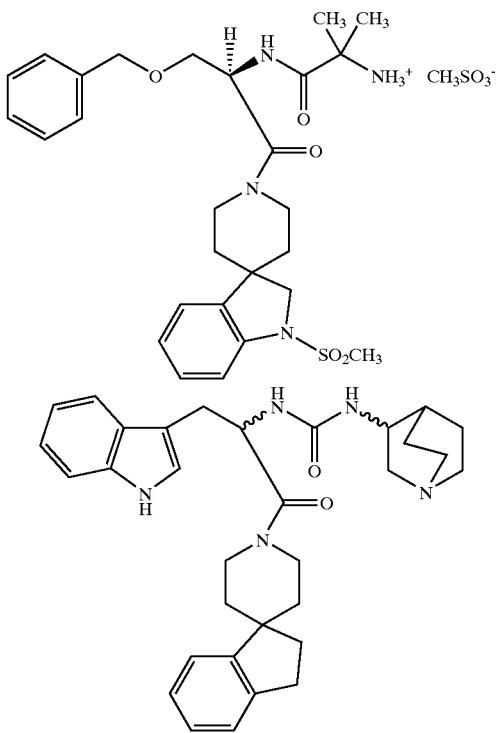

The present invention provides a series of compounds that have activity as growth hormone secretagogues. These compounds are non-peptidyl in nature and are, therefore, more metabolically stable than growth hormone, growth hormone releasing hormone, or analogs of either of these proteins. The compounds employed in the present invention are preferred for human pharmaceutical uses as well as veterinary uses, particularly in cattle, swine, sheep, poultry and fish.

SUMMARY OF THE INVENTION

The present invention relates to compounds of Formula I, as follows:

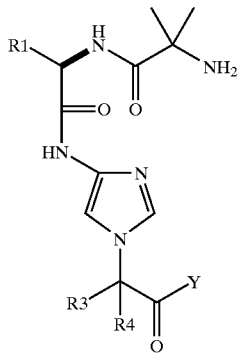

wherein R1 is $C_6H_5CH_2OCH_2$—, $C_6H_5(CH_2)_3$— or indol-3-ylmethyl; Y is pyrrolidin-1-yl, 4-$C_1$-$C_6$ alkylpiperidin-1-yl or NR2R2; R2 are each independently a C1 to $C_6$ alkyl; R3 is 2-napthyl or phenyl para-substituted by W; W is H, F, $CF_3$, $C_1$–$C_6$ alkoxy or phenyl; and R4 is H or $CH_3$, or a pharmaceutically acceptable salt or solvate thereof.

The present invention further relates to pharmaceutical formulations containing compounds of Formula I, alone or in combination with other growth hormone secretagogue compounds, and/or in combination with suitable bone-antiresorptive agents, and the use of said compounds and/or formulations at least for the increase in endogenous levels of growth hormone in a mammal.

The present invention yet further relates to methods for the treatment or prevention of a physiological condition which may be modulated by an increase in endogenous growth hormone, which method comprises administering to an animal in need of said treatment an effective amount of a compound of Formula I.

The present invention still further relates to processes for the preparation of compounds of Formula I.

DETAILED DESCRIPTION

In a preferred embodiment, compounds of the present invention are those compounds of Formula I wherein R3 is a methyl group.

In another preferred embodiment, compounds of the present invention are those compounds of Formula I wherein Y is 4-methylpiperidin-1-yl.

It is also preferred that the stereochemistry, at the two chiral centers, of the compounds of Formula I is (R,R).

The terms and abbreviations used in the instant examples have their normal meanings unless otherwise designated For example "° C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "FDMS" refers to field desorption mass spectrometry; "UV" refers to ultraviolet spectroscopy; "IR" refers to infrared spectroscopy; and "NMR" refers to nuclear magnetic resonance spectroscopy.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_4$ alkyl".

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

The term "carboxy-protecting group" as used herein refers to substituents of the carboxy group commonly employed to block or protect the carboxy functionality while reacting other functional groups on the compound. Examples of such protecting groups include methyl, ethyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxy-benzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)-ethyl, p-toluenesulfonylethyl, 4-nitrobenzylsulfonylethyl, allyl, cinnamyl, 1-(trimethylsilylmethyl)prop-1-en-3-yl, and the like.

A preferred carboxy-protecting group for the practice of the present invention is methyl or ethyl. Further examples of these groups may be found in E. Haslam, supra, at Chapter 5, and T. W. Greene, et al., supra, at Chapter 5.

The term "amino-protecting group" as used herein refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, n-butoxycarbonyl, (NBoc) t-butoxycarbonyl, 1,1-diphenyl-eth-1-yloxycarbonyl, 1,1-diphenylprop-1-yloxycarbonyl, 2-phenylprop-2-yloxycarbonyl,2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenyl-methoxycarbonyl (FMOC), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)-benzyloxycarbonyl, isobornyloxycarbonyl, 1-piperidyloxycarbonyl, and the like; benzoylmethylsulfonyl group, 2-nitrophenylsulfenyl, diphenylphosphine oxide and like amino-protecting groups.

The amino-protecting group employed is usually not critical so long as the derivatized amino group is stable to the condition of subsequent reactions on other positions of the intermediate molecule, and may be selectively removed at the appropriate point without disrupting the remainder of the molecule including any other amino-protecting groups. A preferred amino-protecting group for the practice of the present invention is t-butoxycarbonyl (NBoc). Further examples of groups referred to by the above terms are described by E. Haslam, *Protective Groups in Organic Chemistry*, (J. G. W. McOmie, ed., 1973), at Chapter 2; and T. W. Greene and P. G. M. Wuts, *Protective Groups in Organic Synthesis* (1991), at Chapter 7.

The term "leaving group" (Q) refers to a group of atoms that is displaced from a carbon atom by the attack of a nucleophile in a nucleophilic substitution reaction. Suitable leaving groups include bromo, chloro, and iodo, benzenesulfonyloxy, methanesulfonyloxy, and toluenesulfonyloxy. The term "leaving group" (Q) includes activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, azido, or —O—CO—($C_4$–$C_7$ alkyl).

The compounds used in the method of the present invention have two chiral centers. As a consequence of these chiral centers, the compounds of the present invention occur as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in *Nomenclature of Organic Compounds: Principles and Practice*, (J. H. Fletcher, et al., eds., 1974) at pages 103–120.

In addition to the (R)-(S) system, the older D-L system is also used in this document to denote absolute configuration, especially with reference to amino acids. In this system, a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, a number of routes are available. As an example, a mixture of enantiomers may be prepared, and then the two enantiomers may be separated A commonly employed method for the resolution of the racemic mixture (or mixture of enantiomers) into the individual enantiomers is to first convert the enantiomers to diastereomers by way of forming a salt with an optically active acid or base. These diastereomers may then be separated using differential solubility, fractional crystallization, chromatography, or the like. Further details regarding resolution of enantiomeric mixtures may be found in J. Jacques, et al., *Enantiomers, Racemates, and Resolutions*, (1991).

During any of the following synthetic sequences it may be necessary or desirable to protect sensitive or reactive groups on any of the molecules concerned. This may be achieved by employing conventional protecting groups as described, supra.

The compounds of the present invention may be prepared by a number of routes, many of which are known to those of skill in the art. The particular order of steps to be employed in the synthesis of compounds of formula I is dependent upon the compound to be synthesized, the starting material employed, and the relative lability of the various substituted moieties. Examples of such synthetic routes may be found in Schemes I through IV provided below, as well as in the Examples.

One synthetic route to compounds of the present invention is provided in Scheme IA–IC below. The compounds of formula IV' and IV are commercially available, or may be prepared using techniques known in the art. A compound of Formula IV may be prepared from a compound of Formula IV, through an intermediate acid chloride prepared by standard methods using thionyl chloride or oxalyl chloride. Treatment of the resulting acid chloride with a bromine source, such as N-bromosuccinimide, followed by quenching of the acid chloride with ethanol, results in compounds of Formula IV. It is to be understood that the bromine group on the compound of Formula IV may in fact be any suitable leaving group (Q), as defined herein. This preparation is provided below in Scheme IA.

Scheme IA

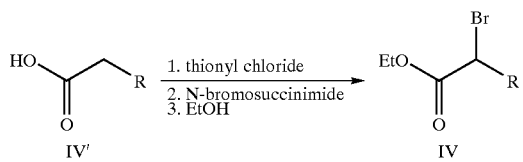

wherein R is representative of E as defined in a compound of Formula I above.

As shown in Scheme IB, the starting material further includes compounds of Formula V, which are commercially available, or may be routinely synthesized using techniques readily known in the art. Compounds of Formula IV may be coupled with a compound of formula V (4-nitroimidazole) by methods known in the art to generate a compound of Formula IIb'. Suitable agents to be employed in the coupling of these compounds include the treatment of a compound of Formula IV with an organic or inorganic base, followed by reaction with the bromo compound of Formula IV. Standard organic bases include trialkylamines, potassium hexamethyldisilazide, lithium hexamethyldisilazide, lithium diisopropylamide, potassium carbonate, and the like. Preferred for the practice of the present invention is sodium hydride or potassium carbonate in dimethylformamide.

A compound of Formula IIb' is then deprotected to provide a compound of Formula IIb, using lithium hydroxide, although other deprotecting reagents may be employed in this reaction. Such deprotecting agents include standard saponification reagents such as sodium hydroxide, potassium hydroxide, and lithium hydroxide.

Substantially pure (R) enantiomers of compounds of Formula IIb may also be synthesized by methods provided in U.S. Pat. Nos. 5,344,937 and 5,380,866, the disclosures of which are herein incorporated by reference.

A compound of Formula IIb is then converted to the corresponding amide under appropriate conditions with a compound of formula VI to generate a compound of Formula IIa. In general, amidation of primary or secondary amines of Formula VI may be accomplished by a number of methods known in the art in which activation of the acid to form a better leaving group. Suitable activating agents for this are also known in the art and include dicyclohexycarbodiimide (DCC), 1-(3-dimethylaminopropyl)-3-ethylcarbodiimide hydrochloride (EDC) with hydroxybenzotriazole (HOBT), oxalyl chloride, thionyl chloride, PyBOP® (benzotriazol-1-yl-oxytripyrrolidine-phosphonium hexafluorophosphate), and the like. Preferred for the practice of the present invention is hydroxybenzotriazole (HOBT). The nitro group on the resulting compound of Formula IIa may then be reduced to an amino group using any suitable means, employing a suitable reducing agent. Preferred for the practice of the present invention is a catalytic reduction employing hydrogen and 5% palladium on carbon. A compound of Formula II is produced by this reduction reaction.

The preferred reaction temperature range employed in these reactions is between −40 and 150° C., and the most preferred range is between 10 and 40° C. These reactions may be conveniently carried out in situ, without isolation of the particular compound after its preparation.

Examples of these reactions are provided below in Scheme IB wherein R is representative of E as previously defined, and $R_2R_1N$ is $R_6$ as previously defined.

Scheme IB

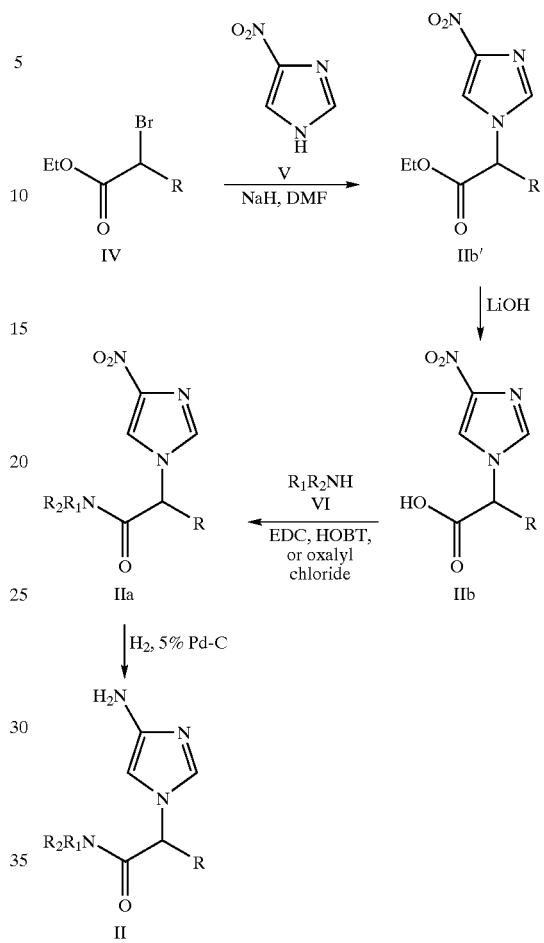

A second portion of the overall synthesis of compounds of Formula I is provided in Scheme IC below.

Representative starting material for this synthesis is a compound of Formula IIIb', which is a chemically-protected form of the amino acid O-serine. By chemically-protected it is meant that both the amino- and carboxy- functional groups have been suitably protected in order to facilitate further reactions with this molecule. Such protection reactions are known to those of skill in the art, and may be applied to other suitable starting materials. Intermediates of formula IIIb' are commercially available, or may be prepared by standard syntheses of amino acids. Such syntheses are well known to persons of ordinary skill in the art and are described, for example, in *Chemistry and Biochemistry of Amino Acids*, (G. C. Chapman ed., 1985). The protected amino group may be specifically deprotected using trifluoroacetic acid and methylene chloride to allow for further reactions with this amino functional group. This deprotection reaction results in a compound of Formula IIIb.

A compound of Formula IIIb may then be N-acylated with an amino-protected compound of formula X to produce a compound of Formula IIIa'. Suitable activating agents for this N-acylation reaction are known in the art and include DCC, HOBT, EDC, and oxalyl chloride. Preferred for the practice of the present invention is HOBT. Compounds of formula X are commercially available, or are readily prepared from suitable available starting materials. The protected carboxy group on the compound of Formula IIIa' is then selectively deprotected, typically using lithium hydroxide, to generate a compound of Formula III. Compounds of Formula III in which the starting material IIIb' is 2-Nboc-amino-pentanoic acid methyl ester may also be prepared by the route described in Scheme IC.

A compound of Formula III is then coupled with a compound prepared from the reduction of IIb' with hydrogen and a palladium catalyst employing a coupling reaction to generate a compound of Formula Ia. Again, typical reagents for this N-acylation are known in the art, and include DCC and HOBT, which is the preferred method of coupling employed in the practice of the present invention. A compound of Formula Ia is then selectively deprotected at the carboxy group, coupled at this site with a compound of Formula VI, and then further deprotected at the amino group to generate a compound of Formula Ia. Suitable agents for these deprotection and coupling reactions are discussed, infra, and are known in the art. Compounds of Formula Ia are encompassed by Formula I, and are pharmaceutically active.

The preferred reaction temperature range employed in these reactions is between −40 and 150° C., and the most preferred range is between 10 and 40° C. These reactions may be conveniently carried out in situ, without isolation of the particular compound after its preparation.

Alternatively, compounds of Formula IIa can be coupled with compounds of Formula III to provide intermediates which can be deprotected to give compounds of Formula Ia.

Representative reactions are provided below in Scheme IC, wherein R is E as previously defined, and $R_2R_1N$ is $R_6$ as previously defined.

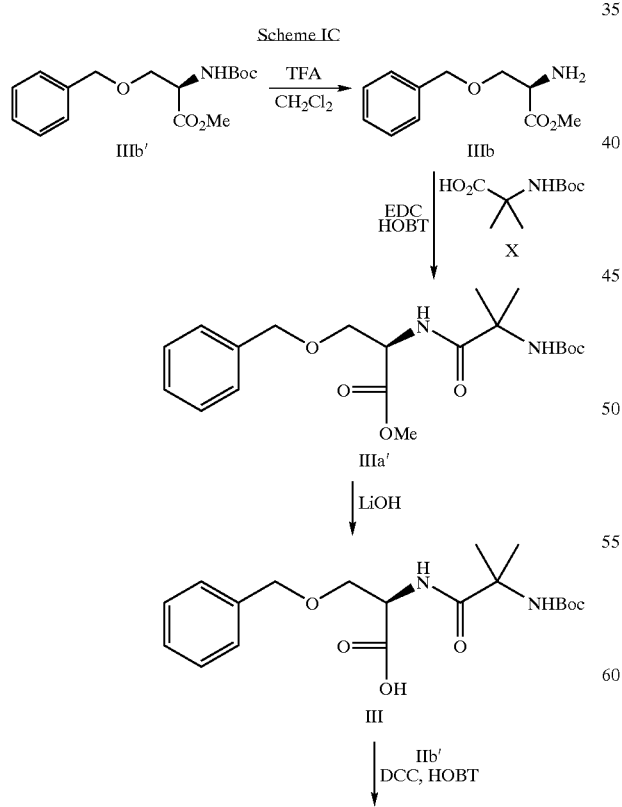

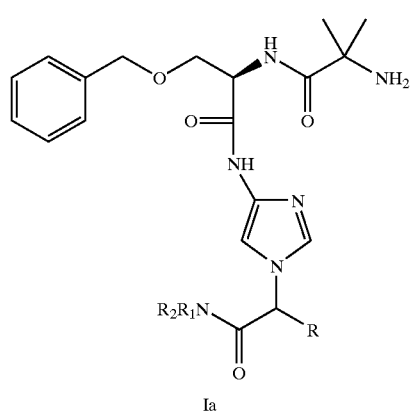

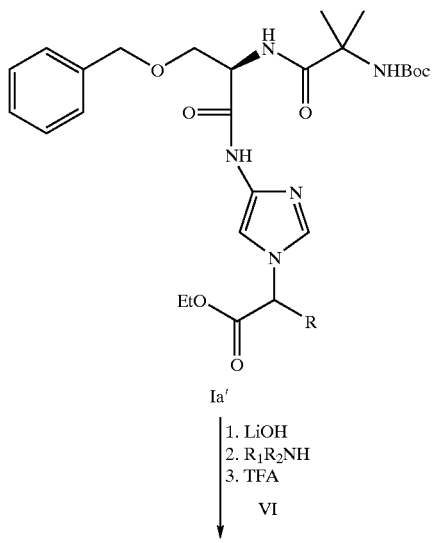

In addition to the synthetic scheme described hereinabove, an enantiospecific protocol for the preparation of the compounds of Formula I may be employed. Typically, a synthetic reaction design which maintains the chiral center present in the starting material in a desired orientation is chosen. The preferred reaction schemes are those that generally produce compounds in which greater than 95 percent of the product is the desired enantiomer. In Scheme II below, R-substituted phenyl is representative of the E substituents as provided in compounds of Formula I above.

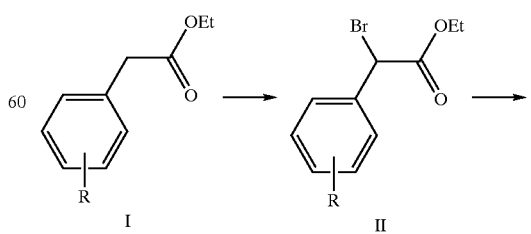

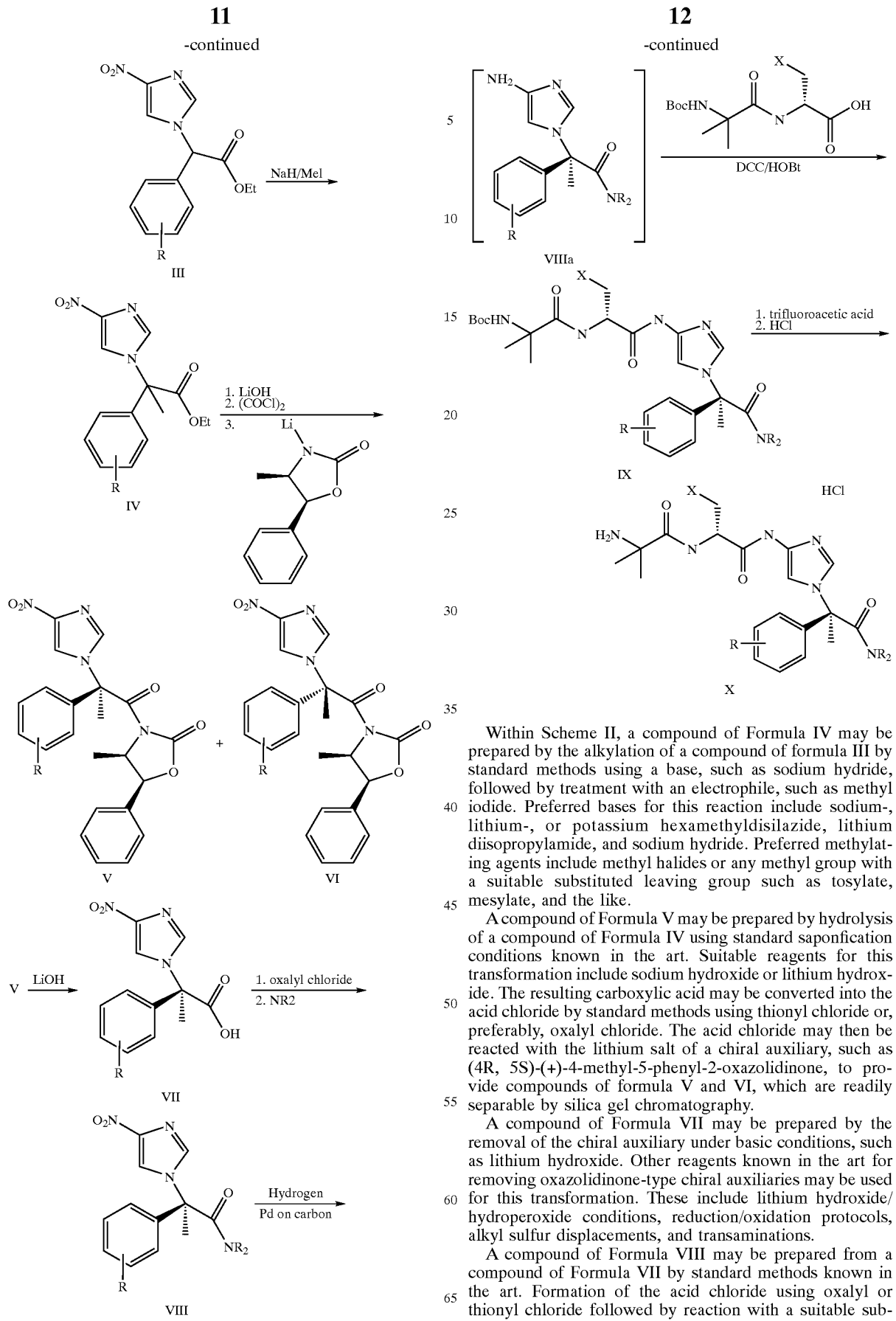

Within Scheme II, a compound of Formula IV may be prepared by the alkylation of a compound of formula III by standard methods using a base, such as sodium hydride, followed by treatment with an electrophile, such as methyl iodide. Preferred bases for this reaction include sodium-, lithium-, or potassium hexamethyldisilazide, lithium diisopropylamide, and sodium hydride. Preferred methylating agents include methyl halides or any methyl group with a suitable substituted leaving group such as tosylate, mesylate, and the like.

A compound of Formula V may be prepared by hydrolysis of a compound of Formula IV using standard saponfication conditions known in the art. Suitable reagents for this transformation include sodium hydroxide or lithium hydroxide. The resulting carboxylic acid may be converted into the acid chloride by standard methods using thionyl chloride or, preferably, oxalyl chloride. The acid chloride may then be reacted with the lithium salt of a chiral auxiliary, such as (4R, 5S)-(+)-4-methyl-5-phenyl-2-oxazolidinone, to provide compounds of formula V and VI, which are readily separable by silica gel chromatography.

A compound of Formula VII may be prepared by the removal of the chiral auxiliary under basic conditions, such as lithium hydroxide. Other reagents known in the art for removing oxazolidinone-type chiral auxiliaries may be used for this transformation. These include lithium hydroxide/ hydroperoxide conditions, reduction/oxidation protocols, alkyl sulfur displacements, and transaminations.

A compound of Formula VIII may be prepared from a compound of Formula VII by standard methods known in the art. Formation of the acid chloride using oxalyl or thionyl chloride followed by reaction with a suitable substituted amine ($NR_2$) provide compounds of Formula VIII.

A compound of Formula IX may be prepared by the reduction of a compound of Formula VIII using hydrogen with palladium on carbon. Other methods known in the art which may be employed for the reduction of the nitro group include the use of tin(II)chloriide, iron in an acidic solution, ferrous sulfate and aqueous alkali, activated alumina, and sodium sulfite. The resulting 4-amino imidazole compound of Formula VIIa is then reacted directly with the appropriate dipeptide acid (a compound of Formula IIX) under standard peptide coupling conditions involving formation of the active ester of the dipeptide followed by reaction with amine VIIa. Conditions suitable for amide formation include DCC, EDC, with HOBT. A compound of Formula IIX may be prepared from the methyl ester of unnatural D-amino acids it such as D-benzyloxyserine, D-tryptophan, and D-2-amino-5-phenyl-pentanoic acid and the like which are known in the art. Standard coupling protocols involving formation of the active ester of the amino acid using DCC/HOBT followed by reaction with N-Boc-aminoisobutyric acid provide dipeptide acids of Formula IIX.

The Boc protecting group of a compound of Formula IX may be removed under standard acidic conditions such as hydrochloric acid in acetic acid or ethyl acetate, trifluoroacetic acid, tetramethyliodosilane, aluminum chloride, sulfuric acid in dioxane, and methanesulfonic acid.

An additional method of preparing diastereomeric compounds of Formula I involves the use of a chromatographic column which employs a chiral phase. An example of such a preparation may be found in Examples Part 6 as provided hereinbelow.

Two additional Schemes for providing chiral intermediates are provided hereinbelow as Schemes IIIA and IIIB. As described in Scheme IIIA, optically pure aryl glycine amino acids may be protected at the amino position by reaction with a suitable protecting group, such as Boc. Reaction of the Boc protected intermediate with a standard methylating agent, such as methyl iodide, may provide the corresponding phenolic methyl ether. The carboxamide may be prepared by coupling with an amine, such as dimethylamine, pyrrolidine, or 4-methyl piperidine, using standard coupling techniques. Preferred coupling agents for the invention are diethyl cyanophosphorane (DECP), triethylamine and the amine at 0° C. The Boc protecting group may be removed under standard acidic conditions, with trifluoroacetic acid being preferred. The desired 4-nitroimidazole compounds can be prepared by reaction of the free amine with 1,4-dinitroimidazole to give optically pure compounds, as determined by chiral HPLC. Such chiral intermediates can be processed as described in Schemes I and II to provide diastereomerically pure products. For example, the chiral nitroimidazoles described in Scheme IIIA or IIIB may be reduced under standard conditions, such as hydrogenation with a palladium catalyst, to provide the corresponding chiral amino intermediate II. Such intermediates may be subsequently coupled with compounds of formula III of Scheme II as previously described to provide a chiral intermediate which can be deprotected to give diastereomerically pure compounds of formula Ia.

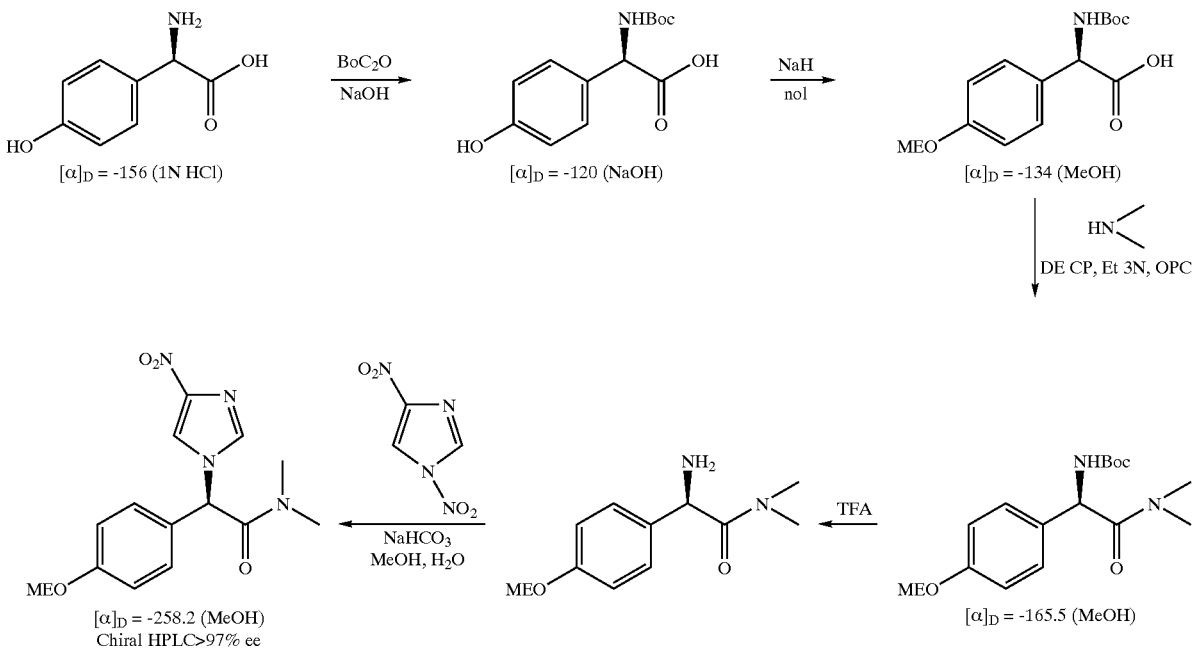

Scheme IIIA CHIRAL SYNTHESIS of D-Phenylglycine Imidazole Subunit

Scheme IIIB Chiral Synthesis of L-Phenylglycine Imidazole
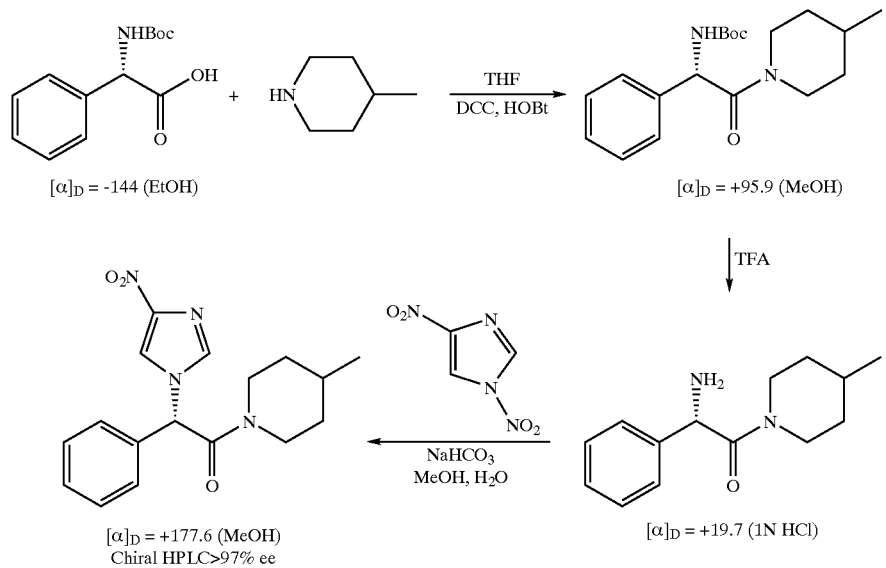
An additional approach and corresponding synthetic scheme for the preparation of compounds of the instant invention is provided below in Scheme IV:
Scheme IV
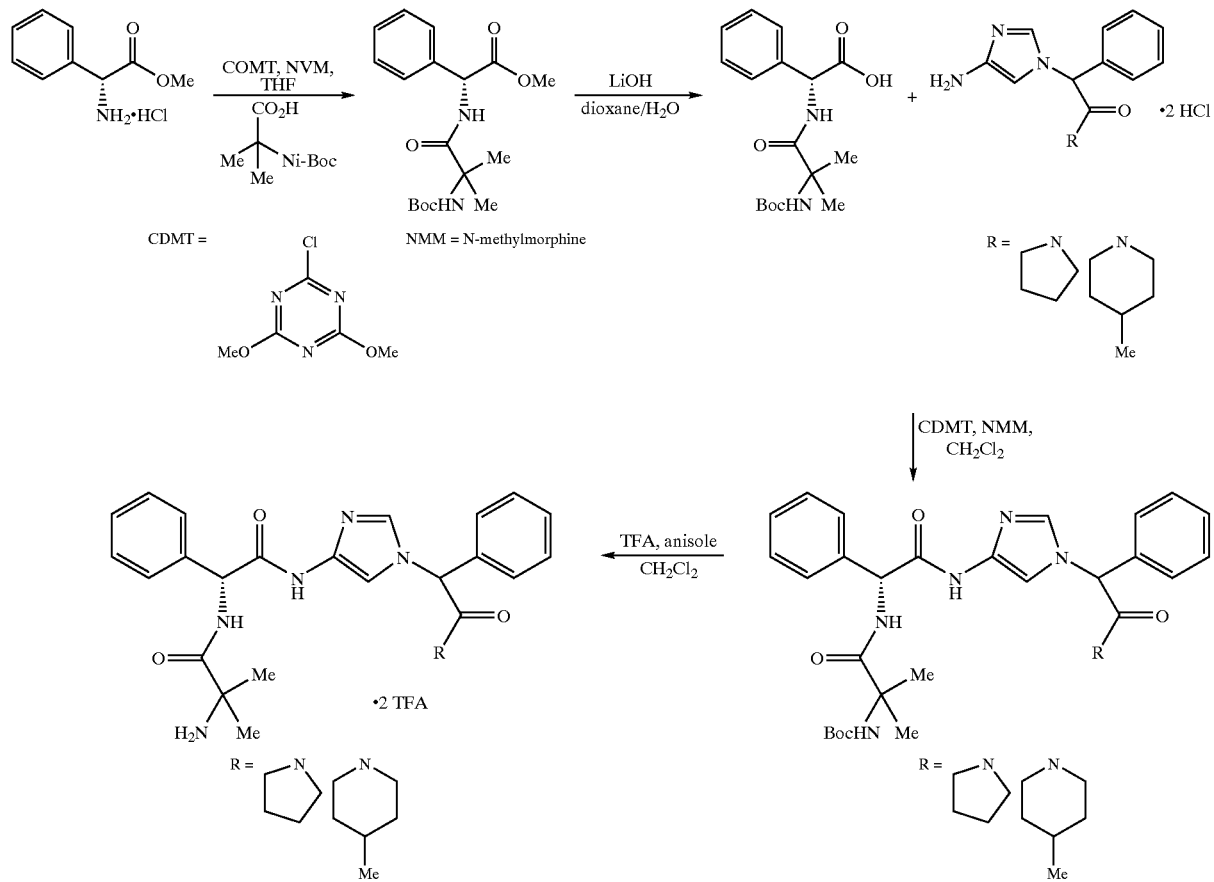

Compounds of Formula I may be conveniently screened for growth hormone secretagogue activity. A typical assay may employ pituitary cells established in culture, followed by a challenge with the various compounds of formula I, and the levels of growth hormone determined accordingly. Growth hormone levels may be calculated using various radioimmunoassay techniques known to those of skill in the art. Screening of compounds for growth hormone secretagogue activity may conveniently be scaled up for high throughput screening.

The invention further encompasses methods employing the pharmaceutically acceptable salts of the compounds defined by Formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein refers to salts of the compounds of Formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, naphthalene-2-sulfonate, mandelate, mesylate, and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary amonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further encompasses methods employing pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

This invention also encompasses methods employing the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:

1) ester or amide derivatives which may be cleaved by esterases or lipases;

2) peptides which may be recognized by specific or nonspecific proteases; or 3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, *Design of Prodrugs*, (1985).

As used herein, the term "effective amount" means an amount of compound of the instant invention which is capable of inhibiting, alleviating, ameliorating, treating, or preventing further symptoms in mammals, including humans, which may be due to decreased levels of endogenous growth hormone.

By "pharmaceutically acceptable formulation" it is meant that the carrier, diluent, excipients and salt must be compatible with the active ingredient (a compound of Formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, sachets, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

In addition, the growth hormone secretagogue compounds as disclosed herein may be administered to a patient in need of treatment in combination with other growth hormone secretagogues known in the art, and/or with a suitable bone anti-resorptive agent or agents for the prevention or treatment of osteoporosis and/or loss of muscle strength. Said suitable bone anti-resorptive agents include selective estrogen receptor modulators, bisphophonates, calcitonin, and hormone replacement therapeutic agents. Additionally, PTH may be administered in combination with said growth hormone secretagogues. Said combination therapy may be administered concomitantly or sequentially.

Suitable dosing ranges of compounds of Formula I include 0.01 µg/kg/day to 60 mg/kg/day.

The present invention also relates to methods for the modulation of cardiac function which comprise the administration of a compound of Formula I.

The present invention further relates to methods for the treatment or prevention of congestive heart failure by administering, to an animal in need thereof, an effective amount of a compound of Formula I.

The present invention additionally relates to pharmaceutical formulations containing a growth hormone secretagogue alone or in combination with additional therapeutic agents useful for the treatment or prevention of congestive heart failure.

The use of growth hormone secretagogue compounds, for the modulation of cardiac function and for the treatment or prevention of congestive heart failure, are described in copending U.S. patent application Ser. No. 09/137,255, filed Aug. 19, 1998, titled "Treatment of Congestive Heart Failure With Growth Hormone Secretagogues", the teachings of which are incorporated herein in their entirety by reference.

The particular dosage of a compound required to treat, inhibit, or prevent the symptoms and/or disease of congestive heart failure in a mammal, including humans, according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy.

Representative pharmaceutical formulations containing compounds of formula I are provided below. The formulations which follow are given for purposes of illustration and are not intended to be limiting in any way. The total active ingredients in such formulations comprises from 0.1% to 99.9% by weight of the formulation. The term "active ingredient" means a compound of Formula I.

Formulation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation 6

Suppositories, each containing 25 mg of active ingredient are made as follows:

| Ingredient | Amount |
| --- | --- |
| Active Ingredient | 25 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation 9

An intravenous formulation may be prepared as follows:

| Ingredient | Quantity |
| --- | --- |
| Active Ingredient | 250.0 mg |
| Isotonic saline | 1000 ml |

Formulation 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C.

When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another formulation employed in the methods of the present invention employs transdermal delivery devices or patches. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, the disclosure of which is herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, the disclosure of which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The following Examples and Preparations are illustrative of the processes employed in the synthesis of the compounds of the present invention. As would be understood by persons skilled in the art, other synthetic schemes may be employed to prepare the compounds of the instant invention.

Exemplification

EXAMPLE 1

Preparation of Chemical Intermediates

EXAMPLE 1A

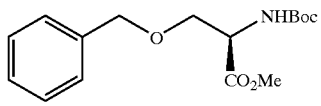

Preparation 1A

To a solution of tert-butyloxycarbonyl-O-benzyl (boc-OBz)-D-Ser-OH (25.0 g, 84.7 mmol), while stirring in anhydrous N,N-dimethylformamide (500 mL) at room temperature, was added sodium bicarbonate (14.2 g, 169 mmol) followed by methyl iodide (26.4 mL, 424 mmol). After 18 hours, the reaction mixture was concentrated to approximately 100 mL Ethyl acetate was added and the mixture washed with aqueous sodium bicarbonate and brine. The organic extract was dried and concentrated to give the above-identified product (25 g, 96%) as a light yellow oil:

$^1$H NMR (300 MHz, CDCl$_3$) d 1.45 (s, 9H), 3.70 (m, 1H), 3.75 (s, 3H), 3.85 (m, 1H), 4.50 (m, 3H), 7.30 (m, 5H); MS (FD) m/e 310; Anal. calc'd for C$_{16}$H23NO5: C, 62.12; H, 7.49; N, 4.53. Found: C, 62.31; H, 7.49; N, 4.43.

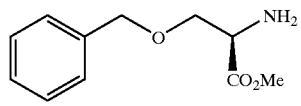

Preparation 1B

To a solution of a compound of Preparation 1A (5.0 g, 16 mmol), stirring in dichloromethane (25 mL) [or 40 mL?] and anisole (1 mL) at 0° C. was added trifluoroacetic acid. After 4 hours at room temperature, saturated sodium bicarbonate solution was added and the mixture extracted with ethyl acetate. The combined organic extracts were washed with brine, dried over sodium sulfate, and concentrated. The above-identified crude product was used in the next step without further purification.

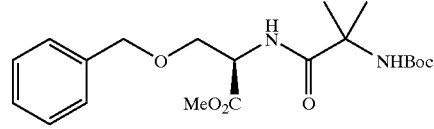

Preparation 1C

To a solution of a compound of Preparation 1B (65.4 mmol), boc-α-aminoisobutyric acid (13.2 g, 65.4 mmol), 1-hydroxybenzotriazole (8.8 g, 65.4 mmol), and N,N-diisopropylethylamine (22.8 mL, 130.7 mmol) stirring in dichloromethane (500 mL) at 0° C. was added 1-(3-dimethyl-aminopropyl)-3-ethylcarbodiimide (12.3 g, 71.9 mmol). After 18 hours, ethyl acetate and saturated ammonium chloride were added and the mixture extracted with ammonium chloride, sodium bicarbonate, and brine. The organic extracts were dried over sodium sulfate and concentrated. Purification by silica gel chromatography (25% ethyl acetate/hexanes) yielded the above-identified product (21.6 g, 83%) as a white solid: $^1$H NMR (300 MHz, CDCl$_3$) d 1.39 (s, 9H), 1.48 (s, 6H), 3.62 (dd, J=3.4, 9.1 Hz, 1H), 3.70 (s, 3H), 3.85 (dd, J=3.4, 9.1 Hz, 1H), 4.48 (dd, J=12.5, 22.7 Hz, 2H), 4.75 (m, 1H), 4.92 (s, 1H), 7.11 (d, J=8.6 Hz, 1H), 7.35 (m, 5H); MS (FD) m/e 395; Anal. calc'd for C$_{20}$H$_{30}$N$_2$O$_6$: C, 60.90; H, 7.67; N, 7.10. Found: C, 61.02; H, 7.78; N, 7.10.

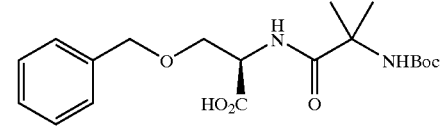

Preparation 1

To a solution of a compound of Preparation 1C (5.30 g, 13.4), stirring in dioxane (100 mL)/water (50 mL) at room temperature was added lithium hydroxide (2.80 g, 67.3 mmol). After 18 hours, water was added and the solution concentrated. The resulting mixture was extracted with diethyl ether. Sodium chloride was added to the aqueous layer and the pH adjusted to 3.5 with 1 N HCl. The resulting mixture was extracted with ethyl acetate and the combined organic extracts dried over sodium sulfate then concentrated to yield the above-identified product (4.40 g, 86%) as a white foam: $^1$H NMR (300 MHz, CDCl$_3$) d 1.39 (s, 9H), 1.45 (s, 3H), 1.47 (s, 3H), 3.68 (m, 1H), 3.95 (m, 1H), 4.54

(s, 2H), 4.70 (m, 1H), 5.51 (bs, 1H), 7.18 (d, J=9.1 Hz, 1H), 7.25 (m, 5H), 9.90 (bs, 1H); MS (FD) m/e 381; Anal. calc'd for $C_{19}H_{28}N_2O_6$: C, 59.99; H, 7.42; N, 7.36. Found: C, 59.74; H, 7.26; N, 7.30.

EXAMPLE 1B

Preparation 2A

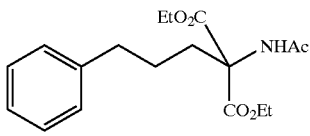

A solution of sodium ethoxide was generated by the addition of sodium metal (52.89 grams, 2.3007 mol), over 3 hours, to ethanol (1500 mL). To the sodium ethoxide solution, at ambient temperature, was added a solution of diethylacetamidomalonate (499.75 grams, 2.3007 mol) dissolved in ethanol (225 mL). The reaction mixture was stirred for 1.5 hours at ambient temperature. 1-bromo-3-phenylpropane (458.07 grams, 2.3007 mol) was then added over 15 minutes and the reaction mixture was refluxed until complete as determined by HPLC (16 hours). The reaction mixture was concentrated to dryness and the residue partitioned between ethyl acetate (1×1500 mL and 2×500 mL) and water (1500 mL). The ethyl acetate layers were combined, washed with saturated sodium chloride solution (4×500 mL), dried using sodium sulfate, and concentrated to give 752.1 grams (98%) of the above-identified product as a light yellow solid: A 1.0 gram sample was recrystallized from hexane:ethyl acetate (19:1, v:v) to give a mp 84–86° C.

$^1$H nmr (CDCl$_3$): δ 1.18–1.23 (t, 6H), 1.37–1.50 (m, 2H), 2.02 (s, 3H), 2.34–2.41 (m, 2H), 2.58–2.62 (t, 2H), 4.16–4.24 (q, 4H), 6.76 (s, broad, 1H), 7.11–7.28 (m, 5H). $^{13}$C nmr (CDCl$_3$): δ 13.95, 23.03, 25.67, 31.85, 35.45, 62.46, 66.49, 125.40, 125.90, 128.27, 128.35, 141.77, 168.11, 168.94. MS (FIA ) m/z 336.3 ([M+H]+). IR (KBr, cm$^{-1}$) 1645.98 (amide), 1744.76 (C=O). Anal. Calc'd. for $C_{18}H_{25}NO_5$: C, 64.46; H, 7.51; N, 4.17. Found: C, 64.60; H, 7.37; N, 4.39.

Preparation 2B

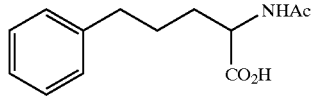

A slurry consisting of the product of Preparation 2A (249.15 grams, 0.7428 mol) and 2.5 N sodium hydroxide solution was then heated at 100° C. for three hours. The reaction mixture was cooled to 30° C. and the pH adjusted to 5.0 using concentrated hydrochloric acid. The solution was then heated to 100° C. and the pH was held at 5.0 using concentrated hydrochloric acid as needed until the reaction was complete as determined by HPLC. The solution was filtered while hot through diatomaceous earth. The filtrate was cooled to 5–10° C. and the pH adjusted to 1.0 using concentrated hydrochloric acid. The resulting slurry was stirred for 1 hour at 5° C., filtered, and dried in vacuum at 50° C. to give 160.34 grams (92%) of above-identified product, (DL)-N-acetyl-2-amino-5-phenylpentanoic acid, as a white powder, mp 145–148° C. $^1$H nmr (DMSO-d$_6$): δ 1.60–1.71 (m, 4H), 1.86 (s, 3H), 2.56–2.59 (m, 2H), 4.19–4.23 (m, 1H), 7.16–7.30 (m, 5H), 8.14 (d, 1H). $^{13}$C nmr (DMSO-d$_6$): δ 23.17, 28.25, 31.55, 35.51, 52.55, 126.60, 129.14, 142.64, 170.25, 174.65. MS (FIA) m/z 236.2 (M+). IR (KBr, cm$^{-1}$) 1609.17 (amide), 1741.12 (C=O). Anal. Calc'd. for $C_{13}H_{17}NO_3$: C, 66.36; H, 7.28; N, 5.95. Found: C, 66.41; H, 7.15; N, 5.96.

Preparation 2C

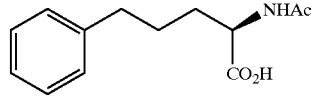

A solution consisting of (DL)-N-acetyl-2-amino-5-phenylpentanoic acid (Preparation 2B) (438.0 grams, 1.862 mol), cobalt chloride (1.10 grams), 2N potassium hydroxide solution (931 mL, 1.862 mol), and water (8000 mL) was adjusted to a pH of 8.0 by the addition of 2N potassium hydroxide solution. To the reaction mixture was added Acylase I (aspergillus melleus, 39.42 grams) which was then vigorously stirred for 24 hours at 40° C. while maintaining a pH of 8.0 by addition of 2N potassium hydroxide. The resulting slurry was filtered. The filtrate was adjusted to a pH of 2.0 giving a thick slurry. The product was isolated by filtration, washed with hexane (2000 mL) and dried in vacuum at 50° C. to give 188.52 grams (43%) of the above-identified product, (D)-N-acetyl-2-amino-5-phenylpentanoic acid: $^1$H nmr (DMSO-d$_6$): δ 1.59–1.74 (m, 4H)., 1.86 (s, 3H), 2.57–2.60 (m, 2H), 4.22–4.26 (m, 1H), 7.16–7.30 (m, 5H), 8.02 (d, 1H), 12.39 (s, broad, 1H). $^{13}$C nmr (DMSO-d$_6$): δ 23.18, 28.13, 31.66, 35.54, 52.58, 126.56, 129.10, 142.67, 170.12, 174.48. MS (FIA ) m/z 236.1 (M$^+$). IR (KBr, cm$^{-1}$) 1625.08 (amide), 1700.24 (C=O). Anal. Calc'd. for $C_{13}H_{17}NO_3$: C, 66.36; H, 7.28; N, 5.95. Found: C, 66.49; H, 7.00; N, 6.03.

Preparation 2D

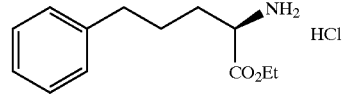

A solution consisting of (D)-N-acetyl-2-amino-5-phenylpentanoic acid (Preparation 2C)(188.8 grams, 0.8024 mol), ethanol (535 mL), and concentrated hydrochloric acid (268 mL, 3.21 mol) was warmed to 85° C. The reaction was determined to be incomplete by HPLC at 14.5 hours and additional concentrated hydrochloric acid (50 mL) was then added. This reaction was determined to be complete by HPLC after 22.5 hours. Subsequently, water was azeotropically distilled from the reaction by continuous addition and distillation of 8000 mL of ethanol. The ethanol was azeotropically distilled from the reaction by the continuous addition and distillation of ethyl acetate (2000 mL). Upon cooling the solution to 0° C. the product crystallized. The solution containing the product was stirred for 1 hour at 0° C., filtered, and the cake dried in vacuum at 40° C. to give 199.0 grams (96%) of the above-identified product, 2-amino-5-phenylpentanoic acid, ethyl ester hydrochloride: (mp 117–121° C. $^1$H nmr (DMSO-d$_6$): δ 1.15–1.21 (t, 3H), 1.50–1 89 (m, 4H), 2.48–2.67 (m, 2H), 3.92–3.98 (t, 1H), 4.08–4.25 (m, 2H), 7.12–7.29 (m, 5H), 8.76 (s, broad, 3H). $^{13}$C nmr (DMSO-d$_6$): δ 13.90, 25.97, 29.52, 34.41, 51.71, 61.56, 124.91, 125.81, 128.24, 141.27, 169.35. MS (FIA ) m/z 222.3 (M$^+$). IR (KBr, cm$^{-1}$) 1741.14 (C=O). $[α]^{20}_D$=−11.17(c=30.62 mg/3mL, MeOH). Anal. Calc'd. for $C_{13}H_{20}NO_2Cl$: C, 60.58; H, 7.82; N, 5.43. Found: C, 60.45; H, 7.67; N, 5.55.

Preparation 2E

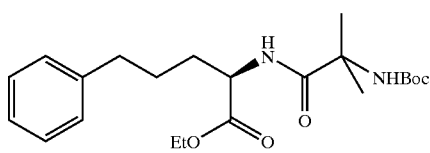

A slurry consisting of N-t-BOC-α-aminoisobutyric acid (90.64 grams, 0.446 mol), 2-chloro-4,6-dimethoxy-1,3,5-triazine (75.90 grams, 0.425 mol), N-methyl morpholine (88.13 grams, 0.871 mol), and diethyl ether (1000 mL) was stirred at ambient temperature until complete as determined by HPLC (3 hours). The D-2-amino-5-phenylpentanoic acid, ethyl ester hydrochloride (Preparation 2D), (109.55 grams, 0.425 mol) was added and the reaction mixture stirred for 16 hours at ambient temperature. The reaction mixture was partitioned between 10% citric acid solution (1000 mL) and ethyl acetate (3×500 mL). The organic phase was washed with 10% citric acid solution (3×500 mL), saturated sodium bicarbonate solution (3×500 mL), water (1×500 mL), dried using sodium sulfate, and concentrated to dryness. The residue was recrystallized from hexane (3000 mL) to give 155.11 grams of the above-identified product: mp 97–99° C.

$^1$H nmr (CDCl$_3$): δ 1.25–1.28 (t, 3Hz, 1.43 (s, 9H), 1.48 (s, 3H), 1.50 (s, 3H), 1.70–1.73 (m, 3H), 1.87–1.93 (m, 1H), 2.62–2.67 (m, 2H), 4.16–4.21 (m, 2H), 4.57–4.62 (m, 1H), 4.95 (s, 1H), 6.96 (s, broad, 1H), 7.16–7.19 (m, 3H), 7.26–7.33 (m, 2H). $^{13}$C nmr (CDCl$_3$): δ 14.53, 26.32, 27.17, 28.67, 32.47, 35.73, 52.54, 57.17, 61.62, 126.21, 128.69, 128.79, 142.12, 154.99, 172.81, 174.69. MS (FIA ) m/z 407.5 ([M+H]$^+$). IR (KBr, cm$^{-1}$) 1652.75, 1685.52 (amides), 1741.73 (C=O). [α]$^{20}_D$=7.83 (c =10.22 mg/1 mL, MeOH). UV (0.1% trifluoroacetic acid in water : acetonitrile) λ$_{max}$ 215;6 nm. Anal. Calc'd. for C$_{22}$H$_{34}$N$_2$O$_5$: C, 65.00; H, 8.43; N, 6.89. Found: C, 65.23; H, 8.34; N, 6.94.

Preparation 2

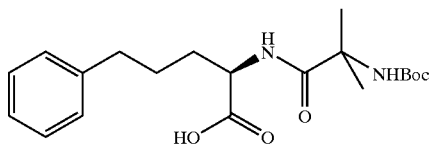

A solution consisting of the product of Preparation 2E (152.53 grams, 0.3752 mol) and tetrahydrofuran (884 mL) was cooled to 5° C. A solution consisting of lithium hydroxide (26.96 grams, 1.126 mol) and water (1419 mL) was added to the reaction dropwise over 10 minutes while maintaining a temperature of 5–10° C. Ethanol (183 mL) was added and the reaction stirred at 5–10° C. until complete as determined by HPLC (2 hours). The pH of the reaction mixture was then adjusted to 2.0 using 6 N hydrochloric acid solution while maintaining 5–10° C. The product was extracted from solution with ethyl acetate (3×500 mL). The ethyl acetate extracts were combined, dried using sodium sulfate, and concentrated to dryness to give 141.51 grams (100%) of the above-identified product: $^1$H nmr (DMSO-d$_6$): δ 1.32–1.37 (m, 15H), 1.57–1.75 (m, 4H), 2.51–2.58 (m, 2H), 4.23–4.27 (m, 1H), 6.85 (s, broad, 1H), 7.15–7.28 (m, 5H), 7.42 (d, 1H), 12.5 (s, broad, 1H). $^{13}$C nmr (DMSO-d$_6$): δ 26.31, 27.85, 29.00, 31.86, 35.60, 52.53, 56.60, 78.95, 126.52, 129.05, 129.10, 142.69, 155.06, 174.40, 175.17. MS (FIA) m/z 379.5 ([M+H]$^+$). IR (KBr, cm$^{-1}$) 1641.98, 1692.22 (amides), 1719.72 (C=O). [α]$^{20}_D$=−5.73 (c =10.48 mg/1 mL, MeOH). Anal. Calc'd. for C$_{20}$H$_{30}$N$_2$O$_5$: C, 63.47; H, 7.99; N, 7.40. Found: C, 63.25; H, 7.84; N, 7.46.

EXAMPLE 1C

Preparation 3A

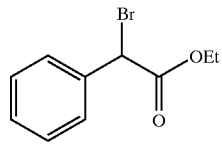

To a solution of α-bromophenylacetic acid (100 g, 466 mmol), stirring in absolute ethanol (500 mL) at room temperature, was added p-toluenesulfonic acid monohydrate (10 g, 53 mmol). This solution was heated to reflux and, after 8 hours, concentrated to dryness. The resulting residue was dissolved in ethyl acetate, washed with saturated aqueous sodium bicarbonate, brine, dried over sodium sulfate, filtered, and concentrated to yield 77 g (68%) of the above-identified product as an orange oil:

$^1$H-NMR is consistent with structure; MS (FD) 241.9, 243.9.

Preparation 3

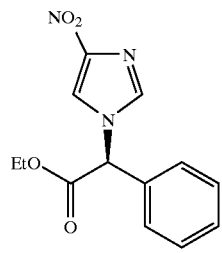

To a slurry of sodium hydride (13.6 g of a 60% dispersion in mineral oil, 341 mmol) stirring in N,N-dimethylformamide (240 mL) was carefully added 4-nitroimidazole (38.6 g, 341 mmol) such that the temperature during the addition was maintained below 40° C. This resulting slurry was stirred for 1 hour and then cooled to 5° C. To this mixture was slowly added Preparation 3A (76 g, 310 mmol) at a rate such that the reaction temperature was maintained below 20° C. After 4 hours, the reaction was concentrated and subsequently extracted with ethyl acetate. The combined organic extracts were filtered, washed with water, brine, dried over sodium sulfate, filtered and concentrated. The resulting residue was purified by silica gel chromatography (methanol/chloroform gradient) to yield the 60.1 g (70%) of the above-identified product as a white solid: $^1$H-NMR is consistent with structure; MS (FD) 275 (M+); Anal. Calc'd. for: C, 56.73; H, 4.73; N, 15.27. Found: C, 56.48; H, 4.78; N, 15.08.

EXAMPLE 1D

Preparation 4A

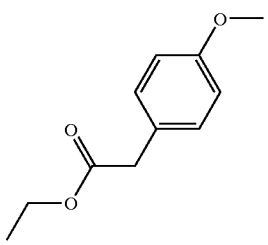

To a solution of 4-methoxyphenylacetic acid (98 g, 590 mmol), in absolute ethanol (300 mL), was added of p-toluenesulfonic acid (20 g, 105 mmol). The reaction mixture was heated to reflux and maintained at that temperature for 5 hours then cooled to room temperature and concentrated to dryness. The resulting oil was purified by flash chromatography (silica gel, 20% ethyl acetate/hexanes) to give 102 g (89%) of the above-identified product as a colorless oil: $^1$H-NMR (d, DMSO) 1.17 (t, J=8.7 Hz, 3H), 3.56 (s, 2H), 3.73 (s, 3H), 4.05 (q, J=7.2 Hz, 2H), 6.87 (d, J=8.7 Hz, 2H), 7 17 (d, 8.7 Hz, 2H); MS (ion spray) 195.3 (M+1); Anal. Calc'd for $C_{11}H_{14}O_3$: C, 68.02; H, 7.27. Found: C, 67.95, 7.17.

Preparation 4B

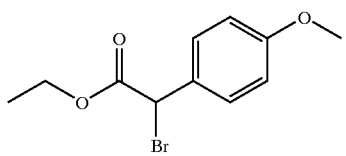

To a solution of the product of Preparation 4A (40 g, 200 mmol) in carbon tetrachloride (500 mL) was added N-bromosuccinimide (37 g, 206 mmol) and hydrobromic acid (4 drops of 48% aqueous solution). The resulting mixture was heated to reflux and maintained at that temperature for 5 hours then cooled to room temperature, filtered, and concentrated. The resulting oil was purified by flash chromatography (silica gel, chloroform) to give 51.1 g (94%) of the above-identified product as a colorless oil: $^1$H-NMR (d, DMSO) 1.19 (t, J=8.4 Hz, 3H), 3.77 (s, 3H), 4.18 (m, 2H), 5.88 (s, 1H), 6.95 (d, J=8.4 Hz, 2H), 7.50 (d, J=8.4 Hz, 2H); MS (FD) 272, 274 (M+); Anal. Calc'd for $C_{11}H_{13}BrO_3$: C, 48.37; H, 4.80. Found: C, 48.52, 4.77.

Preparation 4

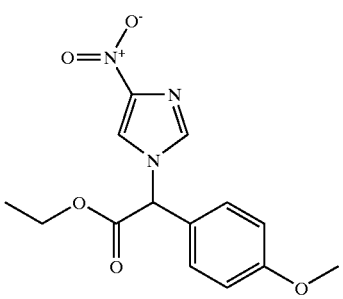

To a solution of the product of Preparation 4B (49.5 g, 181 mmol), stirring in dimethylformamide (500 mL) at room temperature, was added 4-nitroimidazole (20.5 g, 181 mmol) and potassium carbonate (75 g, 543 mmol). After 16 hours, the reaction mixture was filtered and concentrated. The resulting oil was partitioned between ethyl acetate and water and extracted with ethyl acetate. The combined organic extracts were washed with brine, dried over sodium sulfate, filtered and concentrated. The resulting oil was purified by flash chromatography (silica gel, 30–70% ethyl acetates/hexanes gradient) to yield 33.6 g (61%) of the above-identified product as an orange oil that solidifies upon standing: $^1$H-NMR (d, DMSO) 1.17 (t, J=7.2 Hz, 3H), 3.78 (s, 3H), 4.25 (q, J=7.2 Hz, 2H), 6.57 (s, 1H), 7.02 (d, J=8.7 Hz, 2H), 7.46 (d, J=8.7 Hz, 2H), 7.92 (s, 1H), 8.38 (s, 1H); MS (ion spray) 306 (M+1); Anal. Calc'd for $C_{14}H_{15}N_3O_5$: C, 55.08; H, 4.95; N, 13.76. Found: C, 54.93; H, 4.89; N, 13.82.

EXAMPLE 1E

Preparation 5A

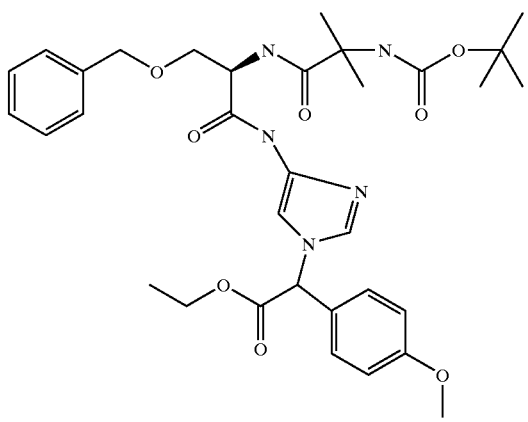

To a slurry of 10% palladium on carbon (6.0 g) was added a slurry of the product of Preparation 4 (8.4 g, 27.5 mmol) in tetrahydrofuran (30 mL). The reaction mixture was placed under a hydrogen atmosphere (40 mm Hg) using a Parr apparatus, until the reduction was complete. The reaction mixture was then filtered through celite. To the resulting solution, stirring at room temperature, was added the product of Preparation 1 (10.5 g, 27.5 mmol), 1-hydroxybenzotriazole (4.1 g, 30.3 mmol) and 1-(3-dimethylaminopropyl)-3-ethylcarbodiimide (6.3 g, 30.3 mmol). After 16 hours, the reaction mixture was concentrated and the resulting oil was slurried in ethyl acetate and filtered. The solution was diluted with water and then extracted with ethyl acetate. The combined organic extracts were washed with brine, dried over sodium sulfate, filtered and concentrated. The resultant crude material was purified by flash chromatography (silica gel, 3% methanol/chloroform) to give 14.4 g (83%) of the above-identified product as a tan foam: $^1$H-NMR (d, DMSO) 1.78 (t, J=7.2 Hz, 3H), 1.27–1.32 (m, 15H), 3.60 (m, 1H), 3.67 (m, 1H), 3.76 (s, 3H), 4.20 (d, J=7.2 Hz, 2H), 4.44 (d, J=3.0 Hz, 2H), 4.57 (m, 1H), 6.35 (s, 1H), 6.97 (d, J=7.2 Hz, 2H), 7.20–7.35 (m, 10H), 7.40 (m, 1H), 7.52 (s, 1H); MS (ion spray) 638 (M+1); Anal. Calc'd for $C_{33}H_{43}N_5O_8$: C, 62.15; H, 6.80; N, 10.98 Found: C, 62.41; H, 6.85; N, 11.09.

Preparation 5

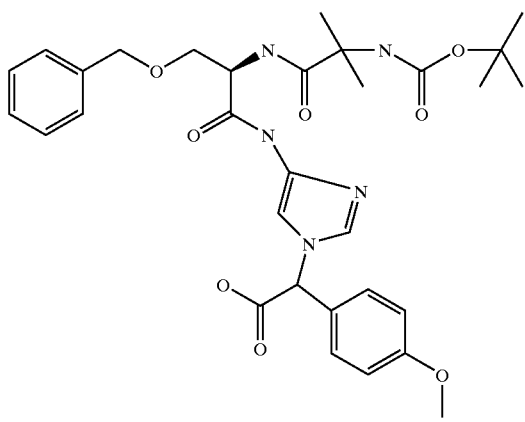

To a solution of the product of Preparation 5A (14.4 g, 23 mmol), stirring in dioxane (150 mL) at room temperature, was added a solution of lithium hydroxide (0.65 g, 27.6 mmol) in water (75 mL). After 20 minutes reaction mixture was acidified to a pH of 2.9 using 1 N hydrochloric acid. To the resulting solution was added water and ethyl acetate. The mixture was then extracted with ethyl acetate. The combined organic extracts were washed with brine, dried over sodium sulfate and concentrated to yield 13.0 g (93%) of the above-identified product as a yellow foam: 1H NMR (d, DMSO) 1.25–1.40 (m, 15H), 3.65–3.70 (m, 2H), 3.76 (s, 3H), 4.44 (d, J=3.4 Hz, 2H), 4.57 (m, 1H), 6.20 (s, 1H), 6.97 (d, J=3.4 Hz, 2H), 7.15–7.35 (m, 10H), 7.42 (m, 1H), 7.53 (s, 1H), 10.2 (s, 1H); MS (ion spray) 610.7 (M+1); Anal. Calc'd for $C_{31}H_{39}N_5O_8$: C, 61.07; H, 6.45; H, 11.49. Found: C, 60.90; H, 6.43; N, 11.32.

EXAMPLE 1F

Preparation 6A

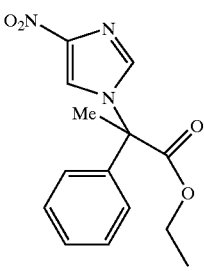

A solution of the product of Preparation 3 (10.00 g, 36.36 mmol) in DMF (50 mL) was added dropwise to a suspension of sodium hydride (1.60 g, 40.00 mmol) in DMF (50 mL) under nitrogen at 0° C. The mixture was stirred 10 minutes. Ethyl iodide (2.5 mL, 40.00 mmol) was then added dropwise. The reaction mixture was subsequently stirred thirty minutes at 0° C., and then for 1 hour at ambient temperature. The mixture was quenched with a saturated solution of sodium bicarbonate. Ethyl acetate was added and the mixture washed with bicarbonate followed by brine. The organic layer was dried over sodium sulfate, filtered, and concentrated in vacuo. The resulting foam was purified by flash chromatography (300 g silica, 2:3 ethyl acetate/hexanes) to yield the above-identified product (8.81 g, 84%) as a light yellow foam: $^1$H NMR (300 Mz, CDCl$_3$)—consistent with structure; Anal. Calc'd. for $C_{14}H_{15}N_3O_4$; 58.13 C, 5.23 H, 14.53 N; found 57.88 C, 5.36 H, 14.39 N; FDMS (M+)–289.

Preparation 6B

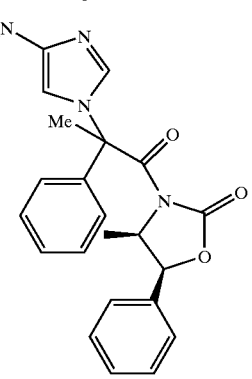

A solution of the product of Preparation 6A (8.35 g, 28.89 mmol) in THF (100 mL) was treated with lithium hydroxide (1.82 g, 43.34 mmol) and water (50 mL). The w reaction was stirred at ambient temperature for 30 minutes. Water was added and the mixture washed with diethyl ether. The pH of the aqueous layer was adjusted to 3.0 with 10% sodium bisulfate. The mixture was saturated with sodium chloride and washed with ethyl acetate. The ethyl acetate washes were combined, dried over sodium sulfate, filtered, and concentrated in vacuo. The resulting crude solid was dissolved in anhydrous dichloromethane (100 mL) under nitrogen. To this solution was added catalytic DMF (0.1 mL) and excess oxalyl chloride (25 g). This mixture was stirred for 3 hours, then concentrated in vacua. The resulting crude foam was dissolved in THF (20 mL) and added dropwise to a solution of lithium (4R,5S)-(+)-4-methyl-5-phenyl-2-oxazolidinone which was generated by adding n-BuLi (1.6M in hexanes, 19.9 mL, 31.82 mmol) dropwise to a solution of (4R, 5S)-(+)-4-methyl-5-phenyl-2-oxazolidinone (5.64 g, 31.82 mmol) in THF (50 mL) at –78° C. under nitrogen and stirred for 20 minutes; and then used without further purification.

The resulting mixture was stirred at –78° C. for 30 minutes, then warmed to 0° C. The mixture was quenched with saturated sodium bicarbonate. Ethyl acetate and water were added and the mixture washed with sodium bicarbonate and brine. The organic layer was dried over sodium sulfate, filtered, and concentrated in vacuo. The resulting foam was purified by flash chromatography (400 g silica, 5% diethyl ether/dichloromethane) to yield diastereomer 1 (3.76 g, 31% yield) and diastereomer 2 (4.32 g, 36%) of above-identified product as colorless foams:

diastereomer 1—$^1$H NMR (300 MHz, CDCl$_3$)—consistent with structure; Anal. Calc'd. for $C_{22}H_{20}N_4O_5$; 62.85 C, 4.80 H, 13.33 N; found 60.97 C, 4.64 H, 12.44 N; FDMS (M+)—420: diastereomer 2—$^1$H NMR (300 MHz, CDCl$_3$)—consistent with structure; Anal. Calc'd. for $C_{22}H_{20}N_4O_5$; 62.85 C, 4.80 H, 13.33 N; found 62.41 C, 4.82 H, 11.92 N; FDMS (M+)—420.

EXAMPLE 1G

Preparation 7A

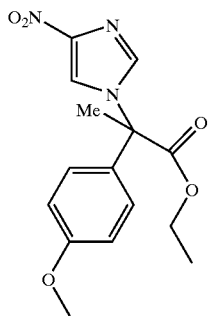

Preparation 7A was prepared, using the method of Preparation 6A, using the product of Preparation 4 (5.00 g, 16.39 mmol) in DMF (25 mL) and sodium hydride (0.72 g, 18.03 mmol) and methyl iodide 1.12 ml, 18.03 mmol) in DMF (25 mL) to yield above-identified product (4.81 g, 92%) as a light yellow foam: $^1$H NMR (300 MHz, CDCl$_3$)—consistent with structure: Anal. calc'd. for C$_{15}$H$_{17}$N$_3$O$_5$; 56.42 C, 5.37 H, 13.16 N; found 56.13 C, 5.35 H, 13.01 N; ISMS (M+)—320.

Preparation 7

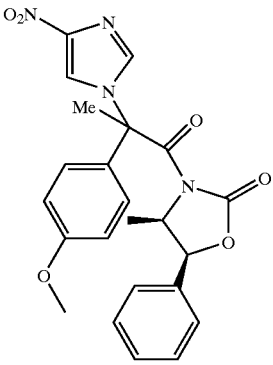

Preparation 7 was prepared, as described in Preparation 6B, using the product of Preparation 7A (4.80 g, 15.03 mmol) in THF (50 mL) and lithium hydroxide (1.26 g, 30.06 mmol) in water (25 mL) to give the crude acid. This material was immediately reacted with anhydrous dichloromethane (100 mL), catalytic DMF (0.5 mL), and excess oxalyl chloride (12 mL) to give the crude acid chloride. This crude product was then reacted with THF (20 mL), n-BuLi (1.6M in hexanes, 14.1 mL, 22.54 mmol), and (4R, 5S)-(+)-4-methyl-5-phenyl-2-oxazolidinone (4.00 g, 22.54 mmol) in THF (50 mL) to yield diastereomer 1 (2.79 g, 41% yield) and diastereomer 2 (2.80 g, 41%) of the above-identified product as colorless foams: 2) diastereomer 1—$^1$H NMR (300 MHz, CDCl$_3$)—consistent with structure; Anal. calc'd. for C$_{23}$H$_{22}$N$_4$O$_6$; 61.33 C, 4.92 H, 12.44 N; found 60.92 C, 4.82 H, 12.03 N; ISMS (M+)—451: H$^1$NMR (300 MHz, CDCl$_3$)—consistent with structure; Anal. calc'd. for C$_{23}$H$_{22}$N$_4$O$_6$; 61.33 C, 4.92 H, 12.44 N; found 61.57 C, 4.98 H, 12.47 N; ISMS (M+)—451.

EXAMPLE 1H

Preparation 8A

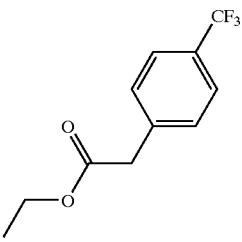

Reaction of 4-trifluoromethylphenyl acetic acid (15.0 g, 73.4 mmol) and p-toluenesulfonic acid (2.8 g, 14.7 mmol) in absolute ethanol (100 mL) as described in Preparation 4A gave 16.3 g (95%) of the above-identified product, as a colorless oil: $^1$H-NMR (d, DMSO) 1.18 (t, J=7.0 Hz, 3H), 3.80 (s, 2H), 4.10 (q, J=7.0 Hz, 2H), 7.49 (d, J=7.9 Hz, 2H), 7.69 (d, J=7.9 Hz, 2H); MS (FD) 232 (M+); Anal. Calc'd for C$_{11}$H$_{11}$F$_3$O$_2$: C, 56.90; H, 4.77. Found: C, 56.81; H,

Preparation 8B

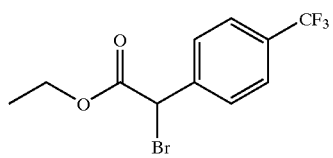

Reaction of the product of Preparation of 8A (15.8 g, 68.0 mmol), N-bromosuccinimide (12.5 g, 70 mmol) and 48% HBr (3 drops) in carbon tetrachloride (80 mL) as described in Preparation 4B, gave 19.8 g (94%) of the above-identified product as a colorless oil: $^1$H-NMR (d, DMSO) 1.19 (t, J=7.2 Hz, 3H), 4.15–4.25 (m, 2H), 6.07 (S, 1H), 7.78 (s, 4H); MS (FD) 309, 311 (M+); Anal. Calc'd for C$_{11}$H$_{10}$BrF$_3$O$_2$: C, 42.47; H, 3.24. Found: C, 42.38; H, 3.13.

Preparation 8

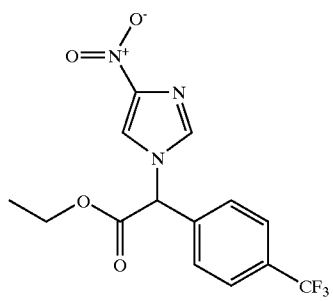

Reaction of the product of Preparation 8B (51.8 g, 167 mmol), 4-nitroimidazole (18.8 g, 167 mmol), and potassium carbonate (51 g, 368 mmol) in N,N-dimethylformamide (600 mL), as described in Preparation 4, gave 21.7 g (38%) of the above-identified product as a viscous orange oil:

$^1$H-NMR (d, DMSO) 1.19 (t, J=7.2 Hz, 3H), 4.26 (q, J=7.2 Hz, 2H), 6.80 (s, 1H), 7.76 (d, J=8.3 Hz, 2H), 7.83 (d, J=8.3 Hz, 2H), 8.01 (s, 1H), 8.51 (s, 1H); MS (ion spray) 344 (M+1); Anal. Calc'd for C$_{14}$H$_{12}$F$_3$N$_3$O$_4$: C, 48.99; H, 3.52; N, 12.24. Found: C, 49.03; H, 3.74; N, 11.96.

EXAMPLE 1I

Preparation 9A

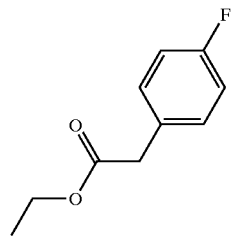

Reaction of 4-fluorophenylacetic acid (15.0 g, 97.0 mmol), p-toluenesulfonic acid (2.0 g, 10.5 mmol) and absolute ethanol (100 mL), as described in Preparation 4A, gave 15.4 g (87%) of the above-identified product as a colorless oil: $^1$H-NMR (d, DMSO) 1.17 (t, J=7.2 Hz, 3H), 3.66 (s, 2H), 4.06 (q, J=7.2 Hz, 2H), 7.10–7.20 (m, 2H), 7.25–7.35 (m, 2H); MS (FD) 182 (M+); Anal. Calc'd for $C_{30}H_{11}FO_2$: C, 65.92; H, 6.09. Found: C, 65.67; H, 5.96.

Preparation 9B

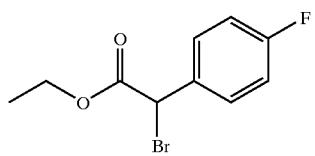

Reaction of the product of Preparation 9A (14.9 g, 82 mmol), N-bromosuccinimide (14.9 g, 84.5 mmol) and 48% HBr (4 drops) in carbon tetrachloride (80 mL) as described in Preparation 4B gave 18.3 g (85%) of the above-identified product, as follows, as a colorless oil: $^1$H-NMR (d, DMSO) 1.19 (t, J=7.2 Hz, 3H), 4.15–4.25 (m, 2H), 5.95 (s, 1H), 7.15–7.30 (m, 2H), 7.56–7.70 (m, 2H); MS (FD) 260, 262 (M+); Anal. Calc'd for $C_{10}H_{10}BrFO_2$: C, 46.00; H, 3.96. Found: C, 46.10; H, 3.95.

Preparation 9

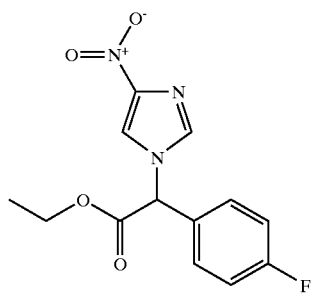

Reaction of the product of Preparation 9B (68 g, 260 mmol), 4-nitroimidazole (35.0 g, 312 mmol) and potassium carbonate (108 g, 780 mmol) in dimethylformamide (300 mL), as described in Preparation 4 gave 39.8 g (52%) of the above-identified product as an orange oil: $^1$H-NMR (d, DMSO) 1.83 (t, J=7.2 Hz, 3H), 4.25 (q, J=7.2 Hz, 2H), 6.66 (s, 1H), 7.25–7.35 (m, 2H), 7 55–7.65 (m, 2H), 7.95 (d, 1;13 Hz, 1H), 8.44 (d, J=1.5 Hz, 1H); MS (ion spray) 294.2 (M+1); Anal. Calc'd for $C_{13}H_{12}FN_3O_4$: C, 53.24; H, 4.12; N, 14.33. Found: C, 53.51; H, 4.07; N, 14.42.

EXAMPLE 1J

Preparation 10A

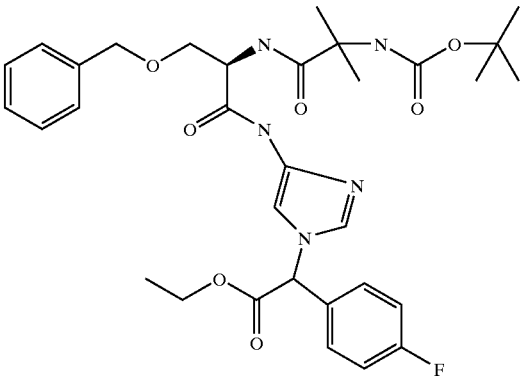

Reduction of the product of Preparation 9 (8.9 g, 30.3 mmol) with 10% palladium on carbon (6.0 g) in tetrahydrofuran (120 mL) followed by coupling with the product of Preparation 1 (11.4 g, 30 mmol), 1-hydroxybenzotriazole (4.5 g, 33 mmol) and 1-(3-dimethylaminopropyl)-3-ethylcarbodiimide (6.8 g, 33 mmol), as described in Preparation 5A, gave 10.8 g (58%) of the above-identified product as a tan foam: $^1$H-NMR (d, DMSO) 1.18 (t, J=7.2 Hz, 3H), 1.25–1.35 (m, 15H), 3.60 (m, 1H), 3.70 (m, 1H), 4.25 (q, J=7.2 Hz, 2H), 4.44 (d, J=2.6 Hz, 2H), 4.60 (m, 1H), 6.47 (s, 1H), 7.20–7.40 (m, 9H), 7.40–7.50 (m, 3H), 7.56 (s, 1H), 10.25 (br s, 1H); MS (ion spray) 626.1 (M+l); Anal. Calc'd for $C_{32}H_{40}FN_5O_7$: C, 61.43; H, 6.44; N, 11.19. Found: C, 61.63; H, 6.42; N, 11.26.

Preparation 10

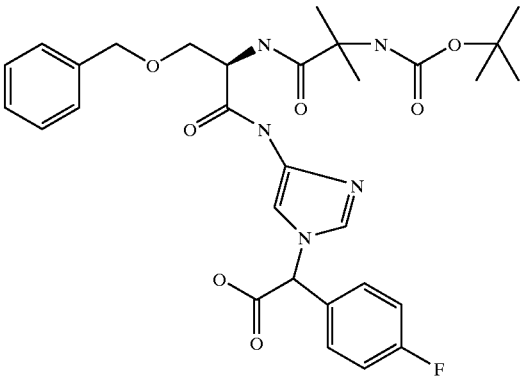

Reaction of the product of Preparation 10A (10.5 g, 17.0 mmol) and lithium hydroxide (0.48 g, 20.4 mmol) in dioxane (200 mL) and water (100 mL) as described in Preparation 5 gave 10.1 g (100%) of the above-identified product as a tan foam: $^1$H-NMR (d, DMSO) 1.25–1.40 (m, 15H), 3.35 (br s, 1H), 3.60 (m, 1H), 3.70 (m, 1H), 4.44 (d, J=2.6 Hz, 2H), 4.60 (m, 1H), 6.33 (s, 1H), 7.20–7.35 (m, 9H), 7.40–7.50 (m, 3H), 7.56 (s, 1H), 10.20 (br s, 1H); MS (ion spray) 598.5 (M+l); Anal. Calc'd for $C_{30}H_{36}FN_5O_7$: C, 60.29; H, 6.07; N, 11.72. Found: C, 60.38; H, 6.29; N, 11.49.

EXAMPLE 1K

Preparation 11A

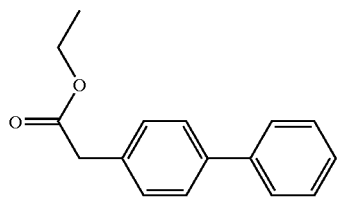

Reaction of biphenylacetic acid (25.2 g, 119 mmol) and p-toluenesulfonic acid (3.3 g, 17 mmol) in absolute ethanol at (250 mL), as described in Preparation 4A gave 25.4 g (89%) of the above-identified product as a yellow oil: $^1$H-NMR is consistent with structure; MS (FD) 240.1 (M+); Anal. Calc'd for $C_{16}H_{16}O_2$: C, 79.97; H, 6.71. Found: C, 79.75; H, 6.59.

Preparation 11B

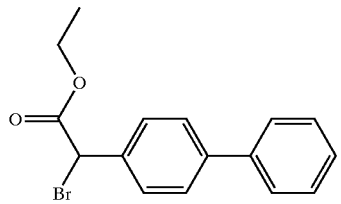

Reaction of the product of Preparation 11A (18.0 g, 75.0 mmol), N-bromosuccinimide (13.7 g, 77.25 mL) and 48% HBr (4 drops) in carbon tetrachloride (80 mL), as described in Preparation 4B, gave 22.56 g (94%) of above-identified product as a yellow oil: $^1$H-NMR is consistent with structure; MS (FD) 318, 320 (M+); Anal. Calc'd for $C_{16}H_{15}BrO_2$ 0.05Chydrochloric acid$_3$: C, 60.2i; H, 4.74. Found: C, 59.50; H, 4.75.

Preparation 11

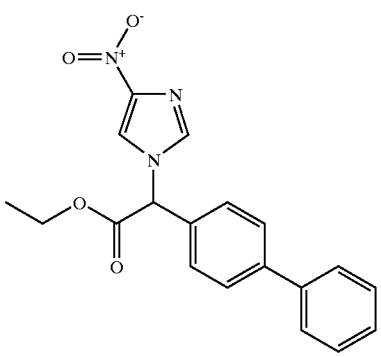

To a slurry of sodium hydride (2.42 g, 60.5 mmol) stirring in dimethylformamide (200 mL) at room temperature, was added 4-nitroimidazole (6.9 g, 60.5 mmol). After 10 minutes, the product of Preparation 11B (17.62 g, 55.0 mmol) was added. After 16 hours, the reaction mixture was concentrated and the residue was slurried in ethyl acetate then filtered. The resulting oil was partitioned between ethyl acetate and water then extracted with ethyl acetate. The combined organic extracts were washed with brine, dried over sodium sulfate, filtered and concentrated. The resulting oil was absorbed onto silica gel and purified by flash chromatography (silica gel, 30–50% ethyl acetate/hexanes) to yield 12.0 g (62%) of the above-identified product as a yellow viscous oil: $^1$H-NMR is consistent with structure; MS (FD) 351 (M+).

EXAMPLE 1L

Preparation 12A

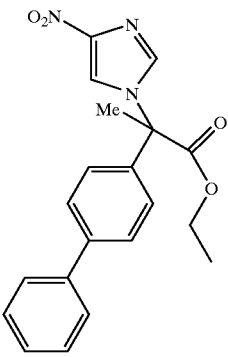

Preparation 12A was prepared as described in Preparation 3, using the product of Preparation 11 (11.03 g, 31.39 mmol) in DMF (50 mL) and sodium hydride (1.25 g, 31.39 mmol) and methyl iodide (1.9 ml, 31.39 mmol) in DMF (50 mL) to yield the above-identified product (10.25 g, 89%) as a light yellow foam: $^1$H NMR (300 MHz, CDCl$_3$)—consistent with the following structure: Anal. calc'd. for $C_{20}H_{19}N_3O_4$; 65.75 C, 5.26 H, 11.50 N; found 63.84 C, 5.16 H, 10.94 N; ISMS (M+)—366.

Preparation 12

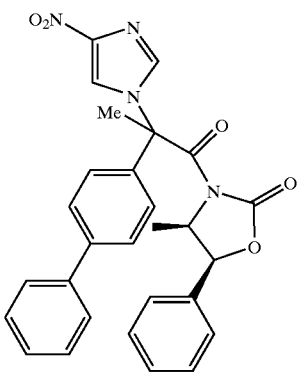

Preparation 12 was prepared as described in Preparation 6B, using the product of Preparation 12A, (10.20 g, 27.92 mmol) in THF (100 mL) and lithium hydroxide (2.34 g, 55.84 mmol) in water (50 mL) to give the crude acid. The resulting crude solid was dissolved in anhydrous dichloromethane (150 mL) and reacted with catalytic DMF (0.5 mL) and excess oxalyl chloride (23 mL). The resulting crude foam was dissolved in THF (50 mL) and reacted with n-BuLi (1.6M in hexanes, 25.1 mL, 40.28 mmol), (4R, 5S)-(+)-4-methyl-5-phenyl-2-oxazolidinone (7.14 g, 40.28 mmol), and THF (150 mL) to yield diastereomer 1 (6.21 g, 45% yield) and diastereomer 2 (6.20 g, 45%) of the above-identified product as colorless foams: $^1$H NMR (300 MHz, CDCl$_3$)—consistent with the structure: Anal. calc'd. for $C_{28}H_{24}N_4O_5$; 66.93 C, 4.99 H, 11.56 N; found 65.32 C, 5.06 H, 10.66 N; ISMS (M+)—497: $^1$H NMR (300 MHz, CDCl$_3$)—consistent with structure; Anal. calc'd. for $C_{28}H_{24}N_4O_5$; 66.93 C, 4.99 H, 11.56 N; found 65.05 C, 4.92 H, 10.61 N; FDMS (M+)—497.

EXAMPLE 1b

Preparation 13A

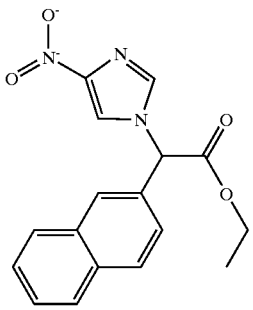

A suspension of 2-naphthyl acetic acid (49.37 g, 265.0 mmol) and thionyl chloride (80 mL) in carbon tetrachloride (55 mL) was heated to reflux for 20 minutes at which time all material went into solution. The reaction was cooled to ambient temperature. Carbon tetrachloride (125 mL), N-bromosuccinamide (56.60 g, 318.0 mmol), and hydrobromic acid (48% aq., catalytic, 0.5 mL) were added. The mixture was heated to reflux for 30 minutes, cooled to ambient temperature, filtered, and concentrated in vacuo. The material was redissolved in dichloromethane (200 mL) and excess ethanol (100 mL) was added dropwise. The mixture was stirred at ambient temperature for 1 hour, then concentrated in vacuo. The crude material was chromatographed (700 g silica, 30% ethyl acetate/hexane) to yield a crude tan solid. This crude material was dissolved dimethylformamide (200 mL) and 4-nitroimidazole (29.78 g, 263.5 mmol) and potassium carbonate (72.70 g, 526.8 mmol) were added. The reaction was stirred at ambient temperature, then concentrated in vacuo to 100 mL. Ethyl acetate and water were added and the mixture washed with sodium bicarbonate and brine. The organic layer was dried over sodium sulfate and concentrated in vacuo. The crude material was chromatographed (1.0 kg silica, 30% ethyl acetate/hexane) to yield the above-identified product (Preparation 13A)(40.2 g, 47%), as follows, as a brown foam: $^1$H NMR (300 MHz, CDCl$_3$)—consistent with structure; Anal. calc'd. for $C_{17}H_{15}N_3O_4$; 62.76 C, 4.65 H, 12.92 N; found 60.54 C, 4.35 H, 12.04 N; ISMS (M+)—326.

Preparation 13

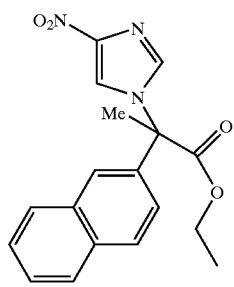

Preparation 13 was prepared, as described in Preparation 6A, using the product of Preparation 13A (13.9 g, 42.65 mmol) in DMF (50 mL) and sodium hydride (1.71 g, 42.65 mmol) and methyl iodide (2.64 ml, 42.65 mmol) in DMF (50 mL) to yield the above-identified product (10.94 g, 77%) as a light yellow oil: $^1$H NMR (300 MHz, CDCl$_3$)—consistent with structure; Anal. calc'd. for $C_{18}H_{17}N_3O_4$; 63.71 C, 5.05 H, 12.38 N; found 63.80 C, 4.98 H, 12.41 N; ISMS (M+)—340.

EXAMPLE 1N

Preparation 14

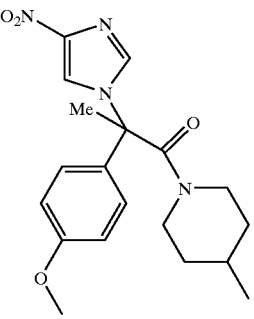

isomer 1

The product of Preparation 7, diastereomer 1 (1.00 g, 2.22 mmol) in THF (50 mL) was added to a solution of lithium hydroxide (0.10 g, 2.44 mmol) in water (25 mL). The resulting mixture was stirred at ambient temperature for 30 minutes. Water was added and the mixture washed with diethyl ether. The pH of the aqueous layer was adjusted to 3.0 with 10% aqueous sodium bisulfate. The mixture was saturated with sodium chloride and washed with ethyl acetate. The ethyl acetate washes were combined, dried over sodium sulfate, filtered, and concentrated in vacuo. The resulting crude solid was dissolved in anhydrous dichloromethane (50 mL) under nitrogen. To this solution was added catalytic DMF (0.1 mL) and excess oxalyl chloride (5 g). This mixture was stirred 3 hours, then concentrated in vacuo.

The resulting crude foam was dissolved in anhydrous dichloromethane (50 mL) and cooled to 0° C. 4-dimethylaminopyridine (catalytic, 10 mg) and 4-methylpiperidine (0.34 mL, 2.71 mmol) were added and the resulting solution stirred for 18 hours. The resulting crude foam was dissolved in anhydrous dichloromethane (50 mL) washed with sodium bicarbonate and brine. The organic layer was dried over sodium sulfate, filtered, and concentrated in vacuo. The crude foam was purified by flash chromatography (silica, 100 g, 5% methanol/dichloromethane) to yield the above-identified product (0.38 g, 50% yield) as a colorless foam: $^1$H NMR (300 MHz, CDCl$_3$)—consistent with structure; Anal. calc'd. for $C_{19}H_{24}N_4O_4$; 61.28 C, 6.50 H, 15.05 N; found 61.38 C, 6.40 H, 15.11 N; FDMS (M+)—372.

EXAMPLE 10

Preparation 15A

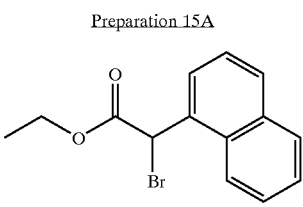

Reaction of 1-naphthylacetic acid (9.3 g, 50 mmol) in carbon tetrachloride (35 mL) was added thionyl chloride (14.4 mL, 200 mmol). The reaction was heated to reflux. After 30 minutes, the mixture was cooled to 20° C. and a solution, of N-bromosuccinimide (8.9 g, 50 mmol) and 48% HBr in carbon tetrachloride, (8 drops) was then added. The reaction was heated to reflux and after 30 minutes, cooled to ambient temperature, filtered and concentrated. The resulting oil was added to absolute ethanol at 0° C. and then concentrated. The residue was purified by flash chromatography (silica gel, 3% ethyl acetate/hexanes) to yield 12.6 g (86%) of the above-identified product as an oil: $^1$H-NMR is consistent with structure.

Preparation 15B

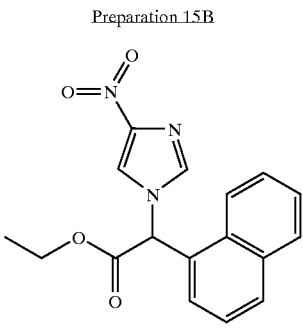

To a slurry of sodium hydride (1.6g, 40 mmol) stirring in dimethylformamide (50 mL) at room temperature was added 4-nitroimidazole (4.5 g, 40 mmol). The reaction was cooled to 0° C. and then the product of Preparation 15A (11.8 g, 40 mmol) was added. The mixture was then slowly warmed to ambient temperature. The reaction was poured into an ice/water mixture and extracted with ethyl acetate. The combined organic extracts were washed with water, brine, dried over sodium sulfate, and concentrated. The residue was purified by flash chromatography (silica gel, 40% ethyl acetate/hexanes) to yield 6.03 g (50%) of above-identified product as an oil: $^1$H-NMR is consistent with structure; MS (ion spray) 325.1 (M+1); Anal. Calc'd for $C_{17}H_{15}N_3O_4 \cdot 0.37H_2O$: C, 61.50; H, 4.78; N, 12.66. Found: C, 61.46; H, 4.60; N, 12.73.

Preparation 15C

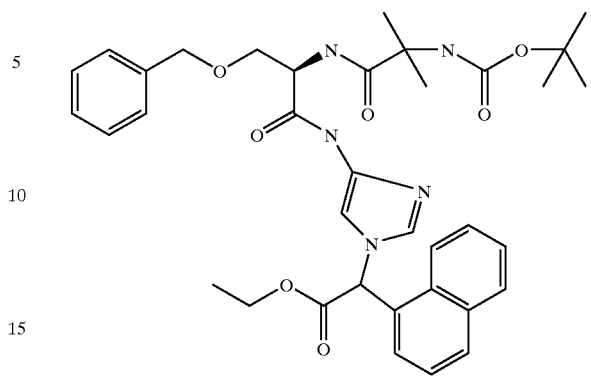

To a slurry of 10% palladium on carbon (0.6 g) in tetrahydrofuran was added a solution of the product of Preparation 15B (1.28 g, 4.0 mmol) in tetrahydrofuran (20 mL). The mixture was reacted under a hydrogen atmosphere (40 psi) on a Parr apparatus for 3 hours and subsequently filtered through celite. To this solution was added of the product of Preparation 1 (1.5 g, 3.96 mmol), 1-hydroxybenzotriazole (0.59 g, 4.35 mmol) and 1-(3-dimethylaminopropyl)-3-ethylcarbodiimide (0.9 g, 4.35 mmol) in tetrahydrofuran (30 mL). After 16 hours, the reaction mixture was filtered and concentrated. The resulting residue was purified by flash chromatography (silica gel, chloroform to 1% methanol/chloroform gradient) to yield 1.99 g (77%) of the above-identified product as an orange foam:

$^1$H-NMR is consistent with structure; MS (ion spray) 657 (M+1); Anal. Calc'd for $C_{36}H_{43}N_5O_7$: C, 65.74; H, 6.59; N, 10.65. Found: C, 65.67; H, 6.53; N, 10.87.

Preparation 15

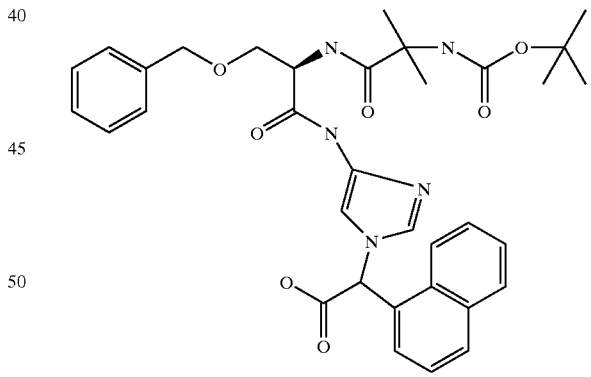

To a solution of the product of Preparation 15C (1.97g, 3.0 mmol) stirring in dioxane (20 mL) at room temperature was added a solution of lithium hydroxide (0.08 g, 3.3 mmol) in water (10 mL). After 15 minutes, the reaction was acidified to pH =3.0 with 1 N hydrochloric acid and extracted with ethyl acetate. The combined organic extracts were washed with brine, dried over sodium sulfate, filtered and concentrated to yield 1.8 g (95%) of the desired product (Preparation 15). $^1$H-NMR is consistent with structure; MS (ion spray) 630 (M+1); Anal. Calc'd for $C_{34}H_{39}N_5O_7 \cdot 1.05H_2O$: C, 62.96; H, 6.39; N, 10.80. Found: C, 63.09; H, 6.39; N, 10.40.

EXAMPLE 1P

Preparation 466

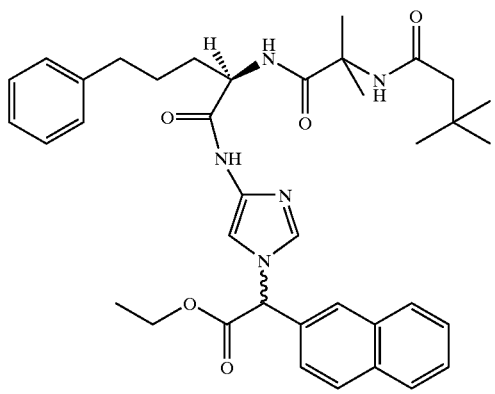

To a suspension of 5% palladium on carbon (2.60 g) and tetrahydrofuran (100 mL), in a Parr reaction bottle, was added the product of Preparation 136 from Examples Part 2A (5.00 g, 15.3 mmol) as a solid. The reaction bottle was placed on a Parr shaker, and shaken at room temperature for 2 h under a hydrogen atmosphere (40 psi). The reaction was filtered through a pad of Celite 521 and the filtrate was then added to a previously prepared mixture of the product of Preparation 2 from Examples Part 2A (5.80 g, 15.3 mmol), 1,3-dicyclohexylcarbodiimide (3.48 g, 16.9 mmol) and 1-hydroxybenzotriazole hydrate (2.29 g, 16.9 mmol) in 50 mL tetrahydrofuran at 0C. The reaction was stirred for 16 h at room temperature, then the solvent was evaporated under reduced pressure. The residue was dissolved in ethyl acetate and the 1,3-dicyclohexylurea was filtered away. The filtrate was purified by flash chromatography (silica gel, 80% ethyl acetate/hexanes—5% methanol/ethyl acetate) to give the desired product as a light yellow solid foam (7.96 g, 80%): $^1$H NMR consistent with structure; MS (IS) m/e 656 (M+1); Anal. Calc'd for $C_{37}H_{45}N_5O_6$: C, 67.77; H, 6.92; N, 10.68. Found: C, 67.49; H, 6.88; N, 11.71.

Preparation 467

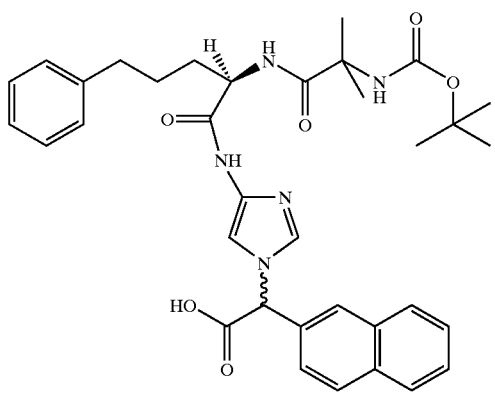

To a solution of the product of Preparation 466 (8.73 g, 13.3 mmol) in tetrahydrofuran (120 mL) and water (60 mL) at room temperature was added lithium hydroxide (2.23 g, 53.2 mmol). The reaction stirred 35 min at room temperature, at which time the tetrahydrofuran was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light yellow solid foam that was used without further purification (8.18 g, 98%): $^1$H NMR consistent with structure; MS (IS) m/e 628 (M+1); Anal. Calc'd for $C_{35}H_{41}N_5O_6$: C, 66.97; H, 6.58; N, 11.16. Found: C, 66.68; H, 6.75; N, 11.12.

EXAMPLE 1Q

Preparation 136

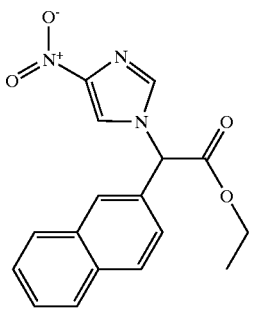

To a suspension of 2-naphthyl acetic acid (49.37 g, 265.0 mmol) in carbon tetrachloride (55 mL) was added and thionyl chloride (80 mL). The mixture was heated to reflux for 20 minutes then cooled to ambient temperature. Carbon tetrachloride (125 mL), N-bromosuccinimide (56.60 g, 318.0 mmol) and hydrobromic acid (48% aq., 0.5 mL) were added. The mixture was heated to reflux for 30 min, cooled to ambient temperature, filtered, and concentrated. The resulting material was dissolved in dichloromethane (200 mL) and excess ethanol (100 mL) was added dropwise. After 1 h, the reaction was concentrated and the resulting crude material was purified by flash chromatography(silica gel, 30% ethyl acetate/hexane) to yield a tan solid. This crude material was dissolved dimethylformamide (200 mL) and 4-nitroimidazole (29.78 g, 263.5 mmol) and potassium carbonate (72.70 g, 526.8 mmol) were added. After 16 h, the reaction was concentrated to 100 mL. Ethyl acetate and water were added and the mixture washed with sodium bicarbonate and brine. The organic layer was dried over sodium sulfate and concentrated. The crude material was purified by flash chromatography (silica, 30% ethyl acetate/hexane) to yield 40.2 g (47%) of the desired product as a brown foam: $^1$H NMR (300 MHz, CDCl$_3$)—consistent with structure; Anal. calc'd. for $C_{17}H_{15}N_3O_4$; 62.76 C. 4.65 H, 12.92 N; found 60.54 C, 4.35 H, 12.04 N; ISMS (M+)—326.

EXAMPLE 1R

Preparation 74

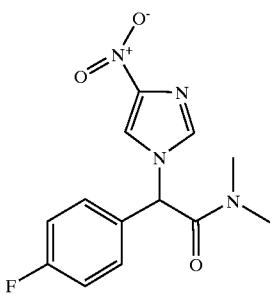

To a solution of the compound of Preparation 9 (17.0 g, 58.0 mmol) stirring at room temperature was added to sodium hydroxide (125 mL of a 2N aqueous solution) along with tetrahydrofuran (10 mL) and ethanol (10 mL). After hydrolysis was complete, the mixture was cooled in an bath and acidified to pH 2.75 with aqueous hydrochloric acid and extracted with ethyl acetate. The combined organic extracts were washed with water, dried over sodium sulfate and concentrated to provide 15.0 g (99%) of the desired carboxylic acid. The crude material was combined with aqueous N,N-dimethyl amine (40%, 9.0 mL, 71.8 mmol), 1-hydroxybenzotriazole hydrate (7.64 g, 56.6 mmol) and 1,3-dicyclohexylcarbodiimide (11.7 g, 56.6 mmol) in tetrahydrofuran (150 mL). After 18 h, the mixture was concentrated and the residue slurried in ethyl acetate, filtered, and the filtrate concentrated. Purification of the concentrate by flash chromatography (silica gel, chloroform/methanol) provided 10.2 g (62%) of the desired product: ESMS: (M+H)$^+$ 293.1. $^1$H NMR (300 MHz, DMSO-d$_6$) δ 8.21 (d, 1H, J=1.51 Hz) 7.80(d, 1H, J=1.13 Hz), 7.60–7.50 (m, 2H,), 7.38–7.25 (m, 2H), 6.88 (s, 1H), 2.92 (s, 3H), 2.86 (s, 3H). Anal. Calc'd. for $C_{13}H_{13}N_4O_3$: C, 53.43; H, 4.48; N, 19.17. Found: C, 53.43; H, 4.71; N, 19.07.

Preparation 75

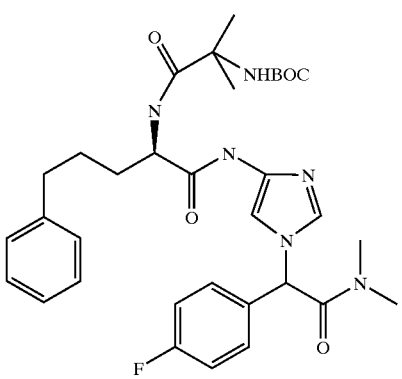

The product of Preparation 74 (2.0 g (6.85 mmol) was combined with 10% palladium/carbon (1.80 g) and palladium/black (0.20 g) in tetrahydrofuran(75 mL)and the mixture shaken under a hydrogen atmosphere (38 psi) in a Parr apparatus. After reduction was complete, the catalyst was removed by filtration through celite and the resulting solution was immediately added to a solution of 1,3-dicyclohexylcarbodiimide (1.51 g, 7.3 mmol), 1-hydroxybenzotriazole (1.0 g, 7.3 mmol), the product of Preparation 2 (2.77 g, 7.3 mmol) in tetrahydrofuran (50 mL) at room temperature. After 16 h, the mixture was concentrated and the residue slurried in ethyl acetate then filtered. The filtrate was concentrated and resulting crude product purified by flash chromatography (silica gel, chloroform/methanol) which afforded 3.47 g (81%) of the desired product: ESMS: (M+H)$^+$ 623.5, 624.6. $^1$H NMR was consistent with product. Anal. Calc'd. for $C_{33}H_{43}N_6O_4F \cdot 0.02$ CHC13: C, 63.44; H, 6.94; N, 13.44. Found: C, 63.04; H, 7.41; N, 11.93.

EXAMPLE 1S

Preparation 1L

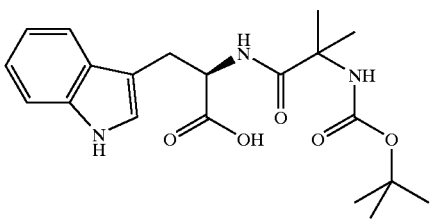

N-Methyl morpholine (4.79 mL, 2 eq, 47.3 mm) was added to a stirred slurry of N-Boc-a-aminoisobutyric acid (4.43 g, 21.7 mm, 1 eq) and 3.89 g (21.7 mm, 1.0 eq) of 2-chloro-(4,6)-dimethoxy-1,3,5-triazine (CDMT) in 100 mL of diethyl ether. After stirring the reaction mixture at ambient temperature for 1.5 hours, D-tryptophan ester hydrochloride was added. After stirring overnight, the reaction mixture was quenched by the addition of 150 mL of 10% aqueous citric acid solution. The layers were separated and the ether layer was washed with 50 mL of saturated sodium bicarbonate solution and 50 mL of water. Lithium hydroxide (2.43 g, 5 eq) was dissolved in 100 ml of water and the solution was added to the diethyl ether solution and stirred vigorously for 4 hours at room temperature. The layers were separated and the pH of the aqueous layers was adjusted to 5.6 with 1M HCl. The pH was then adjusted to 3.95 with 10% citric acid solution and the aqueous layer was extracted with 100 mL of ethyl acetate. The ethyl acetate layers were washed with brine, dried over magnesium sulfate and filtered. The volatiles were removed under vacuum to give 82% yield of the desired product as a white foam. $^1$H-NMR consistent with structure.

EXAMPLE 1T

Preparation R1

Ethyl 2-(2-Naphthyl)acetate

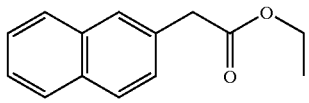

A steady stream of anhydrous hydrochloric acid was bubbled subsurface into a solution of 2-naphthylacetic acid (251.38 grams, 1.35 mol) dissolved in ethanol (1760 mL) over a period of 10 minutes. The resulting solution was stirred at ambient temperature until complete as determined by hplc (2 hours). The reaction mixture was concentrated to dryness. The resulting oil was dissolved in ethyl acetate (200 mL) and filtered through silica gel (300 grams) eluting the product with ethyl acetate (1400 mL). The filtrate was concentrated to give 286.33 grams (99%) of ethyl 2-(2-naphthyl)acetate as a colorless oil. MS (FIA) m/z 215.3 [(M+H)$^+$] . $^1$H nmr (DMSO-d$_6$) δ1.15–1.24 (t, 3H), 3.81–3.86 (d, 2H), 4.07–4.15 (q, 2H), 7.41–7.55 (m, 3H), 7.80–7.92 (m, 4H).

Preparation R2

Ethyl 2-Bromo-2-(2-naphthyl)acetate

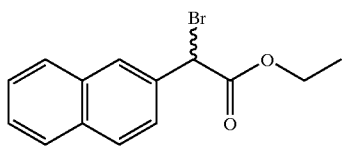

A solution consisting of ethyl 2-(2-naphthyl)acetate (1.07 grams, 5.0 mmol), N-bromosuccinimide (0.89 grams, 5.0 mmol), benzoyl peroxide (0.05 grams), and carbon tetrachloride (50 mL) was heated at reflux until complete as determined by hplc (3 hours). The reaction was cooled to ambient temperature, washed with water (2×25 mL), dried using sodium sulfate, and filtered. The filtrate was concentrated to dryness. The residue was purified using a Biotage Flash 40M system eluting with hexane: ethyl acetate (49:1) to give 1.20 grams (82%) of ethyl 2-bromo-2-(2-naphthyl) acetate, mp 80–82° C. MS (FIA) m/z 293.0 [(M+H)$^+$]. Anal. calcd. for $C_{14}H_{13}O_2Br$: C: 57.36; H: 4.47. Found: C: 57.62; H: 4.54. $^1$H nmr (CDCl$_3$): δ1.27–1.33 (t, 3H), 4.18–4.36 (m, 2H), 5.56 (s, 1H), 7.52–7.55 (m, 2H), 7.71–7.76 (m, 1H), 7.82–7.92 (m, 3H), 7.97 (s, 1H).

Preparation R3

Ethyl 2-(2-Naphthyl)-2-(4-nitroimidazolyl)acetate

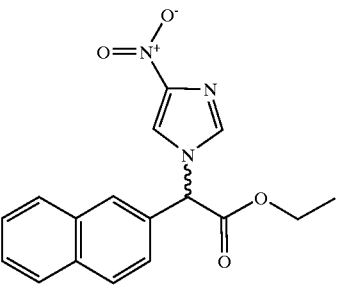

A yellow slurry consisting of ethyl 2-bromo-2-(2-naphthyl) acetate (384.04 grams, 1.31 mol), 4-nitroimidazole (148.13 grams, 1.31 mol), potassium carbonate (362.11 grams, 2.62 mol), and dimethyl formamide (2500 mL) was stirred at ambient temperature until complete as determined by hplc (16 hours). The reaction mixture was diluted with water (2000 mL) and extracted with ethyl acetate (4×500 mL). The organic extracts were combined and washed with saturated sodium bicarbonate solution (2×500 mL), 10% citric acid solution (2×500 mL), saturated sodium chloride solution (2×500 mL), dried using sodium sulfate, and evaporated. A portion (50 grams) of the crude product was purified by column chromatography on silica gel eluting with dichloromethane: heptane (16:3) gradient to dichloromethane: heptane: methanol (16:3:0.2) giving 30.99 grams of ethyl 2-(2-naphthyl)-2-(4-nitroimidazolyl)acetate which was 90% pure by hplc. A 1 gram sample of the product was purified a second time using a Biotage Flash 40S system eluting with dichloromethane: heptane: methanol (16.9:3:0.1) to give 0.90 grams (46%) of ethyl 2-(2-naphthyl)-2-(4-nitroimidazolyl)acetate as a tan oil. MS (FIA) m/z 326.4 [(M+H)$^+$]. $^1$H nmr (CDCl$_3$): δ 1.25–1.31 (t, 3H), 4.28–4.39 (m, 2H), 6.16 (s, 1H), 7.36–7.44 (dd, 1H), 7.54–7.62 (m, 3H), 7.84–7.90 (m, 3H), 7.90–7.95 (m, 2H).

Preparation R4

Ethyl 2-[4-((2R)-2-{2-[(Tert-butoxy) carbonylaminol]-2-methyl propanoylamino}-3-indol-3-ylpropanoylamino)imidazolyl]-2-(2-naphthyl)acetate

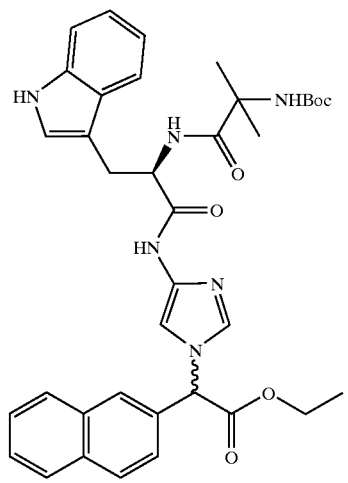

A mixture of ethyl 2-(2-naphthyl)-2-(4-nitroimidazolyl) acetate (2.04 grams, 6.27 mmol), tetrahydrofuran (20 mL), and 10% palladium on carbon (2.04 gram) was hydrogenated at ambient temperature and pressure until complete as determined by hplc (20 hours). The catalyst was removed by filtration and rinsed with tetrahydrofuran (10 mL). The filtrate was added to a slurry consisting of 1-[3-(dimethyl amino)propyl-3-ethylcarbodiimide hydrochloride (1.20 grams, 6.27 mmol), tetrahydrofuran (10 mL), and (2R)-2-{2-[(tert-butoxy)carbonylamino]-2-methylpropanoylamino}-3-indol-3-ylpropanoic acid (2.44 grams, 6.27 mmol) and stirred 16 hours at ambient temperature. The reaction mixture was partitioned between water (150 mL) and ethyl acetate (3×50 mL). The organic extracts were combined, washed with saturated sodium chloride solution, dried using sodium sulfate, and evaporated. The resulting crude oil was purified by column chromatography on silica gel with hexane ethyl acetate: methanol (10:10:1) as an eluent giving 1.72 grams (41%) of ethyl 2-[4-((2R)-2-{2-[(tert-butoxy) carbonylamino]-2-methylpropanoylamino}-3-indol-3-ylpropanoyl amino) imidazolyl]-2-(2-naphthyl)acetate. A 0.2 gram sample was further purified using preparative reverse phase hplc to give 0.16 grams of ethyl 2-[4-{(2R)-2-{2-[(tert-butoxy) carbonylamino]-2-methylpropanoylamino}-3-indol-3-ylpropanoyl amino)imidazolyl]-2-(2-naphthyl)acetate for analytical study. MS (FIA) m/z 667.4 [(M+H)$^+$]. Anal. calcd. exact mass for $C_{37}H_{43}N_6O_6$ [((M+H)$^+$]=667.3244. Exact mass found by mass spectrometry: $C_{37}H_{43}N_6O_6$ [(M+H)$^+$]= 667.3254. $^1$H nmr (CDCl$_3$): 1.25–1.42 (m, 19H), 3.24–3.33 (m, 2H), 4.28–4.33 (m, 2H), 4.98–5.01 (m, 1H), 5.94 (s, 1H), 6.85–7.01 (m, 3H), 7.18–7.21 (m, 2H), 7.35–7.39 (m, 2H), 7.49–7.58 (m, 4H), 7.78–7.84 (m, 4H), 8.69 (s, 1H), 10.65 (s, broad, 1H).

Preparation R5

Ethyl 2-[4-((2R)-2-{2-[(Tert-butoxy)carbonylamino]-2-methyl propanoylamino)-3-indol-3-ylpropanoylamino)imidazolyl]-2-phenylacetate

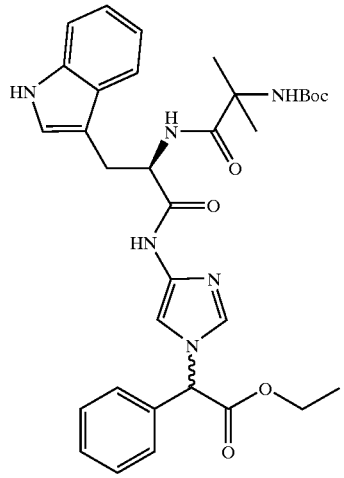

This compound was obtained from the reduction of ethyl 2-(4-nitroimidazolyl)-2-phenylacetate and subsequent reaction with (2R)-2-{2-[(tert-butoxy) carbonylaminol]-2-methyl propanoylamino}-3-indole-3-ylpropanoic acid as a yellow foam in 73% yield after purification by flash chromatography using dichloromethane: methanol (19:1) as the eluent. MS (FIA) m/z 617.5 [(M+H)$^+$]. $^1$H nmr (CDCl$_3$): δ 1.19–1.32 (m, 18H), 3.10–3.12 (m, 1H), 3.16–3.17 (m, 1H), 3.32 (s, 1H), 4.22–4.27 (m, 2H), 4.69 (s, broad, 1H), 6.44 (s, 1H), 6.85–6.91 (m, 2H), 7.00 (t, 1H), 7.07–7.08 (m, 1H), 7.38–7.40 (m, 1H), 7.42–7.45 (m, 6H), 7.55–7.56 (m, 2H), 10.16 (s, broad, 1H), 10.75 (s, 1H).

EXAMPLE 2

Synthesis of Formula I Compounds

Compounds of the present invention were synthesized as described below.

Preparation EX1A

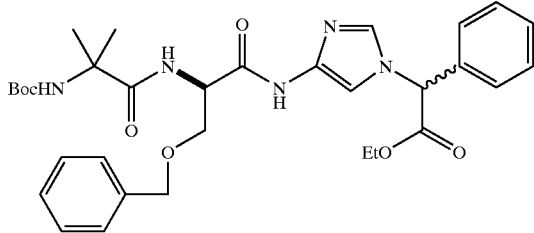

To a suspension of 5% Pd/C (0.85 g) and a compound of Preparation 3 (2.13 g, 7.21 mmol) stirring in dioxane (50 mL) at room temperature was added hydrogen (g) (35 psi) on a Parr apparatus. After 4 hours, the mixture was purged with nitrogen, celite added, and the solution filtered through a pad of celite. To the resulting filtrate, under nitrogen atmosphere, was added a compound of Preparation 1 (2.74 g, 7.21 mmol), 1-hydroxybenzotriazole (0.97 g, 7.21 mmol), N,N-diisopropylethylamine (2.5 mL, 14.4 mmol), and 1-(3-dimethylaminopropyl)-3-ethylcarbodiimide (1.36 g, 7.93 mmol). After 18 hours, ethyl acetate was added and the mixture washed with saturated aqueous ammonium chloride, saturated aqueous sodium bicarbonate, and brine. The organic extract was dried over sodium sulfate and concentrated. Purification by silica gel chromatography (5% methanol/dichloromethane) yielded the above-identified compound (1.25 g, 29%) as a yellow foam: $^1$H NMR (300 MHz, CDCl$_3$) d 1.30 (t, J=6.9 Hz, 3H), 1.40 (s, 9H), 1.42 (s, 3H), 1.51 (s, 3H), 3.60 (dd, J=5.1, 9.7 Hz, 1H), 4.05 (m, 1H), 4.28 (m, 2H), 4.54 (dd, J=14.08, 26.3 Hz, 2H), 4.62 (m, 1H), 5.08 (bs, 1H), 5.82 (s, 1H), 7.12 (d, J=11.5 Hz, 1H), 7.35 (m, 12H), 9.75 (bs, 1H); MS (FD) m/e 607; Anal. calc'd for C$_{32}$H$_{41}$N$_5$O$_7$: C, 63.29; H, 6.80; N, 11.52. Found: C, 63.07; H, 6.81; N, 11.74.

Preparation EX1B

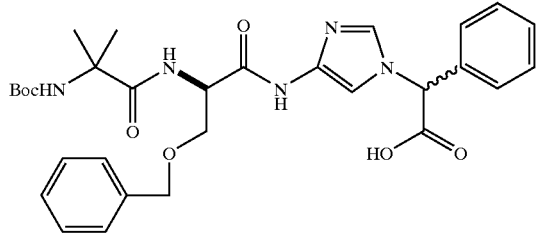

To a solution of a compound of Preparation EX1A (5.3 g, 8.75), stirring in dioxane (50 mL)/water (25 mL) at room temperature, was added lithium hydroxide (0.73 g, 17.50 mmol). After 20 minutes, water was added and the reaction concentrated to approximately 30 mL. The resulting mixture was extracted with diethyl ether and the aqueous layer saturated with sodium chloride then adjusted to pH 3.5 with 1 N HCl. The mixture was extracted with ethyl acetate and the combined organic extracts dried over sodium sulfate and concentrated to yield the above-identified compound (4.90 g, 97%) as a light orange foam: $^1$H NMR (300 MHz, CDCl$_3$) d ; MS (FD) m/e ; Anal. calc'd for: C, ; H,; N, . Found: C, ; H, ; N,.

Preparation EX1C

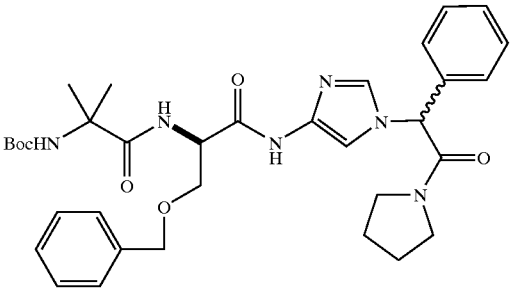

To a solution of Preparation EX1B (2.09 g, 3.61 mmol), pyrrolidine (0.30 mL, 3.61 mmol), and 1-hydroxybenzotriazole (0.54 g, 3.97 mmol) stirring in anhydrous DMF (50 mL) at 0° C. was added 1,3-dicyclohexyl carbodiimide (0.82 g, 3.97 mmol). After 18 hours at room temperature, the reaction mixture was concentrated, dissolved in dichloromethane, filtered, and concentrated. Purification by silica gel chromatography (5% methanol/dichloromethane) yielded the above-identified compound (1.74 g, 76%) as a light orange solid: ¹H NMR (300 MHz, CDCl3) d 1.41 (s, 9H), 1.43 (s, 3H), 1.52 (s, 3H), 2.88 (m, 4H), 3.42 (m, 1H), 3.50 (m, 4H), 4.08 (m, 1H), 4.55 (dd, J=14.9, 27.4 Hz, 2H), 4.70 (m, 1H), 4.96 (d, J=4.0 Hz, 1H), 5.86 (s, 1H), 7.15 (d, J=6.9 Hz, 1H), 7.35 (m, 12H), 9.28 (bs, 1H); MS (FD) m/e 632; Anal. calc'd for $C_{34}H_{44}N_6O_6$: C, 64.54; H, 7.01; N, 13.28. Found: C, 63.48; H, 6.95; N, 12.19.

Compound 1

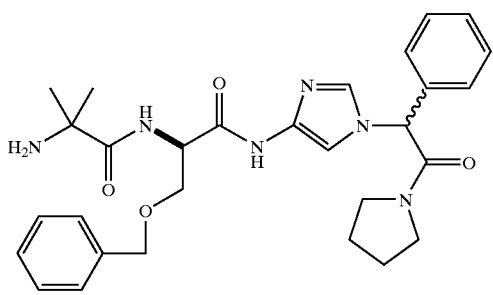

To a solution of a compound of Preparation EX1C (1.00 g, 1.58 mmol) and anisole (0.3 mL), stirring in anhydrous dichloromethane (12 mL) at 0° C., was added trifluoroacetic acid (3 mL) and the reaction mixture was then warmed to room temperature. After 4 hours, the dichloromethane was removed in vacuo and excess diethyl ether added. After 20 minutes, the reaction mixture was filtered to yield the above-identified compound (1.02 g, 85%) as a white solid: ¹H NMR (300 MHz, CDCl₃) d 1.60 (s, 6H), 1.90 (m, 4H), 3.08 (m, 1H), 3.58 (m, 3H), 3.88 (m, 2H), 4.52 (m, 2H), 4.72 (m, 1H), 6.10 (m, 2H), 7.25 (m, 6H), 7.46 (m, 5H), 7.70 (m, 1H), 8.00 (m, 1H), 8.40 (m, 1H), 11.15 (m, 1H); MS (FD) m/e 532 (M-2TFA); Anal. calc'd for $C_{33}H_{38}F_6N_6O_8$: C, 52.10; H, 5.03; N, 11.05. Found: C, 51.54; H, 5.25; N, 11.21.

EXAMPLE 2-2

Preparation EX2A

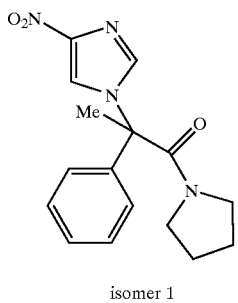

isomer 1

A solution of the product of Preparation 6B, diastereomer 1 (2.30 g, 5.48 mmol) in THF (50 mL) was added to a solution of lithium hydroxide (0.25 g, 6.03 mmol) in water (25 mL). The resulting mixture was stirred at ambient temperature for 30 minutes. Water was added and the mixture washed with diethyl ether. The pH of the aqueous layer was adjusted to 3.0 with 10% aqueous sodium bisulfate. The mixture was saturated with sodium chloride and washed with ethyl acetate. The ethyl acetate washes were combined, dried over sodium sulfate, filtered, and concentrated in vacuo. The resulting crude solid was dissolved in anhydrous dichloromethane (50 mL) under nitrogen. To this solution was added catalytic DMF (0.1 mL) and excess oxalyl chloride (5 g). This mixture was stirred for 3 hours, then concentrated in vacuo. The resulting crude foam was dissolved in anhydrous dichloromethane (50 mL) and cooled to 0° C. 4-Dimethylaminopyridine (catalytic, 10 mg) and pyrrolidine (1.8 mL, 18.74 mmol) were added and the resulting solution was stirred for 18 hours. Dichloromethane was then added and the mixture washed with sodium bicarbonate and brine. The organic layer was dried over sodium sulfate, filtered, and concentrated in vacuo. The crude foam was purified by flash chromatography (silica, 100 g, 5% methanol/dichloromethane) to yield the above-identified product (1.73 g, 88% yield) as a colorless foam:

¹H NMR (300 MHz, CDCl₃)—consistent with structure; Anal. calc'd. for $C_{16}H_{18}N_4O_3$; 61.14 C, 5.77 H, 17.82 N; found 60.67 C, 5.78 H, 16.03 N; FDMS (M+)—314.

Preparation EX2B

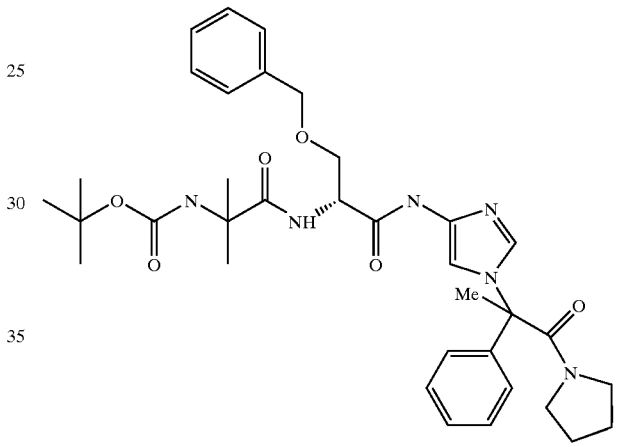

isomer 1

A solution of the product of Preparation EX2A (1.66 g, 5.29 mmol) in THF (5 mL) was added to a suspension of 5% palladium on carbon (0.80 g, catalytic, 25 mL THF) under inert atmosphere. The resulting mixture was placed under hydrogen (40 psi) on a Parr shaker for 1.5 hours. The resulting mixture was placed under nitrogen and celite added. The mixture was then filtered and rinsed with THF. The filtrate was place under nitrogen and HOBT (0.71 g. 5.29 mmol), the product of Preparation 1 (2.01 g, 5.29 mmol), EDC (1.00 g, 5.81 mmol), and DIEA (1.0 mL, 5.81 mmol) were added. The resulting mixture was stirred for 18 hours at ambient temperature, then concentrated in vacuo. The crude material was dissolved in ethyl acetate and washed with sodium bicarbonate and brine. The organic layer was dried over sodium sulfate, filtered, and concentrated in vacuo. The resulting crude foam was purified by flash chromatography (silica, 100 g, 2% methanol/dichloromethane) to yield the above-identified product (0.66 g, 19% yield) as a light yellow foam: ¹H NMR (300 MHz, CDCl₃)—consistent with structure; Anal. calc'd. for $C_{35}H_{46}N_6O_6$; 65.00 C, 7.17 H, 12.99 N; found 63.21 C, 6.92 H, 12.54 N; FDMS (M+)—646.

Compound 2

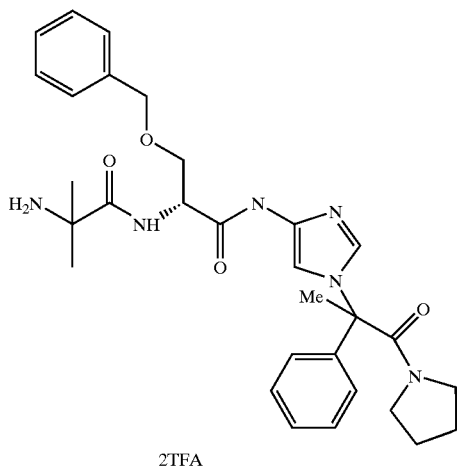

2TFA

A solution of the product of Preparation EX2B (0.52 g, 0.80 mmol) in dichloromethane (20 mL) was stirred under nitrogen with anisole (0.4 mL) and trifluoroacetic acid (4.0 mL) at ambient temperature for 3 hours. The mixture was concentrated in vacuo to approximately 5 mL and excess diethyl ether added. The mixture was filtered and rinsed with diethyl ether to yield the above-identified product (0.40 g, 65% yield) as an off white solid: $^1$H NMR (300 MHz, CDCl$_3$)—consistent with structure; Anal. calc'd. for $C_{34}H_{40}N_6O_8F_6$; 52.71 C, 5.20 H, 10.85 N; found 52.60 C, 5.08 H, 10.69 N; FDMS (M+)—546.

Preparation 193

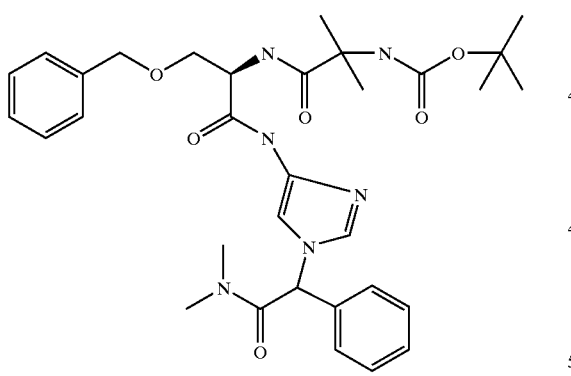

To a solution of Preparation EX1B (1.0 g, 1.7 mmol), N,N-dimethylamine hydrochloride, 0.14 g (1.7 mmol), triethylamine, 0.26 mL (1.9 mmol) and 1-hydroxybenzotriazole, 0.26 g (1.9 mmol) in 70 mL of dimethylformamide was added 0.4 g (1.9 mmol) of 1-(3-dimethylaminopropyl)-3-ethylcarbodiimide. The reaction mixture was stirred overnight then concentrated. The residue was slurried in ethyl acetate, filtered and water was added. The mixture was extracted with ethyl acetate. The combined organic extracts were washed with brine, dried over sodium sulfate, filtered and concentrated. The residue was chromatographed on silica gel using 4% methanol/chloroform as eluant to yield 0.58 g (56%) of the above-identified product as a white foam: $^1$H-NMR is consistent with structure; MS (FD) 606 (M+); Anal. Calc'd for $C_{32}H_{42}N_6O_6$: C, 63.35; H, 6.98; N, 13.85. Found: C, 63.18; H, H7.03; N, 13.84.

Compound 3

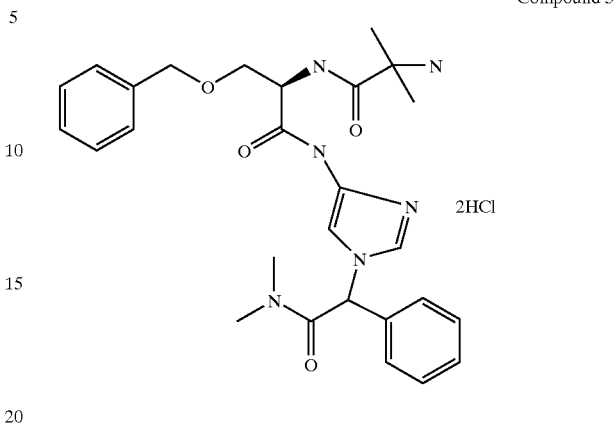

2HCl

To a solution of the product of Preparation 193, 0.5 g (0.82 mmol) in 12 mL of dichloromethane was added 4 mL of trifluoroacetic acid. After stirred for 1 hour, water was added. The reaction was quenched with solid sodium bicarbonate and was extracted with chloroform. The combined organic extracts were washed with brine, dried over sodium sulfate, filtered and concentrated. The residue was dissolved in ethyl acetate and hydrochloric acid-saturated ether was added. The resulting slurry was concentrated to yield 0.4 g (85%) of the above-identified product as a yellow solid: $^1$H-NMR is consistent with structure; MS (FD) 506.4 (M+); Anal. Calc'd for $C_{27}H_{34}N_6O_4$ 2.9HCl: C, 53.85; H, 4.50; N, 13.95. Found: C, 53.91; H, 6.14; N, 13.76.

EXAMPLE 2-4

Preparation 194

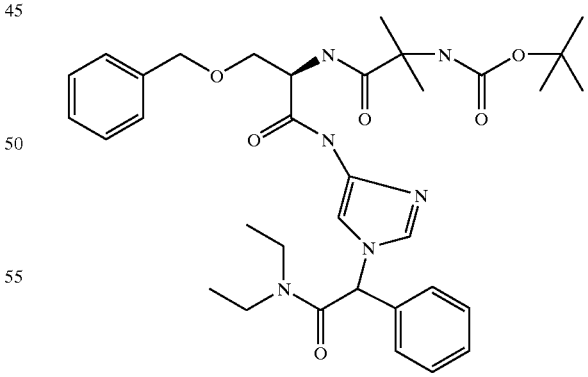

Reaction of the product of Preparation EX1B (1.0 g, 1.7 mmol), diethylamine (0.18 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193 gave 0.53 g (49%) of the above-identified product as a yellow foam: $^1$H-NMR is consistent with structure; MS (FD) 634.3 (M+).

Compound 4

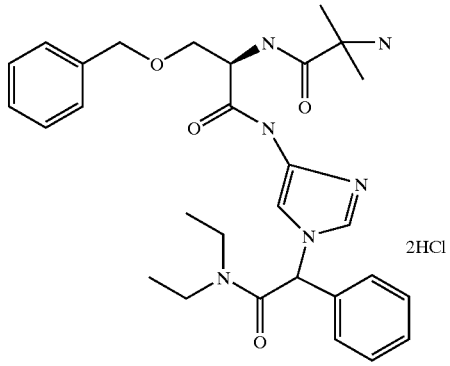

2HCl

Reaction of the product of Preparation 194 (0.52 g, 0.82 mmol), trifluoroacetic acid (4 mL), dichloromethane (12 mL) as described in Compound 3, gave 0.47 g (100%) of the above-identified product as a white solid: $^1$H-NMR is consistent with structure; MS (FD) 534.1 (M+); Anal. Calc'd for $C_{29}H_{38}N6O_4 \cdot 2.4HCl$: C, 55.99; H, 6.54; N, 13.51. Found: C, 55.88; H, 6.91; N, 13.32.

EXAMPLE 2-5

Preparation 195

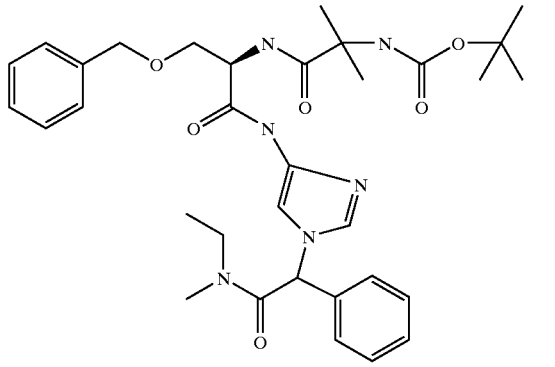

Reaction of the product of Preparation EX1B (1.0 g, 1.7 mmol), N,N-methylethylamine (0.15 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (40 mL), as described in Preparation 193, gave 0.56 g (56%) of the above-identified product as a tan foam: $^1$H-NMR is consistent with structure; MS (FD) 620 (M+); Anal. Calc'd for $C_{33}H_{44}N_6H_6$: C, 63.85; H, 7.15; N, 13.54. Found: C, 63.45; H, 7.19; N, 13.15.

Compound 5

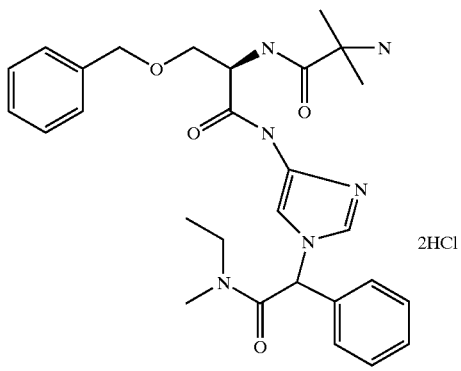

2HCl

Reaction of the product of Preparation 195 (0.4 g, 0.64 mmol), trifluoroacetic acid (2 mL), dichloromethane (6 mL), as in Compound 3 gave 0.32 g (84%) of the above-identified product as a yellow solid: 1H-NMR is consistent with structure; MS (FD) 520 (M+); Anal. Calc'd for $C_{28}H_{36}N_6O_4 \cdot 2.2HCl$: C, 55.97; H, 6.41; N, 13.99. Found: C, 56.11; H, 6.23; N, 13.60.

EXAMPLE 2-6

Preparation EX3A

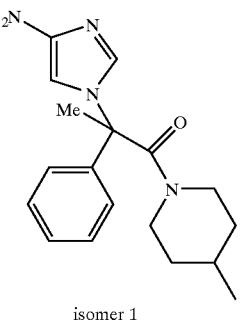

isomer 1

Prepared as in Preparation EX2A using the product of Preparation 6B, diastereomer 1 (1.88 g, 5.44 mmol) in THF (50 mL) and lithium hydroxide (0.23 g, 5.63 mmol) in water (25 mL) to give a crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg), L-proline methyl ester hydrochloride (0.90 g, 5.44 mmol), and N,N-diethylisopropylamine (2.8 mL, 16.31 mmol) to yield the above-identified product (1.21 g, 65% yield) as a colorless foam: $^1$H NMR (300 MHz, CDCl$_3$)— consistent with structure; Anal. calc'd. for $C_{18}H_{22}N_4O_3$; 63.14 C, 6.48 H, 16.36 N; found 63.29 C, 6.45 H, 15.29 N; FDMS (M+)—342.

Preparation EX3B

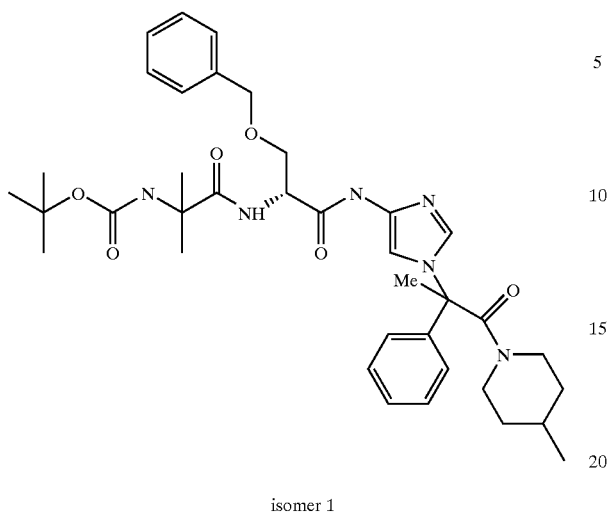

isomer 1

Prepared as in Preparation EX2B using the product of Preparation EX3A (1.21 g, 3.53 mmol) and 5% palladium on carbon (0.80 g, catalytic, 25 mL THF) to give the crude amine. The resulting filtrate was reacted with HOBT (0.48 g, 3.53 mmol), the product of Preparation 1 (1.34 g, 3.53 mmol), diisopropylethylamine (0.6 mL, 3.53 mmol), and EDCI (0.67 g, 3.88 mmol) to yield the above-identified product (0.97 g, 41% yield) as a light yellow foam: $^1$H NMR (300 MHz, CDCl$_3$)—consistent with structure: Anal. calc'd. for C$_{37}$H$_{50}$N$_6$O$_6$; 65.85 C, 7.47 H, 12.45 N; found 64.96 C, 7.48 H, 12.04; FDMS (M+)—675.

Compound 6

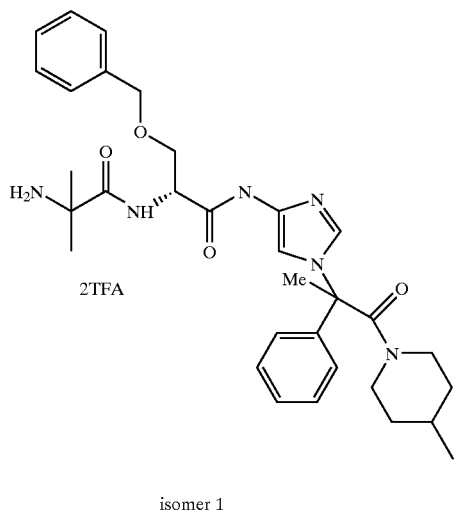

2TFA isomer 1

Prepared as in Example 2-2 using the product of Preparation EX3B (0.95 g, 1.41 mmol), trifluoroacetic acid (4.0 mL), anisole (0.4 mL), and dichloromethane (20 mL) to yield the desired product (Preparation 3) (0.82 g, 92%) as a pale yellow solid: $^1$H NMR (300 MHz, CDCl$_3$)—consistent with structure above: Anal. calc'd. for C$_{36}$H$_{44}$N$_6$O$_8$F$_6$; 53.86 C, 5.53 H, 10.47 N; found 52.73 C, 5.50 H, 10.07 N; FDMS (M+)—574.

EXAMPLE 2-7

Preparation EX4A

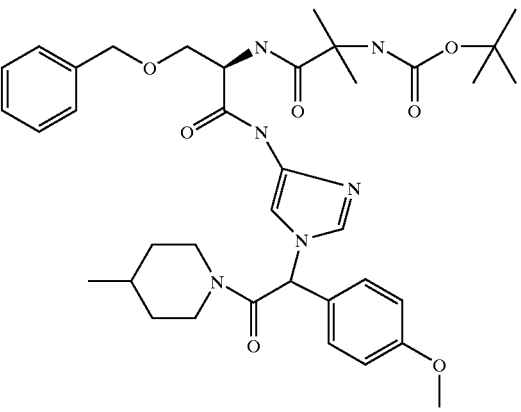

To a solution of the product of Preparation 5 (8.0 g, 13.0 mmol), stirring in dimethylformamide (150 mL) at room temperature, was added 4-methylpiperidine (1.6 mL, 13.0 mmol), 1-hydroxybenzotriazole (2.0 g, 14.3 mmol) and 1-(3-dimethylaminopropyl)-3-ethylcarbodiimide (3.0 g, 14.3 mmol). After 16 hours, the reaction mixture was filtered and concentrated. The resulting material was partitioned between ethyl acetate and water and extracted with ethyl acetate. The combined organic extracts were washed with brine, dried over sodium sulfate, filtered and concentrated to dryness. The resulting crude material was purified by flash chromatography (silica gel, 3% methanol/chloroform) to yield 7.65 g (85%) of the above-identified product as a yellow foam: $^1$H-NMR (d, DMSO) 0.2 (m, 1H), 0.50 (d, J=6.0 Hz, 1.5 H), 0.80 (d, J=6.0 Hz, 1.5 H), 1.05 (m, 1H), 1.22–1.45 (m, 15H), 1.50–1.65 (m, 4H), 2.65 (m, 1H), 3.00 (m, 1H), 3.55 (m, 1H), 3.65 (m, 1H), 3.75 (s, 3H), 4.37 (m, 1H), 4.40–4.50 (m, 2H), 4.60 (m, 1H), 6.62 (d, J=13 Hz, 1H), 6.98 (t, J=9.4 Hz, 2H), 7.10–7.45 (m, 11H), 10.15 (br s, 1H); MS (ion spray) 691.3 (M+l); Anal. Calc'd for C$_{37}$H$_{50}$N$_6$O$_7$·0.6H$_2$O: C, 63.34; H, 7.35; N, 11.98. Found: C, 63.25; H, 7.03; 11.87.

Compounds 7 and 8

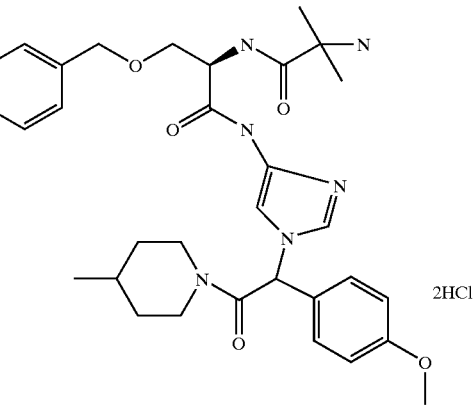

2HCl

To a solution of the product of Preparation EX4A (7.26 g, 10.5 mmol), stirring in dichloromethane (25 mL) at room temperature, was added trifluoroacetic acid (10 mL). After 4 hours, the reaction mixture was poured into a saturated solution of sodium bicarbonate extracted with chloroform.

The combined organic extracts were washed with brine, dried over sodium sulfate, filtered and concentrated to yield 6.12 g (99%) of the free base as a tan foam. The diastereomeric material (3.0 g) was chromatographed on an 8×15 cm Prochrom column packed with Kromasil CHI-DMP chiral phase using an eluent mixture of 3A alcohol (13% by v), dimethylethylamine (0.2% by v) in heptane at a flow rate of 250 mL/min to provide the individual diastereomers in pure form:

Compound 7 Isomer: To a solution of the purified isomer in ethyl acetate was added a saturated solution of hydrochloric acid in diethyl ether. The resulting slurry was concentrated to dryness to yield 1.1 g (37%) of the desired product as a white solid: $^1$H NMR (d, DMSO) 0.50 (d, J=6.0 Hz, 1.5 H), 0.80 (d, J=6.0 Hz, 1. 5 H), 1.16 (m, 1H), 1.35 (m, 1H), 1.50–1.70 (m, 8H), 2.60–2.70 (m, 2H), 3.03 (m, 1H), 3.65–3.80 (m, 6H), 4.40 (m, 1H), 4.53 (s, 2H), 4.75 (m, 1H), 6.90–7.08 (m, 3H), 7.25–7.45 (m, 9H), 8.20–8.40 (m, 4H), 8.61 (d, J.=7.5 Hz, 1H), 11.15 (br s, 1H); $t_R$ =7.93 min; MS (ion spray) 591.6 (M+1); Anal. Calc'd for $C_{32}H_{42}N_6O_5$.2HCl: C, 57.92; H. 6.69; N, 12.66. Found: C, 57.72; H, 6.47; N, 12.42.

Compound 8 Isomer: To a solution of the purified isomer in ethyl acetate was added a saturated solution of hydrochloric acid in diethyl ether. The resulting slurry was concentrated to yield 0.98 g (33%) of the desired product as a white solid: $^1$H NMR (d, DMSO) 0.50 (d, J=6.0 Hz, 1.5 H), 0.80 (d, J=6.0 Hz, 1. 5 H), 1.16 (m, 1H), 1.35 (m, 1H), 1.50–1.70 (m, 8H), 2.60–2.70 (m, 2H), 3.03 (m, 1H), 3.65–3.80 (m, 6H), 4.40 (m, 1H), 4.53 (s, 2H), 4.75 (m, 1H), 6.90–7.08 (m, 3H), 7.25–7.45 (m, 9H), 8.20–8.40 (m, 4H), 8.61 (d, J=7.5 Hz, 1H), 11.15 (br s, 1H); $t_R$=11.78 min; MS (ion spray) 591.6 (M+1); Anal. Calc'd for $C_{32}H_{42}N_6O_5$.2HCl: C, 57.29; H, 6.64; N, 12.53. Found: C, 57.23; H, 6.29; N, 12.57.

EXAMPLE 2-8

Preparation EX5A

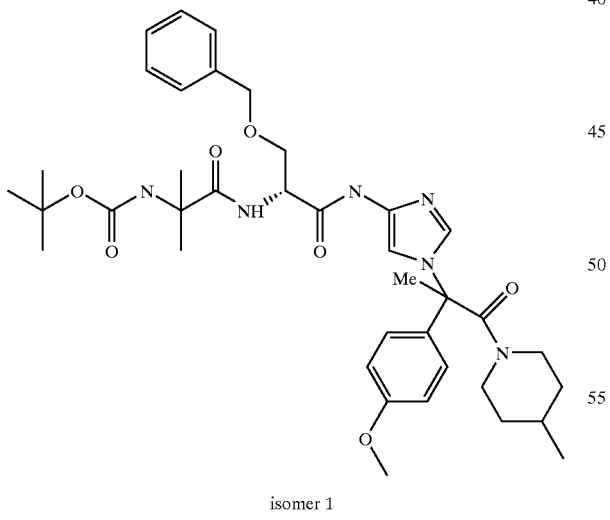

isomer 1

Preparation EX5A was prepared as in Preparation EX2B using the product of Preparation 14 (1.32 g, 3.55 mmol) and 5% palladium on carbon (1.4 g, catalytic, 50 mL THF) to give the crude amine. The resulting filtrate was reacted with HOBT (0.48 g, 3.55 mmol), the product of Preparation 1 (1.35 g, 3.55 mmol), and DCC (0.81 g, 3.91 mmol) to yield the above-identified product (0.82 g, 33% yield), as follows, as a light yellow foam: $^1$H NMR (300 MHz, CDCl$_3$)— consistent with the structure; Anal. calc'd. for $C_{38}H_{52}N_6O_7$; 64.75 C, 7.44 H, 11.92 N; found 66.19 C, 7.17 H, 12.10 N; ISMS (M+)—705.

Compound 8

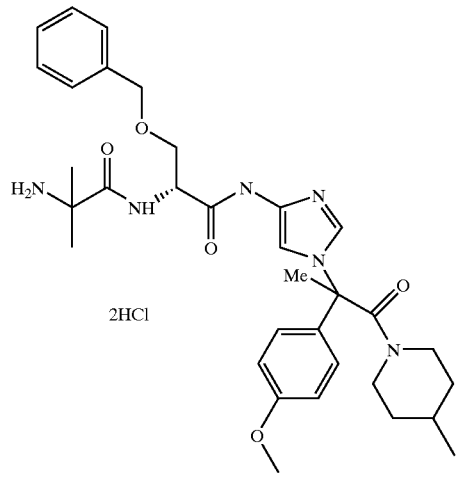

2HCl

A solution of the product of Preparation EX5A (0.82g, 1.16 mmol), in dichloromethane (20 mL), was stirred under nitrogen with anisole (0.4 mL) and trifluoroacetic acid at ambient temperature for 3 hours. The mixture was quenched with saturated sodium bicarbonate and stirred for 10 minutes at ambient temperature Dichloromethane was added and the mixture was washed with bicarbonate and brine. The organic layer was dried over sodium sulfate, concentrated in vacuo, and redissolved in 2 mL ethyl acetate. Diethyl ether (saturated HCl(g), 5 mL) was added and the mixture was then stirred for 12 minutes. The mixture was filtered to yield the above-identified product (0.71 g, 90%) as a pale yellow solid: $^1$H NMR (300 MHz, CDCl$_3$)—consistent with structure; Anal. calc'd. for $C_{33}H_{46}N_6O_5Cl_2$; 58.49 C, 6.84 H, 12.40 N; found 55.40 C, 6.48 H, 11.80 N; ISMS (M+)—605.

EXAMPLE 2-9

Preparation EX6A

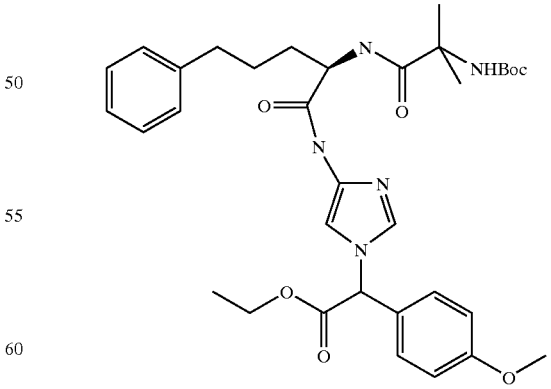

To a suspension of 5% palladium on carbon (1.75 g) and tetrahydrofuran (120 mL) was added the product of Preparation 4 (3.51 g, 11.5 mmol). The reaction mixture was placed under a hydrogen atmosphere (40 mm Hg) on a Parr apparatus for 2 hours then filtered through celite. The filtrate was subsequently added to a solution of the product of Preparation 2 (4.33 g, 11.5 mmol), 1-(3-dimethylaminopropyl)-3-ethylcarbodiimide (2.60 g, 12.6 mmol) and 1-hydroxybenzotriazole (1.72 g, 12.6 mmol) stirring in tetrahydrofuran (50 mL) at 0° C. After 16 hours at room temperature, the reaction mixture was concentrated. The resulting residue was dissolved in ethyl acetate, filtered and the resulting filtrate concentrated. The crude residue was purified by flash chromatography (silica gel, 90% ethyl acetate/hexanes to 10% methanol/ethyl acetate gradient) to give 4.5 g (62%) the desired product (Preparation EX6A), as follows, as a light orange foam: $^1$H NMR: consistent with structure; MS (IS) m/e 636 (M+1). Anal. ($C_{34}H_{45}N_5O_7$) C, H, N.

Preparation EX6B

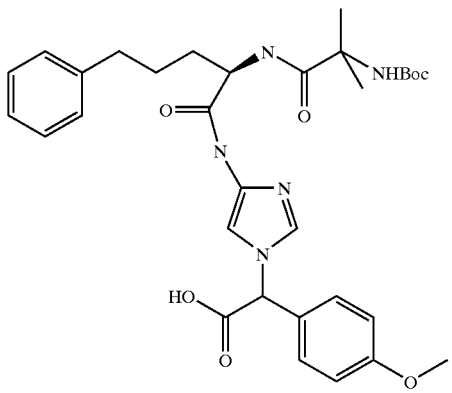

To a solution of the product of Preparation EX6A (1.01 g, 1.59 mmol), stirring in tetrahydrofuran (30 mL) and water m (15 mL) at room temperature, was added lithium hydroxide (0.26 g, 6.30 mmol). After 25 minutes, the reaction mixture was concentrated and the resulting residue was diluted with water and extracted with diethyl ether. The aqueous extracts were acidified to pH 2–3 with 1N hydrochloric acid and then extracted with ethyl acetate. The combined organic extracts were washed with brine, dried with sodium sulfate and concentrated to provide 0.96 g (99%) of the desired compound (Preparation EX6B), as follows, as a light tan foam that was used without further purification: $^1$H NMR consistent with structure; MS (IS) m/e 608 (M+1). Anal. ($C_{32}H_{41}N_5O_7$) C: calc'd, 63.25; found, 62.68, H, N.

Preparation EX6C

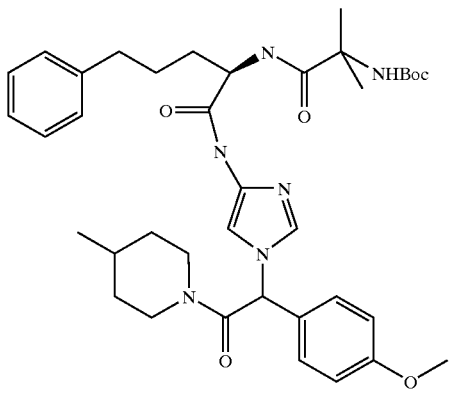

To a solution of the product of Preparation EX6B (0.93 g, 1.53 mmol), stirring in dichloromethane (25 mL) at room temperature, was added N-methylmorpholine (0.20 mL, 1.83 mmol) and 2-chloro-(4,6)-dimethoxy-1,3,5-triazine (0.35 g, 1.99 mmol). After 1 hour, 4-methylpiperidine (0.20 mL, 1.68 mmol) was added and the resulting mixture was stirred room temperature for 2 hours at which time 2-chloro-(4,6)-dimethoxy-1,3,5-triazine (0.10 g, 0.70 mmol) was added. After 1 hour, the reaction mixture was concentrated and the resulting residue purified by flash chromatography (silica gel, ethyl acetate/methanol gradient) to give the desired compound (Preparation EX6C), as follows, as a light yellow solid foam (0.875 g, 83%): $^1$H NMR consistent with structure; MS (IS) m/e 689 (M+1) Anal. ($C_{38}H_{52}N_6O_6$) C,H,N.

Compound 10

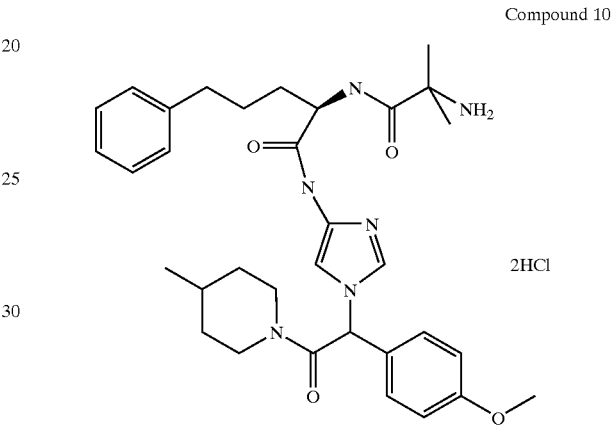

2HCl

To a solution of the product of Preparation Ex6C (0.77 g, 1.12 mmol) and anisole (0.13 mL, 1.13 mmol) stirring in dichloromethane (20 mL) at 0° C., was added trifluoroacetic acid. After 3–4 hours, the reaction mixture was warmed to room temperature and then quenched by pouring over cold saturated aqueous sodium bicarbonate. The organic layer was collected and the aqueous layer was extracted twice with dichloromethane. The combined organic extracts were washed with aqueous sodium bicarbonate, water, brine, then dried over sodium sulfate and concentrated. The resulting material was purified by flash chromatography (silica gel, 5% methanol/ 95% ethyl acetate gradient to 5% triethylamine/10% methanol/ 85% ethyl acetate) to provide 0.63 g (95%) of the desired mixture of diastereomers as an off-white solid foam. The mixture (190 mg) was resolved by chiral HPLC [Kromasil packing material, 15% 3A alcohol/ 85% heptane (w/0.2% dimethylamine)] to provide the two desired diastereomers. To a solution of diastereomer 2 (65 mg) (retention time=9.00 min) stirring in ethyl acetate (5 mL) was added saturated solution of hydrochloric acid in diethyl ether. The resulting white precipitate was collected by vacuum filtration and rinsed with diethyl ether to provide the desired compound (60 mg) as a white amorphous solid: $^1$H NMR consistent with structure; MS (IS) m/e 589 (M+1). Anal. ($C_{33}H_{44}N_6O_4 \cdot 2HCl$) C, H, N.

EXAMPLE 2-10

Preparation EX7A

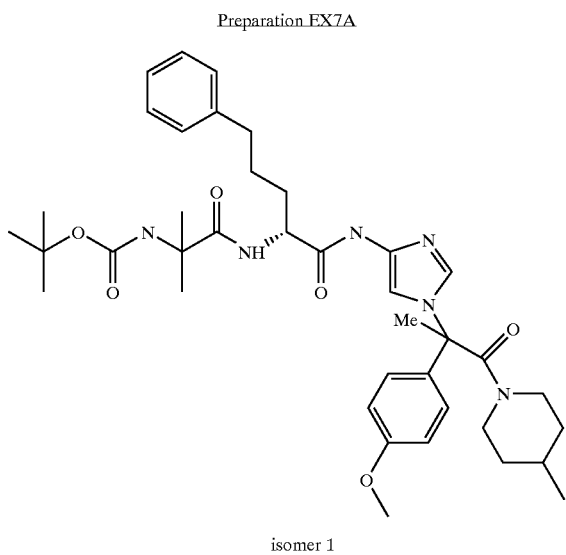

isomer 1

Prepared as in Preparation EX2B using the product of Preparation 14 (0.92 g, 2.47 mmol) and 5% palladium on carbon (1.00 g, catalytic, 30 mL THF) to give the crude amine. The resulting filtrate was reacted with HOBT (0.35 g, 2.47 mmol), the product of Preparation 2 (0.94 g, 2.47 mmol), and DCC (0.56 g, 2.72 mmol) to yield the desired product (Preparation EX7A), as follows, (0.92 g, 53% yield) as a light yellow foam: $^1$H NMR (300 MHz, CDCl$_3$)—consistent with structure; Anal. calc'd. for C$_{39}$H$_{54}$N$_6$O$_6$; 66.64 C, 7.74 H, 11.96 N; found 66.65 C, 7.65 H, 12.02 N; ISMS (M+)—702.

Compound 11

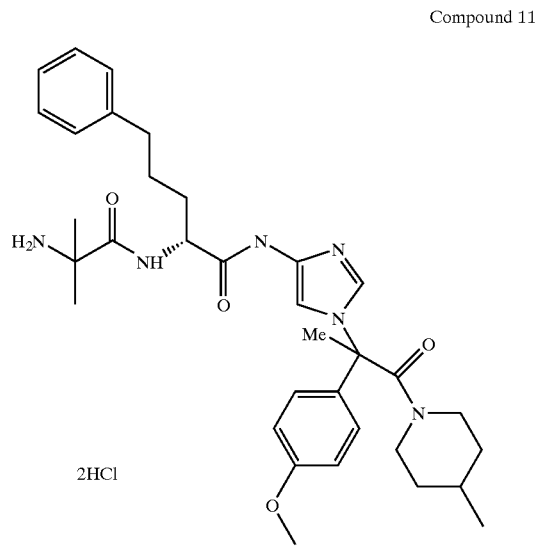

2HCl

Prepared as in Example 2-8 using the product of Preparation EX7A (0.26 g, 0.37 mmol), trifluoroacetic acid (4.0 mL), anisole (0.4 mL), and dichloromethane (20 mL) to yield the desired product (Example 7) (0.19 g, 76%) as a pale yellow solid: $^1$H NMR (300 MHz, CDCl$_3$)—consistent with structure; Anal. calc'd. for C$_{34}$H$_{48}$N$_6$O$_4$Cl$_2$; 60.44 C, 7.16 H, 12.44 N; found 60.08 C, 7.03 H, 12.06 N; ISMS (M+)—603.

EXAMPLE 2-11

Preparation EX8A

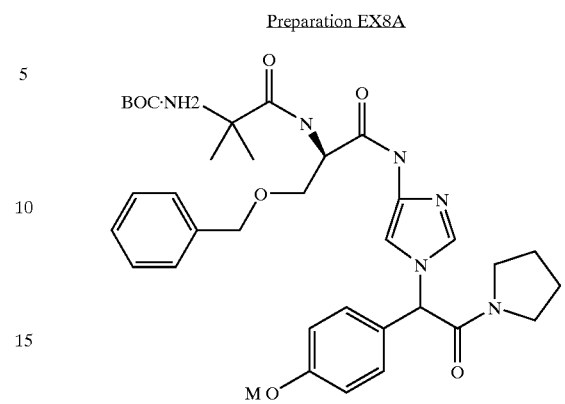

To a solution of the product of Preparation 5 (10.0 g, 16.4 mmol), stirring in tetrahydrofuran (150 mL) at room temperature was added 1-hydroxybenzotriazole (2.22 g, 16.4 mmol) and 1,3-dicyclohexylcarbodiimide (3.38 g, 16.4 mmol). After 15 minutes, pyrrolidine (1.37 mL, 16.4 mmol) was added. After 16 hours, the reaction mixture was filtered and concentrated. The resulting crude material was purified by flash chromatography (silica gel, 5% inethanol/dichloromethane) to yield 7.05 g (65%) of the desired product (Preparation EX8A), as follows, as a yellow foam: $^1$H-NMR consistent with product; MS (ion spray) 663 (M+1); Anal. Calc'd for C$_{35}$H$_{46}$N$_6$O$_7$: C, 63.43; H, 7.00; N, 12.68. (Found) C, 62.69; H, 6.87; N, 129.1.

Compounds 12 and 13

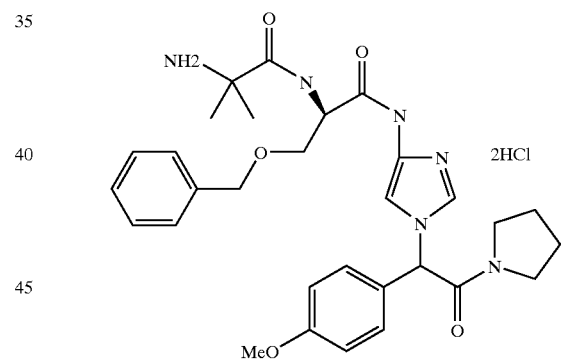

2HCl

To the product of Preparation EX8A (7.0 g, 10.6 mmol) was added a saturated solution of HCl(g)/acetic acid (100 mL). After 4 hours, the reaction mixture was concentrated then partitioned between ethyl acetate and saturated sodium bicarbonate. The organic layer was removed, dried over sodium sulfate and concentrated to yield 5.59 g (94%) of the free base as a light yellow foam. The diastereomeric material (3.45 g) was chromatographed on an 8×15 cm Prochrom column packed with Kromsil CHI-DIMETHYLFORMAMIDE chiral phase using an eluent mixture of 3A alcohol and dimethylethylamine in heptane to provide the individual diastereomers in pure form: $^1$H NMR consistent with product; MS (ion spray) 563 (M+1); Anal. Calc'd. for C$_{30}$H$_{38}$N$_6$O$_5$: C, 64.04; H, 6.81; N, 14.94. (Found) C, 63.98; H, 6.82; N, 14.87.

Compound 12 (Isomer 1) To a solution of the purified isomer in ethyl acetate was added a saturated solution of hydrochloric acid in ethyl acetate. The resulting slurry was concentrated to dryness to yield 1.50 g (39%) of the desired product as an off-white solid: $^1$H NMR consistent with product; MS (ion spray) 563 (M+1); Anal. Calc'd. for $C_{30}H_{38}N_6O_5 \times 2$ HCl: C, 56.69; H, 6.34; N, 13.22. (Found) C, 55.81; H, 6.40; N, 12.68.

Compound 13 (Isomer 2) To a solution of the purified isomer in ethyl acetate was added a saturated solution of hydrochloric acid in ethyl acetate. The resulting slurry was concentrated to dryness to yield 1.43 g (38%) of the desired product as an off-white solid: $^1$H NMR consistent with structure; MS (ion spray) 563 (M+1); Anal. Calc'd. for $C_{30}H_{38}N_6O_5 \times 2$ HCl: C, 56.69; H, 6.34; N, 13.22. (Found) C, 55.71; H, 6.38; N, 12.74.

EXAMPLE 2-12

Preparation EX9A

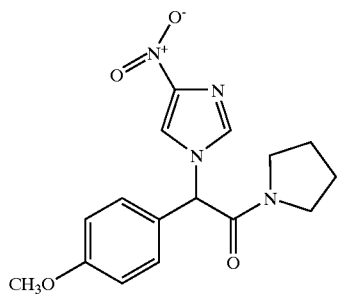

To a solution of Preparation 4 (3.00 g, 9.84 mmol), stirring in tetrahydrofuran (10 mL) and ethanol (5 mL), was added to sodium hydroxide (20 mL of a 5 N aqueous solution). The resulting mixture was stirred at ambient temperature until hydrolysis was complete and subsequently acidified to pH 2.0 with aqueous hydrochloric acid. The reaction mixture was extracted with ethyl acetate, dried over sodium sulfate, and concentrated. The resulting carboxylic acid was combined with pyrrolidine (0.710 g, 10 mmol), 1-hydroxybenzo-triazole hydrate (1.35 g, 10 mmol) and 1,3-dicyclohexyl-carbodiimide (2.06 g, 10.0 mmol) stirring in tetrahydrofuran (100 mL) at room temperature. After 18 hours, the mixture was concentrated, and the residue was then slurried in ethyl acetate then filtered and concentrated. Purification was by flash chromatography (silica gel, chloroform/methanol) provided afford 2.74 g (84%) of the desired product (Preparation EX9A) as follows:

MS: (M+H)$^+$331.2; $^1$H NMR (300 MHz, DMSO-$_6$) δ 8.19 (d, 1H, J=1.51 Hz), 7.80(d, 1H, J=1.51 Hz), 7.45 (d, 2H, J=8.67 Hz),7.02(d, 2H, J=8.67 Hz), 6.58 (s, 1H), 3.77 (s, 3H),3.75–3.60 (m, 1H) 3.45–3.30 (m, 2H), 2.90–2.75 (m, 1H)1.95–1.60 (m, 4H); Anal. Calc'd. for $C_{16}H_{18}N_4O_4$: C, 58.18; H, 5.49; N, 16.96 Found: C, 58.44; H, 5.45; N, 16.87.

Preparation EX9B

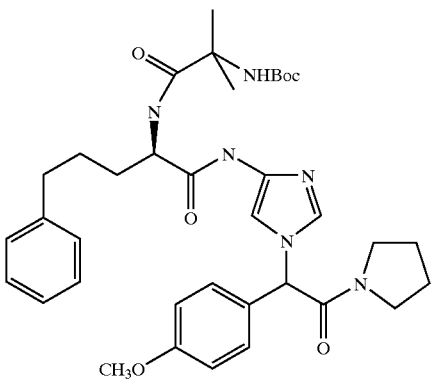

The product of Preparation EX9A (1.13 g, 3.42 mmol) was added to a mixture of 10% palladium/carbon (0.65 g) and palladium/black (0.15 g) in tetrahydrofuran (40 mL). The mixture was shaken under hydrogen (38 psi) in a Parr apparatus. After reduction was complete, the reaction mixture was filtered through celite and then filtrate immediately combined with 1,3-dicyclohexylcarbodiimide (0.71 g, 3.45mmol), 1-hydroxybenzotriazole (0.46 g, 3.40 mmol), the product of Preparation 2 (1.30 g, 3.44 mmol) and additional tetrahydrofuran (60 mL). After stirring overnight at ambient temperature, the mixture was concentrated and the residue slurried in ethyl acetate then filtered. The filtrate was concentrated and the residue purified by flash chromatography (silica gel, chloroform/methanol) which afforded 1.50 g (66%) of the desired product (Preparation EX9B), as follows, which was used without further purification.

Compound 14

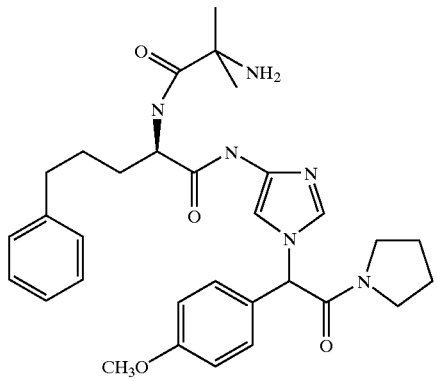

To a solution of the product of Preparation EX9B (1.45 g, 2.20 mmol), in dichloromethane (30 mL), was added trifluoroacetic acid (10 mL). After 2 hours, the mixture was concentrated and the residue treated with excess aqueous sodium bicarbonate and extracted. The combined organic extracts were concentrated and the resulting residue was purified by flash chromatography (silica gel, chloroform/methanol) to provide 0.68 g of the desired product (Example 9) as a yellow solid: MS: (M+H)$^+$561.3. $^1$H NMR was consistent with product (Example 9). Anal. Calc'd. for $C_{31}H_{40}N_6O_4 \cdot 0.2$ CHCl3: C, 64.11; H. 6.93; N, 14.38. Found: C, 64.19; H, 7.19; N, 14.50. The isomeric mixture (1.72 g) was separated as previously described in Example 2-9 to provide 0.64 g of isomer 1 ($t_R$=7.50 min) and 0.49 g of isomer 2 ($t_R$=10.15 min). Isomer 2 (486 mg, 0.87 mmol)

was dissolved in a minimal amount of ethyl acetate and treated with an excess of saturated hydrochloric acid in ethyl acetate. Concentration and subsequent evaporation from diethyl ether allowed for recovery of 580 mg of an off-white solid: MS: (M+H)+561.3, 562.4. $^1$H NMR was consistent with product. Anal. Calc'd. for $C_{31}H_{40}N_6O_4 \cdot 3.0$ HCl: C, 55.57; H, 6.47; N, 12.54. Found: C, 56.40; H, 6.43; N, 12.20.

EXAMPLE 2-13

Preparation EX10A

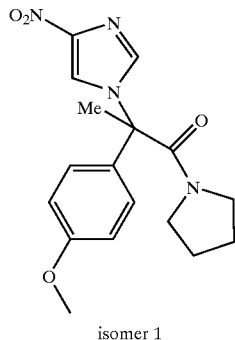

isomer 1

Prepared as in Preparation EX2A using the product of Preparation 7, diastereomer 1 (1.25 g, 2.78 mmol) in THF (50 mL) and lithium hydroxide (0.14 g, 3.33 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg) and pyrrolidine (0.24 mL, 2.89 mmol) to yield the desired product (Preparation EX10A), as follows, (0.78 g, 86% yield) as a colorless foam: $^1$H NMR (300 MHz, CDCl$_3$)—consistent with structure; Anal. calc'd. for $C_{17}H_{20}N_4O_4$; 59.59 C, 5.85 H, 16.27 N; found 59.59 C, 5.96 H, 16.19 N; ISMS (M+)—345.

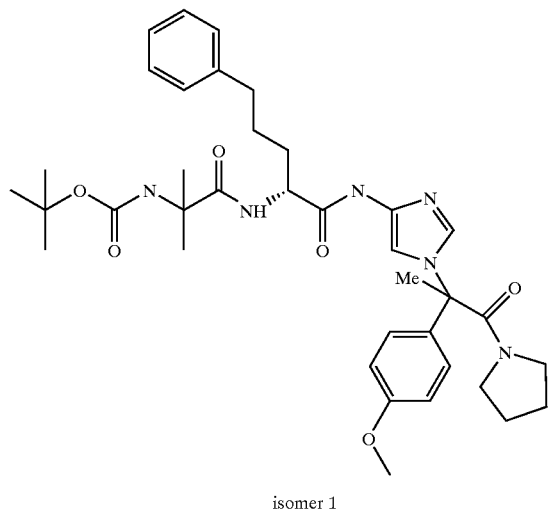

isomer 1

Prepared as in Preparation EX2B using the product of Preparation EX10A (0.77 g, 2.24 mmol) and 5% palladium on carbon (0.80 g, catalytic, 25 mL THF) to give the crude amine. The resulting filtrate was reacted with HOBT (0.30 g, 2.46 mmol), the product of Preparation 2 (0.85 g, 2.24 mmol), and DCC (0.51 g, 2.46 mmol) to yield the desired product (Preparation EX10B), as follows, (0.70 g, 46% yield) as a light yellow foam: $^1$H NMR (300 MHz, CDCl$_3$)—consistent with structure; Anal. calc'd. for $C_{37}H_{50}N_6O_6$; 65.85 C, 7.47 H, 12.45 N; found 65.83 C, 7.27 H, 12.38 N; ISMS (M+)—675.

Compound 15

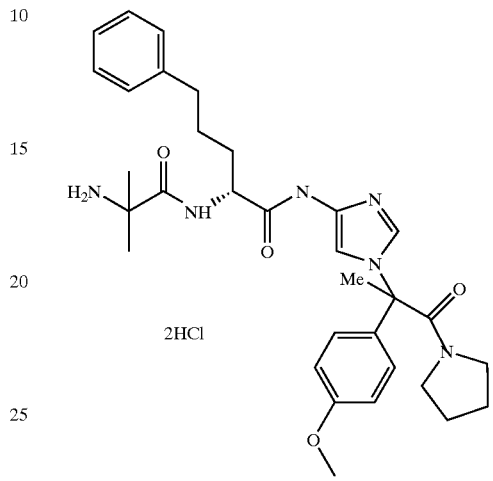

2HCl

A solution of the product of Preparation EX10B (0.69 g, 1.02 mmol) in dichloromethane (10 mL) was stirred under nitrogen with anisole (02 mL) and trifluoroacetic acid (4.0 mL) at ambient temperature for 3 hours. The mixture was quenched with saturated sodium bicarbonate and stirred 10 minutes at ambient temperature. Dichloromethane was added and the mixture was washed with bicarbonate and brine. The organic layer was dried over sodium sulfate, concentrated in vacuo, and redissolved in 2 mL ethyl acetate. Diethyl ether (saturated HCl (g), 5 mL) was added and the mixture stirred 10 minutes. The mixture was filtered to yield the desired product (Example 10) (0.57 g, 86% yield) as a white solid:

$^1$H NMR (300 MHz, CDCl$_3$)—consistent with structure; Anal. calc'd. for $C_{32}H_{42}N_6O_4Cl_2$; 59.35 C, 6.85 H, 12.98 N; found 58.74 C, 6.77 H, 12.85 N; ISMS (M+)—575.

EXAMPLE 2-14

Preparation 473

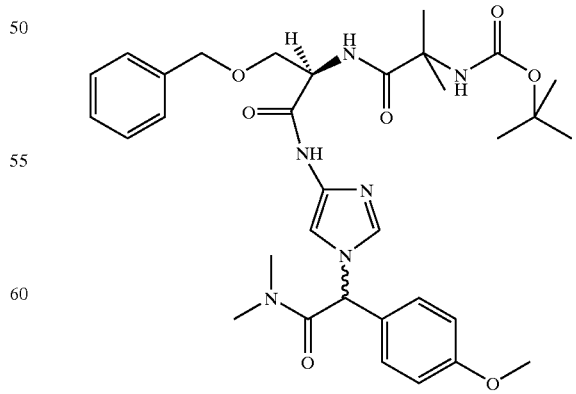

To a solution of the product of Preparation 5 (3.60 g, 5.90 mmol) in anhydrous dichloromethane (60 mL) at 0° C. was added N-methylmorpholine (0.78 mL, 7.08 mmol) and 2-chloro-4,6-dimethoxy-1,3,5-triazine (1.35 g, 7.67 mmol). This mixture stirred for 1 h, warming to room temperature, at which time a 2M solution of N,N-dimethylamine (3.30 mL, 6.49 mmol) was added. The reaction stirred for 2 h at room temperature, then more 2-chloro-4,6-dimethoxy-1,3,5-triazine (0.30 g) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (2.93 g, 78%): $^1$H NMR consistent with structure; MS (IS) m/e 637 (M+1); Anal. Calc'd for $C_{33}H_{44}N_6O_7$: C, 62.25; H, 6.97; N, 13.20. Found: C, 61.02; H, 6.67; N, 13.72.

Compound 16

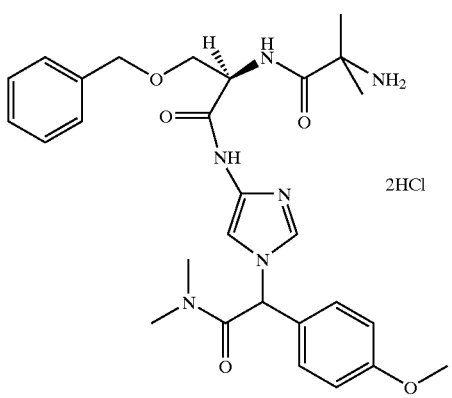

2HCl

To a stirring solution of the product of Preparation 473 (3.60 g, 5.65 mmol) and anisole (0.65 mL, 5.93 mmol) in anhydrous dichloromethane (130 mL) at 0° C. was added trifluoroacetic acid (13 mL) via syringe. The reaction was stirred for 4 hours warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 5% methanol/ethyl acetate—5% triethylamine/10% methanol/ethyl acetate) to provide the desired product as an off-white solid foam (2.20 g, 73%). $^1$H NMR consistent with structure; MS (IS) m/e 537 (M+1); Anal. Calc'd for $C_{28}H_{36}N_6O_5$: C, 62.67; H, 6.76; N, 15.66. Found: C, 62.53; H, 6.62; N, 15.57.

Diastereomeric separation: the product was resolved by HPLC [Kromasil packing material, 15% 3A alcohol/ 85% heptane (w/0.2% DMEA)] to provide two diastereomers. The second diastereomer (0.45 g) (retention time =10.70 min) was dissolved in ethyl acetate (10 mL) and then a saturated solution of hydrochloric acid in diethyl ether (2 mL) was added, with stirring. The white precipitate was collected by vacuum filtration and rinsed with diethyl ether. Vacuum drying provided Example 254 (0.40 g) as a white amorphous solid: $^1$H NMR consistent with structure; MS (IS) m/e 537 (M+1); Anal. Calc'd for $C_{28}H_{36}N_6O_5 \cdot 2HCl$: C, 55.17; H, 6.28; N, 13.79. Found: C, 56.56; H, 6.38; N, 14.26.

EXAMPLE 2-15

Preparation 76

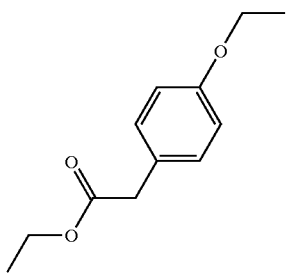

Reaction of 4-ethoxyphenylacetic acid (23.5 g, 130 mmol) and p-toluenesulfonic acid (4.0 g, 21 mmol) in absolute ethanol (150 mL), as described in Preparation 4A, gave 23.2 g (86%) of the desired product as a colorless oil: $^1$H-NMR (d, DMSO) 1.17 (t, J=7.2 Hz, 3H); 1.31 (t, J=7.2 Hz, 3H), 3.56 (s, 2H), 3.99 (q, J=7.2 Hz, 2H), 4.05 (q, J=7.2 Hz, 2H), 6.85 (d, J=8.7 Hz, 2H), 7.14 (d, J=8.7 Hz, 2H); MS (ion spray) 209 (M+1); Anal. Calc'd for $C_{12}H_{16}O_3$: C, 69.21; H, 7.74. Found: C, 68.91; H, 7.55.

Preparation 77

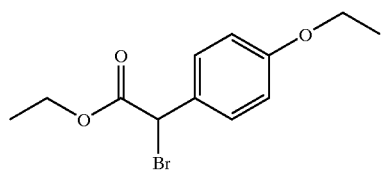

To a solution of the product of Preparation 76 (53 g, 255 mmol), stirring in carbon tetrachloride (600 mL) at room temperature, was added 46.6 g (262 mmol) of N-bromosuccinimide and 3.0 g (18.3 mmol) of 2,2'-azobis (2-methylpropionitrile). The resulting reaction mixture was heated to reflux. After 3.5 h, the solution was cooled to room temperature, filtered and concentrated. The resulting oil was chromatographed on silica gel using chloroform as eluant to afford 70.9 g (97%) of the desired product as a colorless oil: $^1$H-NMR (d, DMSO) 1.17 (t, J=7.2 Hz, 3H), 1.25–1.35 (m, 3H), 4.00–4.10 (m, 2H), 4.13–4.25 (m, 2H), 5.86 (s, 1H), 6.92 (d, J=8.7 Hz, 2H), 7.47 (d, J=9.0 Hz, 2H); MS (FD) 287, 289 (M+).

Preparation 78

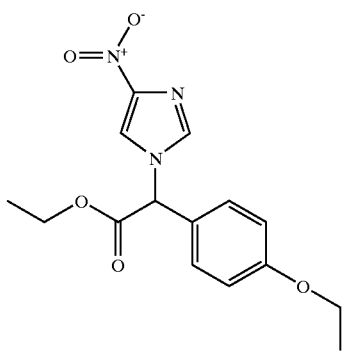

Reaction of the product of Preparation 77 (11.4 g, 40 mmol), 4-nitroimidazole (4.5 g, 40 mmol) and potassium carbonate (16.6 g, 120 mmol) in dimethylformamide (100 mL) as described in Preparation 4 gave 5.47 g (43%) of the desired product as a yellow oil: $^1$H-NMR (d, DMSO) 1. 18 (t, J=7.2 Hz, 3H), 1.29 (t, J=7.2 Hz, 3H), 4.03 (q, J=7.2 Hz, 2H), 4.23 (q, J=7.2 Hz, 2H), 6.54 (s, 1H), 6.70 (d, J=8.7 Hz, 2H), 7.42 (d, J=8.7 Hz, 2H), 7.90 (s, 1H), 8.34 (s, 1H); MS (ion spray) 320.2 (M+1); Anal. Calc'd for $C_{15}H_{17}N_3O_5$: C, 56.42; H, 5.37; N, 13.16. Found: C, 56.29; H, 5.17; N, 13.15.

Preparation 79

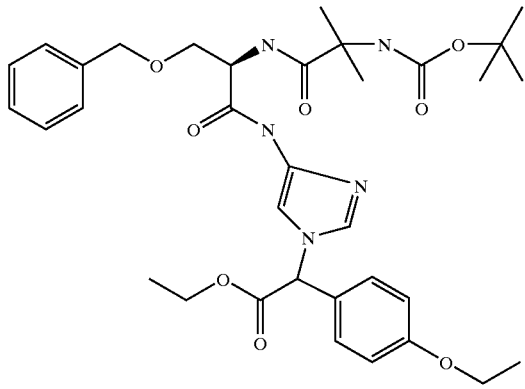

Reduction of the product of Preparation 78 (9.6 g, 30 mmol) with 10% palladium on carbon (7.0 g) in tetrahydrofuran (100 mL) followed by coupling with the product of Preparation 1 (11.5 g, 30 mmol)., 1-hydroxybenzotriazole 4.5.g, 33 mmol) and 1-(3-dimethylaminopropyl)-3-ethylcarbodiimide (6.8 g, 33 mmol), as described in Preparation 5A, gave 9.9 g (50%) of the desired product as a tan foam: $^1$H-NMR (d, DMSO) 1.17 (t, J=7.2 Hz, 3H), 1.25–1.40 (m, 18H), 3.58 (m, 1H), 3.70 (m, 1H), 4.02 (q, J=7.2 Hz, 2H), 4.20 (q, J=7.2 Hz, 2H), 4.44 (d, J=3.4 Hz, 2H), 4.60 (m, 1H), 6.33 (s, 1H), 6.95 (d, J=8.7 Hz, 2H), 7.15–7.35 (m, 9H), 7.43 (m, 1H), 7.51 (m, 1H), 10.2 (br s, 1H); MS (ion spray) 652.4 (M+1); Anal. Calc'd for $C_{34}H_{45}N_5O_8$: C, 62.66; H, 6.96; N, 10.74. Found: C, 62.92; H, 7.00; N, 10.98.

Preparation 80

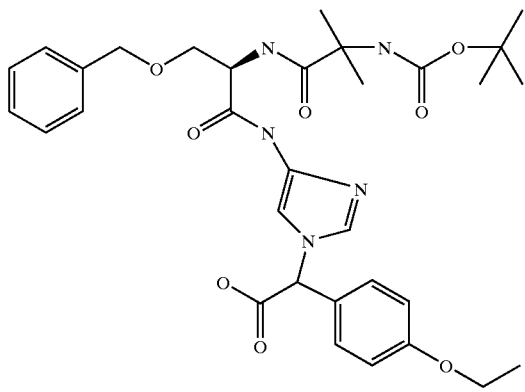

Reaction of the product of Preparation 79 (9.7 g, 15.0 mmol) and lithium hydroxide (0.42 g, 18.0 mmol) in dioxane (200 mL) and water (100 mL), as described in Preparation 5, gave 9.4 g (100%) of the desired product as a tan foam: $^1$H-NMR (d, DMSO) 1.25–1.40 (m, 18H), 3.60 (m, 1H), 3.68 (m, 1H), 4.02 (q, J=7.2 Hz, 2H), 4.44 (d, J=3.0 Hz, 2H), 4.60 (m, 1H), 6.19 (m, 1H), 6.95 (d, J=8.7 Hz, 2H), 7.28–7.35 (m, 9H), 7.40 (m, 1H), 7.51 (s, 1H), 10.2 (br s, 1H), 13.5 (br s, 1H); MS (ion spray) 624.5 (M+1); Anal. Calc'd for $C_{43}H_{41}N_5O_8$: C, 61.62; H, 6.63; N, 11.23. Found: C, 61.58; H, 6.92; N, 10.99.

Preparation 81

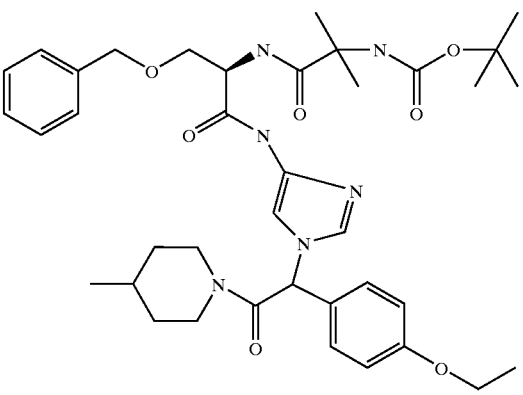

Reaction of the product of Preparation 80 (7.43 g, 12.0 mmol), 4-methylpiperidine (1.42 mL, 12.0 mmol), 1-hydroxybenzotriazole (1.78 g, 13.2 mmol) and 1-(3-dimethylaminopropyl)-3-ethylcarbodiimide (2.72 g, 13.2 mmol) in dimethylformamide (100 mL), as described in Preparation EX4A, gave 6.4 g (76%) of the desired product as a tan foam: $^1$H-NMR (d, DMS0) 0.74 (d, J=6.4 Hz, 1.5 H), 0.87 (d, J=6.0 Hz, 1.5H), 1.05 (m, 1H), 1.25–1.40 (m, 18H), 1.50–1.70 (m, 3H), 2.55–2.70 (m, 2H), 3.00 (m, 1H), 3.57 (m, 1H), 3.65–3.85 (m, 2H), 4.00–4.20 (m, 2H), 4.38 (m, 1H), 4.44 (d, J=3.4 Hz, 2H), 4.60 (m, 1H), 6.61 (d, J=12.0 Hz, 1H), 6.95–7.00 (m, 2H), 7.15–7.20 (m, 2H), 7.20–7.45 (m 9H), 10.15 (br s, 1H); MS (ion spray) 705.5 (M+1); Anal. Calc'd for $C_{38}H_{52}N_6O_7$: C, 64.75; H, 7.44; N, 11.92. Found: C, 64.59; H, 7.21; N, 11.87.

Compounds 17 and 18

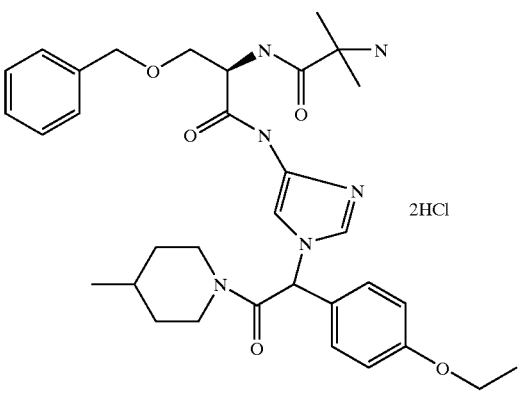

2HCl

Reaction of the product of Preparation 81 (6.4, 9.1 mmol) and trifluoroacetic acid (10 mL) in dichloromethane (25 mL), as described in Example 2-7, gave 4.71 g (77%) of the desired mixture of diastereomers as a tan foam. Resolution of the diastereomers (2.4 g) by HPLC (Kromsil CHI-DMP chiral stationary phase, 3A alcohol/dimethylethylamine/ heptane) provided 200 mg (8%) of isomer 1 and 0.8 g (31%) of isomer 2, both isolated as white solids after acidification with hydrochloric acid as described in Example 2-9:

Compound 17. (Isomer 1) ¹H-NMR (d, DMSO) 0.74 (d, J=6.4 Hz, 1.5H), 0.88 (d, J=6.0 Hz, 1.5H), 1.20 (m, 1H), 1.31 (t, J=6.8 Hz, 3H), 1.45–1.70 (m, 8H), 2.60–2.70 (m, 2H), 3.05 (I, 1H), 3.65–3.80 (m, 3H), 4.00–4.20 (m, 3H), 4.37 (m, 1H), 4.52 (s, 2H), 4.75 (m, 1H), 6.80 (d, J=13.2 Hz, 1H), 6.95–7.05 (m, 2H), 7.25–7.40 (m, 9H), 7.92 (br s, 1H), 8.20–8.30 (m, 3H), 8.53 (d, J=7.2 Hz, 1H), 10.9 (br s, 1H); $t_R$=9.17 min; MS (ion spray) 605 (M+1); Anal. Calc'd for $C_{33}H_{44}N_6O_5$·2HCl·0.1 CHCl3: C, 58.45; H, 6.74; N, 12.74. Found: C, 58.64; H, 6.77; N, 12.36.

Compound 18. (Isomer 2) ¹H-NMR (d, DMSO) 0.74 (d, J=6.4 Hz, 1.5H), D.88 (d, J=6.0 Hz, 1.5H), 1.20 (m, 1H). 1.31 (t, J=6.8 Hz, 3H), 1.45–1.70 (m, 8H), 2.60–2.70 (m, 2H), 3.05 (m, 1H), 3.65–3.80 (m, 3H), 4.00–4.20 (m, 3H), 4.37 (m, 1H), 4.52 (s, 2H), 4.75 (m, 1H), 6.80 (d, J=13.2 Hz, 1H), 6.95–7.05 (m, 2H), 7.25–7.40 (m, 9H), 7.92 (br s, 1H), 8.20–8.30 (m, 3H), 8. 53 (d, J=7.2 Hz, 1H), 10.9 (br s, 1H); $t_R$=12.68 min; MS (ion spray) 605 (M+1); Anal. Calc'd for $C_{33}H_{44}N_6O_5$·¹HCl: C, 59.35; H. 6.85; N, 12.98. Found: C, 59.62; H, 7.01; N, 12.71.

EXAMPLE 2-16

Preparation 83

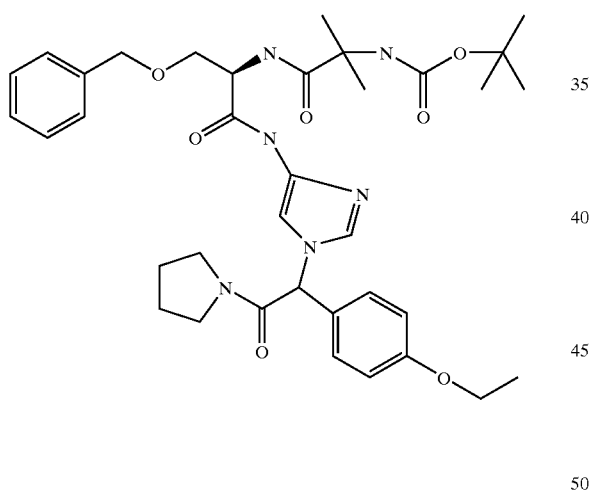

Reaction of the product of Preparation 80 (0.9 g, 1.5 mmol), pyrrolidine (0.13 mL, 1.5 mmol), 1-hydroxybenzotriazole (0.23 g, 1.65 mmol) and 1-(3-dimethylaminopropyl)-3-ethylcarbodiimide (0.34 g, 1.65 mmol) in dimethylformamide (40 mL), as described in Preparation EX4A, gave 0.7 g (74%) of the desired product as a tan foam: ¹H-NMR (d, DMSO) 1.25–1.40 (m, 18H), 1.70–1.90 (m, 4H), 2.95 (m, 1H), 3.30–3.40 (m, 2H), 3.55–3.70 (m, 3H), 4.03 (q, J=7.2 Hz, 2H), 4.44 (d, J=3.4 Hz, 2H), 4.57 (m, 1H), 6.34 (s, 1H), 6.97 (d, J=8.7 Hz, 2H), 7.20–7.35 (m, 9H), 7.40–7.45 (m, 2H), 10.15 (br s, 1H); MS (ion spray) 677.6 (M+1); Anal. Calc'd for $C_{36}H_{48}N_6O_7$·0.2H₂O: C, 63.55; H, 7.17; N, 12.35. Found: C, 63.32; H, 6.96; N, 12.24.

Compound 19

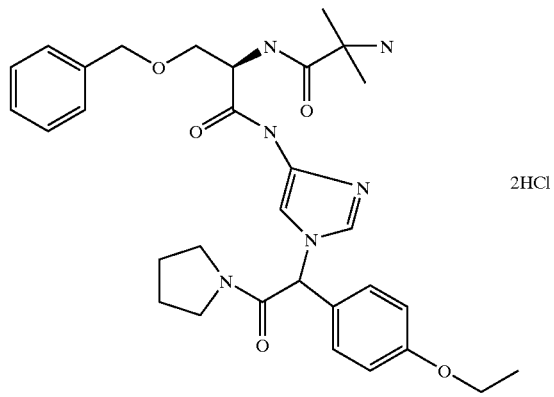

2HCl

Reaction of the product of Preparation 83 (0.59 g, 0.9 mmol) and trifluoroacetic acid (2 mL) in dichloromethane (6 mL), as described in Example 2-7, gave 0.36 g (64%) of the desired product as a mixture of isomers: ¹H-NMR (d, DMSO) 1.32 (t, J=6.8 Hz, 3H), 1.45–1.60 (m, 6H), 1.65–1.90 (m, 4H), 2.90 (m, 1H), 3.25–3.45 (m, 2H), 3.65–3.75 (m, 3H), 4.02 (q, J=6.8 Hz, 2H), 4.45–4.55 (m, 2H), 4.70–4.80 (m, 1H), 6.54 (s, 1H), 6.98 (d, J=8.7 Hz, 2H), 7.20–7.40 (m, 9H), 8.05 (m, 1H), 8.20–8.30 (m, 3H), 8.54 (d, J=7.2 Hz, 1H), 10.95 (br s, 1H); MS (high res) calc'd for $C_{31}H_{40}N_6O_5$: 577.3138. Found: 577.3132. Anal. Calc'd for $C_{31}H_{40}N_6O_5$·2HCl: C, 57.32; H, 6.52; N, 12.94. Found: C, 57.46; H, 6.59; N, 12.91.

EXAMPLE 2-17

Preparation 82

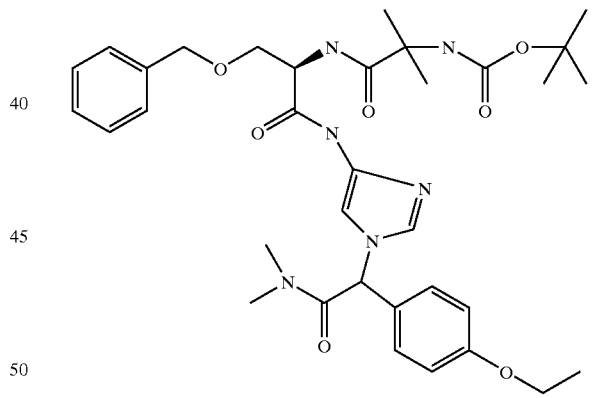

Reaction of the product of Preparation 80 (0.9 g, 1.5 mmol), dimethylamine hydrochloride (0.13 g, 1.5 mmol), triethylamine (0.23 mL, 1.65 mmol), 1-hydroxybenzotriazole (0.23 g, 1.65 mmol) and 1-(3-dimethylaminopropyl)-3-ethylcarbodiimide (0.34 g, 1.65 mmol) in dimethylformamide (50 mL), as described in Preparation EX4A, gave 0.46 g (47%) of the desired product as a tan foam: ¹H-NMR (d, DMSO) 1.25–1.35 (m, 18H), 2.90 (m, 6H), 3.57 (m, 1H), 3.67 (m, 1H), 4.03 (q, J=. 7.2 Hz, 2H), 4.43–4.47 (m, 2H), 4.57 (m, 1H), 6.55 (m, 1H), 6.97 (d, J=8.7 Hz, 2H), 7.15–7.45 (m, 11H), 10.16 (br s, 1H); MS (ion spray) 651.4 (M+1); Anal. Calc'd for $C_{34}H_{46}N_6O_7$: C, 62.75; H, 7.13; N, 12.91. Found: C, 62.55; H, 6.84; N, 12.84.

Compounds 20 and 21

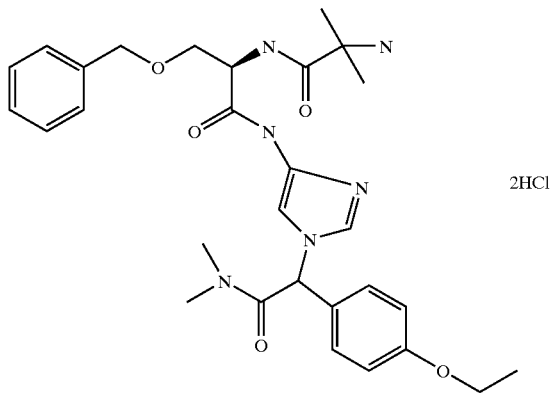

2HCl

Reaction of the product of Preparation 82 (0.44 g, 0.68 mmol) and trifluoroacetic acid (2 mL) in dichloromethane (6 mL), as described in Example 2-7, gave 0.19 g (45%) of the desired product as a tan foam. Resolution of the diastereomers (90 mg, 0.14 mmol) by HPLC (Kromsil CHI-DMP chiral stationary phase, 3A alcohol/dimethylethylamine/heptane) provided 50 mg (50%) of isomer 1 and 27 mg (27%) of isomer 2, both isolated as white solids after acidification with hydrochloric acid as described in Example 2-9:

Compound 20 (isomer 1): $^1$H-NMR (d, DMSO) 1.32 (t, J=6.8 Hz, 3H), 1.50 (s, 6H), 2.86 (s, 3H), 2.90 (s, 3H), 3.70–3.80 (m, 2H), 4.03 (q, J=7.2 Hz, 2H), 4.52 (s, 2H), 4.75 (m, 1H), 6.76 (s, 1H), 7.00 (d, J=8.7 Hz, 2H), 7.25–7.40 (m, 9H), 8.06 (m, 1H), 8.20–8.30 (m, 3H), 8.52–8.60 (m, 1H), 11.00 (br s, 1H) ; $t_R$=7.70 min; MS (high res) calc'd for $C_{29}H_{39}N_6O_5$: 551.2982. Found: 551.2987. Anal. Calc'd for $C_{29}H_{38}N_6O_5$·2.3 HCl·0.3ethyl acetate: C, 54.88; H, 6.51; N, 12.72. Found: C, 54.70; H, 6.49; N, 12.43.

Compound 21 (isomer 2): $^1$H-NMR (d, DMSO) 1.32 (t, J=6.8 Hz, 3H), 1.50 (s, 6H), 2.86 (s, 3H), 2.90 (s, 3H), 3.70–3.80 (m, 2H), 4.03 (q, J=7.2 Hz, 2H), 4.52 (s, 2H), 4.75 (m, 1H), 6.76 (s, 1H), 7.00 (d, J=8.7 Hz, 2H), 7.25–7.40 (m, 9H), 8.06 (m, 1H), 8.20–8.30 (m, 3H), 8.52–8.60 (m, 1H), 11.00 (br s, 1H); $t_R$=9.09 min; MS (high res) calc'd for $C_{29}H_{39}N_6O_5$: 551.2982. Found: 551.2976. Anal. Calc'd for $C_{29}H_{38}N_6O_5$·2HCl·0.3 ethyl acetate: C, 55.18; H, 6.53; N, 12.79. Found: C, 55.01; H, 6.33; N, 12.54.

EXAMPLE 2-18

Preparation 84

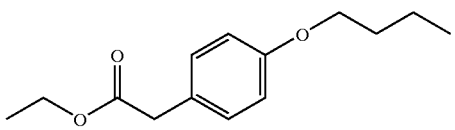

Reaction of 4-butyloxyphenylacetic acid (10.0 g, 48 mmol) and p-toluenesulfonic acid (2.5 g, 13 mmol) in absolute ethanol (100 mL), as described in Preparation 1, gave 11.04 g (98%) of the desired product as a colorless oil: $^1$H-NMR (d, DMS0) 0.94 (t, J=7.4 Hz, 3H), 1.18 (t, J=7.0 Hz, 3H), 1.40–1.50 (m, 2H), 1.60–1.80 (m, 2H), 3.57 (s, 2H), 3.93 (q, J=6.5 Hz, 2H), 4.08 (q, J=7.3 Hz, 2H), 6.86 (d, J=8.4 Hz, 2H), 7.15 (d, J=8.4 Hz, 2H); MS (ion spray) 237 (M+1); Anal. Calc'd for $C_{14}H_{20}O_3$: C, 71.16; H, 8.53. Found: C, 71.33; H, 8.55.

Preparation 85

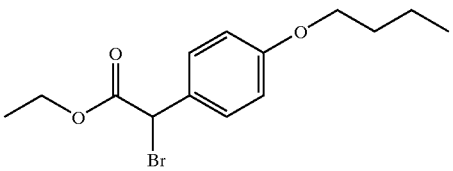

To a solution of the product of Preparation 84, 6.0 g (25 mmol) in 100 mL of carbon tetrachloride was added 4.7 g (25.8 mmol) of N-bromosuccinimide and 0.6 g of 2,2'-azobis(2-methylpropionitrile). The reaction mixture was heated to reflux. After 3.5 hours, the mixture was cooled to room temperature, filtered and concentrated. The resulting oil was purified by flash chromatography (silica gel, 3% methanol/chloroform) to proved 6.9 g (88%) of the desired product as a colorless oil: $^1$H-NMR (d, DMSO) 0.93 (t, J=7.35 H, 3H), 1.20 (t, J=7.2 Hz, 3H), 1.40–1.50 (m, 2H), 1.60–1.80 (m, 2H), 3.95–4.05 (m, 2H), 4.10–4.15 (m, 2H), 5.87 (s, 1H), 6.93 (d, J=8.7 Hz, 2H), 7.45 (d, J=8.7 Hz, 2H); MS (FD) 314, 316 (M+); Anal. Calc'd for $C_{14}H_{19}BrO_3$·0.5CHCl$_3$: C, 52.54; H, 5.98. Found: C, 52.35; H, 5.84.

Preparation 86

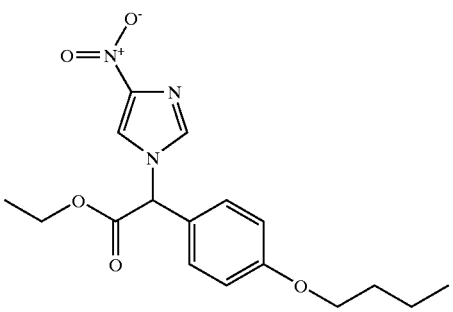

Reaction of the product of Preparation 85 (5.82 g, 19.0 mmol), 4-nitroimidazole (2.1 g, 19.0 mmol) and potassium carbonate (8.0 g, 57 mmol) in dimethylformamide (150 mL), as described in Preparation 4, gave 3.5 g (53%) of the desired product as a yellow oil: $^1$H-NMR (d, DMSO) 0.93 (t, J=7.3 Hz, 3H), 1.19 (t, J=7.0 Hz, 3H), 1.35–1.50 (m, 2H), 1.60–1.80 (m, 2H), 3.92–4.06 (m, 2H), 4.20–4.30 (m, 2H), 6.56 (s, 1H), 6.99 (d, J=8.6 Hz, 2H), 7.44 (d, J=8.6 Hz, 2H), 7.92 (s, 1H), 8.37 (s, 1H); MS (ion spray) 348.3 (M+1); Anal. Calc'd for $C_{17}H_{21}N_3O_5$: C, 58.78; H, 6.09; N, 12.10. Found: C, 59.08; H, 6.21; N, 12.19.

Preparation 87

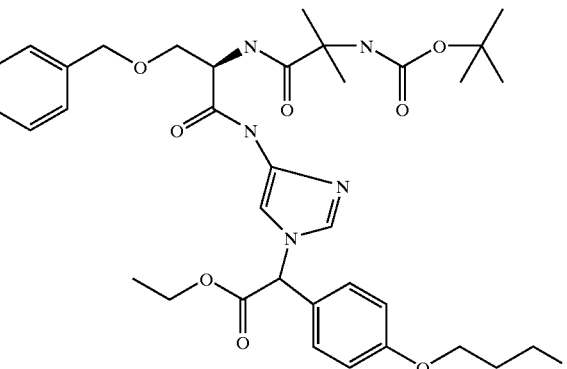

Reduction of the product of Preparation 86 (1.5 g, 4.3 mmol) with 10% palladium on carbon (0.8g) in tetrahydrofuran (40 mL) followed by coupling with the product of Preparation 1 (1.64 g, 4.3 mmol), 1-hydroxybenzotriazole (0.7 g, 4.7 mmol) and 1-(3-dimethylaminopropyl)-3-ethylcarbodiimide (1.04 g, 4.7 mmol), as described in Preparation 5A, gave 1.1 g (38%) of the desired product as a tan foam: 1H-NMR (d, DMSO) 0.92 (t, J=7.5 Hz, 3H), 1.18 (t, J=7.2 Hz, 3H), 1.25–1.40 (m, 15H), 1.40–1.50 (m, 2H), 1.60–1.75 (m, 2H), 3.60 (m, 1H), 3.70 (m, 1H), 3.95–4.00 (m, 2H), 4.20–4.25 (m, 2H), 4.45–4.48 (m, 2H), 4.57 (m, 1H), 6.35 (s, 1H), 6.97 (t, J=9.0 Hz, 2H), 7.15–7.35 (m, 9H), 7.40 (m, 1H), 7.50 (s, 1H), 10.20 (br s, 1H); NS (ion spray) 680.5 (M+1); Anal. Calc'd for C36H49N5O8: C, 63.61; H, 7.27; N, 10.30. Found: C, 63.53; H, 6.99; N, 10.54.

Preparation 88

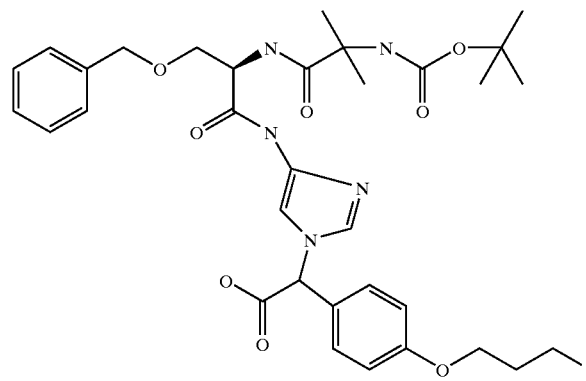

Reaction of the product of Preparation 87 (1.1 g, 1.6 mmol) and lithium hydroxide (0.5 g, 1.92 mmol) in dioxane (50 mL) and water (25 mL), as described in Preparation 5, gave 1.04 g (100%) of the desired product as a tan foam: $^1$H-NMR (d, DMSO) 0.95 (t, J=7.5 Hz, 3H), 1.25–1.35 (m, 15H), 1.35–1.50 (m, 2H), 1.65–1.75 (m, 2H), 3.57 (m, 1H), 3.65 (m, 1H), 3.95 (t, J=6.4 Hz, 2H), 4.57 (m, 1H), 6.19 (d, J=1.5 Hz, 2H), 6.20 (s, 1H), 6.96 (d, J=8.7 Hz, 2H), 7.10–7.35 (m, 9H), 7.40 (m, 1H), 7.50 (s, 1H), 10.20 (br s, 1H), 13.45 (br s, 1H); MS (ion spray) 652.5 (M+1); Anal. Calc'd for $C_{32}H_{45}N_5O_8$: C. 62.66; H. 6.96; N, 10.75. Found: C, 62.45; H, 7.07; N, 10.72.

Preparation 89

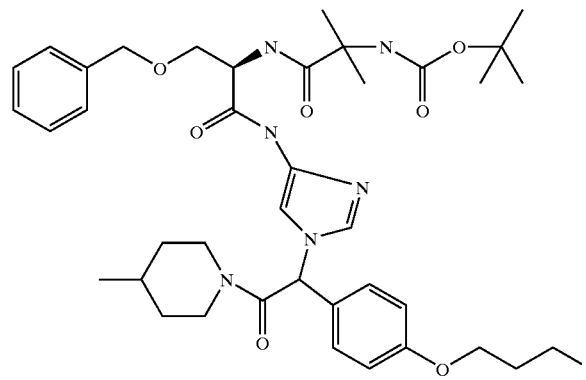

Reaction of the product of Preparation 88 (1.0 g, 1.6 mmol), 4-methylpiperidine (0.19 mL, 1.6 mmol), 1-hydroxybenzotriazole (0.24 g, 1.8 mmol) and 1-(3-dimethylaminopropyl)-3-ethylcarbodiimide (0.35 g, 1.8 mmol) in dimethylformamide (60 mL), as described in Preparation EX4A, gave 0.57 g (48%) of the desired product as a tan foam: $^1$H-NMR (d, DMSO) 0.75 (d, J=6.0 Hz, 1H), 0.85–0.95 (m, 6H), 1.25–1.40 (m, 15H), 1.40–1.75 (m, 7H), 2.55–2.75 (m, 2H), 3.00 (m, 1H), 3.55 (m, 1H), 3.60–3.85 (m, 2H), 3.95–4.00 (m, 2H), 4.60 (m, 1H), 4.85–4.98 (m, 3H), 6.97 (d, J=8.7 Hz, 1H), 6.90–7.00 (m, 2H), 7.15 (m, 1H), 7.20–7.45 (m, 10H), 10.15 (br s, 1H); MS (ion spray) 733.5 (M+1); Anal. Calc'd for $C_{40}H_{56}N_6O_7$: C, 65.55; H, 7.70; N, 11.47. Found: C, 65.44; H, 7.49; N, 11.59.

Compounds 22 and 23

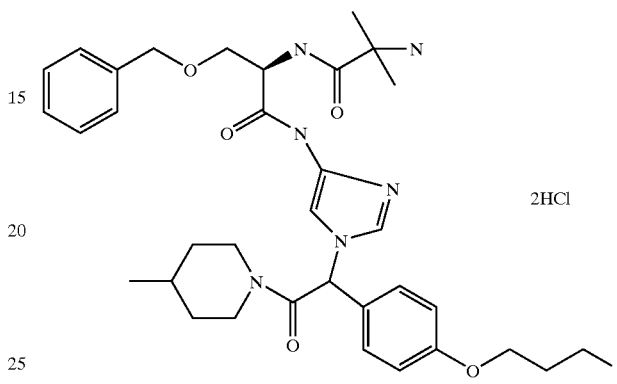

2HCl

Reaction of the product of Preparation 89 (0.55 g, 0.75 mmol) and trifluoroacetic acid (2 mL) in dichloromethane (6 mL), as described in Example 2-7, gave 0.4 g (75%) of the desired product as a mixture diastereomers. This material was resolved by HPLC (Kromsil CHI-DMP chiral stationary phase, 3A alcohol/dimethylethylamine/heptane) to provide the desired diastereomers, both isolated as white solids after acidification with hydrochloric acid as described in Example 2-9:

Compound 22. (isomer 1): $^1$H-NMR (d, DMSO) 0.75 (d, J=6.4 Hz, 1H), 0.85–1.00 (m, 5H), 1.25–1.40 (m, 2H), 1.40–1.50 (m, 2H), 1.50–1.60 (m, 6H), 1.60–1.75 (m, 4H), 2.60=2.70 (m, 2H), 3.00 (m, 1H), 3.60–3.75 (m, 3H), 3.95–4.00 (m, 2H), 4.52 (s, 2H), 4.75 (m, 1H), 4.88 (m, 1H), 6.89 (d, J=14 Hz, 1H), 7.00–7.05 (m, 2H), 7.20–7.40 (m, 9H), 8.10 (m, 1H), 8.20–8.30 (m, 3H), 8.60 (m, 1H), 11.02 (br s, 1H); $t_R$=5.90 min; MS (high res) calc'd for $C_{35}H_{49}N_6O_5$: 633.3764. Found: 633.3768. Anal. Calc'd for $C_{35}H_{48}N_6O_5 \cdot 2.3HCl$: C, 58.66; H, 7.07; N, 11.73. Found: C, 58.59; H, 6.99; N, 11.46.

Compound 23. (isomer 2): $^1$H-NMR (d, DMSO) 0.75 (d, J=6.4 Hz, 1H), 0.85–1.00 (m, 5H), 1.25–1.40 (m, 2H), 1.40–1.50 (m, 2H), 1.50–1.60 (m, 6H), 1.60–1.75 (m, 4H), 2.60=2.70 (m, 2H), 3.00 (m, 1H), 3.60–3.75 (m, 3H), 3.95–4.00 (m, 2H), 4.52 (s, 2H), 4.75 (m, 1H), 4.88 (m, 1H), 6.89 (d, J=14 Hz, 1H), 7.00–7.05 (m, 2H), 7.20–7.40 (m, 9H), 8.10 (m, 1H), 8.20–8.30 (m, 3H), 8.60 (m, 1H), 11.02 (br s, 1H) ; $t_R$=7 .47 min; MS (high res) calc'd for $C_{35}H_{49}N_6O_5$: 633.3764. Found: 633.3762. Anal. Calc'd for $C_{35}H_{49}N_6O_5 \cdot HCl$: C, 59.57; H, 7.14; N, 11.91. Found: C, 59.74; H, 7.30; N, 11.72.

Example 2-19

Preparation EX11A

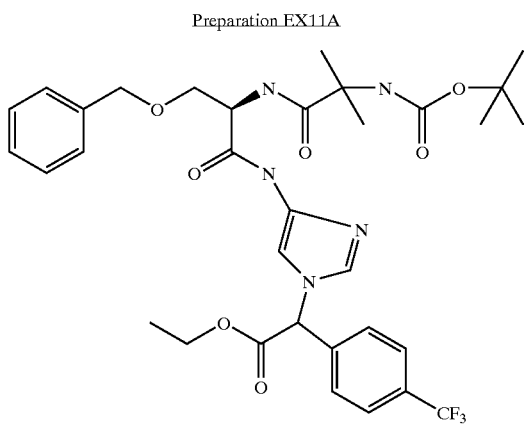

Hydrogenation of the product of Preparation 8 (8.5 g, 24.8 mmol) with 10% palladium on carbon (6.0 g) in tetrahydrofuran (70 mL) followed by coupling with the product of Preparation 1 (9.5 g, 24.8 mmol), 1-hydroxybenzotriazole (3.7 g, 27.3 mmol) and 1-(3-dimethylaminopropyl)-3-ethylcarbodiimide (5.6 g, 27.3 mmol),as described in Preparation 5A, gave 12.8 g (77%) of the above-described product, as a tan foam: $^1$H-NMR (d, DMSO) 1.17 (t, J=7.2 Hz, 3H), 1.25–1.35 (m, 15H), 3.60 (m, 1H), 3.70 (m, 1H), 4.27 (q, J=7.2 Hz, 2H), 4.44 (d, J=2.6 Hz, 2H), 4.60 (m, 1H), 6.63 (s, 1H), 7.23–7.30 (m, 7H), 7.45 (m, 1H), 7.58–7.65 (m, 3H), 7.81 (d, J=8.3 Hz, 2H), 10.25 (br s, 1H); MS (ion spray) 676.5 (M+1); Anal. Calc'd for $C_{33}H_{40}F_3N_5O_7$: C, 58.66; H, 5.97; N, 10.36. Found: C, 58.58; H, 6.17; N, 10.27.

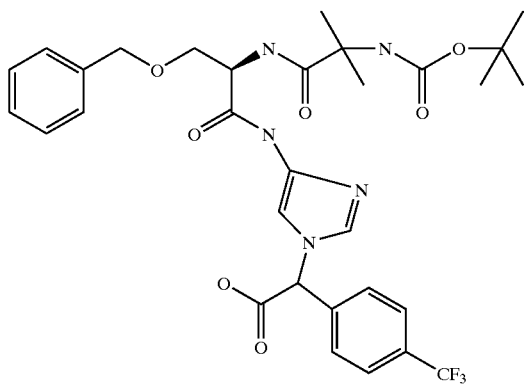

Reaction of the product of Preparation EX11A (12.3 g, 18.2 mmol) and lithium hydroxide (0.52 g, 21.8 mmol) in dioxane (100 mL) and water (75 mL), as described in Preparation 5, gave 11.8 g (100%) of the above-identified product as tan foam: $^1$H-NMR (d, DMSO) 1.20–1.35 (m, 15 H), 3.60 (m, 1H), 3.65 (m, 1H), 4.45 (d, J=2.6 Hz, 2H), 4.60 (m, 1H), 6.46 (s, 1H), 7.15 (m, 1H), 7.20–7.35 (m, 6H), 7.42 (m, 1H)., 7.57–7.65 (m, 3H), 7.79 (d, J=8.3 Hz, 2H), 10.25 (br s, 1H); MS (ion spray) 648.9 (M+1); Anal. Calc'd for $C_{31}H_{36}F_3N_5O_7$: C, 57.41; H, 5.60; N, 10.81. Found: C, 57.31; H, 5.59; N, 10.53.

Preparation EX11C

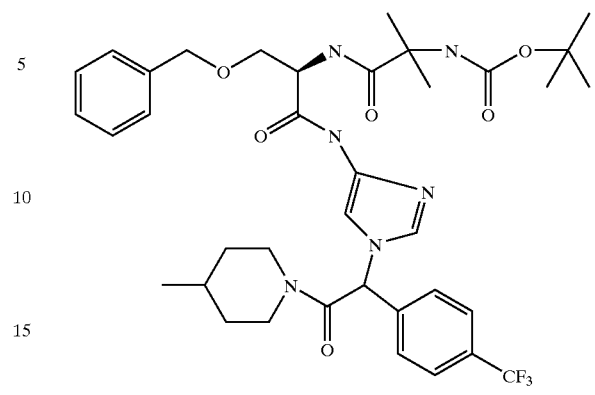

Reaction of the product of Preparation EX11B (8.0 g, 12.3 mmol), 4-methylpiperidine (1.5 mL, 12.3 mmol), 1-hydroxybenzotriazole (1.83 g, 13.5 mmol) and 1-(3-dimethylaminopropyl)-3-ethylcarbodiimide (2.8 g, 13.5 mmol) in N,N-dimethylformamide (150 mL), as described in Preparation 4A, gave 7.33 g (81%) of above-identified product as a tan foam: $^1$H-NMR (d, DMSO) 0.78 (d, J=6.0 Hz, 1.5H), 0.84 (d, J=6.0 Hz, 15H), 0.95 (m, 1H), 1.25-1.35 (m, 16H), 1.50–1.70 (m, 4H), 2.65 (m, 1H). 3.60 (m, 1H), 3.67 (m, 1H), 3.80 (m, 1H), 4.35–4.50 (m, 3H), 4.60 (m, 1H), 6.88 (d, J=9.8 Hz, 1H), 7.20–7.30 (m, 7H), 7.45 (m, 1H), 7.48–7.55 (m, 2H), 7.60 (m, 1H), 7.75–7.85 (m, 2H), 10.25 (br s, 1H); MS (ion spray) 729 (M+1); Anal. Calc'd for $C_{37}H_{47}F_3N_6O_6$: C, 60.98; H, 6.50; N, 11.53. Found: C, 61.24; H, 6.44; N, 11.77.

Compounds 24 and 25

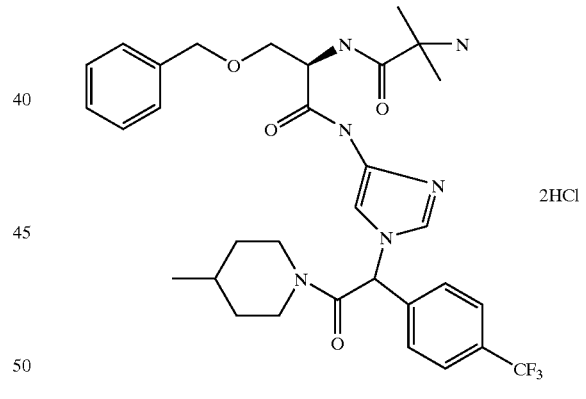

Reaction of the product of Preparation EX11C (7.0 g, 10.0 mmol) and trifluoroacetic acid (10 mL) in dichloromethane (25 mL) as described in Example 2-7 gave 5.62 g (93%) of the desired product (Example 11) (3.0 g) as a tan foam which was purified by HPLC (8×15 cm Prochrom column packed with Kromasil CHI-DMP chiral phase with an eluent mixture of 3A alcohol and dimethylethylamine in heptane) to give 1.5 g (45%) of Example 11, isomer 1 and 1.1 g (30%) of Example 11, isomer 2.

Compound 24 (isomer 1)s $^1$H-NMR (d, DMSO) 0.25 (m, 1H), 0.76 (d, J=6.4 Hz, 1.5H), 0.86 (d, J=6.4 Hz, 1.5H), 1.00 (m, 1H), 1.45–1.70 (m, 8H), 2.65–2.75 (m, 2H), 3.15 (m, 1H), 3.65–3.80 (m, 3H), 4.40 (m, 1H), 4.51 (s, 2H), 4.75 (m, 2H), 7.10 (d, J=12.8 Hz, 1H), 7.20–7.40 (m, 6H), 7.58 (d, J=8.0 Hz, 1H), 7.67 (d, J=8.0 Hz, 1H), 7.80–7.90 (m, 2H), 8.10 (br s, 1H), 8.20–8.35 (m, 3H), 8.55 (d, J=7.5 Hz, 1H), 10.95 (br s, 1H); $t_R$=8.23 min; MS (ion spray) 629.3 (M+1); Anal. Calc'd for $C_{32}H_{39}F_3N_6O_4 \cdot 2HCl$: C, 54.78; H, 5.89; N, 11.98. Found: C, 54.85; H, 5.71; N, 11.70.

Compound 25 (isomer 2): $^1$H-NMR (d, DMSO) 0.25 (m, 1H), 0.76 (d, J=6.4 Hz, 1.5H), 0.86 (d, J=6.4 Hz, 1.5H), 1.00 (m, 1H), 1.45–1.70 (m, 8H), 2.65–2.75 (m, 2H), 3.15 (m, 1H), 3.65–3.80 (m, 3H), 4.40 (m, 1H), 4.51 (s, 2H), 4.75 (m, 2H), 7.10 (d, J=12.8 Hz, 1H), 7.20–7.40 (m, 6H), 7.58 (d, J=8.0 Hz, 1H), 7.67 (d, J=8.0 Hz, 1H), 7.80–7.90 (m, 2H), 8.10 (br s, 1H), 8.20–8.35 (m, 3H), 8.55 (d, J=7.5 Hz, 1H), 10.95 (br s, 1H); $t_R$=10.77 min; MS (ion spray) 629.3 (M+1); Anal. Calc'd for $C_{32}H_{39}F_3N_6O_4 \cdot 2.2HCl$: C, 54.22; H, 5.86; N, 11.85. Found: C, 54.15; H, 5.84; N, 11.64.

EXAMPLE 2-20

Preparation 37

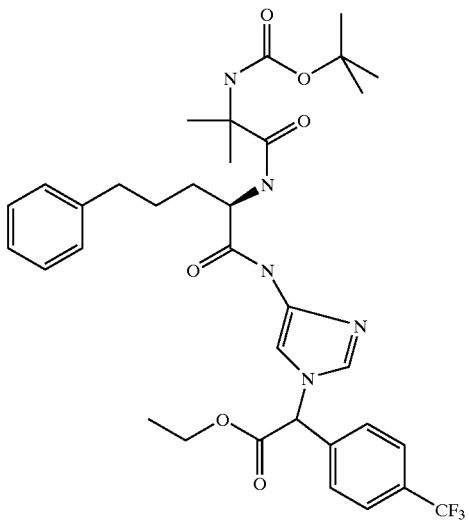

A mixture of the product of Preparation 8 (11.1 g, 32.3 mmol) and 5% palladium on carbon (1.7 g) in tetrahydrofuran (100 mL) was hydrogenated at 60 psi at room temperature using a Parr apparatus. After 1.5 hours, the resulting brown solution was filtered through celite and concentrated to give 8.8 g (87%) crude oil which was used without purification. To a mixture of the amine stirring at 0° C. in tetrahydrofuran (20 mL) was added the product of Preparation 2 (10.6 g, 28.1 mmol) in tetrahydrofuran (30 mL). To this mixture was added 1-hydroxy-7-azobenzotriazole (4.0 g, 29.5 mmol) and 1,3-dicyclohexylcarbodiimide (6.1 g, 29.5 mmol). The solution was allowed to warm to room temperature and the resulting mixture filtered after 3 days. The filtrate was concentrated and subsequently purified by flash chromatography (silica gel, 3.5% methanol/dichloromethane) to provide 12.1 g (64%) of the desired product as an orange solid: $^1$H-NMR (d, DMSO) 1.15 (t, J=7 Hz, 3H), 1.18–1.32 (m, 15H), 1.35–1.70 (m, 4H), 3.23 (m, 2H), 4.19 (q, J=7 Hz, 2H), 4.31 (m, 1H), 6.58 (s, 1H), 7.00 (br s, 1H), 7.05–7.22 (m, 6H), 7.41 (m, 1H), 7.52–7.58 (m, 3H), 7.75 (d, J=8 Hz, 2H), 10.19 (br s, 1H); MS (ion spray) 674.7 (M+1); Anal. Calc'd for $C_{34}H_{42}F_3N_5O_6$: C, 60.61; H, 6.28; N, 10.39.

Found: C, 60.44; H, 6.48; N, 10.36.

Preparation 38

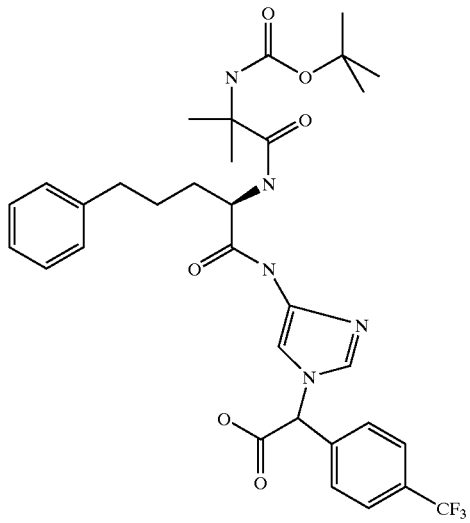

To a solution of the product of Preparation 37 (12.0 g, 17.8 mmol) stirring in dioxane (20 ml) and water (20 ml) at room temperature was added lithium hydroxide (0.84 g, 35.6 mmol). After 90 min with intermittent sonication, the reaction was poured into a solution of sodium bisulfate (12 g/50 mL $H_2O$) and brine (20 mL) then extracted with ethyl acetate. The combined organic extracts were dried over sodium sulfate, filtered, and concentrated to provide 11.5 g (100%) of the desired product as a tan solid: $^1$H-NMR (d, DMSO) 1.17–1.31 (m, 15 H), 1.40–1.70 (m, 4H), 2.45 (m, 2H), 4.33 (m, 1H), 6.40 (s, 1H), 7.00 (m, 1H), 7.05–7.23 (m, 6H), 7.40 (m, 1H), 7.55–7.71 (m, 3H), 7.76 (d, J=8 Hz, 2H), 10.25 (br s, 1H); MS (ion spray) 646.6 (M+1); Anal. Calc'd for $C_{32}H_{38}F_3N_5O_6 \cdot 0.7 H_2O$: C, 58.39; H, 6.03; N, 10.64. Found: C, 58.52; H, 6.01; N, 9.87*.

Preparation 39

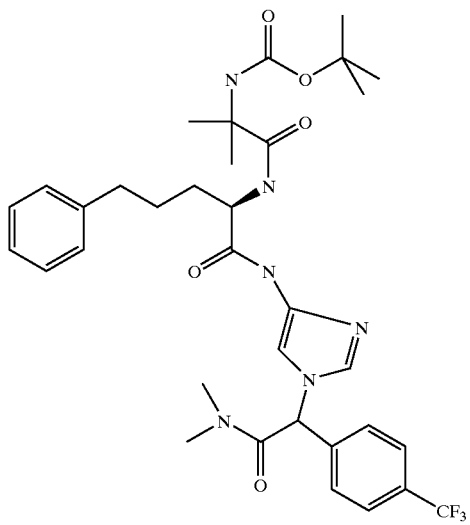

To a solution of the product of Preparation 38 (6.0 g, 9.3 mmol) stirring at 0C in dimethylformamide was added dimethylamine hydrochloride (0.76 g, 9.3 mmol), diethylcyanophosphonate (1.41 mL, 9.3 mmol), and triethylamine (1.29 mL, 9.3 mmol). After 30 min, a second equivalent of dimethylamine hydrochloride, DECP and triethylamine were added. After 30 min, the reaction mixture was diluted with ethyl acetate (300 mL) and washed with aqueous sodium bisulfate and brine. The organic extract was dried over sodium sulfate, filtered, and concentrated. The resulting crude material was purified by radial chromatography (silica gel, 4% methanol in dichloromethane) to give 4.7 g (75%) of the desired product as a tan foam: $^1$H-NMR (d, CDCl$_3$) 1.25(s, 9H), 1.42(s, 6H), 1.60–1.80 (m, 4H), 1.90 (br s, 1H), 2.57 (m, 2H), 2.98 (s, 6H), 4.48 (m, 1H), 7.05–7.21 (m, 6H), 7.50(m, 1H), 7.62–7.76 (m, 5H),8.93 (br s, 1H), 10.93 (br s, 1H); MS (ion spray) 673.7 (M+1).

Compounds 26 and 27

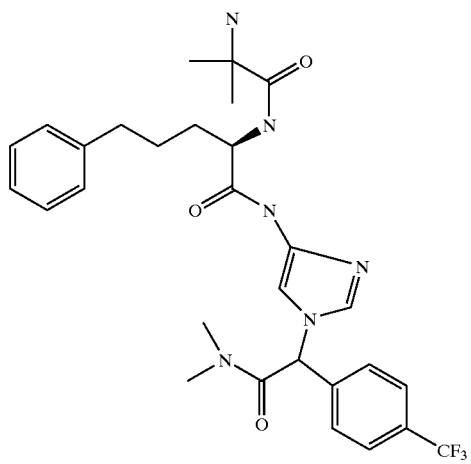

To the product of Preparation 39 (4.7 g, 7.0 mmol) was stirred at room temperature in a saturated solution of hydrochloric acid inglacial acetic acid (30 mL). After 90 min, the mixture was concentrated. The resulting material diluted with ethyl acetate and extracted with aqueous sodium bicarbonate. The organic extract was dried over sodium sulfate, filtered, and concentrated to give 3.7 g (93%) of an orange solid. MS (ion spray) 573.4 (M+1). The diastereomers (3.4 g) were separated by chiral chromatography using a Kromasil-CHI normal phase column to provide 1.40 g (41%) of isomer 1 and 1.26 g (37%) of isomer 2. The individual isomers were dissolved in a saturated solution of hydrochloric acid in glacial acetic acid (4 mL) and subsequently concentrated to provide the desired products as tan solids:

Compound 26 (isomer 1) $^1$H-NMR (d, DMSO) 1.41 (s, 3H), 1.42 (s, 3H), 1.51–1.73 (m, 4H), 2.53 (m, 2H), 2.82 (s, 3H), 2.84 (s, 3H), 4.39 (m, 1H), 6.91 (s, 1H), 7.10 (m, 3H), 7.18–7.29 (m, 3H), 7.55 (d, J=8 Hz, 2H), 7.78 (d, J=8 Hz, 2H), 7.91 (br s, 1H), 8.15 (br s, 3H), 8.38 (d, J=7.5 Hz, 1H), 10.78 (br s, 1H); MS (ion spray) 573.4 (M+1); Anal. Calc'd for C$_{29}$H$_{35}$F$_3$N$_6$O$_3$·2.3HCl: C, 53.06; H, 5.73; N, 12.80. Found: C, 52.90; H, 5.66; N, 12.70.

Compound 27. (isomer 2) $^1$H-NMR (d, DMSO) 1.42 (s, 6H), 1.51–1.73 (m, 4H), 2.53 (m, 2H), 2.82 (s, 3H), 2.84 (s, 3H), 4.39 (m, 1H), 6.91 (s, 1H), 7.10 (m, 3H), 7.18–7.29 (m, 3H), 7.55 (d, J=8 Hz, 2H), 7.78 (d, J=8 Hz, 2H), 7.91 (br s, 1H), 8.15 (br s, 3H), 8.38 (d, J=7.5 Hz, 1H), 10.78 (br s, 1H); MS (ion spray) 573.4 (M+1); Anal. Calc'd for C$_{29}$H$_{35}$F$_3$N$_6$O$_3$·2HCl: C, 53.96; H, 5.78; N, 13.02. Found: C, 53.84; H, 5.71; N, 12.93.

EXAMPLE 2-21

Preparation EX12A

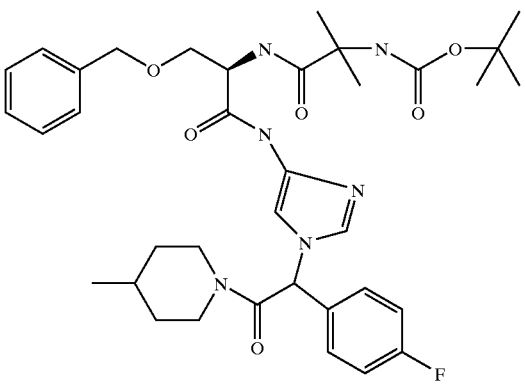

Reaction of product of Preparation 10 (9.2 g, 15.4 mmol), 4-methylpiperidine (1.83 mL, 15.4 mmol), 1-hydroxybenzotriazole (2.3 g, 17 mmol) and 1-(3-dimethylaminopropyl)-3-ethylcarbodiimide (3.5 g, 17 mmol) in dimethylformamide (100 mL) as described in Preparation EX4A gave 9.7 g (93%) of the desired product (Preparation EX12A), as follows, as a tan foam: $^1$H-NMR (d, DMSO) 0.76 (d, J=6.1 Hz, 1.5H), 0.86 (d, J=6.1 Hz, 1.5H), 1.00 (m, 1H), 1.20–1.40 (m, 15H), 1.45–1.70 (m, 3H), 2.55–2.70 (m, 2H), 3.05 (m, 1H), 3.60 (m, 1H), 3.65–3.75 (m, 2H), 4.40 (m, 1H), 4.44 (d, J=2.6 Hz, 2H), 4.60 (m, 1H), 6.73 (d, J=11.3 Hz, 1H), 7.15–7.35 (m, 9H), 7.35–7.50 (m, 4H), 10.20 (br s, 1H). MS (ion spray) 679.6 (M+1); Anal. Calc'd for C$_{36}$H$_{47}$FN$_6$O$_6$: C, 63.70; H, 6.98; N, 12.38. Found: C, 63.44; H, 6.86; N, 12.22.

Compounds 28 and 29

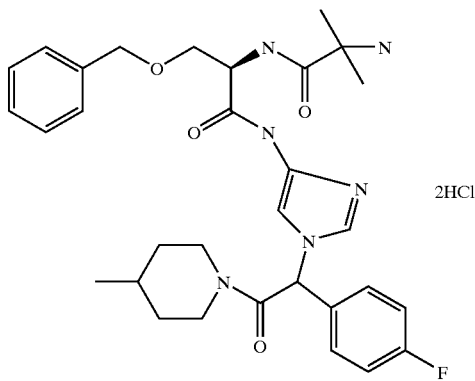

2HCl

Reaction of the product of Preparation EX12A (9.7 g, 14.3 mmol) with trifluoroacetic acid (16 mL) in dichloromethane (40 mL), as described in Example 2-7, gave 6.8 g (73%) of the desired product (Example 12) as a mixture of diastereoisomers. The mixture (3.2 g) was purified by HPLC (8×15 cm Prochrom column packed with Kromasil CHI-DMP chiral phase with an eluent mixture of 3A alcohol and dimethylethylamine in heptane) to give 0.8 g (24%) of isomer 1 and 0.9 g (26%) of isomer 2 as white solids:

Compound 28 (Isomer 1). $^1$H-NMR (d, DMS0) 0.75 (d, J=6.4 Hz, 1.5H), 0.88 (d, J=6.4 Hz, 1.5H), 1.10 (m, 1H), 1.35 (m, 1H), 1.45–1.70 (m, 8H), 2.60–2.75 (m, 2H), 3.15 (m, 1H), 3.65–3.85 (m, 3H), 4.35 (m, 1H), 4.52 (s, 2H), 4.75 (m, 1H), 6.95 (d, J=11.3 Hz, 1H), 7.20–7.49 (m, 9H), 7.45

(m, 1H), 7.52 (m, 1H), 8.05 (br s, 1H), 8.25 (m, 3H), 8.56 (m, 1H), 10.95 (br s, 1H); $t_R$=6.73 min; MS (ion spray) 579.4 (M+1); Anal. Calc'd for $C_{31}H_{39}FN_6O_4$.2HCl.0.2CHCl3: C, 56.29; H, 6.24; N, 12.67. Found: C, 56.47; H, 6.17; N, 12.24.

Compound 29 (Isomer 2) $^1$H-NMR (d, DMSO) 0.75 (d, J=6.4 HZ, 1.5H), 0.88 (d, J=6.4 Hz, 1.5H), 1.10 (mn, 1H), 1.35 (m, 1H), 1.45–1.70 (m, 8H), 2.60–2.75 (mn, 2H), 3.15 (m, 1H), 3.65–3.85 (m, 3H), 4.35 (m, 1H), 4.52 (s, 2H), 4.75 (m, 1H), 6.95 (d, J=11.3 Hz, 1H), 7.20–7.49 (m, 9H), 7.45 (m, 1H), 7.52 (m, 1H), 8.05 (br s, 1H), 8.25 (m, 3H), 8.56 (m, 1H), 10.95 (br s, 1H); $t_R$=9.09 min; MS (ion spray) 579.4 (M+1); Anal. Calc'd for $C_{31}H_{39}FN_6O_4$.2HCl: C, 57.14; H, 6.34; N, 12.90. Found: C, 57.17; H, 6.18; N, 12.79.

EXAMPLE 2-22

Preparation EX13A

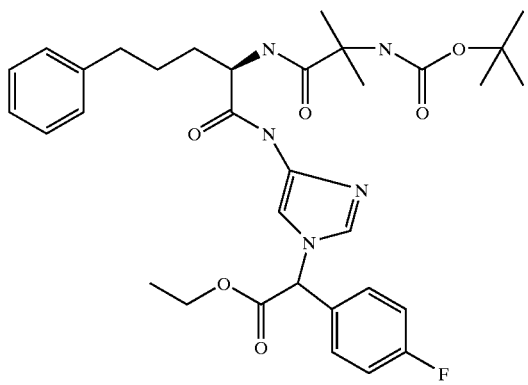

Reduction of the product of Preparation 9 (4.8 g, 16.0 mmol) with 10% palladium on carbon (5.0 g) and tetrahydrofuran (160 mL) followed by coupling with the product of Preparation 2 (6.0 g, 16.0 mmol), 1-hydroxybenzotrlazole (2.4 g, 17.6 mmol) and 1-(3-dimethylaminopropyl)-3-ethylcarbodiimide (3.6 g, 17.6 mmol) as described in Preparation 5A gave 15.4 g (77%) of the above-identified product as a tan foam: 1H-NMR (d, DMSO) 1.17 (t, J=7.2 Hz, 3H), 1.23–1.45 (m, 15H), 1.45–1.57 (m, 6H), 7.16 (q, J=6.8 Hz, 2H), 4.40 (m, 1H), 6.45 (s, 1H), 7.05 (m, 1H), 7.10–7.30 (m, 8H), 7.40–7.48 (m, 3H), 7.54 (s, 1H), 10.20 (br s, 1H); MS (ion spray) 624.4 (M+1); Anal. Calc'd for $C_{33}H_{42}FN_5O_6$: C, 63.55; H, 6.79; N, 11.23. Found: C, 63.83; H, 6.78; N, 11.38.

Preparation EX13B

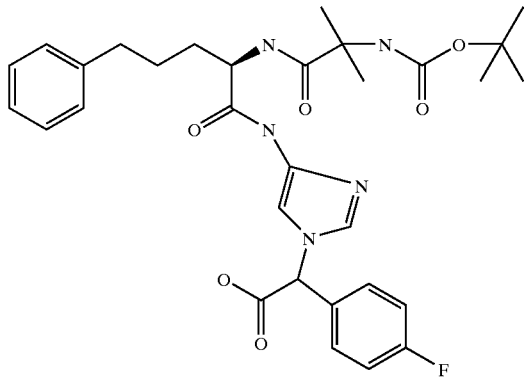

Reaction of the product of Preparation EX 13A (14.8 g, 24.0 mmol) with lithium hydroxide (0.66 g, 29.0 mmol) in dioxane (200 mL) and water (100 mL) as in described in Preparation 5 gave 14.3 g (100%) of the above-identified product as a tan foam: $^1$H-NMR (d, DMSO) 1.25–1.40 (m, 15H), 1.50–1.75 (m, 6H), 4.40 (s, 1H), 6.60 (s, 1H), 7.05 (s, 1H), 7.10–7.30 (m, 8H), 7.40–7.50 (m, 3H), 7.55 (s, 1H), 10.2 (br s, 1H), 13.63 (br s, 1H); MS (ion spray) 596.5 (M+1); Anal. Calc'd for $C_{31}H_{38}FN_5O_6$.0.1 dioxane: C, 62.39; H, 6.47; N, 11.59. Found: C, 62.16; H. 6.56; N, 11.28.

Preparation EX13C

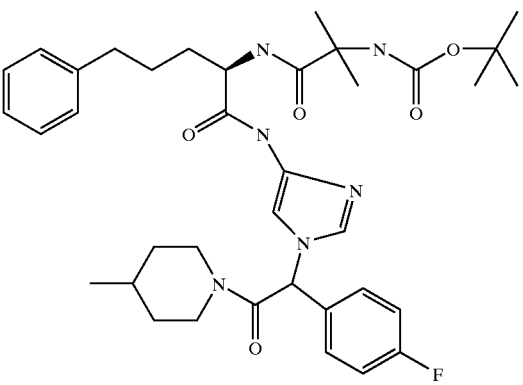

Reaction of the product of Preparation EX13B (13.3 g, 23.1 mmol), 4-methylpiperidine (3 mL, 23.1 mmol), 1-hydroxybenzotriazole (3.4 g, 25.4 mmol) and 1-(3-dimethylaminopropyl)-3-ethylcarbodiimide (5.2 g, 25.4 mmol) in dimethylformamide (100 mL), as described in Preparation EX4A, gave 14.4 g (93%) of the above-identified product as a tan foam: $^1$H-NMR (d, DMSO) 0.76 (d, J=6.4 Hz, 1.5 H), 0.86 (d, J=4.9 Hz, 1.5H), 1.00 (m, 1H), 1.25–1.45 (m, 17H), 1.45–1.75 (m, 8H), 2.60–2.80 (m, 2H), 3.75 (m, 1H), 4.30–4.45 (m, 2H), 6.71 (d J=11.7 Hz, 1H), 7.05 (m, 1H), 7.10–7.30 (m, 9H), 7.30–7.45 (m, 3H), 10.15 (m, 1H); MS (ion spray) 677.5 (M+1) ; Anal. Calc'd for $C_{37}H_{49}FN_6O_5$: C, 65.66; H, 7.30; N, 12.42. Found: C, 65.78; H, 7.19; N, 12.44.

Compounds 30 and 31

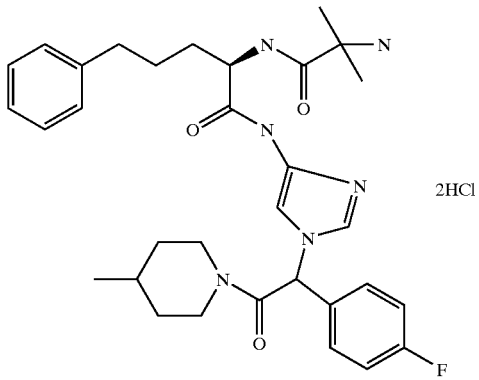

2HCl

Reaction of the product of Preparation EX13C (13.8 g, 20.4 mmol) with trifluoroacetic acid (16 mL) in dichloromethane (40 mL), as described in Example 2-7 gave 10.5 g (89%) of the desired mixture (Example 13) as a tan foam. The mixture (4.0 g) was purified by HPLC (8×15 cm Prochrom column packed with Kromasil CHI-DMP chiral phase with an eluent mixture of 3A alcohol and dimethylethylamine in heptane) to give 1.5 g (38%) of isomer 1 and 0.77 g (20%) of isomer 2 as white solids:

Compound 30 (isomer 1) $^1$H-NMR (d, DMSO) 0.75 (t, J=6.4 Hz, 1.5 H), 0.87 (t, J=6.0 Hz, 1.5 H), 1.15 (m, 1H), 1.35 (m, 1H), 1.45–1.80 (m, 12H), 2.55–2.75 (m, 3H), 3.05 (m, 1H), 3.65–3.75 (m, 2H), 4.30–4.50 (m, 2H), 6.94 (d, J=12 Hz, 1H), 7.10–7.20 (m, 2H), 7.20–7.40 (m, 7H), 7.45 (m, 1H), 7.55 (m, 1H), 8.08 (m, 1H), 8.15–8.30 (m, 3H), 8.44 (t, J=7.2 Hz, 1H), 10.90 (br s, 1H); $t_R$=6.62 min; MS (ion spray) 578.3 (M+1); Anal. Calc'd for $C_{32}H_{41}FN_6O_3 \cdot 2.3HCl$: C, 58.81; H, 6.61; N, 12.72. Found: C, 57.91; H, 6.55; N, 12.72.

Compound 31 (isomer 2) $^1$H-NMR (d, DMSO) 0.75 (t, J=6.4 Hz, 1.5 H), 0.87 (t, J=6.0 Hz, 1.5 H), 1.15 (m, 1H), 1.35 (m, 1H), 1.45–1.80 (m, 12H), 2.55–2.75 (m, 3H), 3.05 (m, 1H), 3.65–3.75 (m, 2H), 4.30–4.50 (m, 2H), 6.94 (d, J=12 Hz, 1H), 7.10–7.20 (m, 2H), 7.20–7.40 (m, 7H), 7.45 (m, 1H), 7.55 (m, 1H), 8.08 (m, 1H), 8.15–8.30 (m, 3H), 8.44 (t, J=7.2 Hz, 1H), 10.90 (br s, 1H); $t_R$=8.95 min; MS (ion spray) 578.3 (M+1); Anal. Calc'd for $C_{32}H_{41}FN_6O_3 \cdot 2.3HCl$: C, 58.81; H, 6.61; N, 12.72. Found: C, 58.05; H, 6.64; N, 12.43.

EXAMPLE 2-23

Preparation EX14A

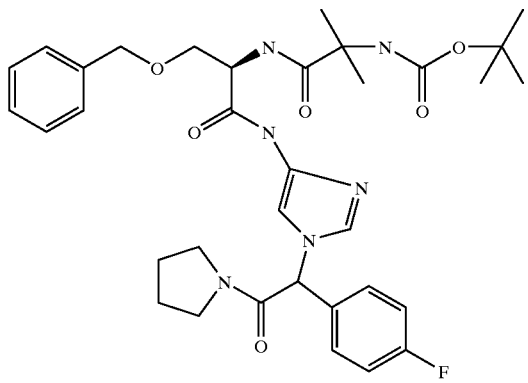

Reaction of the product of Preparation 10B (0.6 g, 1.0 mmol), pyrrolidine (0.08 mL, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (20 mL) as described in Preparation EX4A gave 0.27g (41%) of the above-identified product as a white foam: $^1$H-NMR is consistent with structure; MS (FD) 650.5 (M+); Anal. Calc'd for $C_{34}H_{43}FN_6O_6 \cdot 0.6H_2O$: C, 61.73; H, 6.73; N, 1212.70. Found: C, 61.98; H, 6.43; N, 12.66.

Compound 32

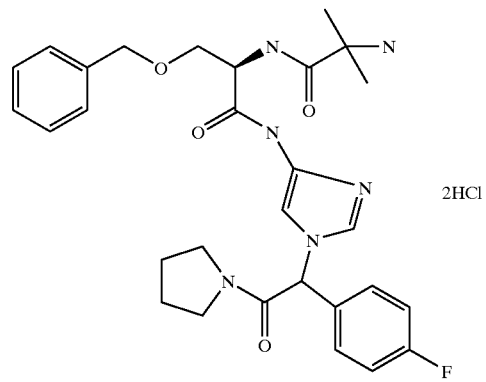

2HCl

Reaction of the product of Preparation EX14A (0.2 g, 0.3 mmol) and trifluoroacetic acid (4 mL) in dichloromethane (6 mL), as described in Example 2-7, gave 0.16 g (84%) of the desired mixture of isomers as a yellow solid: $^1$H-NMR is consistent with structure. MS (high res) calc'd for $C_{29}H_{36}FN_6O_4$: 551.2782. Found: 551.2790.

EXAMPLE 2-24

Compound 33

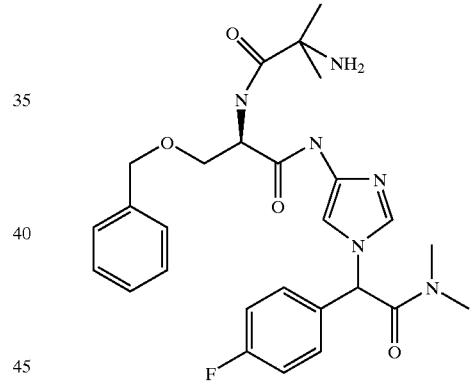

To a solution of the product of Preparation 75 (3.30 g, 5.3 mmol) stirring in dichloromethane (30 mL) at room temperature was added trifluoroacetic acid (10 m). After 3 h, the mixture was concentrated and the residue treated with excess aqueous sodium bicarbonate. The resulting mixture was extracted with ethyl acetate and the combined organic extracts were washed with 1N aqueous sodium hydroxide, dried over sodium sulfate, and concentrated. The residue was purified by flash chromatography (silica gel, chloroform/methanol) to provide 1.40 g (51%) of the desired product as a light tan solid: ESMS: (M+H)$^+$525.3. $^1$H NMR was consistent with product. Anal. Calc'd. for $C_{27}H_{33}N_6O_4F \cdot 1.3$ methanol: C, 60.03; H, 6.80; N, 14.84. Found: C, 60.19; H, 6.81; N, 14.56. The isomeric mixture (3.20 g) was separated as previously described in Example 2-9 to give 1.57 g of isomer 1 ($t_R$=7.57 min) and 0.88 g of isomer 2 ($t_R$=10.43 min). For isomer 2, 0.88 g (1.68 mmol)

was dissolved in ethyl acetate and treated with a saturated solution of hydrochloric acid in diethyl ether. The resulting mixture was concentrated, washed with diethyl ether to give 0.97 g of the desired product: ESMS: (M+H)+525.4, 526.7. $^1$H NMR was consistent with product. Anal. Calc'd. for $C_{25}H_{33}N_6O_4F \cdot 2.75$ HCl: C, 51.73; H, 6.07; N, 13.41. Found: C, 51.62; H, 5.74; N, 13.34.

EXAMPLE 2-25

Preparation 54

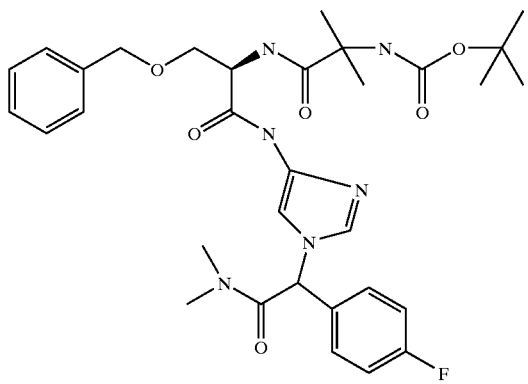

Reaction of the product of Preparation 10 (1.0 g, 1.7 mmol), dimethylamine hydrochloride (0.14 g, 1.7 mmol), triethylamine (0.26 mL, 1.9 mmol), 1-hydroxybenzotriazole (0.26 g, 1.9 mmol) and 1-(3-dimethylaminopropyl)-3-ethylcarbodiimide (0.4 g, 1.9 mmol) in dimethylformamide (30 mL) as described in Preparation EX4A gave 0.55 g (52%) of the desired product as a tan foam: $^1$H-NMR is consistent with structure; MS (ion spray) 625.4 (M+1); Anal. Calc'd for $C_{32}H_4FN_6O_6$: C, 61.53; H, 6.61; N, 13.45. Found: C, 61.22; H, 6.33; N, 13.44.

Compound 34

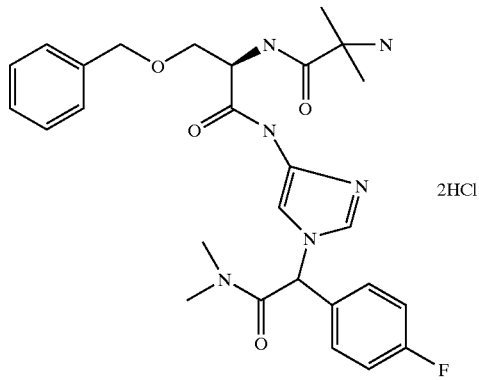

2HCl

Reaction of the product of Preparation 54 (0.54 g, 0.86 mmol) and trifluoroacetic acid (2 mL), dichloromethane (6 mL) as described in Example 2-7 gave 0.4 g (77%) of the desired product as a mixture of isomers: $^1$H-NMR is consistent with structure. MS (ion spray) 525.4 (M+1); Anal. Calc'd for $C_{27}H_{33}FN_6O_6 \cdot 2HCl$: C, 54.27; H, 5.90; N, 14.06. Found: C, 53.11; H, 5.70; N, 13.58.

Compound 35

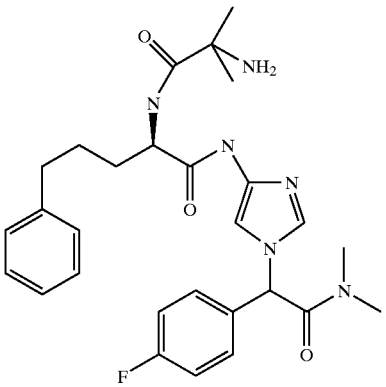

To a solution of the product of Preparation 75 (1.45 g, 2.29 mmol) stirring at room temperature in dichloromethane (50 mL) was added trifluoroacetic acid (15 mL) After 3 hours, the mixture was concentrated and the material treated with excess aqueous sodium bicarbonate. The aqueous mixture was extracted with ethyl acetate and the combined organic extracts concentrate. The resulting residue was purified by flash chromatography (silica gel, chloroform/methanol) to provide 1.55 g of the desired product: ESMS: (M+H)+523.3. The isomeric mixture (3.44 g) was separated as previously described in Example 2-9 to provide 0.98 g of pure isomer 1 ($t_R$=7.94 min) and 0.81 g of isomer 2 ($t_R$=10.57 min). For isomer 2, 0.80 g (1.53 mmol) was dissolved in ethyl acetate/methanol and treated with a saturated solution of hydrochloric acid in diethyl ether. The resulting mixture was concentrated to provide 0.90 g (92%) of the desired product as a light tan solid: ESMS: (M+H)+ 523.4, 524.5. $^1$H NMR was consistent with product. Anal. Calc'd. for $C_{28}H_{35}N_6O_3F \cdot 3.25$ HCl: C, 52.46; H, 6.01; N, 13.11. Found: C, 52.49; H, 6.23; N, 11.80.

EXAMPLE 2-27

Preparation EX15A

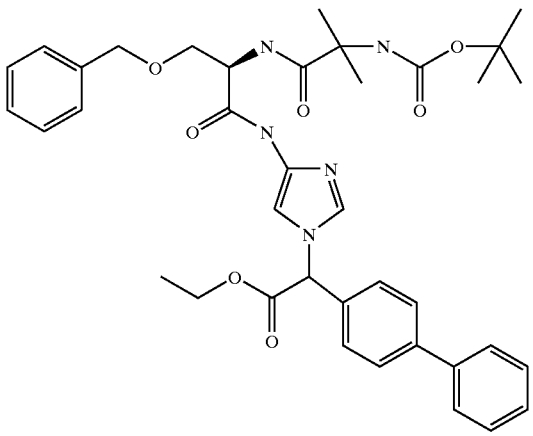

Reduction of the product of Preparation 11 (2.0 g, 5.8 mmol) under a hydrogen atmosphere with 10% palladium on carbon (0.8 g) and tetrahydrofuran (70 mL) followed by coupling with the product of Preparation 1 (2.2 g, 5.8 mmol), 1-hydroxybenzotriazole (0.86 g, 6.4 mmol) and 1-(3-dimethylaminopropyl)-3-ethylcarbodiimide (1.3 g, 6.4 mmol), as described in Preparation 5A, gave 0.7 g (18%) of the desired product (Preparation EX15A), as follows, as a tan foam: $^1$H-NMR is consistent with structure; MS (FD) 683 (M+); Anal. Calc'd for $C_{38}H_{45}N_5O_7$: C, 66.75; H, 6.63; N, 10.34. Found: C, 66.79; H, 6.48; N, 10.32.

Preparation EX15B

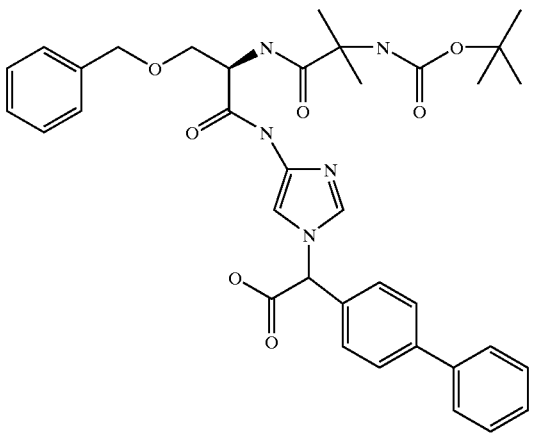

Reaction of the product of Preparation EX15A (0.7 g, 1.0 mmol) and lithium hydroxide (0.03 g, 1.2 mmol) in didxane (20 mL) and water (10 mL), as described in Preparation 5, gave 0.66 g (100%) of the desired product (Preparation EX15B), as follows, as a tan foam: $^1$H-NMR is consistent with structure; MS (FD) 656 (M+); Anal. Calc'd for $C_{36}H_{41}N_5O_7$: C, 65.94; H, 6.30; N, 10.68. Found: C, 65.90; H, 6.37; N, 10.42.

Preparation EX15C

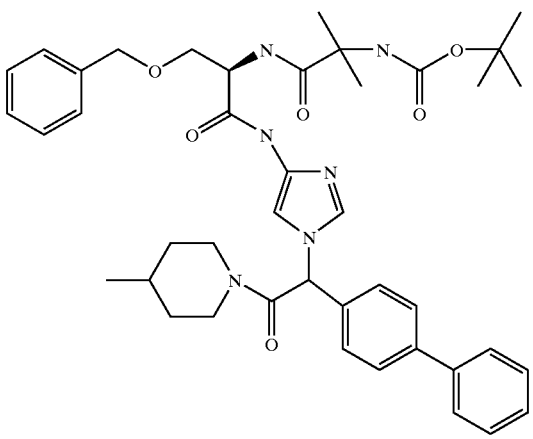

Reaction of the product of Preparation EX15B (0.7 g, 1.1 mmol) with 4-methylpiperidine (0.13 mL, 1.1 mmol), 1-hydroxybenzotriazole (0.17 g, 1.2 mmol) and 1-(3-dimethylaminopropyl)-3-ethylcarbodiimide (0.25 g, 1.2 mmol) in dimethylformamide (40 mL), as described in Preparation EX4A, gave 0.52 g (65%) of the above-identified product as a tan foam: 1H-NMR is consistent with structure; MS (FD) 728.4 (M+); Anal. Calc'd for $C_{37}H_{47}F_3N_6O_6$: C, 60.98; H, 6.50; N, 11.53. Found: C, 61.18; H, 6.35; N, 11.44.

Compounds 38 and 39

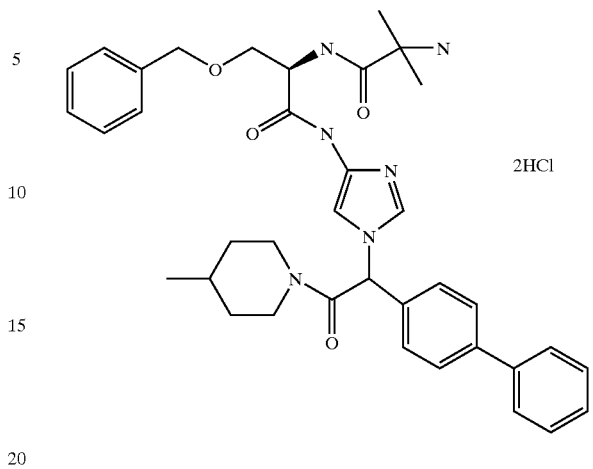

2HCl

Reaction of the product of Preparation EX15C (0.36 g, 0.49 mmol) and trifluoroacetic acid (4 mL) in dichloromethane (12 mL), as described in Example 2-7, gave 0.3 g (88%) of the desired mixture (Example 15) of isomers. Resolution of the diastereomers (4 g, 3.6 mmol) by HPLC (Kromsil CHI-DMP chiral stationary phase, 3A alcohol/dimethylethylamine/heptane eluant) provided 0.6 (16%) of isomer 1 and 0.5 mg (12%) of isomer 2, both isolated as white solids after formation of their respective hydrochloride salts as described in Example 2-9:

Compound 38 (Isomer 1). $^1$H-NMR is consistent with structure; $t_R$=6.9 min; MS (ion spray) 637.4 (M+1); Anal. Calc'd for $C_{37}H_{44}N_6O_4 \cdot 2.5HCl$: C, 61.05; H, 6.44; N, 11.54. Found: C, 60.89; H, 6.53; N, 11.25.

Compound 39 (Isomer 2) $^1$H-NMR is consistent with structure; $t_R$=9.2 min; MS (ion spray) 637.4 (M+1); Anal. Calc'd for $C_{37}H_{44}N_6O_4 \cdot 2.6HCl$: C, 60.75; H, 6.42; N, 11.49. Found: C, 60.67; H, 6.63; N, 11.18.

EXAMPLE 2-28

Preparation EX16A

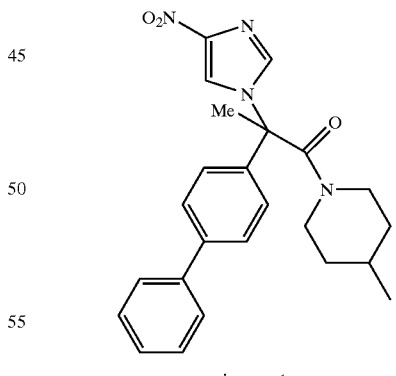

isomer 1

Prepared as in Preparation Ex2A using the product of Preparation 12B, diastereomer 1 (0.40 g, 0.80 mmol) in THF (20 mL) and lithium hydroxide (0.04 g, 0.96 mmol) in water (10 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-dimethylaminopyridine (catalytic, 10 mg) and 4-methylpiperidine (0.24 mL, 2.89 mmol) to yield the desired product (Preparation EX16A), as follows, (0.30 g, 90% yield) as a colorless foam: $^1$H NMR (300 MHz, CDCl$_3$)—consistent with structure; Anal. calc'd. for C$_{24}$H$_{26}$N$_4$O$_3$; 68.88 C, 6.26 H, 13.39 N; found 67.40 C, 6.72 H, 12.45 N; FDMS (M+)—419.

Preparation EX16B

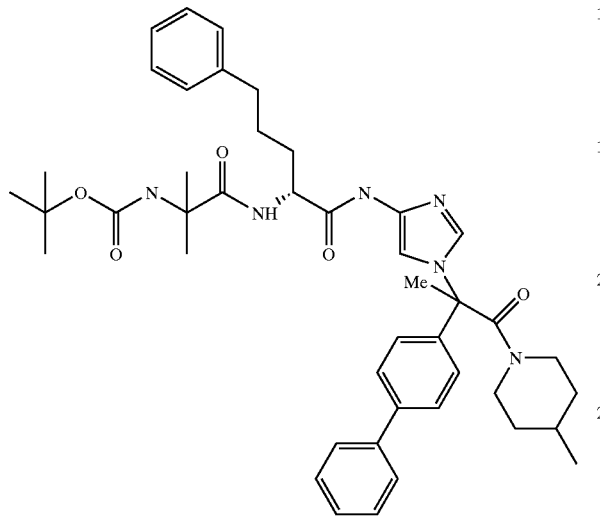

Prepared, as in Preparation EX2B, using the product of Preparation EX16A (0.35 g, 0.84 mmol) and 5% palladium on carbon (0.35 g, catalytic, 25 mL THF) to give the crude amine. The resulting filtrate was reacted with HOBT (0.11 g, 0.84 mmol), the product of Preparation 2 (0.32 g, 0.84 mmol), and DCC (0.17 g, 0.92 mmol) to yield the desired product (Preparation EX16B), as follows, (0.22 g, 35% yield) as a light yellow foam: $^1$H NMR (300 MHz, CDCl$_3$)—consistent with structure; Anal. calc'd. for C$_{44}$H$_{56}$N$_6$O$_5$; 70.56 C, 7.54 H, 11.22 N; found 70.22 C, 7.58 H, 11.21 N; ISMS (M+)—749.

Compound 40

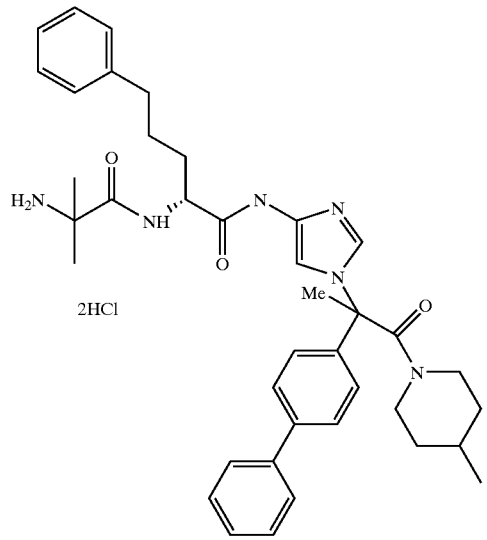

Prepared, as in Example 2-13, using the product of Preparation EX16B (0.22 g, 0.29 mmol), trifluoroacetic acid (4.0 mL), anisole (0.4 mL), and dichloromethane (20 mL) to yield the desired product (Example 16) (0.19 g, %) as a pale yellow solid: $^1$H NMR (300 MHz, CDCl$_3$)—consistent with structure; Anal. calc'd. for C$_{39}$H$_{50}$N$_6$O$_3$Cl$_2$; 64.90 C, 6.98 H, 11.64 N; found 66.48 C, 7.24 H, 11.96 N; FDMS (M+)—649.

EXAMPLE 2-29

Preparation EX17A

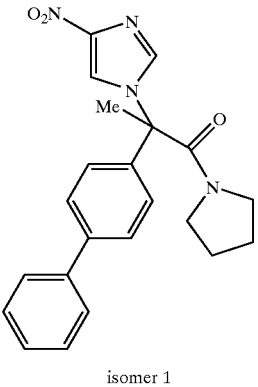

isomer 1

Prepared as in Preparation EX2A using the product of Preparation 12B, diastereomer 1 (1.00 g, 2.02 mmol) in THF (20 mL) and lithium hydroxide (0.13 g, 3.09 mmol) in water (10 mL) to give the crude acid. The resulting crude solid was dissolved in anhydrous dichloromethane (20 mL) and reacted with catalytic DMF (0.1 mL) and excess oxalyl chloride (5 g). The resulting crude foam was dissolved in anhydrous dichloromethane (20 mL) and reacted with 4-Dimethylaminopyridine (catalytic, 10 mg) and pyrrolidine (0.65 mL, 7.76 mmol)to yield the desired product (Preparation EX17A)(0.80 g, 98% yield) as a colorless foam: $^1$H NMR (300 MHz, CDCl$_3$)—consistent with structure; Anal. calc'd. for C$_{22}$H$_{22}$N$_4$O$_3$; 67.68 C, 5.68 H, 14.34 N; found 65.36 C, 5.54 H, 13.43 N; ISMS (M+)—391.

Preparation EX17B

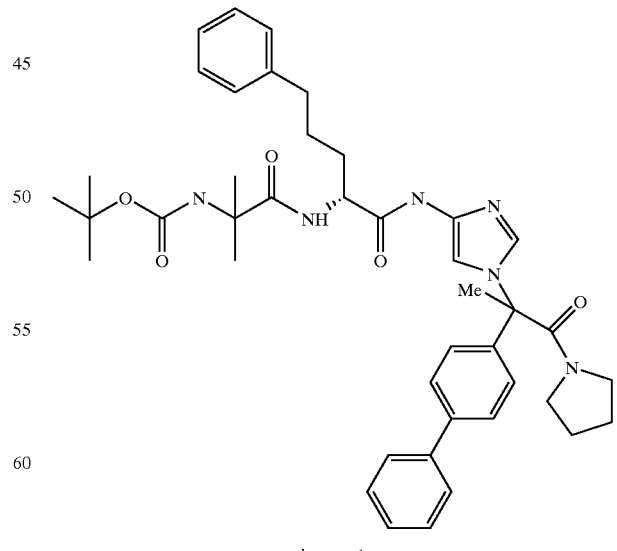

isomer 1

Prepared as in Preparation EX2B using the product of Preparation EX17A (0.80 g, 2.05 mmol) and 5% palladium on carbon (0.80 g, catalytic, 25 mL THF) to yield the crude amine. The filtrate was reacted with HOBT (0.28 g, 2.05 mmol), the product of Preparation 1 (0.78 g, 2.05 mmol), and DCC (0.46 g, 2.05 mmol) to yield the desired product (Preparation EX17B), as follows, (0.76 g, 51% yield) as a light yellow foam: $^1$H NMR (300 MHz, CDCl$_3$)—consistent with structure; Anal. calc'd. for C$_{42}$H$_{50}$N$_6$O$_6$; 68.12 C, 6.97 H, 11.63 N; found 66.93 C, 6.74 H, 11.24 N; ISMS (M+)—723.

on carbon (0.60 g, catalytic, 25 mL THF) to give the crude amine. The resulting filtrate was reacted with HOBT (0.21 g, 1.54 mmol), the product of Preparation 2 (0.58 g, 1.54 mmol), and DCC (0.35 g, 1.69 mmol) to yield the desired product (Preparation EX18A), as follows, (0.56 g, 50% yield) as a light yellow foam: $^1$H NMR (300 MHz, CDCl$_3$)—consistent with structure; Anal. calc'd. for C$_{42}$H$_{52}$N$_6$O$_5$; 69.98 C, 7.27 H, 11.66 N; found 68.71 C, 6.92 H, 11.39 N; ISMS (M+)—721.

Compound 41

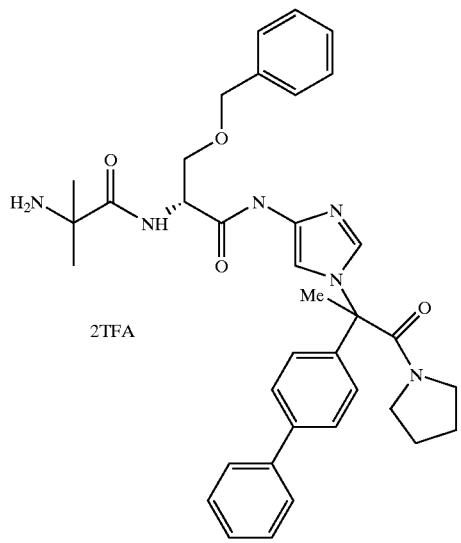

2TFA

Compound 42

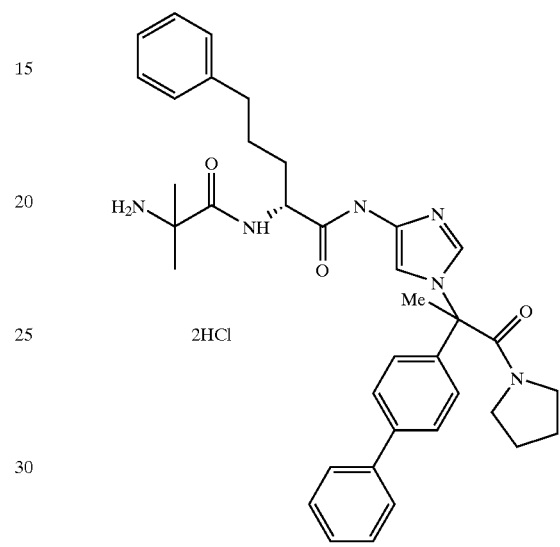

2HCl

Prepared as in Example 2-13 using the product of Preparation EX17B (0. 76 g, 1.05 mmol), trifluoroacetic acid (2.0 mL), anisole (0.2 mL), and dichloromethane (8.0 mL) to yield the desired product (Example 17) (0.76 g, 85% yield) as an off white solid: $^1$H NMR (300 MHz, CDCl$_3$)—consistent with structure; Anal. calc'd. for C$_{40}$H$_{44}$N$_6$O$_8$F$_6$; 56.47 C, 5.21 H, 9.88 N; found 56.24 C, 5.32 H, 9.86 N; ISMS (M+)—623.

Preparation EX18A

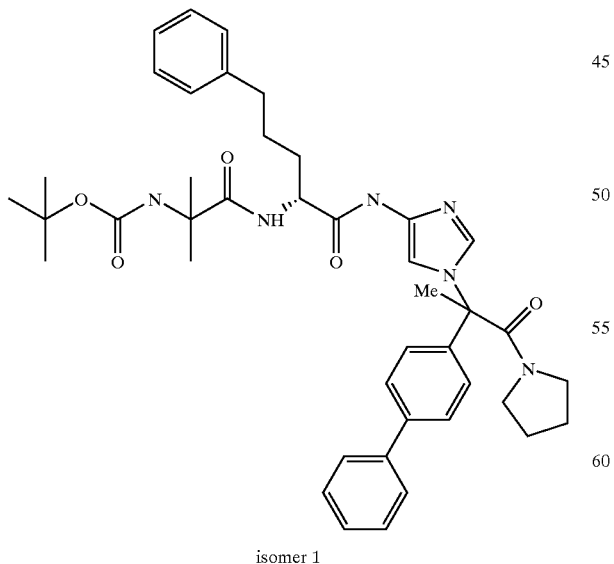

isomer 1

Prepared as in Preparation EX2B using the product of Preparation EX17A (0.60 g, 1.54 mmol) and 5% palladium Prepared as in Example 2-13 using the product of Preparation EX18A (0.52 q, 0.72 mmol), trifluoroacetic acid (4.0 mL), anisole (0.4 mL), and dichloromethane (20 mL) to yield the desired product (Example 18) (0.47 g, 94%) as a pale yellow solid: $^1$H NMR (300 MHz, CDCl$_3$)—consistent with structure; Anal. calc'd. for C$_{37}$H$_{46}$N$_6$O$_3$Cl$_2$; 64.06 C, 6.68 H, 12.11 N; found 62.18 C, 6.59 H. 11.78 N; ISMS (M+)—621.

EXAMPLE 2-31

Preparation 470

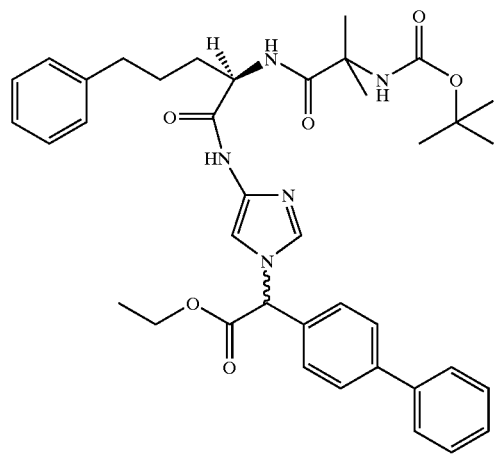

To a suspension of 5% palladium on carbon (2.60 g) and tetrahydrofuran (100 mL), in a Parr reaction bottle, was added the product of Preparation 11 (5.00 g, 15.3 mmol) as a solid. The reaction bottle was placed on a Parr shaker, and shaken at room temperature for 2 h under a hydrogen atmosphere (40 psi). The reaction was filtered through a pad of Celite 521 and the filtrate was then added to a previously prepared mixture of the product of Preparation 2 (5.80 g, 15.3 mmol), 1,3-dicyclohexylcarbodiimide (3.48 g, 16.9 mmol) and 1-hydroxybenzotriazole hydrate (2.29 g, 16.9 mmol) in 50 mL tetrahydrofuran at 0° C. The reaction was stirred for 16 h at room temperature, then the solvent was evaporated under reduced pressure. The residue was dissolved in ethyl acetate and the 1,3-dicyclohexylurea was filtered away. The filtrate was purified by flash chromatography (silica gel, 80% ethyl acetate/hexanes—5% methanol/ethyl acetate) to give the desired product as a light yellow solid foam (7.96 g, 80%): $^1$H NMR consistent with structure; MS (IS) m/e 682 (M +1); Anal. Calc'd for $C_{39}H_{47}N_5O_6$: C, 68.70; H. 6.95; N, 10.27. Found: C, 68.27; H, 6.86; N, 10.77.

Preparation 471

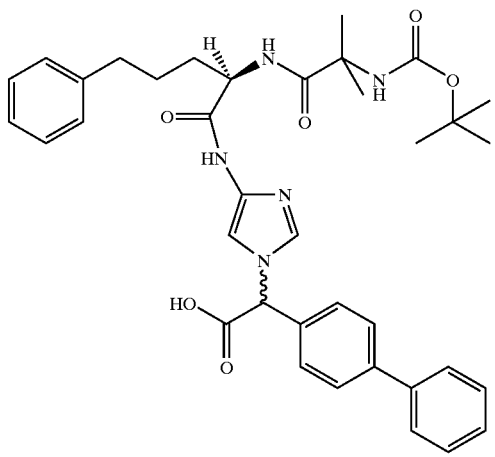

To a solution of the product of Preparation 470 (8.73 g, 13.3 mmol) in tetrahydrofuran (120 mL) and water (60 mL) at room temperature was added lithium hydroxide (2.23 g, 53.2 mmol). The reaction stirred 35 min at room temperature, at which time the tetrahydrofuran was evaporated under reduced pressure. The residue was diluted with water and extracted with diethyl ether (the ether extracts were discarded). The aqueous layer was acidified (pH 2-3) with 1N HCl and then extracted with diethyl ether and ethyl acetate. The combined organic layers were washed with brine, dried (sodium sulfate) and concentrated under reduced pressure to provide the desired product as a light yellow solid foam that was used without further purification (8.18 g, 98%): $^1$H NMR consistent with structure; MS (IS) m/e 654 (M +1); Anal. Calc'd for $C_{37}H_{43}N_5O_6$: C, 67.98; H, 6.63; N, 10.71. Found: C, 66.83; H, 6.59; N, 10.50.

Preparation 472

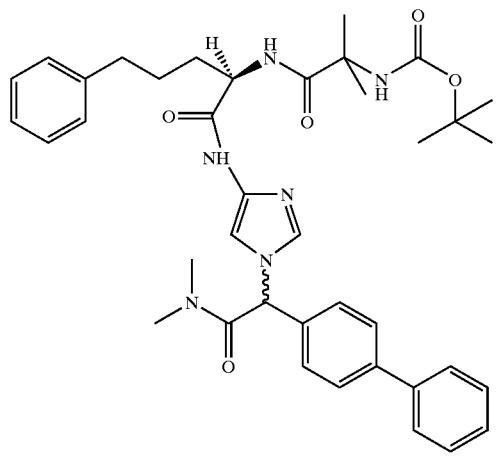

To a solution of the product of Preparation 471 (1.00g, 1.52 mmol) in anhydrous dichloromethane (30 mL) at 0° C. was added N-methylmorpholine (0.20 mL, 1.82 mmol) and 2-chloro-4,6-dimethoxy-1,3,5-triazine (0.35 g, 1.98 mmol). This mixture stirred for 1 h, warming to room temperature, at which time a 2M solution of N,N-dimethylamine (0.84 mL, 1.68 mmol) was added. The reaction stirred for 2 h at room temperature, then more 2-chloro-4,6-dimethoxy-1,3,5-triazine (0.08 g) was added. The reaction was stirred for another 1 h and the solvent was evaporated under reduced pressure. The residue was dissolved in ethyl acetate, the solids were filtered away and the filtrate was purified by flash chromatography (silica gel, 90% ethyl acetate/hexanes—10% methanol/ethyl acetate) to give the desired product as a light yellow solid foam (0.83 g, 80%): $^1$H NMR consistent with structure; MS (IS) m/e 681 (M+1); Anal. Calc'd for $C_{39}H_{48}N_6O_5$: C, 68.80; H, 7.11; N, 12.34. Found: C, 68.23; H, 7.03; N, 12.66.

Compound 43

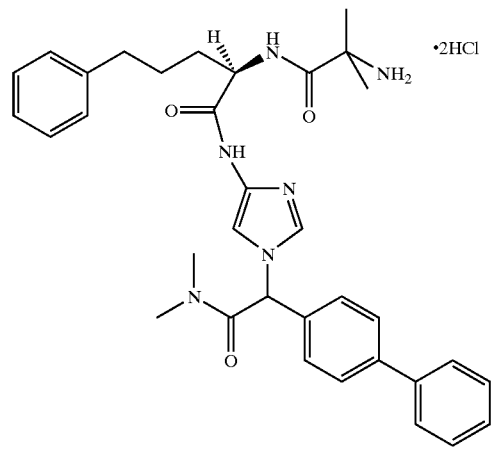

To a stirring solution of the product of Preparation 472 (3.10 g, 4.52 mmol) and anisole (0.52 mL, 4.75 mmol) in anhydrous dichloromethane (100 mL) at 0° C. was added trifluoroacetic acid (10 mL) via syringe. The reaction was stirred for 4 h warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 5% methanol/ethyl acetate—5% triethylamine/10% methanol/ethyl acetate) to provide the desired product as an off-white solid foam (2.40 g, 91%). $^1$H NMR consistent with structure; MS (IS) m/e 581 (M+1); Anal. Calc'd for $C_{34}H_{40}N_6O_3$: C, 70.32; H, 6.94; N, 14.47. Found: C, 69.36; H, 6.71; N, 14.10.

Diastereomeric separation: the desired product was resolved by HPLC [Kromasil packing material, 15% 3A alcohol/85% heptane (w/0.2% DMEA)] to provide two diastereomers. The second diastereomer (0.76 g) (retention time=9.98 min) was dissolved in ethyl acetate (15 mL) and then a saturated solution of hydrochloric acid in diethyl ether (2 mL) was added, with stirring. The white precipitate was collected by vacuum filtration and rinsed with diethyl ether. Vacuum drying provided Example 253 (0.70 g) as a white amorphous solid: $^1$H NMR consistent with structure; MS (IS) m/e 581 (M+1); Anal. Calc'd for $C_{34}H_{40}N_6O_3 \cdot HCl$: C, 66.18; H, 6.70; N, 13.62. Found: C, 64.39; H, 6.69; N. 13.19.

EXAMPLE 2-32

Preparation 137

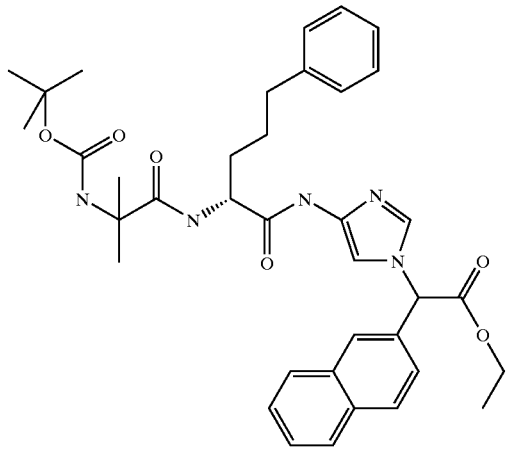

Reaction of the product of Preparation 136 (4.80 g, 14.77 mmol) with 5% palladium on carbon (2.5 g) in tetrahydrofuran (100 mL) under a hydrogen atmosphere followed by coupling with the product of Preparation 1 (5.61 g, 14.77 mmol), EDCI (2.79 g, 16.25 mmol), 1-hydroxybenzotriazole (2.00 g, 14.77 mmol), and N-methylmorpholine (1.6 mL, 14.77 mmol) as described in Preparation 5A gave (6.04 g, 62%) of the desired product as a light orange foam: $^1$H NMR (300 MHz, CDCl$_3$)—consistent with structure; Anal. calc'd. for $C_{36}H_{43}N_5O_7$; 65.74 C, 6.59 H, 10.65 N; found 64.02 C, 6.09 H, 10.13 N; ISMS (M+)—658.

Preparation 138

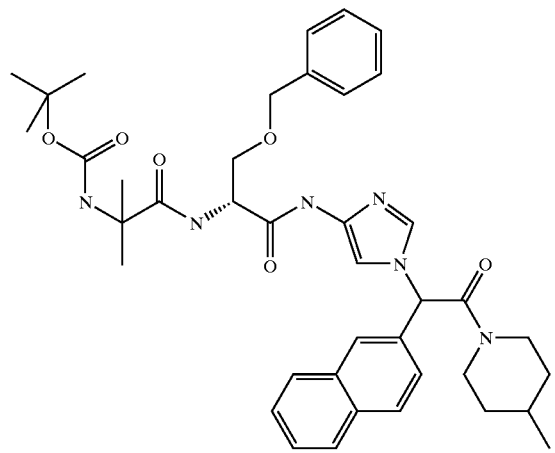

A solution of lithium hydroxide (0.38 g, 9.16 mmol) in water (50 mL) was added to a solution of the product of Preparation 137 (6.04 g, 9.16 mmol) in tetrahydrofuran (100 mL). After 30 min, water was added and the mixture washed with diethyl ether. The aqueous layer was adjusted to pH=3.0 with sodium bisulfate, saturated with sodium chloride, and washed with ethyl acetate. The combined organic extracts were dried over sodium sulfate, and concentrated. To the resulting crude material stirring at room temperature in dimethylformamide (50 mL) was added 1-(3-dimethylaminopropyl)-3-ethylcarbodiimide (2.08 g, 10.01 mmol), 1-hydroxybenzotriazole (1.24 g, 9.16 mmol) and 4-methylpiperidine (1.1 mL, 9.16 mmol). After 18 h, the reaction was quenched with saturated bicarbonate, and washed with ethyl acetate. The combined organic extracts were washed with brine, dried over sodium sulfate, and concentrated. The crude material was purified by flash chromatography (silica gel, 5% methanol/dichloromethane) to yield 4.9 g (75%) of the desired product as a pale yellow foam; $^1$H NMR (300 MHz, CDCl$_3$)—consistent with structure; Anal. calc'd. for $C_{40}H_{50}N_6O_6$; 67.58 C, 7.09 H, 11.82 N; found 65.60 C, 7.09 H. 11.50 N; ISMS (M+)—711.

Compounds 44 and 45

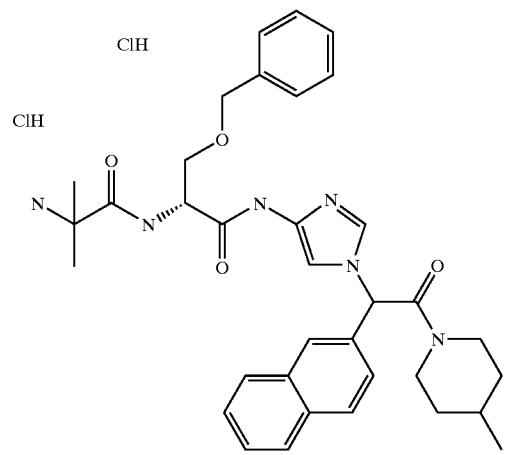

To a solution of the product of Preparation 138 (4.90 g, 6.89 mmol) stirring at room temperature in dichloromethane (40 mL) and anisole (1.0 mL) was added to trifluoroacetic acid (10 mL). After 3 hours, the reaction was quenched with saturated sodium bicarbonate and extracted with ethyl acetate. The combined organic extracts were washed with brine, dried over sodium sulfate and concentrated. The resulting crude material was purified by flash chromatography (silica gel, 5% methanol/dichloromethane) to give the product as a mixture of diastereomers. This material was resolved by HPLC (Kromsil CHI-DMP chiral stationary phase, 3A alcohol/dimethylethylamine/heptane eluant) to provide the free amine of the desired products. The individual diastereomers were dissolved in ethyl acetate and treated with a saturated solution of hydrochloric acid in diethyl ether. The resulting precipitate was filtered to yield the desired products (426779-0.64 g, 14%) (426780-0.43 g, 9%) as tan solids:

Compound 44 $^1$H NMR (300 MHz, CDCl$_3$)—consistent with structure; Anal. calc'd. for C$_{35}$H$_{44}$N$_6$O$_4$Cl$_2$; 61.49 C, 6.49 H, 12.29 N; found 60.28 C, 6.38 H, 11.74 N; ISMS (M+)—611.

Compound 45 $^1$H NMR (300 MHz, CDCl$_3$)—consistent with structure; Anal. calc'd. for C$_{35}$H$_{44}$N$_6$O$_4$Cl$_2$; 61.49 C, 6.49 H, 12.29 N; found 47.81 C, 5.29 H, 9.83 N; ISMS (M+)—611.

EXAMPLE 2-33

Preparation 468

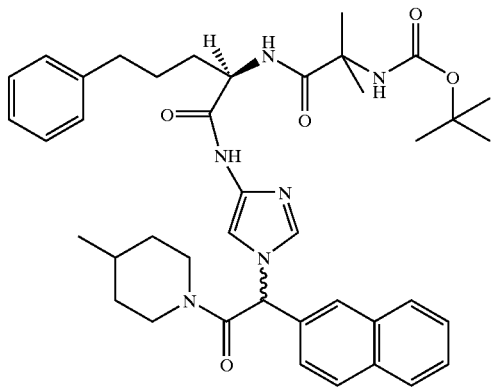

To a solution of the product of Preparation 467 (2.90 g, 4.61 mmol) in anhydrous dichloromethane (40 mL) at 0° C. was added N-methylmorpholine (0.61 mL, 5.53 mmol) and 2-chloro-4,6-dimethoxy-1,3,5-triazine (1.05 g, 5.99 mmol). This mixture stirred for 1 h, warming to room temperature, at which time 4-methylpiperidine (0.60 mL, 5.07 mmol) was added. The reaction stirred for 2 h at room temperature, then more 2-chloro-4,6-dimethoxy-1,3,5-triazine (0.20 g) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (2.99 g, 92%): $^1$H NMR consistent with structure; MS (IS) m/e 709 (M+1); Anal. Calc'd for C$_{41}$H$_{52}$N$_6$O$_5$: C, 69.47; H, 7.39; N, 11.85. Found: C, 69.30; H, 7.47; N, 11.92.

Compounds 46 and 47

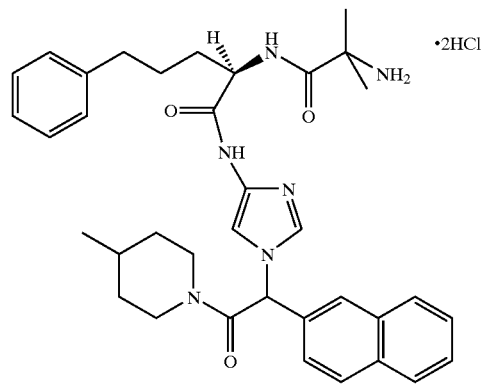

To a stirring solution of the product of Preparation 468 (4.40 g, 6.20 mmol) and anisole (0.71 mL, 6.50 mmol) in anhydrous dichloromethane (140 mL) at 0° C. was added trifluoroacetic acid (14 mL) via syringe. The reaction was stirred for 4 h warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 5% methanol/ethyl acetate—5% triethylamine/10% methanol/ethyl acetate) to provide the desired product as a light yellow solid foam (3.75 g, 99%). $^1$H NMR consistent with structure; MS (IS) m/e 609 (M+1); Anal. Calc'd for C$_{36}$H$_{44}$N$_6$O$_3$: C, 71.03; H, 7.29; N. 13.80. Found: C, 69.83; H, 7.17; N, 13.54.

Diastereomeric separation: the desired product was resolved by HPLC [Kromasil packing material, 15% 3A alcohol/85% heptane (w/0.2% DMEA)] to provide two diastereomers. The first diastereomer (1.30 g) (retention time=6.77 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 249 (1.10 g) as a white amorphous solid: $^1$H NMR consistent with structure; MS (IS) m/e 609 (M+1); Anal. Calc'd for C$_{36}$H$_{44}$N$_6$O$_3$.HCl: C, 67.02; H, 7.03; N, 13.03. Found: C, 66.53; H, 6.96; N, 12.80. The second diastereomer (1.50 g) (retention time=9.17 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 250 (1.47 g) as a white amorphous solid: $^1$H NMR consistent with structure; MS (IS) m/e 609 (M+1); Anal. Calc'd for C$_{36}$H$_{44}$N$_6$O$_3$.HCl: C, 67.02; H, 7.03; N, 13.03. Found: C, 66.08; H, 6.95; N, 12.71.

EXAMPLE 2-34

Preparation 469

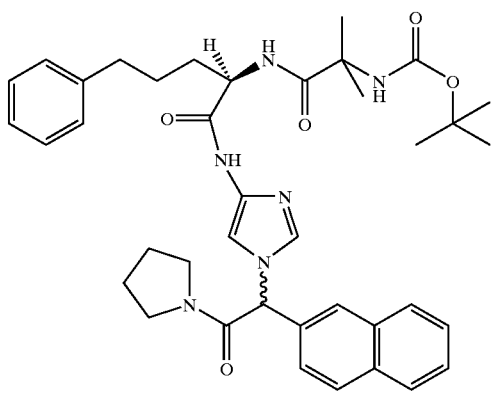

To a solution of the product of Preparation 467 (5.10 g, 8.11 mmol) in anhydrous dichloromethane (75 mL) at 0° C. was added N-methylmorpholine (1.07 mL, 9.73 mmol) and 2-chloro-4,6-dimethoxy-1,3,5-triazine (1.85 g, 10.5 mmol). This mixture stirred for 1 h, warming to room temperature, at which time pyrrolidine (0.75 mL, 8.93 mmol) was added. The reaction stirred for 2 h at room temperature, then more 2-chloro-4,6-dimethoxy-1,3,5-triazine (0.20 g) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (5.30 g, 96%): $^1$H NMR consistent with structure; MS (IS) m/e 681 (M+1); Anal. Calc'd for $C_{39}H_{48}N_6O_5$: C, 68.80; H, 7.11; N, 12.34. Found: C, 68.07; H, 7.10; N, 12.85.

Compounds 48 and 49

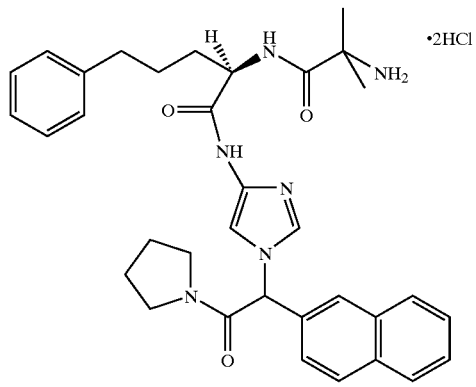

To a stirring solution of the product of Preparation 469 (5.15 g, 7.55 mmol) and anisole (0.86 mL, 7.93 mmol) in anhydrous dichloromethane (150 mL) at 0° C. was added trifluoroacetic acid (15 mL) via syringe. The reaction was stirred for 4 h warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography-(silica gel, 5% methanol/ethyl acetate—5% triethylamine/10% methanol/ethyl acetate) to provide the desired product as an off-white solid foam (4.11 g, 94%). $^1$H NMR consistent with structure; MS (IS) m/e 581 (M+1); Anal. Calc'd for $C_{34}H_{40}N_6O_3$: C, 70.32; H, 6.94; N, 14.47. Found: C, 70.34; H, 6.79; N, 13.70.

Diastereomeric separation: the desired product was resolved by HPLC (Kromasil packing material, 15% 3A alcohol/85% heptane (w/0.2% DMEA)I to provide two diastereomers. The first diastereomer (1.70 g) (retention time=7.72 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 251 (1.27 g) as a off-white amorphous solid: $^1$H NMR consistent with structure; MS (IS) m/e 581 (M+1); Anal. Calc'd for $C_{34}H_{40}N_6O_3 \cdot 2HCl$: C, 66.17; H, 6.70; N, 13.62. Found: C, 65.65; H, 6.90; N, 13.48. The second diastereomer (1.40 g) (retention time=10.81) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 252 (1.47 g) as a off-white amorphous solid: $^1$H NMR consistent with structure; MS (IS) m/e 581 (M+1); Anal. Calc'd for $C_{34}H_{40}N_6O_3 \cdot 2HCl$: C, 66.17; H, 6.70; N, 13.62. Found: C, 65.73; H, 7.03; N, 13.31.

EXAMPLE 2-35

Preparation 142

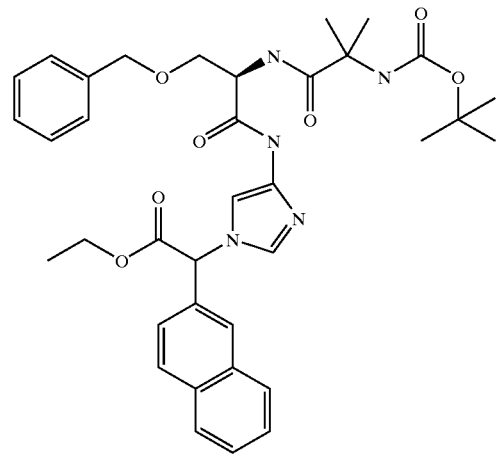

Reaction of the product of Preparation 136 (8.7 g, 27 mmol) with 10% palladium on carbon (4.0 g) under a hydrogen atmosphere followed by coupling with the product of Preparation 1 (10.14 g, 26.7 mmol), 1-hydroxybenzotriazole (4.49 g, 29.3 mmol), and 1-(3-dimethylaminopropyl)-3-ethylcarbodiimide (6.05 g, 29.3 mmol) as described in Preparation 5A gave 5.4 g (31%) of the title compound as a tan solid: $^1$H NMR (d$^6$-DMSO, d): 1.26(t, J=7.4 Hz, 3H), 1.40(s, 9H), 1.55(m, 6H), 3.55(m, 1H), 4.02(s, 1H), 4.25(m, 2H), 4.50(dd, J=10.0 Hz, 2H), 4.86(s, 1H), 5.92(s, 1H), 7.02(d, j=7.0 Hz, 1H), 7.22(m, 8H), 7.33(m, 3H), 7.41(s, 1H), 7.49(m, 1H), 7.80(m, 2H), 9.22 (bs, 1H). Ion spray MS (M$^+$+1): 658. Anal. ($C_{36}H_{43}N_5O_7$): C,H,N.

Preparation 143

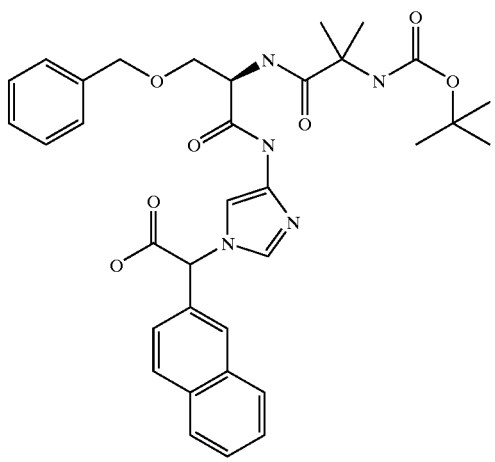

Reaction of the product of Preparation 142 (5.39 g, 8.19 mmol) with lithium hydroxide (361 mg, 8.60 mmol) in dioxane (120 mL) and water (75 mL) as described in Preparation 5 gave 4.92 g (95%) of the title compound as a golden yellow solid: $^1$H NMR (d$^6$-DMSO, d): 1.28 (m, 15H), 3.57(m, 1H), 3.66(m, 1H), 4.43(s, 2H), 4.48(d, J=5.3 Hz, 1H), 4.56(bs, 1H), 5.75(bs, 1H), 7.13(bs, 1H), 7.26(m, 6H), 7.31(d, J=6.0 Hz, 2H), 7.40(m, 1H), 7.45(m, 2H), 7.65(s, 1H), 7.83(m, 3H), 10.10(bs, 1H). Ion spray MS (M$^+$+1): 630.

Preparation 144

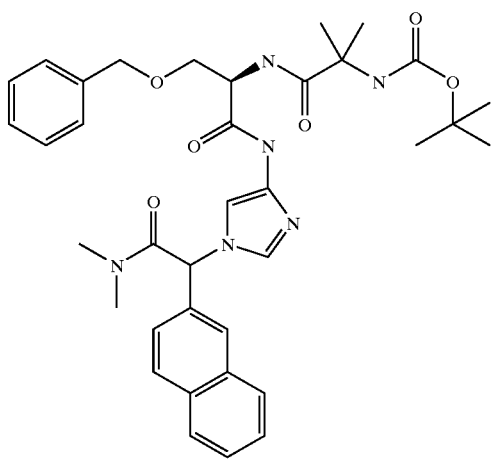

Reaction of the product of Preparation 143 (4.88 g, 7.75 mmol), dimethylamine (4.2 mL, 8.53 mmol, 2.0M in tetrahydrofuran), 1-hydroxy-7-azabenzotriazole(1.16 g, 8.53 mmol) and 1-(3-dimethylaminopropyl)-3-ethylcarbodiimide (1.76 g, 8.53 mmol) in tetrahydrofuran (120 mL) as described in Preparation EX4A gave 2.06 g (40%)of the title compound as a yellow foam: 4$^1$H NMR (d$^6$-DMSO, d): 1.28(m, 15H), 2.92(s, 3H), 2.95(s, 3H), 3.60(m, 1H), 4.43(d, J=4.5 Hz), 4.57(bs, 1H), 6.83(s, 1H), 7.24(m, 8H), 7.39(m, 1H), 7.50(m, 1H), 7.56(m, 2H), 7.88(s, 1H), 7.96(m, 3H). Ion spray MS (M$^+$+1): 657 Anal. (C$_{36}$H$_{44}$N$_6$O$_4$) : H,N;C: calc'd 65.84; found 63.70.

Compound 50

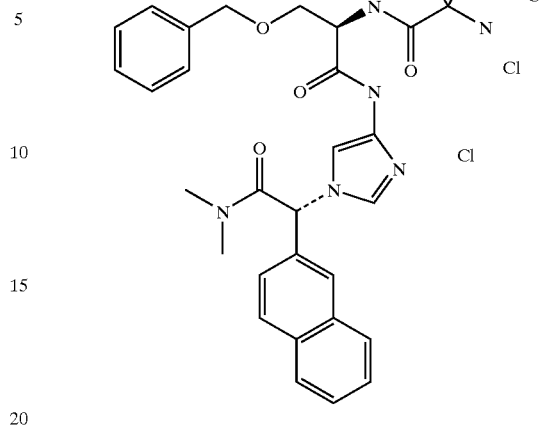

To a solution of glacial acetic acid saturated with dry hydrochloric acid (50 mL, ~3N in hydrochloric acid) stirring at room temperature was added the product of Preparation 144 (1.87 g, 2.85 mmol). After 2 h, the solution was concentrated, washed with aqueous sodium bicarbonate solution, dried over magnesium sulfate and concentrated. The resulting crude material was purified by HPLC (Column) to give 0.5 g of the desired isomer which was dissolved in ethyl acetate and added dropwise to a stirred solution of anhydrous diethyl ether saturated with hydrochloric acid. The resulting white precipitate was collected by filtration and dried to give 474 mg (79%) white solid: $^1$H NMR (d6-DMSO, d): 1.47(m, 6H), 2.90(s, 3H), 2.95(s, 3H), 3.65(dd, J=9 Hz, 2H), 4.49(d, J=7.9 Hz, 2H), 4.73((m, 1H), 6.93(s, 1H), 7.18(s, 1H), 7.26(m, 6H), 7.49(d, J=8.7 Hz, 1H), 7.60(m, 2H), 7.84(d, J=10.5 Hz, 1H), 7.98(m, 3H), 8.14(d, J=9.4 Hz, 2H), 8.45(d, J=6.8 Hz, 1H), 10.74(bs, 1H). FAB+exact MS (M$^+$+1): 557.2876 calculated, 557.2873 found Anal. (C$_{31}$H$_{39}$N$_6$O$_4$Cl$_3$) :H,N;C: calc'd, 56.01; found, 56.72.

EXAMPLE 2-36

Preparation 139

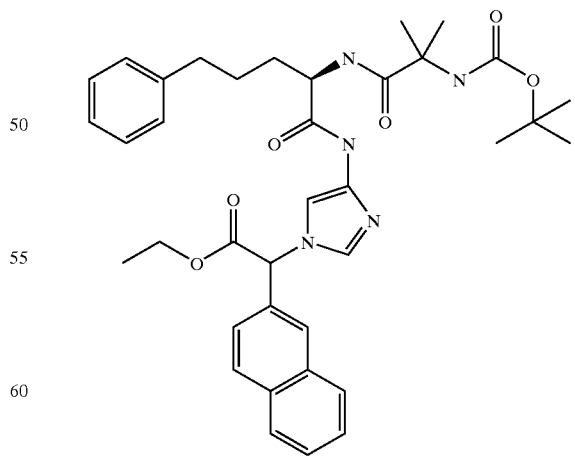

Reaction of the product of Preparation 136 (1.31g, 4.02 mmol) with 10% palladium on carbon (0.5 g) in tetrahydrofuran (50 mL) under a hydrogen atmosphere followed by coupling with the product of Preparation 2 (1.52g, 4.02 mmol), 1-hydroxybenzotriazole (0.68g, 4.42 mmol), and 1-(3-dimethylaminopropyl)-3-ethylcarbodiimide(0.91g, 4.42 mmol) as described in Preparation 5A to give 1.06 g (38%) of the title compound as a tan solid: $^1$H NMR (d$^6$-DMSO, d): 1.22(m, 18H), 1.50(m, 4H), 2.55(m, 2H), 4.26(q, J=9.0 Hz, 2H), 4.37(bs, 1H), 5.75(s, 1H), 6.60(s, 1H), 7.02(bs, 1H), 7.16(m, 3H), 7.22(m, 3H), 7.43(m, 1H), 7.50(d, J=9.3 Hz, 2H), 7.60(m, 2H), 7.97(m, 3H), 10.21(m, 1H). Ion spray MS (M$^+$+1): 656.

Preparation 140

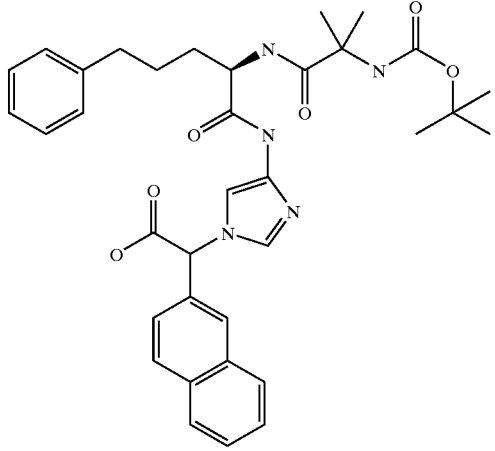

Reaction of the product of Preparation 139 (1.06 g, 1.62 mmol) with lithium hydroxide 75 mg, 1.78 mmol) in dioxane (30 mL) and water (15 mL) as described in Preparation 5 gave 1.01 g (100%) of the title compound as a golden yellow solid: $^1$H NMR (d$^6$-DMSO, d): 1.20(m, 15H), 1.50 (m, 4H), 2.55(m, 2H), 4.38(bs, 1H), 6.58(s, 1H), 7.02(bs, 1H), 7.17(m, 3H), 7.25(m, 3H), 7.35(m, 1H), 7.50(m, 2H), 7.58(m, 2H), 7.98m, 3H), 8.09(m, 1H), 10.36(bs, 1H). Ion spray MS (M$^+$+1): 628.

Preparation 141

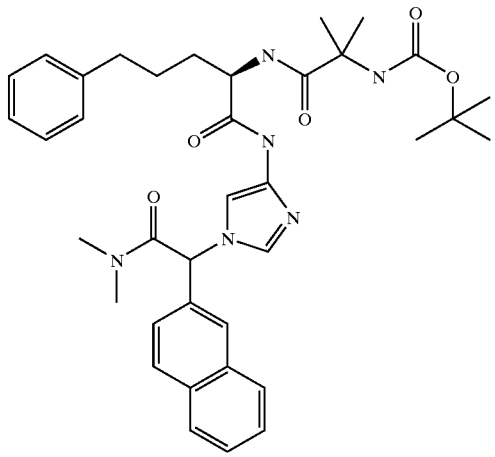

To a solution of the product of Preparation 140 (500 mg, 0.80 mmol) dimethylamine hydrochloric acid (72 mg, 0.88 mmol), triethylamine (0.12 mL, 0.88 mmol), 1-hydroxybenzotriazole (134 mg, 0.88 mmol) and 1-(3-dimethylaminopropyl)-3-ethylcarbodiimide (18 mg, 0.88 mmol) in dimethylformamide (20 mL) as described in Preparation EX4A gave 342 mg (66%) of the title compound as a white solid: "H MMR (d$^6$-DMSO, d): 1.27(m, 15H), 1.57(m, 4H), 2.55(m, 2H), 2.90(s, 3H), 2.95(s, 3H), 4.38(bs, 1H), 6.80(s, 1H), 7.02(bs, 1H), 7.15(m, 3H), 7.22(m, 3H), 7.35(m, 1H), 7.47(m, 2H), 7.57(m, 2H), 7.88(s, 1H), 7.98(m, 3H), 10.15(bs, 1H). Ion spray MS (M$^+$+1) : 655. Anal. (C$_{37}$H$_{46}$N$_6$O$_5$): H,N;C: calc'd 67.87; found 66.19.

Compound 51

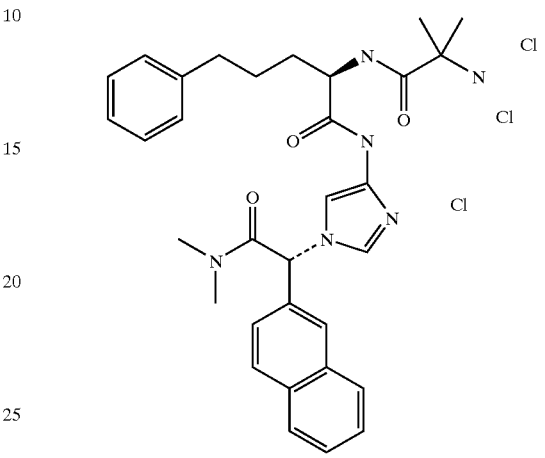

Reaction of the product of Preparation 141 (333 mg, 0.51 mmol) with trifluoroacetic acid (5 mL) in dichloromethane (17 mL) as described in Example 2-7 gave 52 mg (65%) of a tan solid which was purified by HPLC (Kromasil CHI-DMP chiral stationary phase, 3A alcohol/dimethylethylamine/heptane eluant) to give the free amine which was acidified with hydrochloric acid to provide the desired product: $^1$H NMR (d$^6$-DMSO, d): 1.21(m, 6H), 1.57 (m, 4H), 2.54(m, 2H), 2.90(s, 3H), 2.95(s, 3H), 4.41(bs, 1H), 6.82(s, 1H), 7.02(bs, 1H), 7.14(m, 3H), 7.24(m, 3H), 7.48 (m, 2H), 7.57((m, 2H), 7.87(s, 1H), 7.97(m, 3H), 8.12(bs, 1H), 10.40(s, 1H). FAB+exact MS (M$^+$+1): 555.3084 calc'd, 555.3079 found Anal. (C$_{32}$H$_{41}$N$_6$O$_3$Cl$_3$):C,H,N.

EXAMPLE 2-37

Preparation EX20A

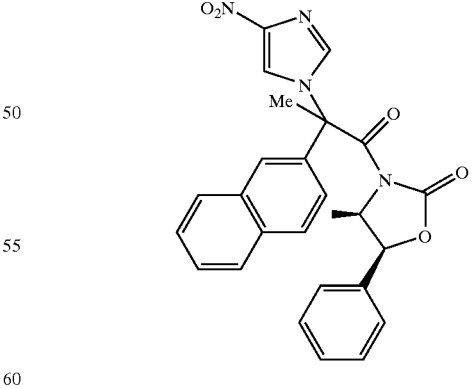

Prepared as in Preparation 6B using the product of Preparation 13B (10.9 g, 32.27 mmol) in THF (150 mL) and lithium hydroxide (1.63 g, 38.73 mmol) in water (75 mL) to give the crude acid. The resulting crude solid was dissolved in anhydrous dichloromethane (150 mL) and reacted with catalytic DMF (0.5 mL) and excess oxalyl chloride (23 mL).

The resulting crude foam was dissolved in THF (50 mL) and reacted with n-BuLi (1.6M in hexanes, 30.1 mL, 48.23 mmol), (4R, 5S)-(+)-4-methyl-5-phenyl-2-oxazolidinone (8.55 g, 48.23 mmol), and THF (150 mL) to yield diastereomer 1 (6.13 g, 41% yield) and diastereomer 2 (4.82 g, 32%) of the desired product (Preparation EX20A), as follows, as colorless foams: diastereomer 1—$^1$H NMR (300 MHz, CDCl$_3$)—consistent with structure; Anal. calc'd. for C$_{26}$H$_{22}$N$_4$O$_5$; 66.38 C, 4.71 H, 11.91 N; found 65.24 C, 4.72 H, 11.59 N; ISMS (M+)—471: diastereomer 2—$^1$H NMR (300 MHz, CDCl$_3$)—consistent with structure; Anal. calc'd. for C$_{26}$H$_{22}$N$_4$O$_5$; 66.38 C, 4.71 H, 11.91 N; found 66.45 C, 4.77 H, 12.20 N; ISMS (M+)—471.

Preparation EX20B

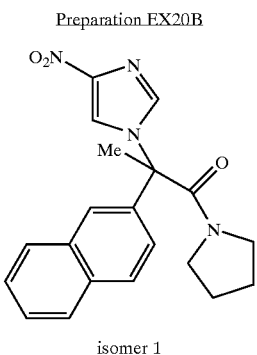

isomer 1

Prepared as in Preparation EX2A using the product of Preparation EX20A, diastereomer 1 (1.00 g, 2.13 mmol) in THF (20 mL) and lithium hydroxide (0.10 g, 2.33 mmol) in water (10 mL) to give the crude acid. The resulting crude solid was dissolved in anhydrous dichloromethane (20 mL) and reacted with catalytic DMF (0.1 mL) and excess oxalyl chloride (5 g). The resulting crude foam was dissolved in anhydrous dichloromethane (20 mL) and reacted with 4-Dimethylaminopyridine (catalytic, 10 mg) and pyrrolidine (0.61 mL, 6.39 mmol) to yield the desired product (Preparation 20B), as follows, (0.42 g, 54% yield) as a colorless foam: $^1$H NMR (300 MHz, CDCl$_3$)—consistent with structure; Anal. calc'd. for C$_{20}$H$_{20}$N$_4$O$_3$; 65.92 C, 5.53 H, 15.38 N; found 61.50 C, 5.41 H, 13.91 N; ISMS (M+)—365.

Preparation EX20C

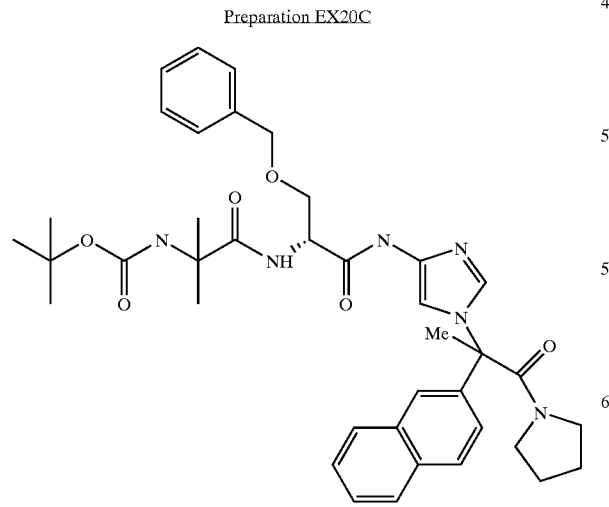

Prepared as in Preparation EX2B using the product of Preparation EX20B (0.42 g, 1.15 mmol) and 5% palladium on carbon (0.40 g, catalytic, 25 mL THF) to yield the crude amine. The filtrate was reacted with HOBT (0.16 g, 1.15 mmol), the product of Preparation 1 (0.44 g, 1.15 mmol), and DCC (0.26 g, 1.28 mmol) to yield the desired product (Preparation EX20C), as follows, (0.41 g, 51% yield) as a light yellow foam: $^1$H NMR (300 MHz, CDCl$_3$)—consistent with structure; Anal. calc'd. for C$_{39}$H$_{48}$N$_6$O$_6$; 67.22 C, 6.94 H, 12.06 N; found 67.66 C, 6.95 H, 11.66 N; ISMS (M+)—697.

Compound 52

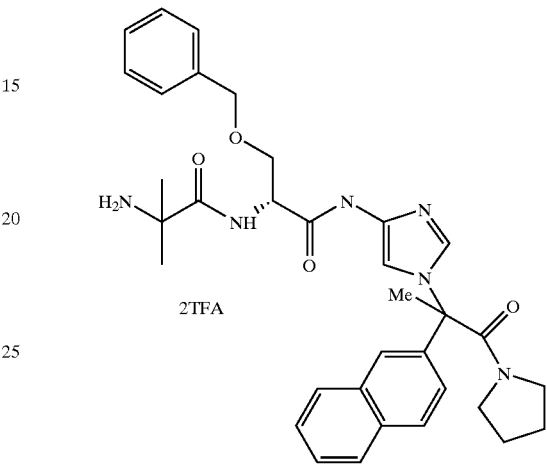

Prepared as in Example Z2 using the product of Preparation EX20C (0.41 g, 0.59 mmol), trifluoroacetic acid (2.0 mL), anisole (0.2 mL), and dichloromethane (8.0 mL) to yield the desired product (Example 20)(0.48 g, 99% yield) as an off white solid: $^1$H NMR (300 MHz, CDCl$_3$)—consistent with structure; Anal. calc'd. for C$_{38}$H$_{42}$N$_6$O$_8$F$_6$; 55.34 C, 5.13 H, 10.19 N; found 55.60 C, 4.92 H, 9.89 N; ISMS (M+)—597.

EXAMPLE 2-38

Preparation 44

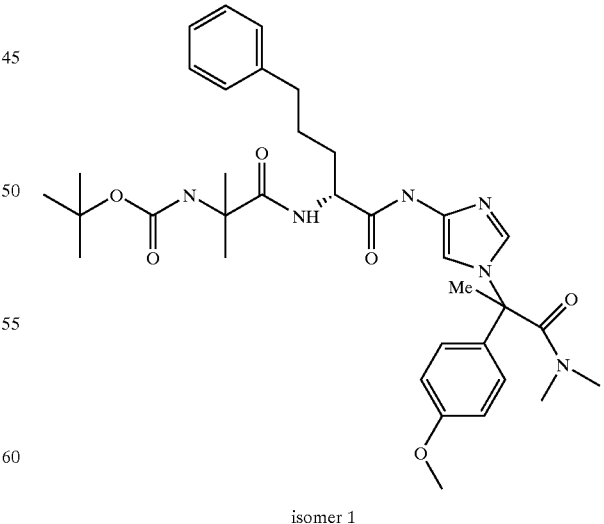

isomer 1

Prepared as in Preparation EX2B using the product of Preparation 21 (0.27 g, 0.85 mmol) and 5% palladium on carbon (0.30 g, catalytic, 20 mL THF) to give the crude amine. The resulting filtrate was reacted with HOBT (0.11 g, 0.85 mmol), the product of Preparation 2 (0.32 g, 0.85 mmol), N-methylmorpholine (0.10 mL, 0.85 mmol), and EDCI (0.16 g, 0.93 mmol) to yield the desired product (0.70 g, 46% yield) as a light yellow foam: $^1$H NMR (300 MHz, CDCl$_3$)—consistent with structure; Anal. calc'd. for C$_{35}$H$_{48}$N$_6$O$_6$; 66.43 C, 7.65 H, 13.28 N; found 63.53 C, 6.83 H, 12.38 N; ISMS (M+)—649.

Compound 53

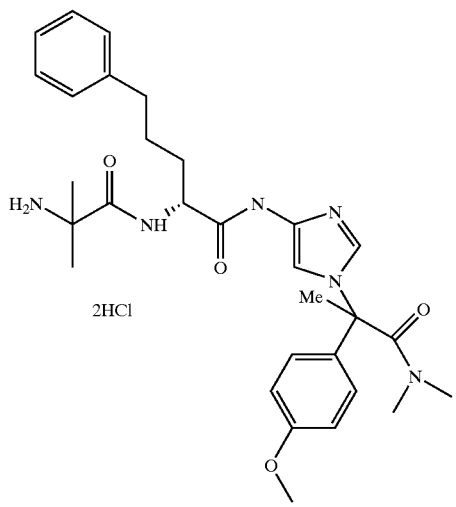

2HCl

Prepared as in Example 2-7 using the product of Preparation 44 (0.19 g, 0.29 mmol), trifluoroacetic acid (4.0 mL), anisole (0.4 mL), and dichloromethane (20 mL) to yield the desired product (0.16 g, 64%) as a pale yellow solid: $^1$H NMR (300 MHz, CDCl$_3$)—consistent with structure; Anal. calc'd. for C$_{30}$H$_{42}$N$_6$O$_4$Cl$_2$; 57.97 C, 6.81 H, 13.52 N; found 57.54 C, 6.36 H, 13.04 N; FDMS (M+)—549.

EXAMPLE 2-39

Preparation 21

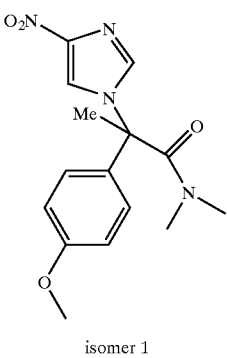

isomer 1

Prepared as in Preparation 17 using the product of Preparation EX9A, diastereomer 1 (2.31 g, 5.15 mmol) in THF (50 mL) and lithium hydroxide (0.26 g, 6.18 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg) and dimethylamine (2.0 M in THF, 7.7 mL, 15.46 mmol) to yield the desired product (1.57 g, 96% yield) as a colorless foam: $^1$H NMR (300 MHz, CDCl$_3$)—consistent with structure; Anal. calc'd. for C$_{15}$H$_{18}$N$_4$O$_4$; 56.60 C, 5.70 H, 17.60 N; found 57.04 C, 6.09 H, 16.82 N; ISMS (M+)—319.

Preparation 45

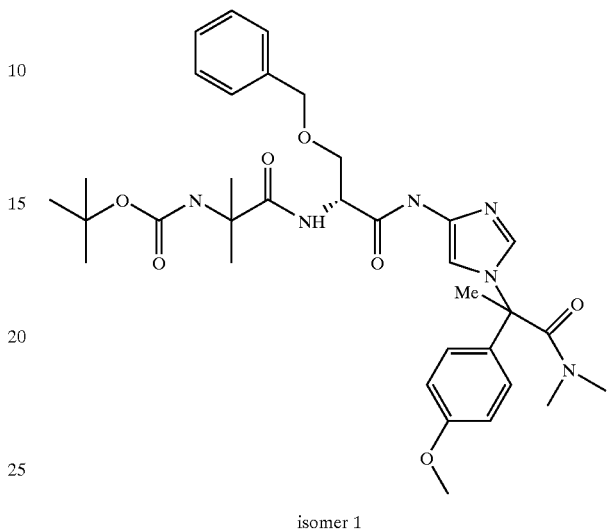

isomer 1

Prepared as in Preparation EX2B using the product of Preparation 21 (0.75 g, 2.36 mmol) and 5% palladium on carbon (0.80 g, catalytic, 25 mL THF) to give the crude amine. The resulting filtrate was reacted with HOBT (0.32 g, 2.36 mmol), the product of Preparation 1 (0.90 g, 2.36 mmol), and DCC (0.54 g, 2.60 mmol) to yield the desired product (0.86 g, 56% yield) as a light yellow foam: $^1$H NMR (300 MHz, CDCl$_3$)—consistent with structure; Anal. calc'd. for C$_{37}$H$_{50}$N$_6$O$_6$; 62.75 C, 7.12 H, 12.91 N; found 62.65 C, 6.95 H, 12.76 N; ISMS (M+)—651.

Compound 54

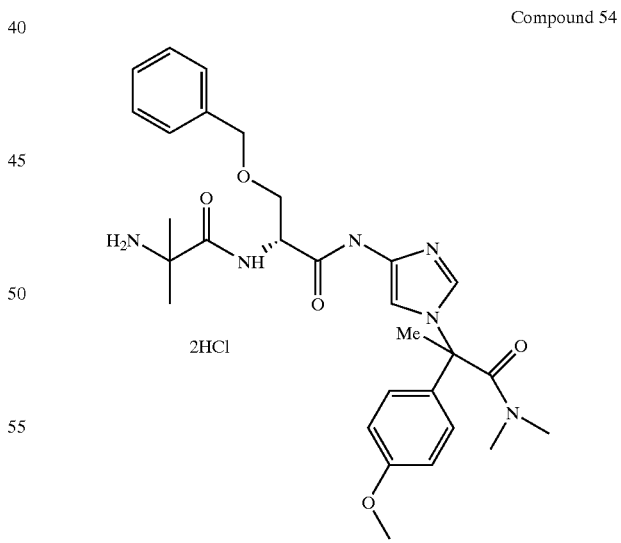

2HCl

Prepared as in Example 2-7 using the product of Preparation 45 (0.84 g, 1.29 mmol), trifluoroacetic acid (4.0 mL), anisole (0.4 mL), and dichloromethane (20 mL) to yield the desired product (0.69 g, 86%) as a pale yellow solid: $^1$H NMR (300 MHz, CDCl$_3$)—consistent with structure; Anal. calc'd. for C$_{29}$H$_{38}$N$_6$O$_5$Cl$_2$; 55.86 C, 6:47 H, 13.48 N; found 55.31C, 6.52 H, 13.01 N; ISMS (M+)—551.

EXAMPLE 2-40

Preparation 46

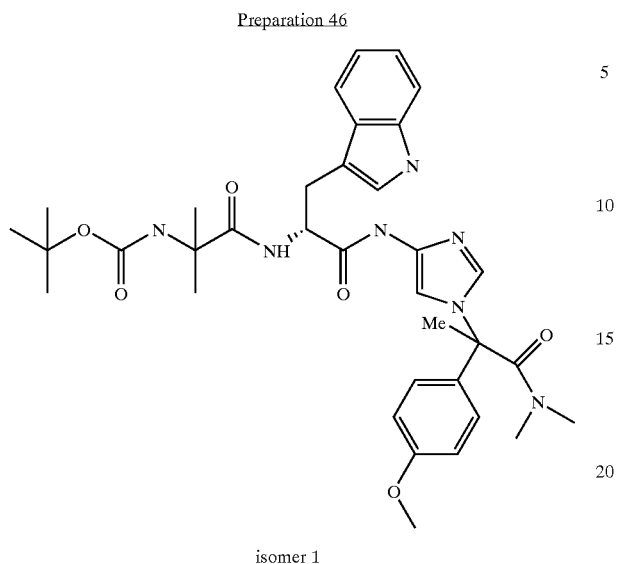

isomer 1

Prepared as in Preparation EX2B using the product of Preparation 21 (0.80 g, 2.52 mmol) and 5% palladium on carbon (0.80 g, catalytic, 25 mL THF) to give the crude amine. The resulting filtrate was reacted with HOBT (0.34 g, 2.52 mmol), the product of Preparation 37 (0.99 g, 2.52 mmol), and DCC (0.57 g, 2.77 mmol) to yield the desired product (0.77 g, 46% yield) as a light yellow foam: $^1$H NMR (300 MHz, CDCl$_3$)—consistent with structure; Anal. calc'd. for C$_{37}$H$_{50}$N$_6$O$_6$; 63.72 C, 6.87 H, 14.86 N; found 63.45 C, 6.86 H, 14.76 N; ISMS (M+)—660.

Compound 55

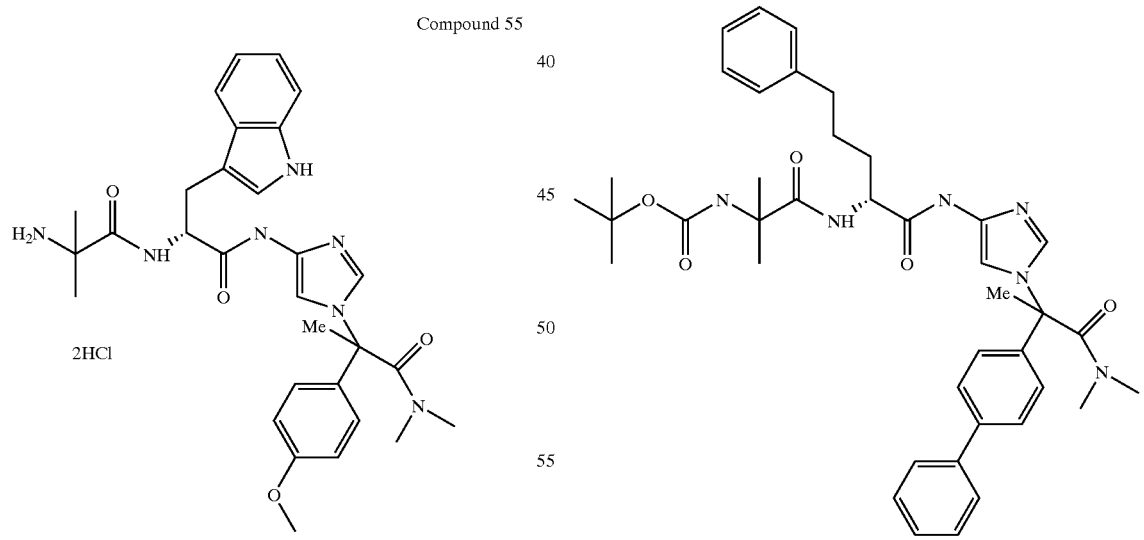

Prepared as in Example 2-7 using the product of Preparation 46 (0.75 g, 1.13 mmol), trifluoroacetic acid (4.0 mL), anisole (0.4 mL), and dichloromethane (20 mL) to yield the desired product (0.62 g, 87%) as a pale yellow solid: $^1$H NMR (300 MHz, CDCl$_3$)—consistent with structure; Anal. calc'd. for C$_{30}$H$_{37}$N$_7$O$_4$Cl$_2$; 56.96 C, 6.21 H, 15.50 N; found 55.48 C, 6.03 H, 14.63 N; ISMS (M+)—560.

EXAMPLE 2-41

Preparation 24

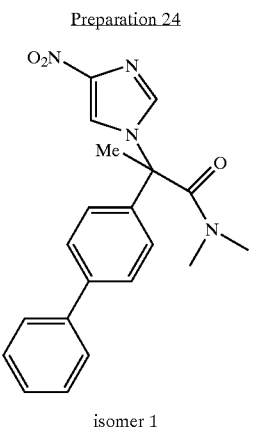

isomer 1

Prepared as in Preparation EX2A using the product of Preparation 12B, diastereomer 1 (0.50 g, 1.00 mmol) in THF (20 mL) and lithium hydroxide (0.05 g, 1.10 mol) in water (10 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg), N-methylmorpholine (0.33 mL, 3.00 mmol), and dimethylamine hydrochloride (0.13 g, 1.50 mmol) to yield the desired product (0.30 g, 82% yield) as a colorless foam: $^1$H NMR (300 MHz, CDCl$_3$)—consistent with structure; Anal. calc'd. for C$_{20}$H$_{20}$N$_4$O$_3$; 65.92 C, 5.53 H, 15.37 N; found 64.17 C, 5.41 H, 14.15 N; ISMS (M+)—365.

Preparation 50

Prepared as in Preparation EX2B using the product of Preparation 24 (0.30 g, 0.82 mmol) and 5% palladium on carbon (0.30 g, catalytic, 25 mL THF) to give the crude amine. The resulting filtrate was reacted with HOBT (0.11 g, 0.82 mmol), the product of Preparation 2 (0.31 g, 0.82 mmol), and DCC (0.19 g, 0.90 mmol) to yield the desired product (0.32 g, 56% yield) as a light yellow foam: $^1$H NMR (300 MHz, CDC$_3$)—consistent with structure; Anal. calc'd.

for $C_{40}H_{50}N_6O_5$; 69.14 C, 7.25 H, 12.09 N; found 67.82 C, 7.07 H, 11.62 N; ISMS (M+)—695.

Compound 56

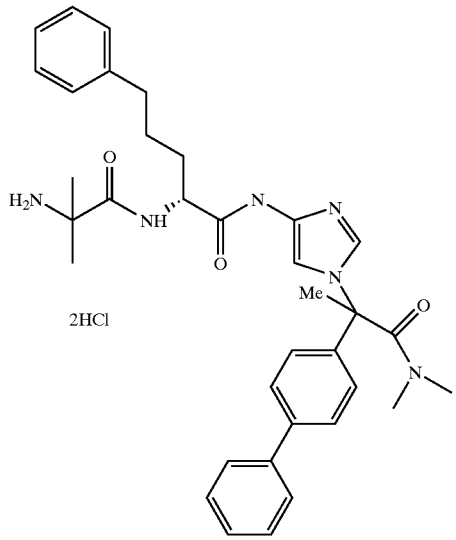

2HCl

Prepared as in Example 2-7 using the product of Preparation 50 (0.32 g, mmol), trifluoroacetic acid (4.0 mL), anisole (0.4 mL), and dichloromethane (20 mL) to yield the desired product (0.26 g, %) as a pale yellow solid: $^1$H NMR (300 MHz, $CDCl_3$)—consistent with structure; Anal. calc'd. for $C_{35}H_{44}N_6O_3Cl_2$; 62.96 C, 6.64 H, 12.59 N; found 60.05 C, 6.31 H, 11.98 N; FDMS (M+)—595.

EXAMPLE 2-42

Preparation 37

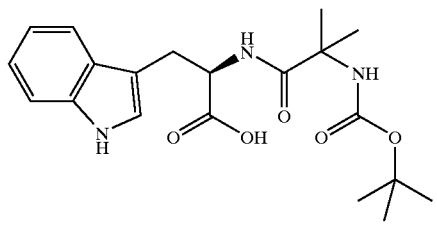

N-Methyl morpholine (4.79 mL, 2 eq, 47.3 mm) was added to a stirred slurry of N-Boc-a-aminoisobutyric acid (4.43 g, 21.7 mm, 1 eq) and 3.89 g (21.7 mm, 1.0 eq) of 2-chloro-(4,6)-dimethoxy-1,3,5-triazine (CDMT) in 100 mL of diethyl ether. After stirring the reaction mixture at ambient temperature for 1.5 hours, D-tryptophan ester hydrochloride was added. After stirring overnight, the reaction mixture was quenched by the addition of 150 mL of 10% aqueous citric acid solution. The layers were separated and the ether layer was washed with 50 mL of saturated sodium bicarbonate solution and 50 mL of water. Lithium hydroxide (2.43 g, 5 eq) was dissolved in 100 ml of water and the solution was added to the diethyl ether solution and stirred vigorously for 4 hours at room temperature. The layers were separated and the pH of the aqueous layers was adjusted to 5.6 with 1M HCl. The pH was then adjusted to 3.95 with 10% citric acid solution and the aqueous layer was extracted with 100 mL of ethyl acetate. The ethyl acetate layers were washed with brine, dried over magnesium sulfate and filtered. The volatiles were removed under vacuum to give 82% yield of the desired product as a white foam. 1H-NMR consistent with structure.

Preparation 49

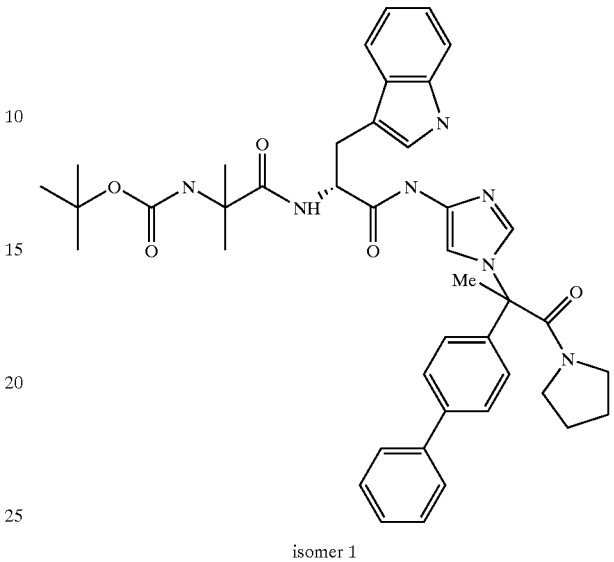

isomer 1

Prepared as in Preparation EX2B using the product of Preparation EX17A (0.20 g, 0.51 mmol) and 5% palladium on carbon (0.20 g, catalytic, 25 mL THF) to give the crude amine. The resulting filtrate was reacted with HOBT (0.07 g, 0.51 mmol), the product of Preparation 37 (0.20 g, 0.51 mmol), and DCC (0.12 g, 0.51 mmol) to yield the desired product (0.17 g, 45% yield) as a light yellow foam: $^1$H NMR (300 MHz, $CDCl_3$)—consistent with structure; Anal. calc'd. for $C_{42}H_{49}N_7O_6$; 68.93 C, 6.75 H, 13.40 N; found 67.02 C, 6.54 H, 12.71 N; ISMS (M+)—732.

Compound 57

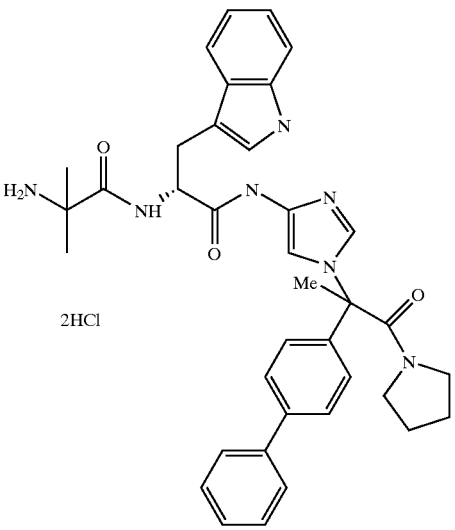

2HCl

Prepared as in Example 2-7 using the product of Preparation 49 (0.96 g, 1.31 mmol), trifluoroacetic acid (4.0 mL), anisole (0.4 mL), and dichloromethane (20 mL) to yield the desired product (0.54 g, 59%) as a pale yellow solid: $^1$H NMR (300 MHz, $CDCl_3$)—consistent with structure; Anal. calc'd. for $C_{37}H_{43}N_7O_3Cl_2$; 63.06 C, 6.15 H, 13.91 N; found 58.22 C, 5.48 H, 12.32 N; ISMS (M+)—632.

EXAMPLE 2-43

Preparation 15

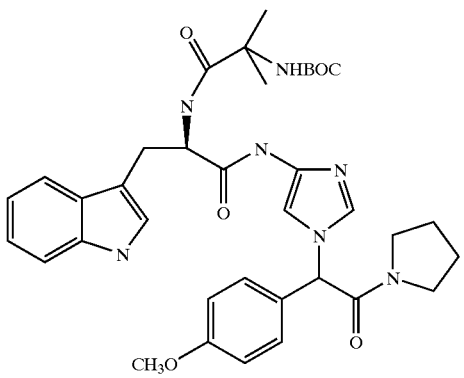

The product of Preparation EX9A (0.85 g, 2.57 mmol) was combined with 10% palladium/carbon (0.50 g) and palladium/black (0.15 g) in tetrahydrofuran (40 mL)and the mixture shaken under a hydrogen atmosphere (38 psi) in a Parr apparatus. After reduction was complete, the catalyst was removed by filtration through celite and the amine/ tetrahydrofuran solution was immediately combined with 1,3-dicyclohexylcarbodiimide (0.53 g, 2.57mmol), 1-hydroxybenzotriazole (0.35 g, 2.57 mmol), the product of Preparation 1L (1.00 g, 2.57 mmol) and additional tetrahydrofuran (60 mL) After stirring overnight at ambient temperature, the mixture was concentrated and the residue slurried in ethyl acetate and filtered. The filtrate was concentrated and the residue purified by flash chromatography (silica gel, chloroform/methanol) which gave 1.62 g of the desired product which was used without further purification.

Compound 58

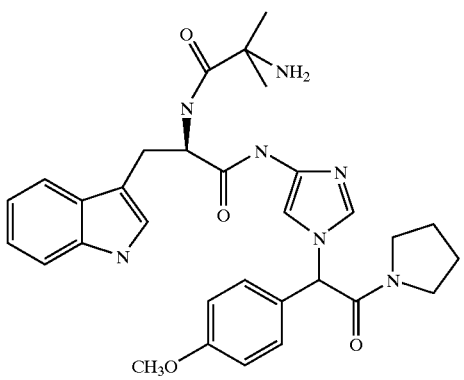

The compound of Preparation 15 (1.57 g, 2.34 mmol) was dissolved in dichloromethane (25 mL) and triflouroacetic acid (10 mL) added. The resulting mixture was stirred at ambient temperature for 2.5 h, concentrated, and the residue treated with excess aqueous sodium bicarbonate. The aqueous mixture was extracted with ethyl acetate and the combined organic extracts concentrated and dried. The residue was chromatographed over silica gel (chloroform/methanol) to provide 0.71 g (53%) of the desired product: MS: (M+H)+ 572.5. $^1$H NMR was consistent with product. Anal. Calcd. for $C_{31}H_{37}N_7O_4$.0.35 $CHCl_3$: C, 61.38; H, 6.14; N, 15.98. Found: C, 61.36; H. 6.11; N, 16.08. The isomeric mixture (2.16 g) was separated as previously described in Example 6 to provide 1.10 g of isomer 1 ($t_R$=10.34 min) and 0.80 g of isomer 2 ($t_R$=13.70 min). The product derived from isomer 2 (0.80 g, 1.40 mmol) was dissolved in a minimal amount of ethyl acetate and the resulting solution treated with an excess of hydrochloric acid in ethyl acetate. The solution was then concentrated to provide 0.88 g (82%) of the desired product as an off white solid: MS: (M+H)+572.3, 573.4. $^1$H NMR was consistent with product. Anal. Calcd. For$C_{31}H_{37}N_7O_4$.3.0 HCl: C, 54.67; H, 5.92; N, 14.40. Found: C, 54.25; H, 5.89; N, 13.35.

EXAMPLE 2-44

Preparation 16

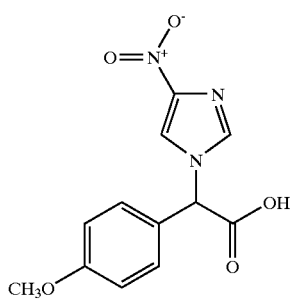

To a solution of the product of Preparation 4 (5.75 g, 18.9 mmol) stirring at room temperature in tetrahydrofuran (10 mL) was added sodium hydroxide (25 mL of a 5 N aqueous solution) along with water (15 mL) and ethanol (10 mL). After hydrolysis was complete, the mixture was acidified to pH 2.0 with aqueous hydrochloric acid and extracted. The combined organic extracts were dried, filtered, and concentrated to give the desired product in quantitative yield as a tan solid: $^1$H NMR (300 MHz, DMSO-$d_6$) δ 14.05–13.60 (bs, 1H), 8.34 (s, 1H) 7.90 (s, 1H), 7.45 (d, 2H, J=8.67 Hz), 7.00 (d, 2H, J=8.67 Hz), 6.42 (s, 1H), 3.77 (s, 3H). FDMS: 277 (M)+ Anal. Calcd. for $C_{12}H_{11}N_3O_5$. 0.67 $H_2O$: C, 49.82; H, 4.30; N, 14.52. Found: C, 50.05; H, 4.01; N, 14.12.

Preparation 17

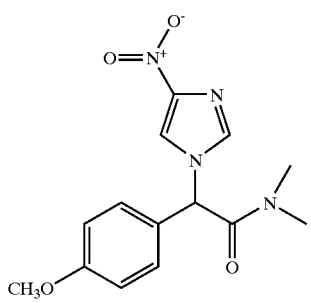

The compound of Preparation 16 (2.50g,9.0 mmol) was combined with aqueous dimethylamine(40%, 1.15 mL,9.0 mmol), 1-hydroxy-benzotriazole hydrate(1.22 g, 9.0 mmol) and 1,3-dicyclohexylcarbodiimide (1.86 g, 9.0 mmol) in tetrahydrofuran (60 mL) and the mixture stirred at ambient temperature. After 18 h, the mixture was concentrated and the residue slurried in ethyl acetate and filtered. The filtrate was concentrated and the resulting residue purified by flash chromatography (silica gel, chloroform/methanol) to afford 1.83 g (67%) of the desired product: $^1$H NMR (300 MHz, DMSO-$d_6$) δ 8.14 (s, 1H) 7.76 (s, 1H), 7.42 (d, 2H, J=8.67 Hz), 7.00 (d, 2H, J=8.67 Hz), 6.78 (s, 1H), 3.77 (s, 3H), 2.91 (2, 3H), 2.85 (s, 3H). ESMS: (M+H)+305.2.

Preparation 19

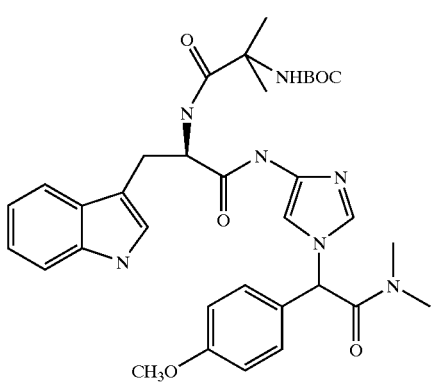

The compound of preparation 17 (0.73 g, 2.38 mmol) was combined with 10% palladium/carbon (0.50 g) and palladium/black (0.10 g) in tetradyrofuran(40 mL)and the mixture shaken under hydrogen (38 psi) in a Parr apparatus. After reduction was complete, the catalyst was removed by filtration through celite and the resulting solution was immediately combined with dicyclohexylcarbodiimide (0.49 g, 2.38 mmol), 1-hydroxybenzotriazole mono-hydrate (0.32 g, 2.37 mmol), the product of Preparation 1L (0.93 g, 2.39 mmol) and additional tetrahydrofuran (60 mL). After stirring overnight at ambient temperature, the mixture was concentrated and the residue slurried in ethyl acetate and filtered. The filtrate was concentrated and the residue purified by silica gel chromatography (chloroform/methanol) to provide 0.76 g (50%) of the desired product as an off white solid which was used without further purification.

Compound 59

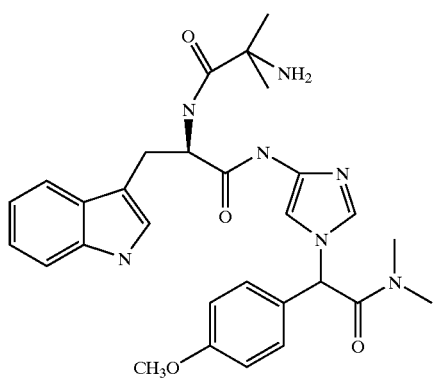

To a solution of the compound of preparation 19 (0.74 g, 115 mmol) stirring at room temperature in dichloromethane (30 mL) was added triflouroacetic acid (10 mL). After 2 h, the mixture was concentrated and the residue treated with excess aqueous sodium bicarbonate. The resulting mixture was extracted with ethyl acetate and the combined organic extracts were concentrated. The residue was purified by flash chromatography (silica gel, chloroform/methanol) to provide 0.23 g (37%) of the desired product: ESMS: (M+H)+ 546.6. $^1$H NMR was consistent with product. Anal. Calcd. for $C_{29}H_{35}N_7O_4 \cdot 0.25$ CHCl3: C, 61.05; H, 6.17; N, 17.04. Found: C, 61.41; H, 6.32; N, 16.52. The isomeric mixture (2.00 g) was separated as described in Example 10 to provide 0.73 g of isomer 1 ($t_R$=9.85 min) and 0.82 g of isomer 2 ($t_R$=12.87 min). To a solution of isomer 2 (0.82 g, 1.50 mmol) stirring in ethyl acetate and methanol was added a saturated solution of hydrochloric acid in ethyl acetate. The resulting mixture was concentrated to provide 0.84 g of the desired product: ESMS: (M+H)+546.2, 547.3. $^1$H NMR was consistent with product. Anal. Calcd. for $C_{29}H_{35}N_7O_4 \cdot$ 3.0 HCl: C, 53.18; H, 5.85; N, 14.97. Found: C, 53.73; H, 6.03; N, 14.04.

EXAMPLE 2-45

Preparation 34

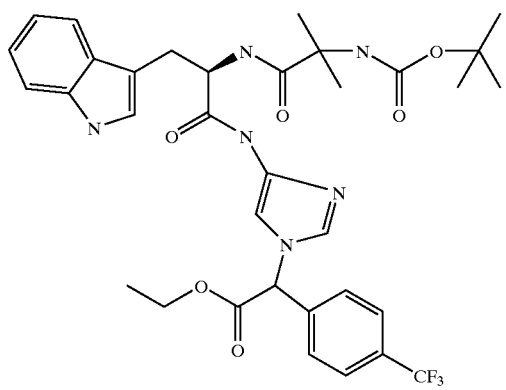

Hydrogenation of the product of Preparation 8 (1.75 g, 5.1 mmol) with 10% palladium on carbon (1.4 g) in tetrahydrofuran (60 mL) followed by reaction with the product of Preparation 1L (2.0 g, 5.1 mmol), 1-hydroxybenzotriazole (0.76 g, 5.6 mmol) and 1-(3-dimethylaminopropyl)-3-ethylcarbodiimide (1.16 g, 5.6 mmol) as described in Preparation 5A gave 2.51 g (72%) of the desired product as a tan foam: $^1$H-NMR (d, DMSO) 1.15–1.35 (m, 18H), 3.05–3.15 (m, 2H), 4.25 (m, 2H), 4.65 (br s, 1H), 6.62 (s, 1H), 6.85 (m, 1H), 6.95–7.08 (m, 2H), 7.20–7.30 (m, 2H), 7.40–7.55 (m, 2H), 7.55–7.65 (m, 3H), 7.82 (d, J=8.3 Hz, 2H), 10.20 (br s, 1H), 10.75 (br s, 1H); MS (ion spray) 685 (M+1); Anal. Calc'd for $C_{34}H_{39}F_3N_6O_6 \cdot H_2O$: C, 58.11; H, 5.88; N, 11.96. Found: C, 58.15; H, 5.59; N, 11.92.

Preparation 35

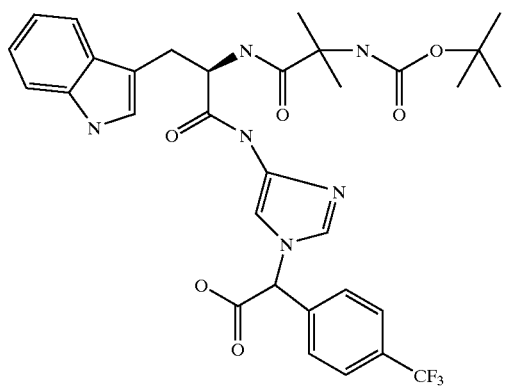

Reaction of the product of Preparation 34 (2.2 g, 3.2 mmol) and lithium hydroxide (0.1 g, 3.9 mmol) in dioxane (50 mL) and water (25 mL) as described in Preparation 5 gave 2.1 g (100%) of the desired product as a tan foam: ¹H-NMR (d, DMSO), 1.15–1.35 (m, 15H), 3.05–3.15 (m, 2H), 4.65 (br s, 1H), 6.97 (s, 1H), 6.90 (m, 1H), 6.98–7.10 (m, 2H), 7.20–7.30 (m, 2H), 7.40–7.55 (m, 4. 2H), 7.57–7.64 (m, 3H), 7.80 (d, J=8.3 Hz, 2H), 10.20 (br s, 1H), 10.75 (br s, 1H), 13.80 (br s, 1H); MS (ion spray) 657.4 (M+1); Anal. Calc'd for $C_{32}H_{35}F_3N_6O_6$: C, 58.53; H, 5.37; N, 12.80. Found: C, 59.28; H, 5.17; N, 12.65.

Preparation 36

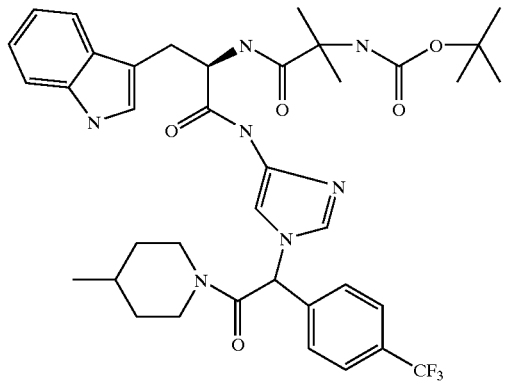

Reaction of the product of Preparation 35 (0.7 g, 1.1 mmol), 4-methylpiperidine (0.13 mL, 1.1 mmol), 1-hydroxybenzotriazole (0.17 g, 1.2 mmol) and 1-(3-dimethylaminopropyl)-3-ethylcarbodiimide (0.26 g, 1.2 mmol) in N,N-dimethylformamide (30 mL) as described in Preparation EX4A provided 0.47 g (58%) of the desired product as a tan foam: ¹H-NMR (d, DMSO) 0.78 (d, J=6.4 Hz, 1.5H), 0.86 (d, J=6.3 Hz, 1.5H), 1.15–1.35 (m, 18H), 1.50–1.70 (m, 3H), 2.60–2.70 (m, 2H), 3.00–3.15 (m, 2H), 3.30 (m, 1H), 4.40 (m, 1H), 4.65 (m, 1H), 6.85–6.95(m, 2H), 7.00–7.10 (m, 2H), 7.17–7.30 (m, 2H), 7.40–7.60 m, 4H), 7.75–7.85 (m, 2H), 10.20 (br s, 1H), 10.75 (br s, 1H); MS (ion spray) 738.5 (M+1); Anal. Calc'd for $C_{38}H_{46}F_3N_7O_5 \cdot 1H_2O$: C, 60.39; H, 6.40; N, 12.97. Found: C, 60.18; H, 6.21; N, 12.99.

Compounds 60 and 61

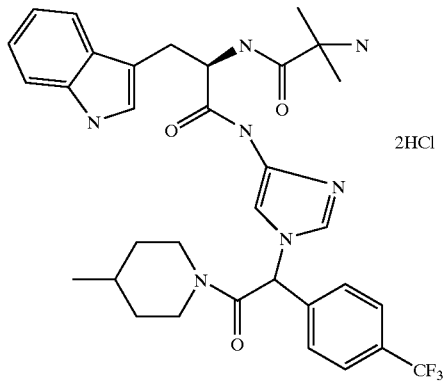

2HCl

Reaction of the product of Preparation 36 (4.8 g, 6.5 mmol) and trifluoroacetic acid (16 mL) in dichloromethane (40 mL) as described in Example 4 gave 2.0 g (44%) of the desired mixture as a tan foam. Purification by HPLC (8 x 15 cm Prochrom column packed with Kromasil CHI-DMP chiral phase with an eluent mixture of 3A alcohol (13% by v), dimethylethylamine (0.2% by v) in heptane at a flow rate of 250 mL/min) gave 0.5 g (12%) of isomer 1 and 0.4 g (9%) of isomer 2. Compound 60 (isomer 1) ¹H-NMR (d, DMSO) 0.77 (d, J=6.5 Hz, 1.5H), 0.87 (d, J=6.0 Hz, 1.5H), 1.00 (m, 1H), 1.32 (s, 3H), 1.50 (s, 3H), 1.50–1.70 (m, 2H), 2.72 (m, 1H), 3.00–3.30 (m, 4H), 3.75 (m, 1H), 4.05–4.33 (m, 3H), 4.20 (m, 1H), 4.78 (m, 1H), 6.94 (m, 3H), 7.20 (s, 1H), 7.30–7.40 (m, 2H), 7.55–7.70 (m, 2H), 7.75–8.00 (m, 4H), 8.05–8.15 (m, 2H), 8.50 (m, 1H), 10.86 (s, 1H), 11.05 (s, 1H); $t_R$=6.01 min; MS (ion spray) 638.2 (M+1). Compound 61 (isomer 2) ¹H-NMR (d, DMSO) 0.77 (d, J=6.5 Hz, 1.5H), 0.87 (d, J=6.0 Hz, 1.5H), 1.00 (m, 1H), 1.32 (s, 3H), 1.50 (s, 3H), 1.50–1.70 (m, 2H), 2.72 (m, 1H), 3.00–3.30 (m, 4H), 3.75 (m, 1H), 4.05–4.33 (m, 3H), 4.20 (m, 1H), 4.78 (m, 1H), 6.94 (m, 3H), 7.20 (s, 1H), 7.30–7.40 (m, 2H), 7.55–7.70 (m, 2H), 7.75–8.00 (m, 4H), 8.05–8.15 (m, 2H), 8.50 (m, 1H), 10.86 (s, 1H), 11.05 (s, 1H); $t_R$=7.5 min; MS (ion spray) 638.2 (M+1).

EXAMPLE 2-46

Preparation 345

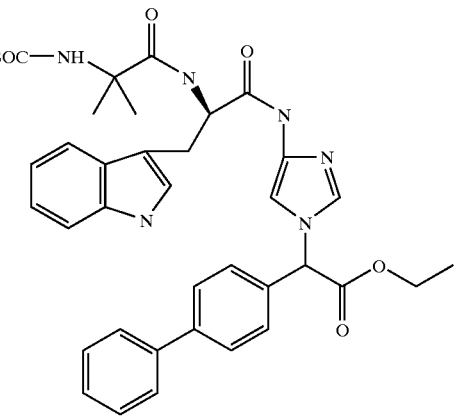

To a mixture of the product of Preparation 11 (6.0 g, 17.1 mmol) and 10% palladium on carbon (6.0 g) in tetrahydrofuran (100 mL). The reaction mixture was placed under a hydrogen atmosphere (40 psi) using a Parr apparatus for 30 min then filtered through Celite. The resulting solution was then added to a previously prepared mixture of the product of Preparation 1L (6.66 g, 17.1 mmol), 1-hydroxybenzotriazole (2.31 g, 17.1 mmol), and 1,3 dicyclohexylcarbodiimide (3.53 g, 17.1 mmol) in tetrahydrofuran (75 mL). After 16 h at room temperature, the reaction mixture was concentrated and the crude material purified by flash chromatography (silica gel, 4% methanol/dichloromethane) to yield 6.17 g (52%) of the desired product as a brown foam: ¹H NMR consistent with structure; MS (ion spray) 693 (M+1).

Preparation 346

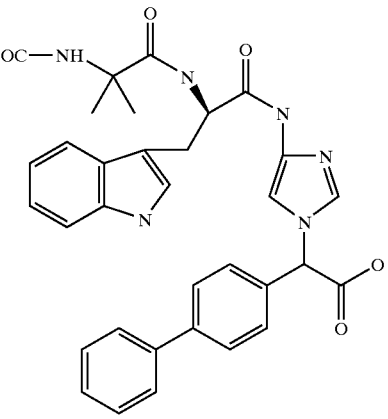

To a solution of the product Preparation 345 (46 g, 6.64 mmol) stirring in tetrahydrofuran (100 mL) at room temperature was added a solution of lithium hydroxide in water (40 mL of 1M). After 30 min, the reaction mixture was acidified with 5N HCl (8.5 mL). The resulting mixture diluted with water and extracted with ethyl acetate. The combined organic extracts were dried over sodium sulfate and concentrated to yield 4.4 g (99%) of the desired product as a yellow foam.

Preparation 347

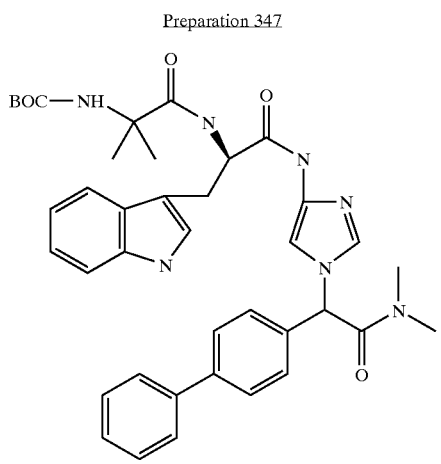

To a solution of the product Preparation 346 (4.0 g, 6.02 mmol) stirring in tetrahydrofuran (50 mL) at room temperature was added 1-hydroxybenzotriazole (813 mg, 6.02 mmol) and 1,3 dicyclohexylcarbodiimide (1.24 g, 6.02 mmol). After 15 min, dimethylamine (3.0 mL of a 2M soln in tetrahydrofuran, 6.02 mmol) was added. After stirring for 16 h in a sealed flask, the reaction mixture was filtered and concentrated. The resulting crude material was purified by flash chromatography (silica gel, 5% methanol/dichloromethane) to yield 2.79 g (68%) of the desired product as a yellow foam.

Compounds 62 and 63

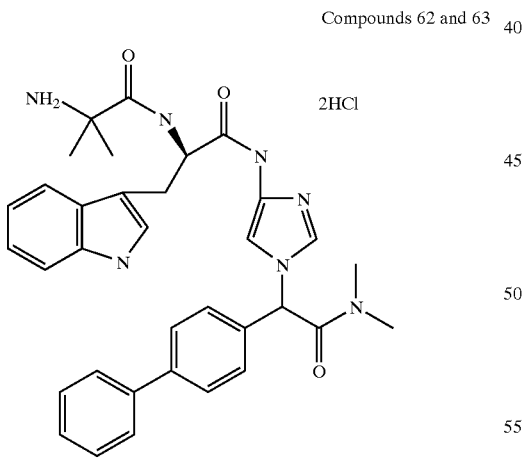

To the product of Preparation 347 (3.4 g, 5.0 mmol) was added a saturated solution of HCl(g)/acetic acid (50 mL). After 1.5 h, the reaction mixture was concentrated then partitioned between ethyl acetate and saturated sodium bicarbonate. The organic layer was removed, dried over sodium sulfate and concentrated to yield 2.45 g (84%) of the free base as a light yellow foam. The diastereomeric material (2.45 g) was chromatographed on an 8×15 cm Prochrom column packed with Kromsil CHI chiral phase using an eluent mixture of 3A alcohol and dimethylethylamine in heptane to provide the individual diastereomers in pure form: $^1$H NMR consistent with product; MS (ion spray) 592 (M+1); Anal. Calcd. for $C_{34}H_{37}N_7O_3$: C, 69.02; H, 6.30; N, 16.57. (Found) C, 67.93; H, 6.29; N, 15.80.

Compound 62 (Isomer 1) To a solution of the purified isomer in ethyl acetate was added a saturated solution of hydrochloric acid in ethyl acetate. The resulting slurry was concentrated to dryness to yield 992 mg (37%) of the desired product as an off-white solid: $^1$H NMR consistent with product; MS (ion spray) 592 (M+1); Anal. Calcd. for $C_{34}H_{37}N_7O_3 \times 2$ HCl: C, 61.44; H, 5.91; N, 14.75. (Found) C, 59.54; H, 5.92; N, 13.76.

Compound 63 (Isomer 2) To a solution of the purified isomer in ethyl acetate was added a saturated solution of hydrochloric acid in ethyl acetate. The resulting slurry was concentrated to dryness to yield 1.17 g (40%) of the desired product as an off-white solid: $^1$H NMR consistent with structure; MS (ion spray) 592 (M+1); Anal. Calcd. for $C_{34}H_{37}N_7O_3 \times 2$ HCl: C, 61.44; H, 5.91; N, 14.75. (Found) C, 59.03; H, 6.04; N, 13.84.

EXAMPLE 2-47

2-[4-((2R)-2-{2-[(Tert-butoxy)carbonylammol-2-methylpropanoylamino)-3-indol-3-ylpropanoylamino) imidazolyll-2-(2-naphthyl)acetic Acid

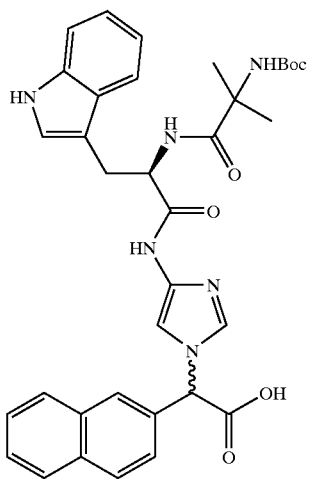

A solution consisting of ethyl 2-[4-((2R)-2-(2-[(tert-butoxy)carbonylamino]-2-methylpropanoylamino)-3-indol-3-ylpropanoylamino)imidazolyl]-2-(2-naphthyl)acetate (1.52 grams, 2.28 mmol), lithium hydroxide (0.11 grams, 4.56 mmol), dioxane (10 mL), and water (10 mL) was stirred at ambient temperature until complete as determined by hplc (30 minutes). The reaction mixture was concentrated to dryness and the residue was dissolved in water (20 mL). The aqueous solution was adjusted to a pH of 3 using a 10% sodium bisulfate solution and extracted with ethyl acetate (3×25 mL). The organic layers were combined, dried using sodium sulfate, filtered, and concentrated to give 1.34 grams (92%) of 2-[4-((2R)-2-(2-[(tert-butoxy)carbonylamino]-2-methyl propanoylamino}-3-indol-3-ylpropanoylamino) imidazolyl]-2-(2-naphthyl)acetic acid.

125

N-[(1R)-2-Indol-3-yl-1-(N-{1-[2-(4-methylpiperidinyl)-1-(2-naphthyl)-2-oxoethyl]imidazol-4-yl}carbamoyl)ethyl]-2-[(tert-butoxy)carbonylamino]-2-methylpropanamide

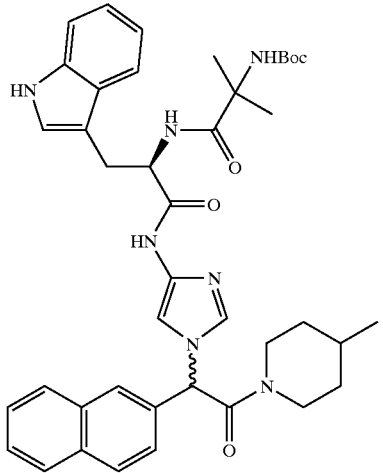

A solution consisting of 2-[4-((2R)-2-{2-[(tert-butoxy)carbonylamino]-2-methylpropanoylarmino}-3-indol-3-yl propanoylamino)imidazolyl]-2-(2-naphthyl)acetic acid (0.55 grams, 0.861 mmol), 4-methylpiperidine (0.085 grams, 0.861 mmol), 1,3-dicyclohexylcarbodiimide (0.195 grams, 0.947 mmol), 1-hydroxybenzotriazole hydrate (0.116 grams, 0.861 mmol) and dimethyl formamide (5 mL) was stirred at ambient temperature until complete as determined by hplc (7 hours). The reaction mixture was diluted with water (40 mL) and extracted with ethyl acetate (4×25 mL). The organic extracts were combined, washed with saturated sodium chloride solution (2×35 mL), dried using sodium sulfate, and concentrated to an oil. The crude product was purified using preparative reverse phase hplc to give 0.32 grams (52%) of N-[(1R)-2-indol-3-yl-1-(N-{1-(2-(4-methyl piperidyl)-1-(2-naphthyl)-2-oxoethyl]imidazol-4-}carbamoyl)ethyl]-2-((tert-butoxy)carbonylammol-2-methylpropanamide. $^1$H nmr (CDCl$_3$): 0.76–0.77 (d, 2H), 0.91–0.95 (m, 2H), 1.23–1.36 (m, 18H), 1.54 (mn, 1H), 1.67 (m, 1H), 2.70–2.72 (m, 2H), 3.25–3.29 (m, 2H), 3.68 (m, 1H), 4.55–4.70 (m, 1H), 4.98 (m, 1H), 6.24 (m, 1H), 6.81–6.83 (d, 1H), 6.92 (m, 1H), 7.00–7.01 (m, 1H), 7.18–7.28 (m, 3H), 7.37–7.55 (m, 5H), 7.76–7.83 (m, 4H), 8.80 (s, broad, 1H), 10.38 (s, broad, 1H). $^{13}$C nmr (CDCl$_3$): δ 14.60, 19.32, 19.47, 21.41, 21.83, 21.90, 25.39, 25.55, 26.04, 28.56, 28.63, 28.84, 31.05, 31.16, 31.21, 33.98, 34.08, 34.29, 34.69, 43.42, 46.28, 46.52, 49.38, 54.55, 56.99, 60.77, 62.31, 69.97, 71.02, 108.80, 110.24, 111.79, 119.02, 119.36, 121.86, 124.10, 125.99, 127.12, 127.36, 127.97, 128.08, 128.10, 128.16, 128.33, 128.63, 128.71, 129.77, 132.26, 133.63, 133.75, 134.02, 136.58, 137.29, 155.16, 157.65, 166.07, 166.18, 166.22, 166.34, 169.40, 171.52, 175.12.

126

Compound 64

N-[(1R)-2-Indol-3-yl-1-(N-{1-[2-(4-methylpiperidyl)-1-(2-naphthyl)-2-oxoethyl]imidazol-4-yl)carbamoyl)ethyl]-2-amino-2-methylpropanamide Dihydrochloride

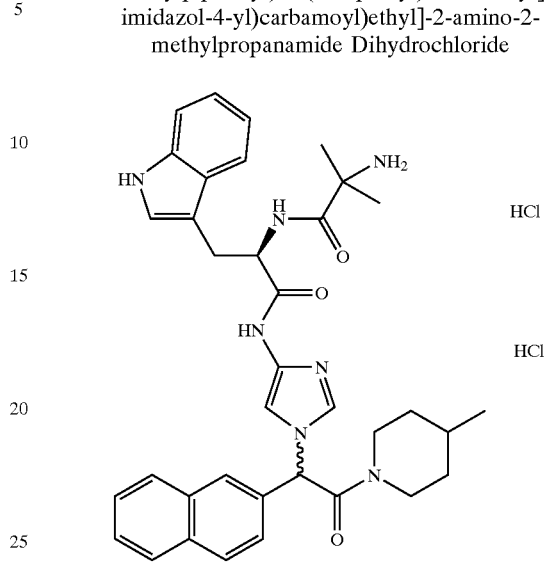

A solution consisting of N-[(1R)-2-indol-3-yl-1-(N-{1-[2-(4-methylpiperidyl)-1-(2-naphthyl)-2-oxoethyl]imidazol-4-yl}carbamoyl)ethyl[-2-[(tert-butoxy)carbonylamino]-2-methyl propanamide (0.32 grams, 0.445 mmol) and anisole (0.25 mL) dissolved in methylene chloride (20 mL) was added trifluoroacetic acid (2.5 mL). The resulting reaction mixture was stirred at ambient temperature until complete as determined by hplc (2.5 hours). The reaction mixture was concentrated to dryness. The residue was dissolved in methanol (5 mL) and applied to a Varian Mega Bond Elut SCX ion exchange column (5 gram). The column was washed with methanol (50 mL). The product was eluted from the column with 2N ammonia in methanol (30 mL). The eluent was concentrated to dryness to give the free base (0.28 grams). A 1.95 M solution of anhydrous HCl in ethyl acetate (0.456 mL, 0.89 mmol) was added to the free base which was dissolved in ethyl acetate (10 mL). The resulting precipitate was collected by filtration and dried in vacuum to give 0.27 grams (87%) of N-[(IR)-2-indol-3-yl-1-(N-(1-[2-(4-methylpiperidyl)-1-(2-naphthyl)-2-oxoethyl]imidazol-4-yl}carbamoyl)ethyl]-2-amino]-2-methylpropanamide dihydrochloride. MS (FIA) m/z 620.7 [(M+H)$^+$]. Anal. calcd. for $C_{36}H_{41}N_7O_3 \cdot 2HCl \cdot 1/2H_2O$: C: 61.62; H: 6.32; N: 13.97. Found: C: 61.42; H: 6.18; N: 13.62. Anal. calcd. exact mass for $C_{36}H_{42}N_7O_3$ [(M+H)$^+$]=620.3349. Exact mass found by mass spectrometry: $C_{36}H_{42}N_7O_3$ [(M+H)$^+$]=620.3355.

$^1$H nmr (DMSO-d$_6$): 0.65–0.67 (d, 2H), 0.89–0.90 (d, 2H), 1.16–1.24 (m, 2H), 1.35–1.36 (d, 4H), 1.51–1.53 (d, 4H), 1.63–1.65 (m, 1H), 2.68–2.74 (m, 1.5H), 3.08 (t. 0.5H), 3.17–3.19 (m, 1H), 3.26–3.27 (m, 1H), 3.71–3.82 (m, 1H), 4.40–4.55 (m, 1H), 4.71–4.72 (t, 1H), 6.90–7.00 (m, 1H), 7.02–7.04 (m, 1H), 7.26–7.33 (m, 3H), 7.52 (m, 1H), 7.59–7.62 (m, 3H), 7.74 (m, 1H), 7.98–8.09 (m, 4H), 8.31–8.32 (d, 3H), 8.49–8.61 (m, 1H), 8.66–8.68 (d, 1H); 10.94 (s, 1H), 11.35 (s, 1H).

EXAMPLE 2-48

N-[(1R)-2-Indol-3-yl-1-(N-{1-(2-(4-methylpiperidyl)-2-oxo-1-phenylethyl]imidazol-4-yl)carbamoyl)ethyl]-2-[(tert-butoxy)carbonylamino]-2-methylpropanamide

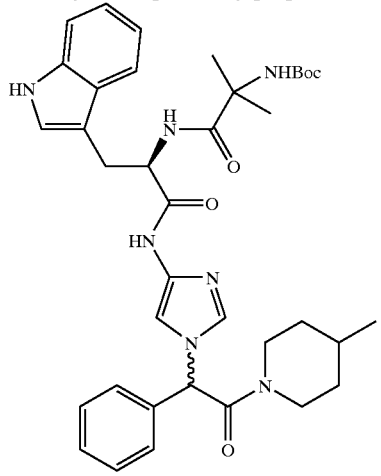

This compound was obtained from the hydrolysis of ethyl 2-[4-((2R)-2-(2-[(tert-butoxy) carbonylamino)-2-methyl propanoylamino}-3-indol-3-ylpropanoylamino) imidazolyl]-2-phenylacetate and subsequent reaction with 4-methyl piperidine in 84% yield after Biotage Flash 40M purification using dichloromethane:methanol (24:1) as the eluent. MS (FIA) m/z 670.5 [(M+H)$^+$]. $^1$H nmr (CDCl$_3$): δ 0.74–0.75 (d, 2H), 0.89–0.90 (d, 2H), 1.17–1.32(m, 18H), 1.53–1.63 (m, 3H), 2.66–2.70 (m, 1H), 3.05 (t, 1H), 3.15–3.20 (m, 1H), 3.69–3.83 (m. 1H), 4.36–4.49 (m, 1H), 4.67 (s, broad, 1H), 6.90–6.93 (m, 2H), 7.01–7.04 (m, 2H), 7.11 (s, 1H), 7.26–7.32 (m, 2H), 7.40–7.54 (m, 5H), 7.67 (s, broad, 1H), 8.16 (m, broad, 1H), 10.49 (s, broad, 1H), 10.84 (s, 1H).

Compound 65

N-[(1R)-2-Indol-3-yl-1-(N-{1-[2-(4-methylpiperidyl)-2-oxo-1-phenylethyl]imidazol-4-yl)carbamoyl)ethyl]-2-amino-2-methyl propanamide Dihydrochloride

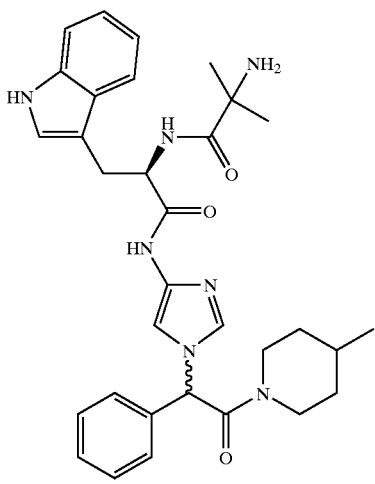

This compound was obtained from N-[(1R)-2-indol-3-yl-1-(N-{1-[2-(4-methylpiperidyl)-2-oxo-1-phenylethyl]imidazol-4-yl)carbamoyl)ethyl]-2-[(tert-butoxy)carbonylamol-2-methyl propanamide as a red foam in 100% yield. MS (FIA) m/z 570.5 [(M+H)$^+$]. $^1$H nmr (d-MeOH): δ 0.81–0.82 (d, 2H), 0.98–0.99 (d, 2H), 1.18–1.21 (m, 2H), 1.34–1.37 (m, 1H), 1.43 (s, 3H), 1.61 (s, 6H), 1.71 (t, 1H), 2.73–2.76 (m, 1.5H), 3.14 (t, 0.5H), 3.27–3.33 (m, 1H), 3.40–3.44 (m, 1H), 3.61–3.65 (m, 1H), 3.75–3.77 (d, 1H), 4.45–4.60 (m, 1H), 4.81 (s, broad, 4H), 6.94–6.99 (m, 1.5H), 7.06–7.07 (m, 1.5H), 7.19 (s, 1H), 7.31–7.35 (m, 2H), 7.52–7.61 (m, 6H), 8.62–8.65 (d, 1H).

EXAMPLE 2-49

N-((1R)-2-Indol-3-yl-1-{N-[1-(2-oxo-1-phenyl-2-pyrrolidinylethyl)imidazol-4-yl]carbamoyl}ethyl)-2-[(tert-butoxy)carbonylamino]-2-methylpropanamide

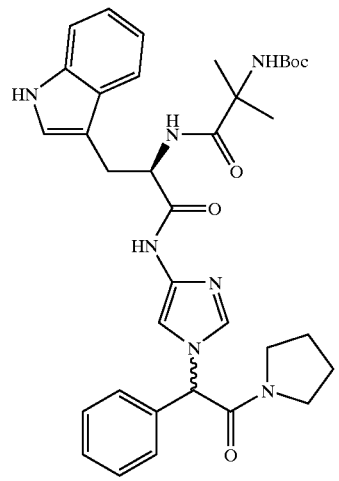

This compound was obtained from the hydrolysis of ethyl 2-[4-((2R)-2-{2-[(tert-butoxy) carbonylamino]-2-methyl propanoylamino}-3-indol-3-ylpropanoylamino) indazolyl]-2-phenylacetate and subsequent reaction with pyrrolidine in 80% yield after purification by flash chromatography using dichloromethane : methanol (19:1) as the eluent. $^1$H nmr (CDCl$_3$): δ 1.10–1.40 (m, 15H), 1.67–1.92 (m, 3H), 2.92–3.60 (m, 5H), 4.90 (s, broad, 1H), 5.33 (s, broad, 1H), 5.85 (d, 1H), 6.80–7.05 (m, 3H), 7.13–7.39 (m, 10H), 7.44–7.80 (m, 2H), 8.96 (s, broad, 1H), 10.20 (s, broad, 1H). $^{13}$C nmr (CDCl$_3$): δ 14.25, 21.11, 24.02, 25.63, 26.08, 28.24, 33.87, 46.39, 46.64, 54.28, 56.67, 60.46, 63.07, 63.09, 108.33, 109.73, 110.69, 111.47, 118.36, 118.56, 119.05, 121.57, 123.77, 125.01, 126.42, 127.60, 128.51, 129.38, 133.14, 133.85, 136.23, 136.45, 136.49, 165.79, 165.85, 169.17, 174.87.

Compound 66

N-((1R)-2-Indol-3-yl-1-{N-[1-(2-oxo-1-phenyl-2-pyrrolidinyl ethyl)imidazol-4-yl]carbamoyl)ethyl)-2-amino-2-methyl propanamide Bistrifluoroacetic Acid

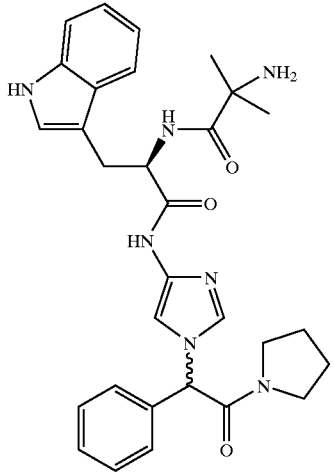
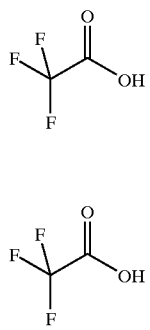

This compound was obtained from N-((1R)-2-indol-3-yl-1-{N-[1-(2-oxo-1-phenyl-2-pyrrolidinylethyl)imidazol-4-yl]carbamoyl)ethyl)-2-[(tert-butoxy)carbonylamino]-2-methylpropanamide as a white solid in 50% yield. MS (FD+) m/z 541 (M+). Anal. calcd. for $C_{30}H_{35}N_7O_3 \cdot 2C_2HF_3O_2$: C: 53.06; H: 4.85; N: 12.74. Found: C: 52.93; H: 4.88; N: 12.55. $^1$H nmr (DMSO-$d_6$): 8 1.29 (s, 3H), 1.46–1.48 (d, 3H), 1.72–1.88 (m, 4H), 2.94 (m, 1H), 3.06–3.07 (m, 1H), 3.19–3.20 (m, 1H), 3.40–3.41 (d, 2H), 3.67–3.69 (m, 1H), 4.78 (s, broad, 1H), 6.53 (s, 1H), 6.93–6.97 (m, 1H), 7.06 (m, 1H), 7.20 (d, 1H), 7.31–7.36 (m, 2H), 7.42–7.42 (m, 4H), 7.73–7.80 (m, 2H), 8.01 (s, broad, 2H), 8.36–8.38 (d, 1H), 10.82–10.85 (d, 2H).

EXAMPLE 2-50

Compound 67

N-[(1R)-1-(N-{1-[(N,N-Dimethylcarbamoyl)-2-naphthylmethyl) imidazol-4-ylicarbamoyl)-2-indol-3-ylethyl]-2-amino-2-methyl propanamide Dihydrochloride

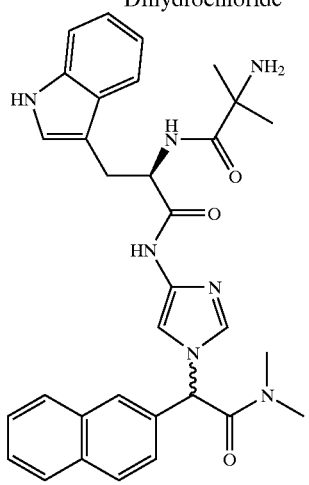

This compound was obtained from the reaction of 2-[4-((2R)-2-{2-[(tert-butoxy)carbonylamino]-2-methylpropanoylamino}-3-indol-3-ylpropanoylamino) imidazolyl]-2-(2-naphthyl)acetic acid and dimethylamine followed by deprotection according to the general procedure as an off white solid in 90% yield. MS (FIA) m/z 566.6 (M+H)+ $^1$H nmr (DMSO-$d_6$) δ 1.36–1.37 (d, 3H), 1.51–1.53 (d, 3H), 2.92 (s, 3H), 2.99 (s, 3H), 3.19–3.22 (m, 1H), 3.27–3.31 (m, 1H), 4.68–4.73 (m, 1H), 6.90–6.94 (m, 1H), 6.97–7.03 (m, 1H), 7.29–7.33 (m, 2H), 7.38 (s, 1H), 7.55 (s, 1H), 7.60–7.62 (t, 3H), 7.73 (t, 1H), 7.98–8.06 (m, 4H), 8.36–8.37 (d, 3H)., 8.72–8.74 (d, 2H), 10.97 (s, 1H), 11.49 (s, 1H).

EXAMPLE 2-51

2-(4-Nitroimidazolyl)-2-phenylacetic acid

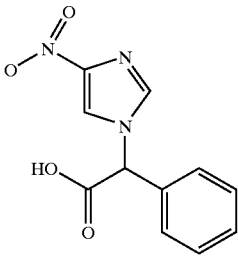

1

Lithium hydroxide (18.1 g, 750 mm, 2 eq) was added to a stirred slurry of ethyl 2-(4-nitroimidazoyl)-2-phenylacetate (104 g, 379 mm) in 250 mL of ethanol. Deionized water was added to the resulting mixture and the stirring was continued for 4 hours. The ethanol was removed under vacuum and the resulting aqueous soltion was washed with 100 mL of diethyl ether. The aqueous layer was diluted with 100 mL of deionized water and the pH was adjusted to 1.8 with concentrated HCl after cooling to 12° C. The resulting slurry was stirred for 30 minutes at less than 5 degrees and filtered. The wet cake was washed with 100 mL of deionized water and dried under a stream of air on the filter overnight to yield 90.34 g (96%) of a brown solid. The product may be recrystallized from isopropyl alcohol to give 72.31 g (80% recovery, 77% overall yield) of a tan solid. Elemental analysis: Calculated: %C 53.45, %H 3.67, %N 16.97; Found: %C 53.67, %H 3.79, %N 16.65. MS: 247 (M$^4$): IR (cm$^{-1}$)1719; H$^1$ nmr (d$^6$ DMSO): d 6.51 (s, 1H), 7.43–7.55 (m,5H), 7.95 (s,1H), 8.40 (s, 1H).

2- (4-Nitroimidazolyl)-2-phenyl-1-pyrrolidinylethane-1-one

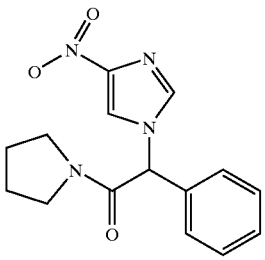

3

N-Methyl morpholine (22.25 ml, 2 eq) was added to a stirred solution of 2-(4-nitroimidazolyl)-2-phenylacetic acid (1) (25.03 g, 101.2 mm) and 2-chloro-4,6-dimethoxy-1,3,5-triazine (18.1 g, 101.2 mm, 1.0 eq) in 50 ml of anhydrous tetrahydrofuran at 25° C. After stirring the reaction mixture at ambient temperature for 1 h, 7.2 mL (101.2 mm, 1.0 eq) of pyrrolidine was added dropwise. The reaction was stirred at room temperature for 2 hours. The reaction mixture was quenched by the addition of 200 mL of ethyl acetate and 200 mL of 1M HCl. The layers were separated and the organic layer was washed with 100 mL of saturated sodium bicarbonate solution. The mixture resulting from the bicarbonate wash was diluted 1:1 with deionized water to dissolve the resulting solids and the layers were separated. The organic layer was washed with brine, dried over magnesium sulfate, filtered and the volatiles were removed under vacuum to give a brown foam. This foam was dissolved in methanol, diethyl ether and methylene chloride. Evaporation of the solvents overnight yielded a brown solid which was slurried in 200 mL of diethyl ether for 4 hours. The resulting slurry was filtered and the cake was washed with diethyl ether. The solids were dried under vacuum overnight to give a cream colored product (21.68 g, 71%) d (d$^6$ DMSO):1.69–1.84 (m, 3H), 2.80–2.85 (m, 0.7H), 3.32–3.41 (m, 3.6H), 3.64–3.67 (m, 0.7H), 6.65 (s, 1H), 7.42–7.50 (m, 5H), 7.83 (s, 1H), 8.22 (s, 1H)

2-(4-aminoimidazolyl)-2-phenyl-1-pyrrolidinylethan-1-one, dihydrochloride

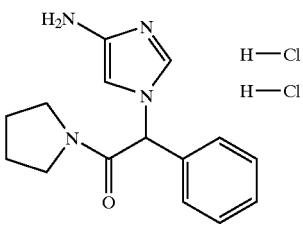

Ethanol (200 mL) was added to a mixture of 2-(4-nitroimidazolyl)-2-phenyl-1-pyrrolidinylethan-1-one (3) (0.752 g, 2.8 mm) and 10% Pd on carbon (75 mg) in a Bradley hydrogenation apparatus. The stirred reaction mixture was subjected to a 60 psi H$_2$ atmosphere and warmed to 60° C. After 2 hours, the reaction mixture was cooled to room temperature and the catalyst was removed by filtration. Anhydrous HCl gas was added to the filtered solution until saturation. The volatiles were then removed under vacuum to give a light yellow foam. Diethyl ether and methylene chloride (25:1) were added to the foam and the resulting mixture was stirred overnight to achieve crystallization. The resulting slurry was filtered and the cake was washed with diethyl ether. The cake was dried under vacuum to give 0.659 g (93%) of a yellow solid. LGD 208.

N-((1R)-2-indol-3-yl-1-(N-[1-(2-oxo-1-phenyl-2-pyrrolidinylethyl)imidazol-4-yl]carbamoyl}ethyl)-2-[(tert-butoxy)carbonylamino]-2-methylpropanamide

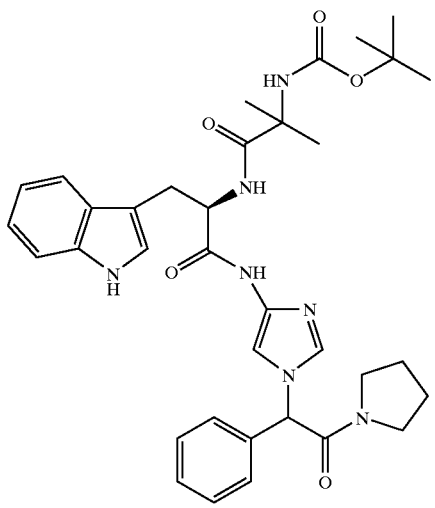

N-Methyl morpholine (0.28 mL, 8.32 mm, 1 eq) was added to a stirred slurry of 2-chloro-4,6-dimethoxy-1,3,5-triazine (0.46 g, 2.57 mm, 1 eq) and (2R)-2-(2-[(tert-butoxy)carbonylamino]-2-methylpropanoylamino}-3-indol-3-ylpropanoic acid (1 g, 2.57 mm) in 10 mL of anhydrous tetrahydrofuran cooled to less than 0° C. After 1.5 hours, 2-(4-aminoimidazolyl)-2-phenyl-1-pyrrolidinylethan-1-one, hydrochloride (0.97 g, 2.82 mm, 1.1 eq) was added and stirring was continued at ice bath temperatures. The reaction was stirred for 4 hours and quenched by the addition of 15 mL of deionized water and ethyl acetate. The ethyl acetate layer was washed with a saturated sodium bicarbonate solution, dried over magnesium sulfate and the volatiles were removed under vacuum to give the crude product as a light purple foam (1.4 g, 84%) The crude product was purified by preparative chromatography to provide 0.52 g (31.5%) of the product as a foam. $^1$H nmr (CDCl$_3$): δ 1.10–1.40 (m, 15H), 1.67–1.92 (m, 3H), 2.92–3.60 (m, %H), 4.90 (s, broad, 1H), 5.33 (s, broad, 1H), 5.85 (d, 1H), 6.80–7.05 (m, 3H), 7.13–7.39 (m, 10H), 7.44–7.80 (m, 2H), 8.96 (s, broad, 1H), 10.20 (s, broad, 1H).

EXAMPLE 2-52

Compound 68

N-((1R)-2-indol-3-yl-1-(N-[1-(2-oxo-1-phenyl-2-pyrrolidinylethyl)imidazol-4-yl]carbamoyl}ethyl)-2-amino-2-methylpropanamide, 2,2,2-trifluoroacetic acid, 2,2,2-trifluoroacetic acid salt

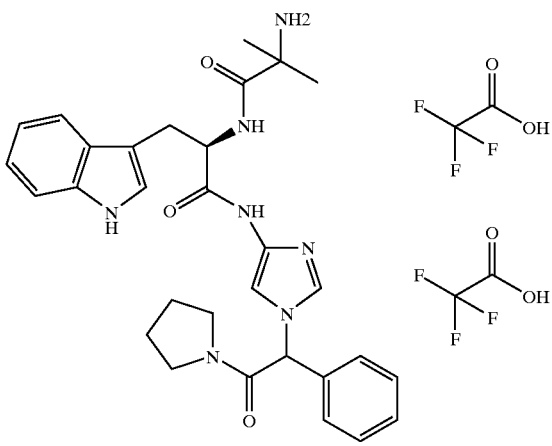

Trifluoroacetic acid (0.57 mL, 7.4 mm, 33 eq) was added to a stirred solution of N-{(1R)-2-indol-3-yl-1-{N-[1-(2-oxo-1-phenyl-2-pyrrolidinylethyl)-imidazol-4-yl] carbamoyl)ethyl)-2-[(tert-butoxy)-carbonylamino]-2-methylpropanamide (8) (0.152 g, 0.22 mm) in 5 mL of methylene chloride. After stirring at room temperature for 3 hours, the reaction mixture was diluted with 50 mL of diethyl ether. The resulting solids were isolated by centrifugation and washed with diethyl ether. The solids were dried under vacuum to give the product as a cream colored solid (0.084 g, 48%) MS (FD+) m/z 541 (M$^+$)Anal. calcd. for C$_{30}$H$_{35}$N$_7$O$_3$.2C$_2$HF$_3$O$_2$: C: 53.06; H: 4.85; N: 12.74. Found: C: 52.93; H: 4.88; N: 12.55. $^1$H nmr (DMSO-d$_6$): δ 1.29 (s, 3H), 1.46–1.48 (d, 3H), 1.72–1.88 (m, 4H), 2.94 (m, 1H), 3.06–3.07 (m, 1H), 3.19–3.20 (m, 1H), 3.40–3.41 (d, 2H), 3.67–3.69 (m, 1H), 4.78 (s, broad, 1H), 6.53 (s, 1H), 6.93–6.97 (m, 1H), 7.06 (m, 1H), 7.20 (d, 1H), 7.31–7.36 (m, 2H), 7.42–7.42 (m, 4H), 7.73–7.80 (m, 2H), 8.01 (s, broad, 2H), 8.36–8.38 (d, 1H), 10.82–10.85 (d, 2H).

EXAMPLE 2-53

Additional Compounds

Additional compounds of Formula I were also synthesizes my methods similar to the foregoing. These compounds included those wherein:

a) R1 is $C_6H_5(CH_2)_3$—, R3 is phenyl, R4 is H, and Y is pyrrolidin-1-yl,
b) R1 is $C_6H_5CH_2OCH_2$—, R3 is phenyl para-substituted by W, W is phenyl, R4 is H, and Y is pyrrolidin-1-yl,
c) R1 is indol-3-ylmethyl, R3 is phenyl para-substituted by W, W is phenyl, R4 is H, and Y is pyrrolidin-1-yl,
d) R1 is indol-3-ylmethyl, R3 is phenyl para-substituted by W, W is —$OCH_3$, R4 is H, and Y is pyrrolidin-1-yl,
e) R1 is $C_6H_5(CH_2)_3$—, R3 is phenyl para-substituted by W, W is $CF_3$, R4 is H, and Y is 4-methylpiperidin-1-yl,
f) R1 is $C_6H_5(CH_2)_3$—, R3 is phenyl para substituted by W, W is phenyl, R4 is H, and Y is pyrrolidin-1-yl,
g) R1 is $C_6H_5(CH_2)_3$—, R3 is phenyl para substituted by W, W is F, R4 is methyl, and Y is pyrrolidin-1-yl,
h) R1 is $C_6H_5CH_2OCH_2$—, R3 is phenyl para substituted by W, W is F, R4 is methyl, and Y is pyrrolidin-1-yl,
i) R1 is $C_6H_5(CH_2)_3$—, R3 is phenyl para substituted by W, W C, is F, R4 is methyl, and Y is 4-methylpiperidin-1-yl,
j) R1 is $C_6H_5(CH_2)_3$—, R3 is 2-naphthyl, R4 is methyl, and Y is 4-methylpiperidin-1-yl,
k) R1 is $C_6H_5CH_2OCH_2$—, R3 is 2-naphthyl, R4 is methyl, and Y is 4-methylpiperidin-1-yl,
l) R1 is $C_6H_5(CH_2)_3$—, R3 is phenyl para-substituted by W, W is $CF_3$, R4 is methyl, and Y is 4-methylpiperidin-1-yl, and
m) R1 is $C_6H_5CH_2OCH_2$—, R3 is phenyl, R4 is H, and Y is 4-methylpiperidin-1-yl

EXAMPLE 3

Pituitary Cell Culture Assay for Growth Hormone Secretion

Thirty-two 250 g male Sprague-Dawley rats were used for each assay. The animals were killed by decapitation and anterior pituitaries were removed and placed into ice cold culture medium. The pituitaries were sectioned into eighths and enzymatically digested using trypsin (Sigma Chemical) to weaken connective tissue. Pituitary cells were dispersed by mechanical agitation, collected, pooled and then seeded into 24-well plates (300,000 cells/well). After 4 days of culture, the cells formed an even monolayer. Cells were then washed with medium and challenged to secrete GH by the addition of GH secretagogues to the medium. After 15 min at 37° C., the medium was removed and stored frozen until radioimmunoassays for rat GH were performed. Doses of secretagogue were added in quadruplicate. Representative data is provided in Table 1 below. Compounds disclosed herein are active in the assay as described. Both EC50 and efficacy values were calculated by the 4-parameter logistic equation. Such values were pooled and represented as mean +/−standard error, when appropriate.

TABLE 1

| EXAMPLES PART 1 Example # | GH secretion $EC_{50}$ ($\mu M$) |
|---|---|
| 6 | 5.53 |
| 8 | 2.39 |

We claim:

1. A compound selected from the group consisting of the following structurally depicted compounds:

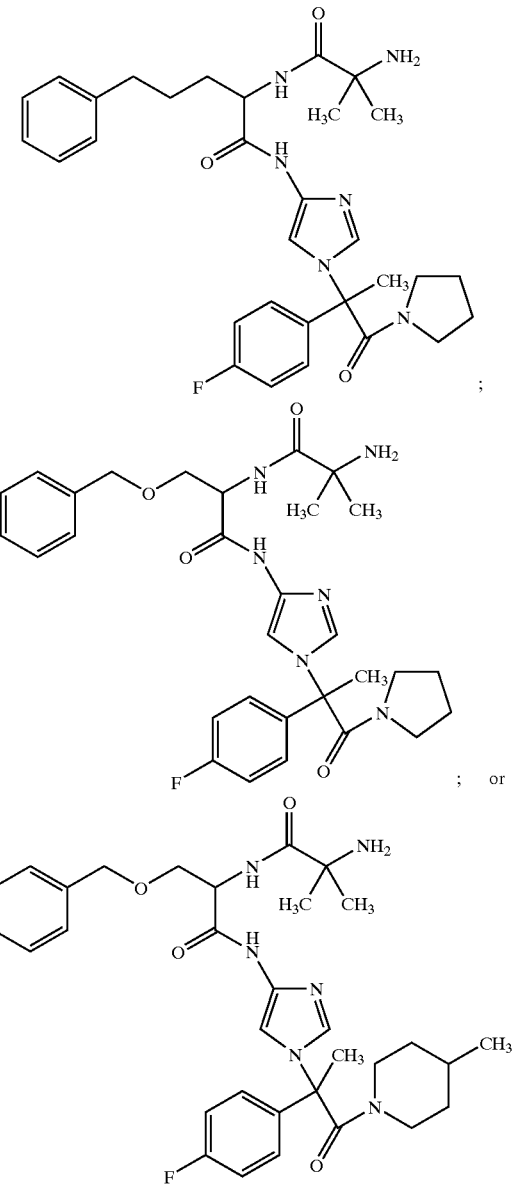

or a pharmaceutically acceptable salt or solvate thereof.

2. A compound according to claim 1 having the formula

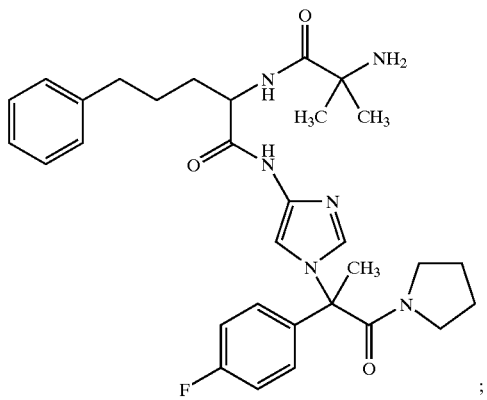

or a pharmaceutically acceptable salt or solvate thereof.

3. A compound according to claim 1 having the formula

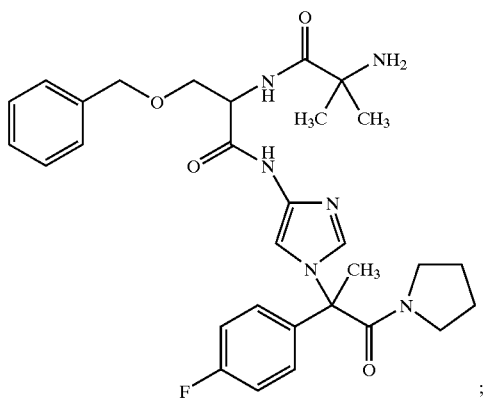

or a pharmaceutically acceptable salt or solvate thereof.

4. A compound according to claim 1 having the formula

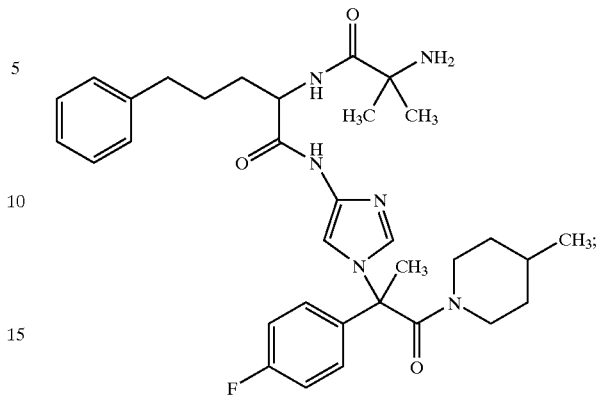

or a pharmaceutically acceptable salt or solvate thereof.

5. A pharmaceutical formulation which comprises, as an active ingredient a compound of claim 1, or a pharmaceutically acceptable salt or solvate thereof, associated with one or more pharmaceutically acceptable carriers, diluents, or excipients.

6. A pharmaceutical formulation which comprises, as an active ingredient a compound of claim 2, or a pharmaceutically acceptable salt or solvate thereof, associated with one or more pharmaceutically acceptable carriers, diluents, or excipients.

7. A pharmaceutical formulation which comprises, as an active ingredient a compound of claim 3, or a pharmaceutically acceptable salt or solvate thereof, associated with one or more pharmaceutically acceptable carriers, diluents, or excipients.

8. A pharmaceutical formulation which comprises, as an active ingredient a compound of claim 4, or a pharmaceutically acceptable salt or solvate thereof, associated with one or more pharmaceutically acceptable carriers, diluents, or excipients.

* * * * *